United States Patent
Grice et al.

(10) Patent No.: US 11,129,827 B2
(45) Date of Patent: Sep. 28, 2021

(54) DUAL MAGL AND FAAH INHIBITORS

(71) Applicant: Abide Therapeutics, Inc., San Diego, CA (US)

(72) Inventors: Cheryl A. Grice, Encinitas, CA (US); Justin S. Cisar, San Diego, CA (US); Katharine K. Duncan, San Diego, CA (US); Yu Feng, San Diego, CA (US); John J. M. Wiener, La Jolla, CA (US); Olivia D. Weber, San Diego, CA (US)

(73) Assignee: Abide Therapeutics, Inc., San Diego, CA (US)

(*) Notice: Subject to any disclaimer, the term of this patent is extended or adjusted under 35 U.S.C. 154(b) by 82 days.

(21) Appl. No.: 16/431,632

(22) Filed: Jun. 4, 2019

(65) Prior Publication Data

US 2019/0282568 A1    Sep. 19, 2019

Related U.S. Application Data

(62) Division of application No. 15/919,113, filed on Mar. 12, 2018, now Pat. No. 10,350,205.

(60) Provisional application No. 62/470,830, filed on Mar. 13, 2017.

(51) Int. Cl.
  *A61K 31/496* (2006.01)
  *A61K 31/506* (2006.01)
  *A61P 25/04* (2006.01)

(52) U.S. Cl.
  CPC .......... *A61K 31/496* (2013.01); *A61K 31/506* (2013.01); *A61P 25/04* (2018.01); *A61K 2121/00* (2013.01)

(58) Field of Classification Search
  CPC ................ A61K 31/496; A61K 31/506; A61K 2121/00; A61P 25/04
  See application file for complete search history.

(56) References Cited

U.S. PATENT DOCUMENTS

| | | | |
|---|---|---|---|
| 7,915,251 B2 | 3/2011 | Kahn et al. | |
| 7,915,261 B2 | 3/2011 | Ishii | |
| 7,919,494 B2 | 4/2011 | Ishii et al. | |
| 8,461,159 B2* | 6/2013 | Breitenbucher | A61P 35/00 514/248 |
| 9,249,102 B2 | 2/2016 | Meng et al. | |
| 2016/0272602 A1 | 9/2016 | Cisar et al. | |

FOREIGN PATENT DOCUMENTS

| | | |
|---|---|---|
| WO | WO 2004/111004 A1 | 12/2004 |
| WO | WO 2010/056309 A2 | 5/2010 |
| WO | WO 2014/127350 A1 | 8/2014 |
| WO | WO 2015/116774 A1 | 8/2015 |
| WO | WO 2016/014975 A2 | 1/2016 |

OTHER PUBLICATIONS

Huntington's Disease in https://www.mayoclinic.org/diseases-conditions/huntingtons-disease/diagnosis-treatment/drc-20356122 (2020) (Year: 2020).*
Yiannopoulou et al. in Therapeutic Advances in Neurological Disorders 6(1), 19-33 (2013) (Year: 2013).*
Amyotrophic Lateral Sclerosis (ALS) in https://www.hopkinsmedicine.org/neurology_neurosurgery/centers_clinics/als/conditions/als_treatment.html (2017) (Year: 2017).*
Kiss et al. disclose in ChemMedChem. 13(20):2177-2188 (2018) (Year: 2018).*
Lodola et al. discloses in Expert Opin Ther Pat. 25(11):1247-66 (2015) (Year: 2015).*
Mallet et al. reviews in Int J Clin Pharmacol Ther. 54(7): 498-501 (2016) (Year: 2016).*
Gil-Ordonez discloses in Biochemical Pharmacology 157, 18-32 (2018) (Year: 2018).*
Ess, KC in Experimental Biology and Medicine 238(3):308-314 (2013) (Year: 2013).*
Garde in FierceBiotech (Jan. 20, 2016) https://www.fiercebiotech.com/r-d/j-j-halts-a-depression-program-shadow-of-a-fatal-french-trial) (Year: 2016).*
Naidoo et al. Neurotherapeutics 9:801-813 (2012) (Year: 2012).*
Berge et al. Pharmaceutical Salts. Journal of Pharmaceutical Sciences 66(1):1-19 (Jan. 1977).
Chang et al. Highly Selective Inhibitors of Monoacylglycerol Lipase Bearing a Reactive Group that is Bioisosteric with Endocannabinoid Substrates. ChemBiol 19(5):579-588 (2012).
Fleisher et al. Improved oral drug delivery: solubility limitations overcome by the use of prodrugs. Advanced Drug Delivery Reviews 19:115-130 (1996).
Long et al. Characterization of tunable piperidine and piperazine carbamates as inhibitors of endocannabinoid hydrolases. J Med chem 53(4):1830-1842 (2010).
Long et al. Selective blockade of 2-arachidonoylglycerol hydrolysis produces cannabinoid behavioral effects. Nat Chem Biol. 5(1):37-44 (2009).
Niphakis et al. O-Hydroxyacetamide Carbamates as a Highly Potent and Selective Class of Endocannabinoid Hydrolase Inhibitors. ACS Chem. Neurosci. 3(5):418-426 (2012/Web2011).
Science IP Report dated Nov. 30, 2017 (103 pgs).
Tichenor et al., "Heteroaryl urea inhibitors of fatty acid amide hydrolase: structure-mutagenicity relationships for arylamine metabolites," Bioorg. Med. Chem. Lett., 22(4):7357-7362 (2012).
D'Addario et al. "Epigenetic Regulation of Fatty Acid Amide Hydrolase in Alzheimer Disease" PLos One (2012), vol. 7, issue 6, e39186.
Scotter et al. "The endocannabinoid system as a target for the treatment of neurodegenerative disease" British Journal of Pharmacology (2010), 160, 480-498.

* cited by examiner

*Primary Examiner* — Dennis Heyer
(74) *Attorney, Agent, or Firm* — Jones Day

(57) ABSTRACT

Provided herein are compounds and pharmaceutical compositions comprising said compounds useful as modulators of MAGL and/or FAAH. The subject compounds and compositions are useful for the treatment of pain and neurological disorders.

16 Claims, No Drawings

DUAL MAGL AND FAAH INHIBITORS

CROSS-REFERENCE

This application is a divisional of U.S. application Ser. No. 15/919,113, filed Mar. 12, 2018, which claims benefit of U.S. Provisional Application No. 62/470,830, filed on Mar. 13, 2017, of each of which are herein incorporated by reference in its entirety.

BACKGROUND OF THE INVENTION

Monoacylglycerol lipase (MAGL) is an enzyme responsible for hydrolyzing endocannabinoids such as 2-AG (2-arachidonoylglycerol), an arachidonate based lipid, in the nervous system. Fatty acid amide hydrolase (FAAH) is another enzyme responsible for hydrolyzing endocannabinoids such as anandamide.

BRIEF SUMMARY OF THE INVENTION

This disclosure provides, for example, compounds and compositions which are modulators of MAGL and/or FAAH, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of MAGL, and/or FAAH, activity in warm-blooded animals such as humans.

In some embodiments is a compound of Formula (I):

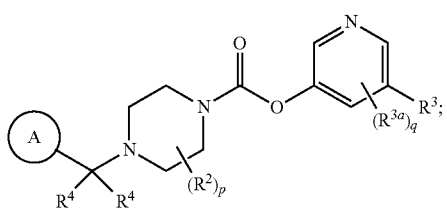

Formula (I)

wherein:

is

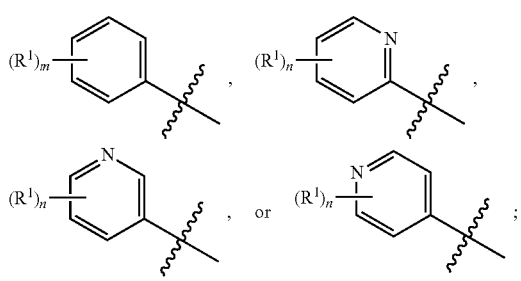

each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$C(O)NR^5R^6$, —$OR^7$, —$SO_2R^{12}$, —$SF_5$, —$SR^8$, aryl, and heteroaryl, wherein aryl and heteroaryl are optionally substituted with one or two groups independently selected from halogen, $C_{1-6}$alkyl, $C_{1-6}$haloalkyl, and —$C(O)NR^8R^9$; or two adjacent $R^1$ form a heterocycloalkyl ring optionally substituted with one or two $R^{11}$;

$R^2$ is $C_{1-6}$alkyl;

$R^3$ is selected from halogen, —CN, $C_{1-6}$alkyl, $C_{1-6}$haloalkyl, —$NR^8R^9$, —$C(O)NR^8R^9$, —$NR^8C(O)R^9$, and —$NR^9SO_2R^8$;

$R^{3a}$ is selected from halogen, $C_{1-6}$alkyl, and $C_{1-6}$haloalkyl;

each $R^4$ is independently selected from H and $C_{1-6}$alkyl;

each $R^5$ and $R^6$ is independently selected from H, $C_{1-6}$alkyl, and $C_{3-8}$cycloalkyl; or $R^5$ and $R^6$, together with the nitrogen to which they are attached, form a heterocycloalkyl optionally substituted with one or two $R^{10}$;

each $R^7$ is independently selected from H, $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl, wherein heterocycloalkyl, aryl, and heteroaryl are optionally substituted with one or two groups independently selected from halogen, $C_{1-6}$alkyl, and $C_{1-6}$haloalkyl;

each $R^8$ and $R^9$ is independently selected from H, $C_{1-6}$alkyl, $C_{3-8}$cycloalkyl, aryl, and heteroaryl;

each $R^{10}$ is independently selected from $C_{1-6}$alkyl, $C_{3-8}$cycloalkyl, $C_{1-6}$haloalkyl, halogen, oxo, —CN, —$C(O)OR^8$, —$C(O)R^8$, —$C(O)NR^8R^9$, —$SO_2R^8$, —$NR^9C(O)R^8$, and —$NR^9SO_2R^8$;

each $R^{11}$ is independently selected from halogen and $C_{1-6}$alkyl;

each $R^{12}$ is independently selected from $C_{1-6}$alkyl and $C_{3-8}$cycloalkyl;

m is 0, 1, 2, 3, 4, or 5;

n is 0, 1, 2, or 3;

p is 0 or 1; and q is 0 or 1;

or a pharmaceutically acceptable salt, solvate, or stereoisomer thereof.

In some embodiments is a compound of Formula (I), or a pharmaceutically acceptable salt, solvate, or stereoisomer thereof, wherein $R^4$ is H.

In some embodiments is a compound of Formula (II):

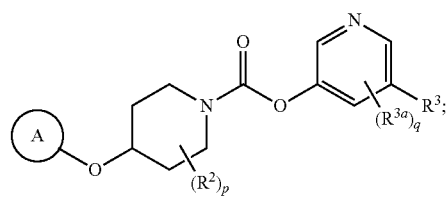

Formula (II)

wherein:

is

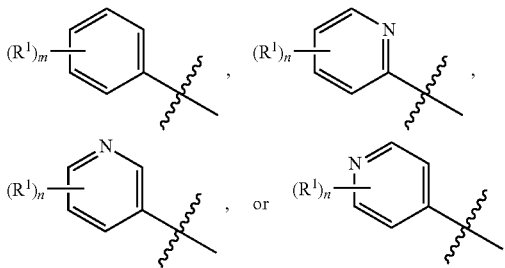

each R¹ is independently selected from halogen, —CN, $C_{1-6}$alkyl, $C_{2-6}$alkynyl, $C_{1-6}$alkyl-OR⁷, $C_{1-6}$haloalkyl, $C_{3-8}$cycloalkyl, —NR⁵R⁶, —C(O)NR⁵R⁶, —OR⁷, —SO₂R¹², —SF₅, —SR⁸, aryl, and heteroaryl, wherein aryl and heteroaryl are optionally substituted with one or two groups independently selected from halogen, $C_{1-6}$alkyl, $C_{1-6}$haloalkyl, and —C(O)NR⁸R⁹; or two adjacent R¹ form a heterocycloalkyl ring optionally substituted with one or two R¹¹;

R² is $C_{1-6}$alkyl;

R³ is selected from halogen, —CN, $C_{1-6}$alkyl, $C_{1-6}$haloalkyl, —NR⁸R⁹, —C(O)NR⁸R⁹, —NR⁸C(O)R⁹, and —NR⁹SO₂R⁸;

R³ᵃ is selected from halogen, $C_{1-6}$alkyl, and $C_{1-6}$haloalkyl;

each R⁵ and R⁶ is independently selected from H, $C_{1-6}$alkyl, and $C_{3-8}$cycloalkyl; or R⁵ and R⁶, together with the nitrogen to which they are attached, form a heterocycloalkyl optionally substituted with one or two R¹⁰;

each R⁷ is independently selected from H, $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl, wherein heterocycloalkyl, aryl, and heteroaryl are optionally substituted with one or two groups independently selected from halogen, $C_{1-6}$alkyl, and $C_{1-6}$haloalkyl;

each R⁸ and R⁹ is independently selected from H, $C_{1-6}$alkyl, $C_{3-8}$cycloalkyl, aryl, and heteroaryl; each R¹⁰ is independently selected from $C_{1-6}$alkyl, $C_{3-8}$cycloalkyl, $C_{1-6}$haloalkyl, halogen, oxo, —CN, —C(O)OR⁸, —C(O)R⁸, —C(O)NR⁸R⁹, —SO₂R⁸, —NR⁹C(O)R⁸, and —NR⁹SO₂R⁸;

each R¹¹ is independently selected from halogen and $C_{1-6}$alkyl;

each R¹² is independently selected from $C_{1-6}$alkyl and $C_{3-8}$cycloalkyl;

m is 0, 1, 2, 3, 4, or 5;

n is 0, 1, 2, or 3;

p is 0 or 1; and q is 0 or 1;

or a pharmaceutically acceptable salt, solvate, or stereoisomer thereof.

In some embodiments is a compound of Formula (I) or (II), or a pharmaceutically acceptable salt, solvate, or stereoisomer thereof, wherein p is 0. In some embodiments is a compound of Formula (I) or (II), or a pharmaceutically acceptable salt, solvate, or stereoisomer thereof, wherein p is 1. In some embodiments is a compound of Formula (I) or (II), or a pharmaceutically acceptable salt, solvate, or stereoisomer thereof, wherein R² is $C_{1-6}$alkyl. In some embodiments is a compound of Formula (I) or (II), or a pharmaceutically acceptable salt, solvate, or stereoisomer thereof, wherein R² is —CH₃. In some embodiments is a compound of Formula (I) or (II), or a pharmaceutically acceptable salt, solvate, or stereoisomer thereof, wherein

is

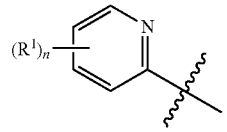

In some embodiments is a compound of Formula (I) or (II), or a pharmaceutically acceptable salt, solvate, or stereoisomer thereof, wherein

is

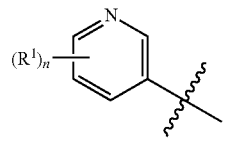

In some embodiments is a compound of Formula (I) or (II), or a pharmaceutically acceptable salt, solvate, or stereoisomer thereof, wherein

is

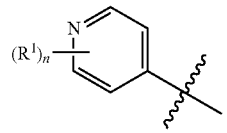

In some embodiments is a compound of Formula (I) or (II), or a pharmaceutically acceptable salt, solvate, or stereoisomer thereof, wherein n is 1. In some embodiments is a compound of Formula (I) or (II), or a pharmaceutically acceptable salt, solvate, or stereoisomer thereof, wherein

is

In some embodiments is a compound of Formula (III):

Formula (III)

wherein:
each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$C(O)NR^5R^6$, —$OR^7$, —$SO_2R^{12}$, —$SF_5$, —$SR^8$, aryl, and heteroaryl, wherein aryl and heteroaryl are optionally substituted with one or two groups independently selected from halogen, $C_{1-6}$alkyl, $C_{1-6}$haloalkyl, and —$C(O)NR^8R^9$; or two adjacent $R^1$ form a heterocycloalkyl ring optionally substituted with one or two $R^1$;

$R^3$ is selected from halogen, —CN, $C_{1-6}$alkyl, $C_{1-6}$haloalkyl, —$NR^8R^9$, —$C(O)NR^8R^9$, —$NR^8C(O)R^9$, and —$NR^9SO_2R^8$;

$R^{3a}$ is selected from halogen, $C_{1-6}$alkyl, and $C_{1-6}$haloalkyl;

each $R^5$ and $R^6$ is independently selected from H, $C_{1-6}$alkyl, and $C_{3-8}$cycloalkyl; or $R^5$ and $R^6$, together with the nitrogen to which they are attached, form a heterocycloalkyl optionally substituted with one or two $R^{10}$;

each $R^7$ is independently selected from H, $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl, wherein heterocycloalkyl, aryl, and heteroaryl are optionally substituted with one or two groups independently selected from halogen, $C_{1-6}$alkyl, and $C_{1-6}$haloalkyl;

each $R^8$ and $R^9$ is independently selected from H, $C_{1-6}$alkyl, $C_{3-8}$cycloalkyl, aryl, and heteroaryl; each $R^{10}$ is independently selected from $C_{1-6}$alkyl, $C_{3-8}$cycloalkyl, $C_{1-6}$haloalkyl, halogen, oxo, —CN, —$C(O)OR^8$, —$C(O)R^8$, —$C(O)NR^8R^9$, —$SO_2R^8$, —$NR^9C(O)R^8$, and —$NR^9SO_2R^8$;

each $R^{11}$ is independently selected from halogen and $C_{1-6}$alkyl;

each $R^{12}$ is independently selected from $C_{1-6}$alkyl and $C_{3-8}$cycloalkyl;

m is 0, 1, 2, 3, 4, or 5;
q is 0 or 1;
w is 1 or 2;
x is 0 or 1;
y is 0 or 1; and
z is 0 or 1;
wherein when y and z are 0, then x is 1 and w is 2;
when y and z are 1, then w is 1; and
when y is 1 and z is 0, or y is 0 and z is 1, then x is 1;

or a pharmaceutically acceptable salt, solvate, or stereoisomer thereof.

In some embodiments is a compound of Formula (III) having the structure of Formula (IIIa):

Formula (IIIa)

In some embodiments is a compound of Formula (III) having the structure of Formula (IIIb):

Formula (IIIb)

In some embodiments is a compound of Formula (IV):

Formula (IV)

wherein:
each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$C(O)NR^5R^6$, —$OR^7$, —$SO_2R^{12}$, —$SF_5$, —$SR^8$, aryl, and heteroaryl, wherein aryl and heteroaryl are optionally substituted with one or two groups independently selected from halogen, $C_{1-6}$alkyl, $C_{1-6}$haloalkyl, and —$C(O)NR^8R^9$; or two adjacent $R^1$ form a heterocycloalkyl ring optionally substituted with one or two $R^{11}$;

$R^3$ is selected from halogen, —CN, $C_{1-6}$alkyl, $C_{1-6}$haloalkyl, —$NR^8R^9$, —$C(O)NR^8R^9$, —$NR^8C(O)R^9$, and —$NR^9SO_2R^8$;

$R^{3a}$ is selected from halogen, $C_{1-6}$alkyl, and $C_{1-6}$haloalkyl;

each $R^5$ and $R^6$ is independently selected from H, $C_{1-6}$alkyl, and $C_{3-8}$cycloalkyl; or $R^5$ and $R^6$, together with the nitrogen to which they are attached, form a heterocycloalkyl optionally substituted with one or two $R^{10}$;

each $R^7$ is independently selected from H, $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl, wherein heterocycloalkyl, aryl, and heteroaryl are optionally substituted with one or two groups independently selected from halogen, $C_{1-6}$alkyl, and $C_{1-6}$haloalkyl;

each $R^8$ and $R^9$ is independently selected from H, $C_{1-6}$alkyl, $C_{3-8}$cycloalkyl, aryl, and heteroaryl;

each $R^{10}$ is independently selected from $C_{1-6}$alkyl, $C_{3-8}$cycloalkyl, $C_{1-6}$haloalkyl, halogen, oxo, —CN, —C(O)OR$^8$, —C(O)R$^8$, —C(O)NR$^8$R$^9$, —SO$_2$R$^8$, —NR$^9$C(O)R$^8$, and —NR$^9$SO$_2$R$^8$;

each $R^{11}$ is independently selected from halogen and $C_{1-6}$alkyl;

each $R^{12}$ is independently selected from $C_{1-6}$alkyl and $C_{3-8}$cycloalkyl;

m is 0, 1, 2, 3, 4, or 5; and q is 0 or 1;

or a pharmaceutically acceptable salt, solvate, or stereoisomer thereof.

In some embodiments is a compound of Formula (I), (II), (III), (IIIa), (IIIb), or (IV), or a pharmaceutically acceptable salt, solvate, or stereoisomer thereof, wherein m is 1. In some embodiments is a compound of Formula (I), (II), (III), (IIIa), (IIIb), or (IV), or a pharmaceutically acceptable salt, solvate, or stereoisomer thereof, wherein m is 2. In some embodiments is a compound of Formula (I), (II), (III), (IIIa), (IIIb), or (IV), or a pharmaceutically acceptable salt, solvate, or stereoisomer thereof, wherein $R^3$ is $C_{1-6}$haloalkyl. In some embodiments is a compound of Formula (I), (II), (III), (IIIa), (IIIb), or (IV), or a pharmaceutically acceptable salt, solvate, or stereoisomer thereof, wherein $R^3$ is —CF$_3$. In some embodiments is a compound of Formula (I), (II), (III), (IIIa), (IIIb), or (IV), or a pharmaceutically acceptable salt, solvate, or stereoisomer thereof, wherein $R^3$ is halogen. In some embodiments is a compound of Formula (I), (II), (III), (IIIa), (IIIb), or (IV), or a pharmaceutically acceptable salt, solvate, or stereoisomer thereof, wherein $R^3$ is —C(O)NH$_2$. In some embodiments is a compound of Formula (I), (II), (III), (IIIa), (IIIb), or (IV), or a pharmaceutically acceptable salt, solvate, or stereoisomer thereof, wherein $R^3$ is —CN. In some embodiments is a compound of Formula (I), (II), (III), (IIIa), (IIIb), or (IV), or a pharmaceutically acceptable salt, solvate, or stereoisomer thereof, wherein q is 0. In some embodiments is a compound of Formula (I), (II), (III), (IIIa), (IIIb), or (IV), or a pharmaceutically acceptable salt, solvate, or stereoisomer thereof, wherein q is 1. In some embodiments is a compound of Formula (I), (II), (III), (IIIa), (IIIb), or (IV), or a pharmaceutically acceptable salt, solvate, or stereoisomer thereof, wherein each $R^1$ is independently selected from halogen, —CN, $C_{1-6}$alkyl, $C_{1-6}$haloalkyl, —NR$^5$R$^6$, —OR$^7$, and heteroaryl. In some embodiments is a compound of Formula (I), (II), (III), (IIIa), (IIIb), or (IV), or a pharmaceutically acceptable salt, solvate, or stereoisomer thereof, wherein each $R^1$ is independently selected from halogen, $C_{1-6}$haloalkyl, —NR$^5$R$^6$, and —OR$^7$. In some embodiments is a compound of Formula (I), (II), (III), (IIIa), (IIIb), or (IV), or a pharmaceutically acceptable salt, solvate, or stereoisomer thereof, wherein $R^5$ and $R^6$, together with the nitrogen to which they are attached, form a heterocycloalkyl optionally substituted with one or two $R^{10}$. In some embodiments is a compound of Formula (I), (II), (III), (IIIa), (IIIb), or (IV), or a pharmaceutically acceptable salt, solvate, or stereoisomer thereof, wherein $R^5$ and $R^6$, together with the nitrogen to which they are attached, form a heterocycloalkyl substituted with one or two $R^{10}$ independently selected from $C_{1-6}$alkyl and —C(O)NR$^8$R$^9$. In some embodiments is a compound of Formula (I), (II), (III), (IIIa), (IIIb), or (IV), or a pharmaceutically acceptable salt, solvate, or stereoisomer thereof, wherein $R^5$ and $R^6$, together with the nitrogen to which they are attached, form an unsubstituted heterocycloalkyl. In some embodiments is a compound of Formula (I), (II), (III), (IIIa), (IIIb), or (IV), or a pharmaceutically acceptable salt, solvate, or stereoisomer thereof, wherein $R^5$ and $R^6$, together with the nitrogen to which they are attached, form a heterocycloalkyl selected from:

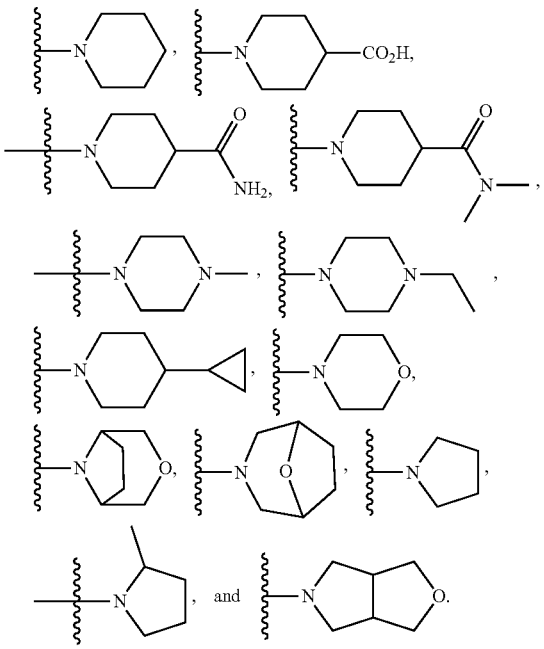

In some embodiments is a compound of Formula (I), (II), (III), (IIIa), (IIIb), or (IV), or a pharmaceutically acceptable salt, solvate, or stereoisomer thereof, wherein each $R^1$ is independently selected from halogen, $C_{1-6}$alkyl, $C_{1-6}$haloalkyl, and —OR$^7$. In some embodiments is a compound of Formula (I), (II), (III), (IIIa), (IIIb), or (IV), or a pharmaceutically acceptable salt, solvate, or stereoisomer thereof, wherein each $R^7$ is independently selected from $C_{1-6}$alkyl, $C_{1-6}$haloalkyl, $C_{3-8}$cycloalkyl, aryl, and heteroaryl. In some embodiments is a compound of Formula (I), (II), (III), (IIIa), (IIIb), or (IV), or a pharmaceutically acceptable salt, solvate, or stereoisomer thereof, wherein each $R^7$ is independently selected from $C_{1-6}$alkyl, $C_{1-6}$haloalkyl, and aryl. In some embodiments is a compound of Formula (I), (II), (III), (IIIa), (IIIb), or (IV), or a pharmaceutically acceptable salt, solvate, or stereoisomer thereof, wherein two adjacent $R^1$ form a heterocycloalkyl ring optionally substituted with one or two $R^{11}$. In some embodiments is a compound of Formula (I), (II), (III), (IIIa), (IIIb), or (IV), or a pharmaceutically acceptable salt, solvate, or stereoisomer thereof, wherein two adjacent $R^1$ form a heterocycloalkyl ring optionally substituted with one or two $R^{11}$ and each $R^{11}$ is independently selected from halogen.

In another embodiment is a pharmaceutical composition comprising a compound of Formula (I), (II), (III), (IIIa), (IIIb), or (IV) described herein, or a pharmaceutically acceptable salt, solvate, or stereoisomer thereof, and at least one pharmaceutically acceptable excipient.

In another embodiment is a method of treating pain in a patient in need thereof, comprising administering to the patient a therapeutically effective amount of a compound of Formula (I), (II), (III), (IIIa), (IIIb), or (IV) described herein, or a pharmaceutically acceptable salt, solvate, or stereoisomer thereof.

In another embodiment is a method of treating a neurological disorder in a patient in need thereof, comprising administering to the patient a therapeutically effective amount of a compound of Formula (I), (II), (III), (IIIa), (IIIb), or (IV) described herein, or a pharmaceutically acceptable salt, solvate, or stereoisomer thereof.

DETAILED DESCRIPTION OF THE INVENTION

This disclosure is directed, at least in part, to modulators or inhibitors of MAGL and/or FAAH. For example, provided herein are compounds capable of inhibiting MAGL and/or FAAH. In some embodiments, the compounds described herein are dual inhibitors capable of inhibiting MAGL and FAAH.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_4$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2), and —$S(O)_tN(R^a)_2$ (where t is 1 or 2), where each $R^a$ is independently hydrogen, alkyl, fluoroalkyl, cycloalkyl, aryl, aralkyl, heterocycloalkyl, heteroaryl, or heteroarylalkyl, and each $R^f$ is independently alkyl, fluoroalkyl, cycloalkyl, aryl, aralkyl, heterocycloalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —$OC(O)$—$R^f$, —$N(R^a)_2$, —$C(O)R^a$, —$C(O)OR^a$, —$C(O)N(R^a)_2$, —$N(R^a)C(O)OR^f$, —$OC(O)$—$NR^aR^f$, —$N(R^a) C(O)R$, —$N(R^a)S(O)_tR^f$ (where t is 1 or 2), —$S(O)_tOR^a$ (where t is 1 or 2), —$S(O)_tR^f$ (where t is 1 or 2), and —$S(O)_tN(R^a)_2$ (where t is 1 or 2), where each $R^a$ is independently hydrogen, alkyl, fluoroalkyl, cycloalkyl, aryl, aralkyl, heterocycloalkyl, heteroaryl, or heteroarylalkyl, and each $R^f$ is independently alkyl, fluoroalkyl, cycloalkyl, aryl, aralkyl, heterocycloalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —$OC(O)R^a$, —$N(R^a)_2$, —$C(O)R^a$, —$C(O)OR^a$, —$C(O)N(R^a)_2$, —$N(R^a)C(O)OR^f$, —OC(O)—NR$^a$R$^f$, —N(R$^a$)C(O)R$^f$, —N(R$^a$)S(O)$_t$R$^f$ (where t is 1 or 2), —S(O)$_t$OR$^a$ (where t is 1 or 2), —S(O)$_t$R$^f$ (where t is 1 or 2), and —S(O)$_t$N(R$^a$)$_2$ (where t is 1 or 2), where each R$^a$ is independently hydrogen, alkyl, fluoroalkyl, cycloalkyl, aryl, aralkyl, heterocycloalkyl, heteroaryl, or heteroarylalkyl, and each R$^f$ is independently alkyl, fluoroalkyl, cycloalkyl, aryl, aralkyl, heterocycloalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) t-electron system in accordance with the Hückel theory. The ring system from which aryl groups are derived include, but are not limited to, groups such as benzene, fluorene, indane, indene, tetralin, and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O) R$^a$, —R$^b$—C(O)OR$^a$, —R$^b$—C(O)N(R$^a$)$_2$, —R$^b$—O—R—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O-aralkyl, where aralkyl is as defined above.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1] heptanyl, and the like. Unless otherwise stated specifically in the specification, the term "cycloalkyl" is meant to include cycloalkyl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O) R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

"Halo" or "halogen" refers to bromo, chloro, fluoro, or iodo substituents.

"Haloalkyl" refers to an alkyl radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Haloalkoxy" refers to an alkoxy radical, as defined above, that is substituted by one or more halo radicals, as defined above.

"Heterocycloalkyl" refers to a stable 3- to 18-membered non-aromatic ring radical that comprises two to twelve carbon atoms and from one to six heteroatoms selected from nitrogen, oxygen, and sulfur. Unless stated otherwise specifically in the specification, the heterocycloalkyl radical is a monocyclic, bicyclic, tricyclic, or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3] dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)$ $R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen, and sulfur. As used herein, the heteroaryl radical is a monocyclic, bicyclic, tricyclic, or tetracyclic ring system, wherein at least one of the rings in the ring system is fully unsaturated, i.e., it contains a cyclic, delocalized (4n+2) t-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$O$—$R$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2) and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl, or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

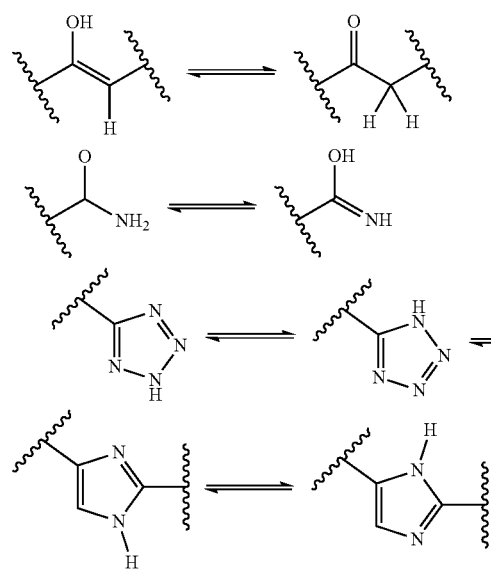
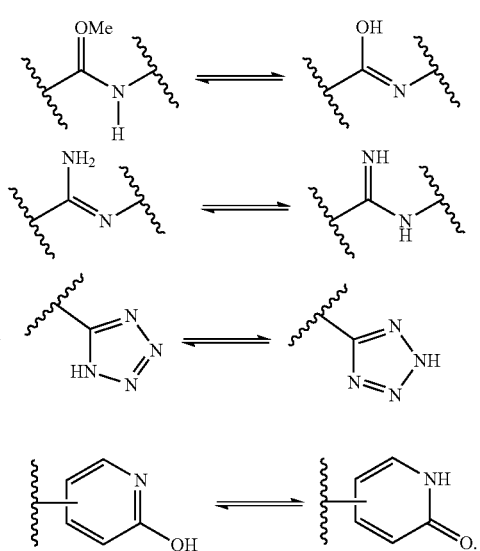

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

For therapeutic use, salts of the compounds of the invention are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The term "addition salt" or "salt", as used herein also is meant to comprise the solvates, which the compounds of the invention as well as the (non-solvate) salts thereof, are able to form. Such solvates are for example hydrates, alcoholates, e.g. methanolates, ethanolates, propanolates, and the like. Preferred are solvates that are pharmaceutically acceptable. Hence the invention also encompasses the pharmaceutically acceptable solvates of the compounds as specified herein.

Compounds of the present invention may exist in N-oxide form. The N-oxide forms are meant to comprise the compounds of the invention wherein one or several nitrogen atoms are oxidized to the so-called N-oxide. The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydroperoxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of the present invention may exist as quaternary amines. The term "quaternary amine" defines the quaternary ammonium salts which the compounds of the invention are able to form by reaction between a basic nitrogen of a compound of the invention and an appropriate quaternizing agent, such as, for example, an optionally substituted alkyl halide, aryl halide or arylalkyl halide, e.g. methyl iodide or benzyl iodide. Other reactants with suitable leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compound of the present invention may have metal binding, chelating, complex forming properties and therefore may exist as metal complexes or metal chelates. Such metalated derivatives of the compounds of the invention are intended to be included within the scope of the present invention.

As used herein, "treatment" or "treating" or "palliating" or "ameliorating" are used interchangeably herein. These terms refer to an approach for obtaining beneficial or desired results including, but not limited to, therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

The compounds of Formula (I), (II), (III), (IIIa), (IIIb), or (IV) described herein are inhibitors of MAGL and/or FAAH. In some embodiments, the compounds are inhibitors of MAGL. In some embodiments, the compounds are inhibitors of FAAH. In some embodiments, the compounds are inhibitors of MAGL and FAAH. The compounds of Formula (I), (II), (III), (IIIa), (IIIb), or (IV) described herein, and compositions comprising these compounds, are useful for the treatment of pain or a neurological disorder.

In some embodiments is a compound of Formula (I):

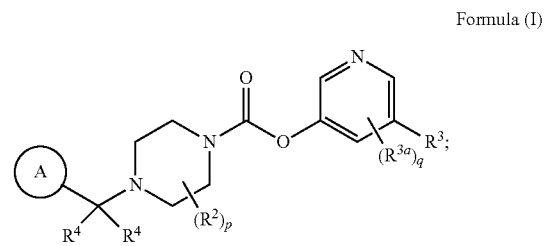

Formula (I)

wherein:

is

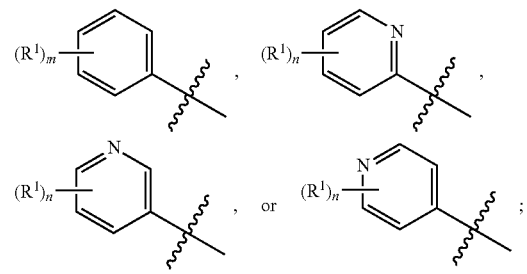

each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$C(O)NR^5R^6$, —$OR^7$, —$SO_2R^{12}$, —$SF_5$, —$SR^8$, aryl, and heteroaryl, wherein aryl and heteroaryl are optionally substituted with one or two groups independently selected from halogen, $C_{1-6}$alkyl, $C_{1-6}$haloalkyl, and —$C(O)NR^8R^9$; or two adjacent $R^1$ form a heterocycloalkyl ring optionally substituted with one or two $R^{11}$;

$R^2$ is $C_{1-6}$alkyl;

$R^3$ is selected from halogen, —CN, $C_{1-6}$alkyl, $C_{1-6}$haloalkyl, —$NR^8R^9$, —$C(O)NR^8R^9$, —$NR^8C(O)R^9$, and —$NR^9SO_2R^8$; $R^{3a}$ is selected from halogen, $C_{1-6}$alkyl, and $C_{1-6}$haloalkyl;

each $R^4$ is independently selected from H and $C_{1-6}$alkyl;

each $R^5$ and $R^6$ is independently selected from H, $C_{1-6}$alkyl, and $C_{3-8}$cycloalkyl; or $R^5$ and $R^6$, together with the nitrogen to which they are attached, form a heterocycloalkyl optionally substituted with one or two $R^{10}$;

each $R^7$ is independently selected from H, $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl, wherein heterocycloalkyl, aryl, and heteroaryl are optionally substituted with one or two groups independently selected from halogen, $C_{1-6}$alkyl, and $C_{1-6}$haloalkyl;

each $R^8$ and $R^9$ is independently selected from H, $C_{1-6}$alkyl, $C_{3-8}$cycloalkyl, aryl, and heteroaryl; each $R^{10}$ is independently selected from $C_{1-6}$alkyl, $C_{3-8}$cycloalkyl, $C_{1-6}$haloalkyl, halogen, oxo, —CN, —C(O)OR$^8$, —C(O)R$^8$, —C(O)NR$^8$R$^9$, —SO$_2$R$^8$, —NR$^9$C(O)R$^8$, and —NR$^9$SO$_2$R$^8$;

each $R^{11}$ is independently selected from halogen and $C_{1-6}$alkyl;

each $R^{12}$ is independently selected from $C_{1-6}$alkyl and $C_{3-8}$cycloalkyl;

m is 0, 1, 2, 3, 4, or 5;

n is 0, 1, 2, or 3;

p is 0 or 1; and q is 0 or 1;

or a pharmaceutically acceptable salt, solvate, or stereoisomer thereof.

In some embodiments is a compound of Formula (I), or a pharmaceutically acceptable salt, solvate, or stereoisomer thereof, wherein each $R^4$ is H. In some embodiments is a compound of Formula (I), or a pharmaceutically acceptable salt, solvate, or stereoisomer thereof, wherein one $R^4$ is H and one $R^4$ is $C_{1-6}$alkyl. In some embodiments is a compound of Formula (I), or a pharmaceutically acceptable salt, solvate, or stereoisomer thereof, wherein one $R^4$ is H and one $R^4$ is —CH$_3$. In some embodiments is a compound of Formula (I), or a pharmaceutically acceptable salt, solvate, or stereoisomer thereof, wherein one $R^4$ is H and one $R^4$ is —CH$_2$CH$_3$. In some embodiments is a compound of Formula (I), or a pharmaceutically acceptable salt, solvate, or stereoisomer thereof, wherein one $R^4$ is H and one $R^4$ is —CH$_2$CH$_2$CH$_3$. In some embodiments is a compound of Formula (I), or a pharmaceutically acceptable salt, solvate, or stereoisomer thereof, wherein one $R^4$ is H and one $R^4$ is —CH(CH$_3$)$_2$. In some embodiments is a compound of Formula (I), or a pharmaceutically acceptable salt, solvate, or stereoisomer thereof, wherein each $R^4$ is $C_{1-6}$alkyl. In some embodiments is a compound of Formula (I), or a pharmaceutically acceptable salt, solvate, or stereoisomer thereof, wherein each $R^4$ is —CH$_3$.

In some embodiments is a compound of Formula (I), or a pharmaceutically acceptable salt, solvate, or stereoisomer thereof, wherein p is 0. In some embodiments is a compound of Formula (I), or a pharmaceutically acceptable salt, solvate, or stereoisomer thereof, wherein p is 1. In some embodiments is a compound of Formula (I), or a pharmaceutically acceptable salt, solvate, or stereoisomer thereof, wherein p is 1 and $R^2$ is —CH$_3$. In some embodiments is a compound of Formula (I), or a pharmaceutically acceptable salt, solvate, or stereoisomer thereof, wherein p is 1 and $R^2$ is —CH$_2$CH$_3$. In some embodiments is a compound of Formula (I), or a pharmaceutically acceptable salt, solvate, or stereoisomer thereof, wherein p is 1 and $R^2$ is —CH$_2$CH$_2$CH$_3$. In some embodiments is a compound of Formula (I), or a pharmaceutically acceptable salt, solvate, or stereoisomer thereof, wherein p is 1 and $R^2$ is —CH(CH$_3$)$_2$.

In some embodiments is a compound of Formula (I), or a pharmaceutically acceptable salt, solvate, or stereoisomer thereof, wherein $R^3$ is halogen. In some embodiments is a compound of Formula (I), or a pharmaceutically acceptable salt, solvate, or stereoisomer thereof, wherein $R^3$ is —CN. In some embodiments is a compound of Formula (I), or a pharmaceutically acceptable salt, solvate, or stereoisomer thereof, wherein $R^3$ is $C_{1-6}$alkyl. In some embodiments is a compound of Formula (I), or a pharmaceutically acceptable salt, solvate, or stereoisomer thereof, wherein $R^3$ is —CH$_3$. In some embodiments is a compound of Formula (I), or a pharmaceutically acceptable salt, solvate, or stereoisomer thereof, wherein $R^3$ is $C_{1-6}$haloalkyl. In some embodiments is a compound of Formula (I), or a pharmaceutically acceptable salt, solvate, or stereoisomer thereof, wherein $R^3$ is —CF$_3$. In some embodiments is a compound of Formula (I), or a pharmaceutically acceptable salt, solvate, or stereoisomer thereof, wherein $R^3$ is —NR$^8$R$^9$. In some embodiments is a compound of Formula (I), or a pharmaceutically acceptable salt, solvate, or stereoisomer thereof, wherein $R^3$ is —NH$_2$. In some embodiments is a compound of Formula (I), or a pharmaceutically acceptable salt, solvate, or stereoisomer thereof, wherein $R^3$ is —C(O)NR$^8$R$^9$. In some embodiments is a compound of Formula (I), or a pharmaceutically acceptable salt, solvate, or stereoisomer thereof, wherein $R^3$ is —C(O)NH$_2$. In some embodiments is a compound of Formula (I), or a pharmaceutically acceptable salt, solvate, or stereoisomer thereof, wherein $R^3$ is —NR$^8$C(O)R$^9$. In some embodiments is a compound of Formula (I), or a pharmaceutically acceptable salt, solvate, or stereoisomer thereof, wherein $R^3$ is —NHC(O)CH$_3$. In some embodiments is a compound of Formula (I), or a pharmaceutically acceptable salt, solvate, or stereoisomer thereof, wherein q is 0. In some embodiments is a compound of Formula (I), or a pharmaceutically acceptable salt, solvate, or stereoisomer thereof, wherein q is 1. In some embodiments is a compound of Formula (I), or a pharmaceutically acceptable salt, solvate, or stereoisomer thereof, wherein q is 1 and $R^{3a}$ is halogen. In some embodiments is a compound of Formula (I), or a pharmaceutically acceptable salt, solvate, or stereoisomer thereof, wherein q is 1 and $R^{3a}$ is $C_{1-6}$alkyl. In some embodiments is a compound of Formula (I), or a pharmaceutically acceptable salt, solvate, or stereoisomer thereof, wherein q is 1 and $R^{3a}$ is $C_{1-6}$haloalkyl.

In some embodiments is a compound of Formula (I), or a pharmaceutically acceptable salt, solvate, or stereoisomer thereof, wherein

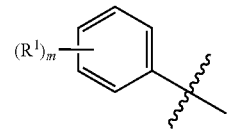

is

In some embodiments is a compound of Formula (I), or a pharmaceutically acceptable salt, solvate, or stereoisomer thereof, wherein m is 0. In some embodiments is a compound of Formula (I), or a pharmaceutically acceptable salt, solvate, or stereoisomer thereof, wherein m is 1. In some embodiments is a compound of Formula (I), or a pharmaceutically acceptable salt, solvate, or stereoisomer thereof, wherein m is 1 and $R^1$ is selected from halogen, —CN, $C_{1-6}$alkyl, $C_{2-6}$alkynyl, $C_{1-6}$alkyl-OR$^7$, $C_{1-6}$haloalkyl, $C_{3-8}$cycloalkyl, —NR$^5$R$^6$, —OR$^7$, —SO$_2$R$^{12}$, —SF$_5$, —SR$^8$, aryl, and heteroaryl. In some embodiments is a compound of Formula (I), or a pharmaceutically acceptable salt, solvate, or stereoisomer thereof, wherein m is 1 and $R^1$ is selected from halogen, $C_{1-6}$alkyl, $C_{1-6}$haloalkyl, $C_{3-8}$cycloalkyl, —NR$^5$R$^6$, and —OR$^7$. In some embodiments is a compound of Formula (I), or a pharmaceutically acceptable salt, solvate, or stereoisomer thereof, wherein m is 1 and $R^1$ is selected from halogen, $C_{1-6}$alkyl, $C_{1-6}$haloalkyl, $C_{3-8}$cycloalkyl, and —$OR^7$. In some embodiments is a compound of Formula (I), or a pharmaceutically acceptable salt, solvate, or stereoisomer thereof, wherein m is 1 and $R^1$ is halogen. In some embodiments is a compound of Formula (I), or a pharmaceutically acceptable salt, solvate, or stereoisomer thereof, wherein m is 1 and $R^1$ is F. In some embodiments is a compound of Formula (I), or a pharmaceutically acceptable salt, solvate, or stereoisomer thereof, wherein m is 1 and $R^1$ is Cl. In some embodiments is a compound of Formula (I), or a pharmaceutically acceptable salt, solvate, or stereoisomer thereof, wherein m is 1 and $R^1$ is —CN. In some embodiments is a compound of Formula (I), or a pharmaceutically acceptable salt, solvate, or stereoisomer thereof, wherein m is 1 and $R^1$ is $C_{1-6}$alkyl. In some embodiments is a compound of Formula (I), or a pharmaceutically acceptable salt, solvate, or stereoisomer thereof, wherein m is 1 and $R^1$ is —$CH_3$. In some embodiments is a compound of Formula (I), or a pharmaceutically acceptable salt, solvate, or stereoisomer thereof, wherein m is 1 and $R^1$ is —C≡CH. In some embodiments is a compound of Formula (I), or a pharmaceutically acceptable salt, solvate, or stereoisomer thereof, wherein m is 1 and $R^1$ is $C_{1-6}$alkyl-$OR^7$. In some embodiments is a compound of Formula (I), or a pharmaceutically acceptable salt, solvate, or stereoisomer thereof, wherein m is 1 and $R^1$ is —$CH_2$—O—$CH_3$. In some embodiments is a compound of Formula (I), or a pharmaceutically acceptable salt, solvate, or stereoisomer thereof, wherein m is 1 and $R^1$ is $C_{1-6}$haloalkyl. In some embodiments is a compound of Formula (I), or a pharmaceutically acceptable salt, solvate, or stereoisomer thereof, wherein m is 1 and $R^1$ is —$CF_3$. In some embodiments is a compound of Formula (I), or a pharmaceutically acceptable salt, solvate, or stereoisomer thereof, wherein m is 1 and $R^1$ is $C_{3-8}$cycloalkyl. In some embodiments is a compound of Formula (I), or a pharmaceutically acceptable salt, solvate, or stereoisomer thereof, wherein m is 1 and $R^1$ is —$NR^5R^6$. In some embodiments is a compound of Formula (I), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl optionally substituted with one or two $R^{10}$. In some embodiments is a compound of Formula (I), or a pharmaceutically acceptable salt, solvate, or stereoisomer thereof, wherein m is 1, $R^1$ is —$NR^5R^6$, and $R^5$ and $R^6$, together with the nitrogen to which they are attached, form an unsubstituted heterocycloalkyl. In some embodiments is a compound of Formula (I), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, $C_{1-6}$haloalkyl, halogen, oxo, —$C(O)NR^8R^9$, —$SO_2R^8$, —$NR^9C(O)R^8$, and —$NR^9SO_2R^8$. In some embodiments is a compound of Formula (I), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, and —$C(O)NR^8R^9$. In some embodiments is a compound of Formula (I), or a pharmaceutically acceptable salt, solvate, or stereoisomer thereof, wherein m is 1 and $R^1$ is —$OR^7$. In some embodiments is a compound of Formula (I), or a pharmaceutically acceptable salt, solvate, or stereoisomer thereof, wherein m is 1, $R^1$ is —$OR^7$, and $R^7$ is selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (I), or a pharmaceutically acceptable salt, solvate, or stereoisomer thereof, wherein m is 1 and $R^1$ is —$OCH_3$. In some embodiments is a compound of Formula (I), or a pharmaceutically acceptable salt, solvate, or stereoisomer thereof, wherein m is 1 and $R^1$ is —$OCF_3$. In some embodiments is a compound of Formula (I), or a pharmaceutically acceptable salt, solvate, or stereoisomer thereof, wherein m is 1 and $R^1$ is —$SO_2R^{12}$. In some embodiments is a compound of Formula (I), or a pharmaceutically acceptable salt, solvate, or stereoisomer thereof, wherein m is 1 and $R^1$ is —$SF_5$. In some embodiments is a compound of Formula (I), or a pharmaceutically acceptable salt, solvate, or stereoisomer thereof, wherein m is 1 and $R^1$ is —$SR^8$. In some embodiments is a compound of Formula (I), or a pharmaceutically acceptable salt, solvate, or stereoisomer thereof, wherein m is 1 and $R^1$ is aryl optionally substituted with one or two groups independently selected from halogen, $C_{1-6}$alkyl, $C_{1-6}$haloalkyl, and —$C(O)NR^8R^9$. In some embodiments is a compound of Formula (I), or a pharmaceutically acceptable salt, solvate, or stereoisomer thereof, wherein m is 1 and $R^1$ is heteroaryl optionally substituted with one or two groups independently selected from halogen, $C_{1-6}$alkyl, $C_{1-6}$haloalkyl, and —$C(O)NR^8R^9$. In some embodiments is a compound of Formula (I), or a pharmaceutically acceptable salt, solvate, or stereoisomer thereof, wherein m is 1 and $R^1$ is selected from thiazole, pyrazine, pyrimidine, and pyridine, optionally substituted with one or two groups independently selected from halogen, $C_{1-6}$alkyl, $C_{1-6}$haloalkyl, and —$C(O)NR^8R^9$. In some embodiments is a compound of Formula (I), or a pharmaceutically acceptable salt, solvate, or stereoisomer thereof, wherein m is 2. In some embodiments is a compound of Formula (I), or a pharmaceutically acceptable salt, solvate, or stereoisomer thereof, wherein m is 2 and each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (I), or a pharmaceutically acceptable salt, solvate, or stereoisomer thereof, wherein m is 2 and each $R^1$ is independently selected from halogen, $C_{1-6}$alkyl, $C_{1-6}$haloalkyl, $C_{3-8}$cycloalkyl, —$NR^5R^6$, and —$OR^7$. In some embodiments is a compound of Formula (I), or a pharmaceutically acceptable salt, solvate, or stereoisomer thereof, wherein m is 2 and each $R^1$ is independently selected from halogen, —CN, $C_{1-6}$alkyl, $C_{1-6}$haloalkyl, —$NR^5R^6$, —$OR^7$, and heteroaryl. In some embodiments is a compound of Formula (I), or a pharmaceutically acceptable salt, solvate, or stereoisomer thereof, wherein m is 2 and each $R^1$ is independently selected from halogen, $C_{1-6}$haloalkyl, —$NR^5R^6$, —$OR^7$, thiazole, pyrazine, pyrimidine, and pyridine. In some embodiments is a compound of Formula (I), or a pharmaceutically acceptable salt, solvate, or stereoisomer thereof, wherein m is 2 and each $R^1$ is independently selected from halogen, $C_{1-6}$alkyl, $C_{1-6}$haloalkyl, $C_{3-8}$cycloalkyl, and —$OR^7$. In some embodiments is a compound of Formula (I), or a pharmaceutically acceptable salt, solvate, or stereoisomer thereof, wherein m is 2, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (I), or a pharmaceutically acceptable salt, solvate, or stereoisomer thereof, wherein m is 2, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$haloalkyl, $C_{3-8}$cycloalkyl, and heterocycloalkyl. In some embodiments is a compound of Formula (I), or a pharmaceutically acceptable salt, solvate, or stereoisomer thereof, wherein m is 3. In some embodiments is a compound of Formula (I), or a pharmaceutically acceptable salt, solvate, or stereoisomer thereof, wherein m is 3 and each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (I), or a pharmaceutically acceptable salt, solvate, or stereoisomer thereof, wherein m is 3 and each $R^1$ is independently selected from halogen, $C_{1-6}$alkyl, $C_{1-6}$haloalkyl, $C_{3-8}$cycloalkyl, —$NR^5R^6$, and —$OR^7$. In some embodiments is a compound of Formula (I), or a pharmaceutically acceptable salt, solvate, or stereoisomer thereof, m is 3 and each $R^1$ is independently selected from halogen, $C_{1-6}$alkyl, $C_{1-6}$haloalkyl, $C_{3-8}$cycloalkyl, and —$OR^7$. In some embodiments is a compound of Formula (I), or a pharmaceutically acceptable salt, solvate, or stereoisomer thereof, wherein m is 3, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (I), or a pharmaceutically acceptable salt, solvate, or stereoisomer thereof, wherein m is 3, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$haloalkyl, $C_{3-8}$cycloalkyl, and heterocycloalkyl.

In some embodiments is a compound of Formula (I), or a pharmaceutically acceptable salt, solvate, or stereoisomer thereof, wherein (A)

is

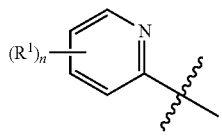

In some embodiments is a compound of Formula (I), or a pharmaceutically acceptable salt, solvate, or stereoisomer thereof, wherein (A)

is

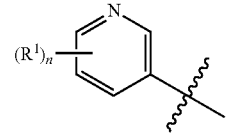

In some embodiments is a compound of Formula (I), or a pharmaceutically acceptable salt, solvate, or stereoisomer thereof, wherein (A)

is

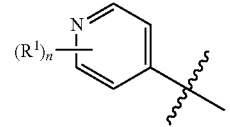

In some embodiments is a compound of Formula (I), or a pharmaceutically acceptable salt, solvate, or stereoisomer thereof, wherein n is 0. In some embodiments is a compound of Formula (I), or a pharmaceutically acceptable salt, solvate, or stereoisomer thereof, wherein n is 1. In some embodiments is a compound of Formula (I), or a pharmaceutically acceptable salt, solvate, or stereoisomer thereof, wherein n is 1 and $R^1$ is selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (I), or a pharmaceutically acceptable salt, solvate, or stereoisomer thereof, wherein n is 1 and $R^1$ is selected from halogen, $C_{1-6}$alkyl, $C_{1-6}$haloalkyl, $C_{3-8}$cycloalkyl, —$NR^5R^6$, and —$OR^7$. In some embodiments is a compound of Formula (I), or a pharmaceutically acceptable salt, solvate, or stereoisomer thereof, wherein n is 1 and $R^1$ is selected from halogen, $C_{1-6}$alkyl, $C_{1-6}$haloalkyl, $C_{3-8}$cycloalkyl, and —$OR^7$. In some embodiments is a compound of Formula (I), or a pharmaceutically acceptable salt, solvate, or stereoisomer thereof, wherein n is 1 and $R^1$ is halogen. In some embodiments is a compound of Formula (I), or a pharmaceutically acceptable salt, solvate, or stereoisomer thereof, wherein n is 1 and $R^1$ is F. In some embodiments is a compound of Formula (I), or a pharmaceutically acceptable salt, solvate, or stereoisomer thereof, wherein n is 1 and $R^1$ is $C_1$. In some embodiments is a compound of Formula (I), or a pharmaceutically acceptable salt, solvate, or stereoisomer thereof, wherein n is 1 and $R^1$ is —CN. In some embodiments is a compound of Formula (I), or a pharmaceutically acceptable salt, solvate, or stereoisomer thereof, wherein n is 1 and $R^1$ is $C_{1-6}$alkyl. In some embodiments is a compound of Formula (I), or a pharmaceutically acceptable salt, solvate, or stereoisomer thereof, wherein n is 1 and $R^1$ is —$CH_3$. In some embodiments is a compound of Formula (I), or a pharmaceutically acceptable salt, solvate, or stereoisomer thereof, wherein n is 1 and $R^1$ is —C≡CH. In some embodiments is a compound of Formula (I), or a pharmaceutically acceptable salt, solvate, or stereoisomer thereof, wherein n is 1 and $R^1$ is $C_{1-6}$alkyl-$OR^7$. In some embodiments is a compound of Formula (I), or a pharmaceutically acceptable salt, solvate, or stereoisomer thereof, wherein n is 1 and $R^1$ is —$CH_2$—O—$CH_3$. In some embodiments is a compound of Formula (I), or a pharmaceutically acceptable salt, solvate, or stereoisomer thereof, wherein n is 1 and $R^1$ is $C_{1-6}$haloalkyl. In some embodiments is a compound of Formula (I), or a pharmaceutically acceptable salt, solvate, or stereoisomer thereof, wherein n is 1 and $R^1$ is —$CF_3$. In some embodiments is a compound of Formula (I), or a pharmaceutically acceptable salt, solvate, or stereoisomer thereof, wherein n is 1 and $R^1$ is $C_{3-8}$cycloalkyl. In some embodiments is a compound of Formula (I), or a pharmaceutically acceptable salt, solvate, or stereoisomer thereof, wherein n is 1 and $R^1$ is —$NR^5R^6$. In some embodiments is a compound of Formula (I), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl optionally substituted with one or two $R^{10}$. In some embodiments is a compound of Formula (I), or a pharmaceutically acceptable salt, solvate, or stereoisomer thereof, wherein n is 1, $R^1$ is —$NR^5R^6$, and $R^5$ and $R^6$, together with the nitrogen to which they are attached, form an unsubstituted heterocycloalkyl. In some embodiments is a compound of Formula (I), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, $C_{1-6}$haloalkyl, halogen, oxo, —$C(O)NR^8R^9$, —$SO_2R^8$, —$NR^9C(O)R^8$, and —$NR^9SO_2R^8$. In some embodiments is a compound of Formula (I), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, and —$C(O)NR^8R^9$. In some embodiments is a compound of Formula (I), or a pharmaceutically acceptable salt, solvate, or stereoisomer thereof, wherein n is 1 and $R^1$ is —$OR^7$. In some embodiments is a compound of Formula (I), or a pharmaceutically acceptable salt, solvate, or stereoisomer thereof, wherein n is 1, $R^1$ is —$OR^7$, and $R^7$ is selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (I), or a pharmaceutically acceptable salt, solvate, or stereoisomer thereof, wherein n is 1 and $R^1$ is —$OCH_3$. In some embodiments is a compound of Formula (I), or a pharmaceutically acceptable salt, solvate, or stereoisomer thereof, wherein n is 1 and $R^1$ is —$OCF_3$. In some embodiments is a compound of Formula (I), or a pharmaceutically acceptable salt, solvate, or stereoisomer thereof, wherein n is 1 and $R^1$ is —$SO_2R^{12}$. In some embodiments is a compound of Formula (I), or a pharmaceutically acceptable salt, solvate, or stereoisomer thereof, wherein n is 1 and $R^1$ is —$SF_5$. In some embodiments is a compound of Formula (I), or a pharmaceutically acceptable salt, solvate, or stereoisomer thereof, wherein n is 1 and $R^1$ is —$SR^8$. In some embodiments is a compound of Formula (I), or a pharmaceutically acceptable salt, solvate, or stereoisomer thereof, wherein n is 1 and $R^1$ is aryl optionally substituted with one or two groups independently selected from halogen, $C_{1-6}$alkyl, $C_{1-6}$haloalkyl, and —$C(O)NR^8R^9$. In some embodiments is a compound of Formula (I), or a pharmaceutically acceptable salt, solvate, or stereoisomer thereof, wherein n is 1 and $R^1$ is heteroaryl optionally substituted with one or two groups independently selected from halogen, $C_{1-6}$alkyl, $C_{1-6}$haloalkyl, and —$C(O)NR^8R^9$. In some embodiments is a compound of Formula (I), or a pharmaceutically acceptable salt, solvate, or stereoisomer thereof, wherein n is 1 and $R^1$ is selected from thiazole, pyrazine, pyrimidine, and pyridine, optionally substituted with one or two groups independently selected from halogen, $C_{1-6}$alkyl, $C_{1-6}$haloalkyl, and —$C(O)NR^8R^9$. In some embodiments is a compound of Formula (I), or a pharmaceutically acceptable salt, solvate, or stereoisomer thereof, wherein n is 2. In some embodiments is a compound of Formula (I), or a pharmaceutically acceptable salt, solvate, or stereoisomer thereof, wherein n is 2 and each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (I), or a pharmaceutically acceptable salt, solvate, or stereoisomer thereof, wherein n is 2 and each $R^1$ is independently selected from halogen, $C_{1-6}$alkyl, $C_{1-6}$haloalkyl, $C_{3-8}$cycloalkyl, —$NR^5R^6$, and —$OR^7$. In some embodiments is a compound of Formula (I), or a pharmaceutically acceptable salt, solvate, or stereoisomer thereof, wherein n is 2 and each $R^1$ is independently selected from halogen, —CN, $C_{1-6}$alkyl, $C_{1-6}$haloalkyl, —$NR^5R^6$, —$OR^7$, and heteroaryl. In some embodiments is a compound of Formula (I), or a pharmaceutically acceptable salt, solvate, or stereoisomer thereof, wherein n is 2 and each $R^1$ is independently selected from halogen, $C_{1-6}$haloalkyl, —$NR^5R^6$, —$OR^7$, thiazole, pyrazine, pyrimidine, and pyridine. In some embodiments is a compound of Formula (I), or a pharmaceutically acceptable salt, solvate, or stereoisomer thereof, wherein n is 2 and each $R^1$ is independently selected from halogen, $C_{1-6}$alkyl, $C_{1-6}$haloalkyl, $C_{3-8}$cycloalkyl, and —$OR^7$. In some embodiments is a compound of Formula (I), or a pharmaceutically acceptable salt, solvate, or stereoisomer thereof, wherein n is 2, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (I), or a pharmaceutically acceptable salt, solvate, or stereoisomer thereof, wherein n is 2, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$haloalkyl, $C_{3-8}$cycloalkyl, and heterocycloalkyl. In some embodiments is a compound of Formula (I), or a pharmaceutically acceptable salt, solvate, or stereoisomer thereof, wherein n is 3.

In some embodiments is a compound of Formula (II):

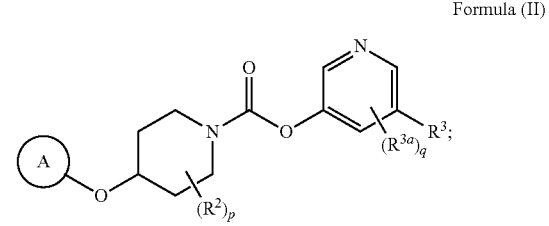

Formula (II)

wherein:

is

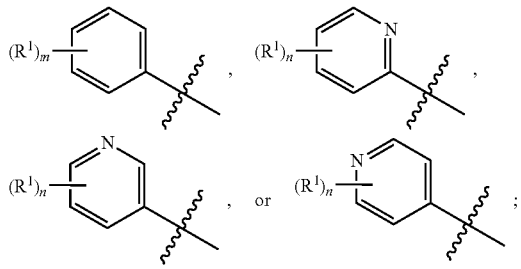

each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$C(O)NR^5R^6$, —$OR^7$, —$SO_2R^{12}$, —$SF_5$, —$SR^8$, aryl, and heteroaryl, wherein aryl and heteroaryl are optionally substituted with one or two groups independently selected from halogen, $C_{1-6}$alkyl, $C_{1-6}$haloalkyl, and —$C(O)NR^8R^9$; or two adjacent $R^1$ form a heterocycloalkyl ring optionally substituted with one or two $R^{11}$;
$R^2$ is $C_{1-6}$alkyl;
$R^3$ is selected from halogen, —CN, $C_{1-6}$alkyl, $C_{1-6}$haloalkyl, —$NR^8R^9$, —$C(O)NR^8R^9$, —$NR^8C(O)R^9$, and —$NR^9SO_2R^8$;
$R^{3a}$ is selected from halogen, $C_{1-6}$alkyl, and $C_{1-6}$haloalkyl;
each $R^5$ and $R^6$ is independently selected from H, $C_{1-6}$alkyl, and $C_{3-8}$cycloalkyl; or $R^5$ and $R^6$, together with the nitrogen to which they are attached, form a heterocycloalkyl optionally substituted with one or two $R^{10}$;
each $R^7$ is independently selected from H, $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl, wherein heterocycloalkyl, aryl, and heteroaryl are optionally substituted with one or two groups independently selected from halogen, $C_{1-6}$alkyl, and $C_{1-6}$haloalkyl;
each $R^8$ and $R^9$ is independently selected from H, $C_{1-6}$alkyl, $C_{3-8}$cycloalkyl, aryl, and heteroaryl;
each $R^{10}$ is independently selected from $C_{1-6}$alkyl, $C_{3-8}$cycloalkyl, $C_{1-6}$haloalkyl, halogen, oxo, —CN, —$C(O)OR^8$, —$C(O)R^8$, —$C(O)NR^8R^9$, —$SO_2R^8$, —$NR^9C(O)R^8$, and —$NR^9SO_2R^8$;
each $R^{11}$ is independently selected from halogen and $C_{1-6}$alkyl;
each $R^{12}$ is independently selected from $C_{1-6}$alkyl and $C_{3-8}$cycloalkyl;
m is 0, 1, 2, 3, 4, or 5;
n is 0, 1, 2, or 3;
p is 0 or 1; and
q is 0 or 1;
or a pharmaceutically acceptable salt, solvate, or stereoisomer thereof.

In some embodiments is a compound of Formula (II), or a pharmaceutically acceptable salt, solvate, or stereoisomer thereof, wherein p is 0. In some embodiments is a compound of Formula (II), or a pharmaceutically acceptable salt, solvate, or stereoisomer thereof, wherein p is 1. In some embodiments is a compound of Formula (II), or a pharmaceutically acceptable salt, solvate, or stereoisomer thereof, wherein p is 1 and $R^2$ is —$CH_3$. In some embodiments is a compound of Formula (II), or a pharmaceutically acceptable salt, solvate, or stereoisomer thereof, wherein p is 1 and $R^2$ is —$CH_2CH_3$. In some embodiments is a compound of Formula (II), or a pharmaceutically acceptable salt, solvate, or stereoisomer thereof, wherein p is 1 and $R^2$ is —$CH_2CH_2CH_3$. In some embodiments is a compound of Formula (II), or a pharmaceutically acceptable salt, solvate, or stereoisomer thereof, wherein p is 1 and $R^2$ is —$CH(CH_3)_2$.

In some embodiments is a compound of Formula (II), or a pharmaceutically acceptable salt, solvate, or stereoisomer thereof, wherein $R^3$ is halogen. In some embodiments is a compound of Formula (II), or a pharmaceutically acceptable salt, solvate, or stereoisomer thereof, wherein $R^3$ is —CN. In some embodiments is a compound of Formula (II), or a pharmaceutically acceptable salt, solvate, or stereoisomer thereof, wherein $R^3$ is $C_{1-6}$alkyl. In some embodiments is a compound of Formula (II), or a pharmaceutically acceptable salt, solvate, or stereoisomer thereof, wherein $R^3$ is —$CH_3$. In some embodiments is a compound of Formula (II), or a pharmaceutically acceptable salt, solvate, or stereoisomer thereof, wherein $R^3$ is $C_{1-6}$haloalkyl. In some embodiments is a compound of Formula (II), or a pharmaceutically acceptable salt, solvate, or stereoisomer thereof, wherein $R^3$ is —$CF_3$. In some embodiments is a compound of Formula (II), or a pharmaceutically acceptable salt, solvate, or stereoisomer thereof, wherein $R^3$ is —$NR^8R^9$. In some embodiments is a compound of Formula (II), or a pharmaceutically acceptable salt, solvate, or stereoisomer thereof, wherein $R^3$ is —$NH_2$. In some embodiments is a compound of Formula (II), or a pharmaceutically acceptable salt, solvate, or stereoisomer thereof, wherein $R^3$ is —$C(O)NR^8R^9$. In some embodiments is a compound of Formula (II), or a pharmaceutically acceptable salt, solvate, or stereoisomer thereof, wherein $R^3$ is —$C(O)NH_2$. In some embodiments is a compound of Formula (II), or a pharmaceutically acceptable salt, solvate, or stereoisomer thereof, wherein $R^3$ is —$NR^8C(O)R^9$. In some embodiments is a compound of Formula (II), or a pharmaceutically acceptable salt, solvate, or stereoisomer thereof, wherein $R^3$ is —$NHC(O)CH_3$. In some embodiments is a compound of Formula (II), or a pharmaceutically acceptable salt, solvate, or stereoisomer thereof, wherein q is 0. In some embodiments is a compound of Formula (II), or a pharmaceutically acceptable salt, solvate, or stereoisomer thereof, wherein q is 1. In some embodiments is a compound of Formula (II), or a pharmaceutically acceptable salt, solvate, or stereoisomer thereof, wherein q is 1 and $R^{3a}$ is halogen. In some embodiments is a compound of Formula (II), or a pharmaceutically acceptable salt, solvate, or stereoisomer thereof, wherein q is 1 and $R^{3a}$ is $C_{1-6}$alkyl. In some embodiments is a compound of Formula (II), or a pharmaceutically acceptable salt, solvate, or stereoisomer thereof, wherein q is 1 and $R^{3a}$ is $C_{1-6}$haloalkyl.

In some embodiments is a compound of Formula (II), or a pharmaceutically acceptable salt, solvate, or stereoisomer thereof, wherein

is $$(R^1)_m \text{―} \underset{}{\overset{}{\bigcirc}} \text{―} \underset{\text{{\tiny \textbackslash}}}{\overset{}{\underset{|}{\text{C}}}}$$

In some embodiments is a compound of Formula (II), or a pharmaceutically acceptable salt, solvate, or stereoisomer thereof, wherein m is 0. In some embodiments is a compound of Formula (II), or a pharmaceutically acceptable salt, solvate, or stereoisomer thereof, wherein m is 1. In some embodiments is a compound of Formula (II), or a pharmaceutically acceptable salt, solvate, or stereoisomer thereof, wherein m is 1 and $R^1$ is selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (II), or a pharmaceutically acceptable salt, solvate, or stereoisomer thereof, wherein m is 1 and $R^1$ is selected from halogen, $C_{1-6}$alkyl, $C_{1-6}$haloalkyl, $C_{3-8}$cycloalkyl, —$NR^5R^6$, and —$OR^7$. In some embodiments is a compound of Formula (II), or a pharmaceutically acceptable salt, solvate, or stereoisomer thereof, wherein m is 1 and $R^1$ is selected from halogen, $C_{1-6}$alkyl, $C_{1-6}$haloalkyl, $C_{3-8}$cycloalkyl, and —$OR^7$. In some embodiments is a compound of Formula (II), or a pharmaceutically acceptable salt, solvate, or stereoisomer thereof, wherein m is 1 and $R^1$ is halogen. In some embodiments is a compound of Formula (II), or a pharmaceutically acceptable salt, solvate, or stereoisomer thereof, wherein m is 1 and $R^1$ is F. In some embodiments is a compound of Formula (II), or a pharmaceutically acceptable salt, solvate, or stereoisomer thereof, wherein m is 1 and $R^1$ is $C_1$. In some embodiments is a compound of Formula (II), or a pharmaceutically acceptable salt, solvate, or stereoisomer thereof, wherein m is 1 and $R^1$ is —CN. In some embodiments is a compound of Formula (II), or a pharmaceutically acceptable salt, solvate, or stereoisomer thereof, wherein m is 1 and $R^1$ is $C_{1-6}$alkyl. In some embodiments is a compound of Formula (II), or a pharmaceutically acceptable salt, solvate, or stereoisomer thereof, wherein m is 1 and $R^1$ is —$CH_3$. In some embodiments is a compound of Formula (II), or a pharmaceutically acceptable salt, solvate, or stereoisomer thereof, wherein m is 1 and $R^1$ is —C≡CH. In some embodiments is a compound of Formula (II), or a pharmaceutically acceptable salt, solvate, or stereoisomer thereof, wherein m is 1 and $R^1$ is $C_{1-6}$alkyl-$OR^7$. In some embodiments is a compound of Formula (II), or a pharmaceutically acceptable salt, solvate, or stereoisomer thereof, wherein m is 1 and $R^1$ is —$CH_2$—O—$CH_3$. In some embodiments is a compound of Formula (II), or a pharmaceutically acceptable salt, solvate, or stereoisomer thereof, wherein m is 1 and $R^1$ is $C_{1-6}$haloalkyl. In some embodiments is a compound of Formula (II), or a pharmaceutically acceptable salt, solvate, or stereoisomer thereof, wherein m is 1 and $R^1$ is —$CF_3$. In some embodiments is a compound of Formula (II), or a pharmaceutically acceptable salt, solvate, or stereoisomer thereof, wherein m is 1 and $R^1$ is $C_{3-8}$cycloalkyl. In some embodiments is a compound of Formula (II), or a pharmaceutically acceptable salt, solvate, or stereoisomer thereof, wherein m is 1 and $R^1$ is —$NR^5R^6$. In some embodiments is a compound of Formula (II), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl optionally substituted with one or two $R^{10}$. In some embodiments is a compound of Formula (II), or a pharmaceutically acceptable salt, solvate, or stereoisomer thereof, wherein m is 1, $R^1$ is —$NR^5R^6$, and $R^5$ and $R^6$, together with the nitrogen to which they are attached, form an unsubstituted heterocycloalkyl. In some embodiments is a compound of Formula (II), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, $C_{1-6}$haloalkyl, halogen, oxo, —C(O)$NR^8R^9$, —$SO_2R^8$, —$NR^9C(O)R^8$, and —$NR^9SO_2R^8$. In some embodiments is a compound of Formula (II), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, and —C(O)$NR^8R^9$. In some embodiments is a compound of Formula (II), or a pharmaceutically acceptable salt, solvate, or stereoisomer thereof, wherein m is 1 and $R^1$ is —$OR^7$. In some embodiments is a compound of Formula (II), or a pharmaceutically acceptable salt, solvate, or stereoisomer thereof, wherein m is 1, $R^1$ is —$OR^7$, and $R^7$ is selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (II), or a pharmaceutically acceptable salt, solvate, or stereoisomer thereof, wherein m is 1 and $R^1$ is —$OCH_3$. In some embodiments is a compound of Formula (II), or a pharmaceutically acceptable salt, solvate, or stereoisomer thereof, wherein m is 1 and $R^1$ is —$OCF_3$. In some embodiments is a compound of Formula (II), or a pharmaceutically acceptable salt, solvate, or stereoisomer thereof, wherein m is 1 and $R^1$ is —$SO_2R^{12}$. In some embodiments is a compound of Formula (II), or a pharmaceutically acceptable salt, solvate, or stereoisomer thereof, wherein m is 1 and $R^1$ is —$SF_5$. In some embodiments is a compound of Formula (II), or a pharmaceutically acceptable salt, solvate, or stereoisomer thereof, wherein m is 1 and $R^1$ is —$SR^8$. In some embodiments is a compound of Formula (II), or a pharmaceutically acceptable salt, solvate, or stereoisomer thereof, wherein m is 1 and $R^1$ is aryl optionally substituted with one or two groups independently selected from halogen, $C_{1-6}$alkyl, $C_{1-6}$haloalkyl, and —C(O)$NR^8R^9$. In some embodiments is a compound of Formula (II), or a pharmaceutically acceptable salt, solvate, or stereoisomer thereof, wherein m is 1 and $R^1$ is heteroaryl optionally substituted with one or two groups independently selected from halogen, $C_{1-6}$alkyl, $C_{1-6}$haloalkyl, and —C(O)$NR^8R^9$. In some embodiments is a compound of Formula (II), or a pharmaceutically acceptable salt, solvate, or stereoisomer thereof, wherein m is 1 and $R^1$ is selected from thiazole, pyrazine, pyrimidine, and pyridine, optionally substituted with one or two groups independently selected from halogen, $C_{1-6}$alkyl, $C_{1-6}$haloalkyl, and —C(O)$NR^8R^9$. In some embodiments is a compound of Formula (II), or a pharmaceutically acceptable salt, solvate, or stereoisomer thereof, wherein m is 2. In some embodiments is a compound of Formula (II), or a pharmaceutically acceptable salt, solvate, or stereoisomer thereof, wherein m is 2 and each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (II), or a pharmaceutically acceptable salt, solvate, or stereoisomer thereof, wherein m is 2 and each R¹ is independently selected from halogen, $C_{1-6}$alkyl, $C_{1-6}$haloalkyl, $C_{3-8}$cycloalkyl, —NR⁵R⁶, and —OR⁷. In some embodiments is a compound of Formula (II), or a pharmaceutically acceptable salt, solvate, or stereoisomer thereof, wherein m is 2 and each R¹ is independently selected from halogen, —CN, $C_{1-6}$alkyl, $C_{1-6}$haloalkyl, —NR⁵R⁶, —OR⁷, and heteroaryl. In some embodiments is a compound of Formula (II), or a pharmaceutically acceptable salt, solvate, or stereoisomer thereof, wherein m is 2 and each R¹ is independently selected from halogen, $C_{1-6}$haloalkyl, —NR⁵R⁶, —OR⁷, thiazole, pyrazine, pyrimidine, and pyridine. In some embodiments is a compound of Formula (II), or a pharmaceutically acceptable salt, solvate, or stereoisomer thereof, wherein m is 2 and each R¹ is independently selected from halogen, $C_{1-6}$alkyl, $C_{1-6}$haloalkyl, $C_{3-8}$cycloalkyl, and —OR⁷. In some embodiments is a compound of Formula (II), or a pharmaceutically acceptable salt, solvate, or stereoisomer thereof, wherein m is 2, each R¹ is independently selected from halogen, $C_{1-6}$alkyl, $C_{1-6}$haloalkyl, $C_{3-8}$cycloalkyl, and —OR⁷, and each R⁷ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (II), or a pharmaceutically acceptable salt, solvate, or stereoisomer thereof, wherein m is 2, each R¹ is independently selected from halogen, $C_{1-6}$alkyl, $C_{1-6}$haloalkyl, $C_{3-8}$cycloalkyl, and —OR⁷, and each R⁷ is independently selected from $C_{1-6}$alkyl, $C_{1-6}$haloalkyl, $C_{3-8}$cycloalkyl, and heterocycloalkyl. In some embodiments is a compound of Formula (II), or a pharmaceutically acceptable salt, solvate, or stereoisomer thereof, wherein m is 3. In some embodiments is a compound of Formula (II), or a pharmaceutically acceptable salt, solvate, or stereoisomer thereof, wherein m is 3 and each R¹ is independently selected from halogen, —CN, $C_{1-6}$alkyl, $C_{2-6}$alkynyl, $C_{1-6}$alkyl-OR⁷, $C_{1-6}$haloalkyl, $C_{3-8}$cycloalkyl, —NR⁵R⁶, —OR⁷, —SO₂R¹², —SF₅, —SR⁸, aryl, and heteroaryl. In some embodiments is a compound of Formula (II), or a pharmaceutically acceptable salt, solvate, or stereoisomer thereof, wherein m is 3 and each R¹ is independently selected from halogen, $C_{1-6}$alkyl, $C_{1-6}$haloalkyl, $C_{3-8}$cycloalkyl, —NR⁵R⁶, and —OR⁷. In some embodiments is a compound of Formula (II), or a pharmaceutically acceptable salt, solvate, or stereoisomer thereof, m is 3 and each R¹ is independently selected from halogen, $C_{1-6}$alkyl, $C_{1-6}$haloalkyl, $C_{3-8}$cycloalkyl, and —OR⁷. In some embodiments is a compound of Formula (II), or a pharmaceutically acceptable salt, solvate, or stereoisomer thereof, wherein m is 3, each R¹ is independently selected from halogen, $C_{1-6}$alkyl, $C_{1-6}$haloalkyl, $C_{3-8}$cycloalkyl, and —OR⁷, and each R⁷ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (II), or a pharmaceutically acceptable salt, solvate, or stereoisomer thereof, wherein m is 3, each R¹ is independently selected from halogen, $C_{1-6}$alkyl, $C_{1-6}$haloalkyl, $C_{3-8}$cycloalkyl, and —OR⁷, and each R⁷ is independently selected from $C_{1-6}$alkyl, $C_{1-6}$haloalkyl, $C_{3-8}$cycloalkyl, and heterocycloalkyl.

In some embodiments is a compound of Formula (II), or a pharmaceutically acceptable salt, solvate, or stereoisomer thereof, wherein

is

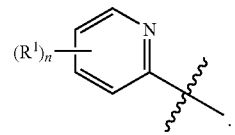

In some embodiments is a compound of Formula (II), or a pharmaceutically acceptable salt, solvate, or stereoisomer thereof, wherein

is

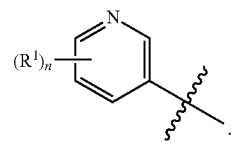

In some embodiments is a compound of Formula (II), or a pharmaceutically acceptable salt, solvate, or stereoisomer thereof, wherein

is

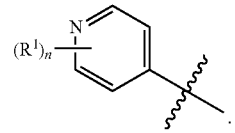

In some embodiments is a compound of Formula (II), or a pharmaceutically acceptable salt, solvate, or stereoisomer thereof, wherein n is 0. In some embodiments is a compound of Formula (II), or a pharmaceutically acceptable salt, solvate, or stereoisomer thereof, wherein n is 1. In some embodiments is a compound of Formula (II), or a pharmaceutically acceptable salt, solvate, or stereoisomer thereof, wherein n is 1 and R¹ is selected from halogen, —CN, $C_{1-6}$alkyl, $C_{2-6}$alkynyl, $C_{1-6}$alkyl-OR⁷, $C_{1-6}$haloalkyl, $C_{3-8}$cycloalkyl, —NR⁵R⁶, —OR⁷, —SO₂R¹², —SF₅, —SR⁸, aryl, and heteroaryl. In some embodiments is a compound of Formula (II), or a pharmaceutically acceptable salt, solvate, or stereoisomer thereof, wherein n is 1 and R¹ is selected from halogen, $C_{1-6}$alkyl, $C_{1-6}$haloalkyl, $C_{3-8}$cycloalkyl, —NR⁵R⁶, and —OR⁷. In some embodiments is a compound of Formula (II), or a pharmaceutically acceptable salt, solvate, or stereoisomer thereof, wherein n is 1 and R¹ is selected from halogen, $C_{1-6}$alkyl, $C_{1-6}$haloalkyl, $C_{3-8}$cycloalkyl, and —OR⁷. In some embodiments is a compound of Formula (II), or a pharmaceutically acceptable salt, solvate, or stereoisomer thereof, wherein n is 1 and $R^1$ is halogen. In some embodiments is a compound of Formula (II), or a pharmaceutically acceptable salt, solvate, or stereoisomer thereof, wherein n is 1 and $R^1$ is F. In some embodiments is a compound of Formula (II), or a pharmaceutically acceptable salt, solvate, or stereoisomer thereof, wherein n is 1 and $R^1$ is $C_1$. In some embodiments is a compound of Formula (II), or a pharmaceutically acceptable salt, solvate, or stereoisomer thereof, wherein n is 1 and $R^1$ is —CN. In some embodiments is a compound of Formula (II), or a pharmaceutically acceptable salt, solvate, or stereoisomer thereof, wherein n is 1 and $R^1$ is $C_{1-6}$alkyl. In some embodiments is a compound of Formula (II), or a pharmaceutically acceptable salt, solvate, or stereoisomer thereof, wherein n is 1 and $R^1$ is —$CH_3$. In some embodiments is a compound of Formula (II), or a pharmaceutically acceptable salt, solvate, or stereoisomer thereof, wherein n is 1 and $R^1$ is —C≡CH. In some embodiments is a compound of Formula (II), or a pharmaceutically acceptable salt, solvate, or stereoisomer thereof, wherein n is 1 and $R^1$ is $C_{1-6}$alkyl-$OR^7$. In some embodiments is a compound of Formula (II), or a pharmaceutically acceptable salt, solvate, or stereoisomer thereof, wherein n is 1 and $R^1$ is —$CH_2$—O—$CH_3$. In some embodiments is a compound of Formula (II), or a pharmaceutically acceptable salt, solvate, or stereoisomer thereof, wherein n is 1 and $R^1$ is $C_{1-6}$haloalkyl. In some embodiments is a compound of Formula (II), or a pharmaceutically acceptable salt, solvate, or stereoisomer thereof, wherein n is 1 and $R^1$ is —$CF_3$. In some embodiments is a compound of Formula (II), or a pharmaceutically acceptable salt, solvate, or stereoisomer thereof, wherein n is 1 and $R^1$ is $C_{3-8}$cycloalkyl. In some embodiments is a compound of Formula (II), or a pharmaceutically acceptable salt, solvate, or stereoisomer thereof, wherein n is 1 and $R^1$ is —$NR^5R^6$. In some embodiments is a compound of Formula (II), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl optionally substituted with one or two $R^{10}$. In some embodiments is a compound of Formula (II), or a pharmaceutically acceptable salt, solvate, or stereoisomer thereof, wherein n is 1, $R^1$ is —$NR^5R^6$, and $R^5$ and $R^6$, together with the nitrogen to which they are attached, form an unsubstituted heterocycloalkyl. In some embodiments is a compound of Formula (II), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, $C_{1-6}$haloalkyl, halogen, oxo, —$C(O)NR^8R^9$, —$SO_2R^8$, —$NR^9C(O)R^8$, and —$NR^9SO_2R^8$. In some embodiments is a compound of Formula (II), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, and —$C(O)NR^8R^9$. In some embodiments is a compound of Formula (II), or a pharmaceutically acceptable salt, solvate, or stereoisomer thereof, wherein n is 1 and $R^1$ is —$OR^7$. In some embodiments is a compound of Formula (II), or a pharmaceutically acceptable salt, solvate, or stereoisomer thereof, wherein n is 1, $R^1$ is —$OR^7$, and $R^7$ is selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (II), or a pharmaceutically acceptable salt, solvate, or stereoisomer thereof, wherein n is 1 and $R^1$ is —$OCH_3$. In some embodiments is a compound of Formula (II), or a pharmaceutically acceptable salt, solvate, or stereoisomer thereof, wherein n is 1 and $R^1$ is —$OCF_3$. In some embodiments is a compound of Formula (II), or a pharmaceutically acceptable salt, solvate, or stereoisomer thereof, wherein n is 1 and $R^1$ is —$SO_2R^{12}$. In some embodiments is a compound of Formula (II), or a pharmaceutically acceptable salt, solvate, or stereoisomer thereof, wherein n is 1 and $R^1$ is —$SF_5$. In some embodiments is a compound of Formula (II), or a pharmaceutically acceptable salt, solvate, or stereoisomer thereof, wherein n is 1 and $R^1$ is —$SR^8$. In some embodiments is a compound of Formula (II), or a pharmaceutically acceptable salt, solvate, or stereoisomer thereof, wherein n is 1 and $R^1$ is aryl optionally substituted with one or two groups independently selected from halogen, $C_{1-6}$alkyl, $C_{1-6}$haloalkyl, and —$C(O)NR^8R^9$. In some embodiments is a compound of Formula (II), or a pharmaceutically acceptable salt, solvate, or stereoisomer thereof, wherein n is 1 and $R^1$ is heteroaryl optionally substituted with one or two groups independently selected from halogen, $C_{1-6}$alkyl, $C_{1-6}$haloalkyl, and —$C(O)NR^8R^9$. In some embodiments is a compound of Formula (II), or a pharmaceutically acceptable salt, solvate, or stereoisomer thereof, wherein n is 1 and $R^1$ is selected from thiazole, pyrazine, pyrimidine, and pyridine, optionally substituted with one or two groups independently selected from halogen, $C_{1-6}$alkyl, $C_{1-6}$haloalkyl, and —$C(O)NR^8R^9$. In some embodiments is a compound of Formula (II), or a pharmaceutically acceptable salt, solvate, or stereoisomer thereof, wherein n is 2. In some embodiments is a compound of Formula (II), or a pharmaceutically acceptable salt, solvate, or stereoisomer thereof, wherein n is 2 and each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (II), or a pharmaceutically acceptable salt, solvate, or stereoisomer thereof, wherein n is 2 and each $R^1$ is independently selected from halogen, $C_{1-6}$alkyl, $C_{1-6}$haloalkyl, $C_{3-8}$cycloalkyl, —$NR^5R^6$, and —$OR^7$. In some embodiments is a compound of Formula (II), or a pharmaceutically acceptable salt, solvate, or stereoisomer thereof, wherein n is 2 and each $R^1$ is independently selected from halogen, —CN, $C_{1-6}$alkyl, $C_{1-6}$haloalkyl, —$NR^5R^6$, —$OR^7$, and heteroaryl. In some embodiments is a compound of Formula (II), or a pharmaceutically acceptable salt, solvate, or stereoisomer thereof, wherein n is 2 and each $R^1$ is independently selected from halogen, $C_{1-6}$haloalkyl, —$NR^5R^6$, —$OR^7$, thiazole, pyrazine, pyrimidine, and pyridine. In some embodiments is a compound of Formula (II), or a pharmaceutically acceptable salt, solvate, or stereoisomer thereof, wherein n is 2 and each $R^1$ is independently selected from halogen, $C_{1-6}$alkyl, $C_{1-6}$haloalkyl, $C_{3-8}$cycloalkyl, and —$OR^7$. In some embodiments is a compound of Formula (II), or a pharmaceutically acceptable salt, solvate, or stereoisomer thereof, wherein n is 2, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (II), or a pharmaceutically acceptable salt, solvate, or stereoisomer thereof, wherein n is 2, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$haloalkyl, $C_{3-8}$cycloalkyl, and heterocycloalkyl. In some embodiments is a compound of Formula (II), or a pharmaceutically acceptable salt, solvate, or stereoisomer thereof, wherein n is 3.

In some embodiments is a compound of Formula (III):

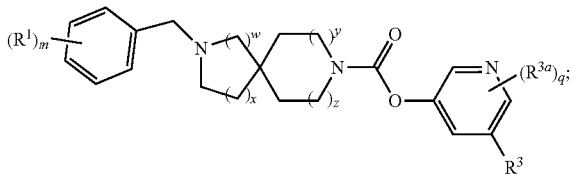

Formula (III)

wherein:
each $R^1$ is independently selected from halogen, —CN, $C_{1-6}$alkyl, $C_{2-6}$alkynyl, $C_{1-6}$alkyl-OR$^7$, $C_{1-6}$haloalkyl, $C_{3-8}$cycloalkyl, —NR$^5$R$^6$, —C(O)NR$^5$R$^6$, —OR$^7$, —SO$_2$R$^{12}$, —SF$_5$, —SR$^8$, aryl, and heteroaryl, wherein aryl and heteroaryl are optionally substituted with one or two groups independently selected from halogen, $C_{1-6}$alkyl, $C_{1-6}$haloalkyl, and —C(O)NR$^8$R$^9$; or two adjacent $R^1$ form a heterocycloalkyl ring optionally substituted with one or two $R^{11}$;
$R^3$ is selected from halogen, —CN, $C_{1-6}$alkyl, $C_{1-6}$haloalkyl, —NR$^8$R$^9$, —C(O)NR$^8$R$^9$, —NR$^8$C(O)R$^9$, and —NR$^9$SO$_2$R$^8$;
$R^{3a}$ is selected from halogen, $C_{1-6}$alkyl, and $C_{1-6}$haloalkyl;
each $R^5$ and $R^6$ is independently selected from H, $C_{1-6}$alkyl, and $C_{3-8}$cycloalkyl; or $R^5$ and $R^6$, together with the nitrogen to which they are attached, form a heterocycloalkyl optionally substituted with one or two $R^{10}$;
each $R^7$ is independently selected from H, $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl, wherein heterocycloalkyl, aryl, and heteroaryl are optionally substituted with one or two groups independently selected from halogen, $C_{1-6}$alkyl, and $C_{1-6}$haloalkyl;
each $R^8$ and $R^9$ is independently selected from H, $C_{1-6}$alkyl, $C_{3-8}$cycloalkyl, aryl, and heteroaryl;
each $R^{10}$ is independently selected from $C_{1-6}$alkyl, $C_{3-8}$cycloalkyl, $C_{1-6}$haloalkyl, halogen, oxo, —CN, —C(O)OR$^8$, —C(O)R$^8$, —C(O)NR$^8$R$^9$, —SO$_2$R$^8$, —NR$^9$C(O)R$^8$, and —NR$^9$SO$_2$R$^8$;
each $R^{11}$ is independently selected from halogen and $C_{1-6}$alkyl;
each $R^{12}$ is independently selected from $C_{1-6}$alkyl and $C_{3-8}$cycloalkyl;
m is 0, 1, 2, 3, 4, or 5;
q is 0 or 1;
w is 1 or 2;
x is 0 or 1;
y is 0 or 1; and
z is 0 or 1;
wherein when y and z are 0, then x is 1 and w is 2;
when y and z are 1, then w is 1; and
when y is 1 and z is 0, or y is 0 and z is 1, then x is 1;
or a pharmaceutically acceptable salt, solvate, or stereoisomer thereof.

In some embodiments is a compound of Formula (III), or a pharmaceutically acceptable salt, solvate, or stereoisomer thereof, wherein y is 1, z is 1, w is 1, and x is 0. In some embodiments is a compound of Formula (III), or a pharmaceutically acceptable salt, solvate, or stereoisomer thereof, wherein y is 1, z is 1, w is 1, and x is 1. In some embodiments is a compound of Formula (III), or a pharmaceutically acceptable salt, solvate, or stereoisomer thereof, wherein y is 1, z is 0, w is 1, and x is 1. In some embodiments is a compound of Formula (III), or a pharmaceutically acceptable salt, solvate, or stereoisomer thereof, wherein y is 1, z is 0, w is 2, and x is 1. In some embodiments is a compound of Formula (III), or a pharmaceutically acceptable salt, solvate, or stereoisomer thereof, wherein y is 0, z is 0, w is 2, and x is 1.

In some embodiments is a compound of Formula (III), or a pharmaceutically acceptable salt, solvate, or stereoisomer thereof, wherein $R^3$ is halogen. In some embodiments is a compound of Formula (III), or a pharmaceutically acceptable salt, solvate, or stereoisomer thereof, wherein $R^3$ is —CN. In some embodiments is a compound of Formula (III), or a pharmaceutically acceptable salt, solvate, or stereoisomer thereof, wherein $R^3$ is $C_{1-6}$alkyl. In some embodiments is a compound of Formula (III), or a pharmaceutically acceptable salt, solvate, or stereoisomer thereof, wherein $R^3$ is —CH$_3$. In some embodiments is a compound of Formula (III), or a pharmaceutically acceptable salt, solvate, or stereoisomer thereof, wherein $R^3$ is $C_{1-6}$haloalkyl. In some embodiments is a compound of Formula (III), or a pharmaceutically acceptable salt, solvate, or stereoisomer thereof, wherein $R^3$ is —CF$_3$. In some embodiments is a compound of Formula (III), or a pharmaceutically acceptable salt, solvate, or stereoisomer thereof, wherein $R^3$ is —NR$^8$R$^9$. In some embodiments is a compound of Formula (III), or a pharmaceutically acceptable salt, solvate, or stereoisomer thereof, wherein $R^3$ is —NH$_2$. In some embodiments is a compound of Formula (III), or a pharmaceutically acceptable salt, solvate, or stereoisomer thereof, wherein $R^3$ is —C(O)NR$^8$R$^9$. In some embodiments is a compound of Formula (III), or a pharmaceutically acceptable salt, solvate, or stereoisomer thereof, wherein $R^3$ is —C(O)NH$_2$. In some embodiments is a compound of Formula (III), or a pharmaceutically acceptable salt, solvate, or stereoisomer thereof, wherein $R^3$ is —NR$^8$C(O)R$^9$. In some embodiments is a compound of Formula (III), or a pharmaceutically acceptable salt, solvate, or stereoisomer thereof, wherein $R^3$ is —NHC(O)CH$_3$. In some embodiments is a compound of Formula (III), or a pharmaceutically acceptable salt, solvate, or stereoisomer thereof, wherein q is 0. In some embodiments is a compound of Formula (III), or a pharmaceutically acceptable salt, solvate, or stereoisomer thereof, wherein q is 1. In some embodiments is a compound of Formula (III), or a pharmaceutically acceptable salt, solvate, or stereoisomer thereof, wherein q is 1 and $R^{3a}$ is halogen. In some embodiments is a compound of Formula (III), or a pharmaceutically acceptable salt, solvate, or stereoisomer thereof, wherein q is 1 and $R^{3a}$ is $C_{1-6}$alkyl. In some embodiments is a compound of Formula (III), or a pharmaceutically acceptable salt, solvate, or stereoisomer thereof, wherein q is 1 and $R^{3a}$ is $C_{1-6}$haloalkyl.

In some embodiments is a compound of Formula (III), or a pharmaceutically acceptable salt, solvate, or stereoisomer thereof, wherein m is 0. In some embodiments is a compound of Formula (III), or a pharmaceutically acceptable salt, solvate, or stereoisomer thereof, wherein m is 1. In some embodiments is a compound of Formula (III), or a pharmaceutically acceptable salt, solvate, or stereoisomer thereof, wherein m is 1 and $R^1$ is selected from halogen, —CN, $C_{1-6}$alkyl, $C_{2-6}$alkynyl, $C_{1-6}$alkyl-OR$^7$, $C_{1-6}$haloalkyl, $C_{3-8}$cycloalkyl, —NR$^5$R$^6$, —OR$^7$, —SO$_2$R$^{12}$, —SF$_5$, —SR$^8$, aryl, and heteroaryl. In some embodiments is a compound of Formula (III), or a pharmaceutically acceptable salt, solvate, or stereoisomer thereof, wherein m is 1 and $R^1$ is selected from halogen, $C_{1-6}$alkyl, $C_{1-6}$haloalkyl, $C_{3-8}$cycloalkyl, —$NR^5R^6$, and —$OR^7$. In some embodiments is a compound of Formula (III), or a pharmaceutically acceptable salt, solvate, or stereoisomer thereof, wherein m is 1 and $R^1$ is selected from halogen, $C_{1-6}$alkyl, $C_{1-6}$haloalkyl, $C_{3-8}$cycloalkyl, and —$OR^7$. In some embodiments is a compound of Formula (III), or a pharmaceutically acceptable salt, solvate, or stereoisomer thereof, wherein m is 1 and $R^1$ is halogen. In some embodiments is a compound of Formula (III), or a pharmaceutically acceptable salt, solvate, or stereoisomer thereof, wherein m is 1 and $R^1$ is F. In some embodiments is a compound of Formula (III), or a pharmaceutically acceptable salt, solvate, or stereoisomer thereof, wherein m is 1 and $R^1$ is $C_1$. In some embodiments is a compound of Formula (III), or a pharmaceutically acceptable salt, solvate, or stereoisomer thereof, wherein m is 1 and $R^1$ is —CN. In some embodiments is a compound of Formula (III), or a pharmaceutically acceptable salt, solvate, or stereoisomer thereof, wherein m is 1 and $R^1$ is $C_{1-6}$alkyl. In some embodiments is a compound of Formula (III), or a pharmaceutically acceptable salt, solvate, or stereoisomer thereof, wherein m is 1 and $R^1$ is —$CH_3$. In some embodiments is a compound of Formula (III), or a pharmaceutically acceptable salt, solvate, or stereoisomer thereof, wherein m is 1 and $R^1$ is —C≡CH. In some embodiments is a compound of Formula (III), or a pharmaceutically acceptable salt, solvate, or stereoisomer thereof, wherein m is 1 and $R^1$ is $C_{1-6}$alkyl-$OR^7$. In some embodiments is a compound of Formula (III), or a pharmaceutically acceptable salt, solvate, or stereoisomer thereof, wherein m is 1 and $R^1$ is —$CH_2$—O—$CH_3$. In some embodiments is a compound of Formula (III), or a pharmaceutically acceptable salt, solvate, or stereoisomer thereof, wherein m is 1 and $R^1$ is $C_{1-6}$haloalkyl. In some embodiments is a compound of Formula (III), or a pharmaceutically acceptable salt, solvate, or stereoisomer thereof, wherein m is 1 and $R^1$ is —$CF_3$. In some embodiments is a compound of Formula (III), or a pharmaceutically acceptable salt, solvate, or stereoisomer thereof, wherein m is 1 and $R^1$ is $C_{3-8}$cycloalkyl. In some embodiments is a compound of Formula (III), or a pharmaceutically acceptable salt, solvate, or stereoisomer thereof, wherein m is 1 and $R^1$ is —$NR^5R^6$. In some embodiments is a compound of Formula (III), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl optionally substituted with one or two $R^{10}$. In some embodiments is a compound of Formula (III), or a pharmaceutically acceptable salt, solvate, or stereoisomer thereof, wherein m is 1, $R^1$ is —$NR^5R^6$, and $R^5$ and $R^6$, together with the nitrogen to which they are attached, form an unsubstituted heterocycloalkyl. In some embodiments is a compound of Formula (III), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, $C_{1-6}$haloalkyl, halogen, oxo, —$C(O)NR^8R^9$, —$SO_2R^8$, —$NR^9C(O)R^8$, and —$NR^9SO_2R^8$. In some embodiments is a compound of Formula (III), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, and —$C(O)NR^8R^9$. In some embodiments is a compound of Formula (III), or a pharmaceutically acceptable salt, solvate, or stereoisomer thereof, wherein m is 1 and $R^1$ is —$OR^7$. In some embodiments is a compound of Formula (III), or a pharmaceutically acceptable salt, solvate, or stereoisomer thereof, wherein m is 1, $R^1$ is —$OR^7$, and $R^7$ is selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (III), or a pharmaceutically acceptable salt, solvate, or stereoisomer thereof, wherein m is 1 and $R^1$ is —OCH3. In some embodiments is a compound of Formula (III), or a pharmaceutically acceptable salt, solvate, or stereoisomer thereof, wherein m is 1 and $R^1$ is —$OCF_3$. In some embodiments is a compound of Formula (III), or a pharmaceutically acceptable salt, solvate, or stereoisomer thereof, wherein m is 1 and $R^1$ is —$SO_2R^{12}$. In some embodiments is a compound of Formula (III), or a pharmaceutically acceptable salt, solvate, or stereoisomer thereof, wherein m is 1 and $R^1$ is —$SF_5$. In some embodiments is a compound of Formula (III), or a pharmaceutically acceptable salt, solvate, or stereoisomer thereof, wherein m is 1 and $R^1$ is —$SR^8$. In some embodiments is a compound of Formula (III), or a pharmaceutically acceptable salt, solvate, or stereoisomer thereof, wherein m is 1 and $R^1$ is aryl optionally substituted with one or two groups independently selected from halogen, $C_{1-6}$alkyl, $C_{1-6}$haloalkyl, and —$C(O)NR^8R^9$. In some embodiments is a compound of Formula (III), or a pharmaceutically acceptable salt, solvate, or stereoisomer thereof, wherein m is 1 and $R^1$ is heteroaryl optionally substituted with one or two groups independently selected from halogen, $C_{1-6}$alkyl, $C_{1-6}$haloalkyl, and —$C(O)NR^8R^9$. In some embodiments is a compound of Formula (III), or a pharmaceutically acceptable salt, solvate, or stereoisomer thereof, wherein m is 1 and $R^1$ is selected from thiazole, pyrazine, pyrimidine, and pyridine, optionally substituted with one or two groups independently selected from halogen, $C_{1-6}$alkyl, $C_{1-6}$haloalkyl, and —$C(O)NR^8R^9$. In some embodiments is a compound of Formula (III), or a pharmaceutically acceptable salt, solvate, or stereoisomer thereof, wherein m is 2. In some embodiments is a compound of Formula (III), or a pharmaceutically acceptable salt, solvate, or stereoisomer thereof, wherein m is 2 and each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (III), or a pharmaceutically acceptable salt, solvate, or stereoisomer thereof, wherein m is 2 and each $R^1$ is independently selected from halogen, $C_{1-6}$alkyl, $C_{1-6}$haloalkyl, $C_{3-8}$cycloalkyl, —$NR^5R^6$, and —$OR^7$. In some embodiments is a compound of Formula (III), or a pharmaceutically acceptable salt, solvate, or stereoisomer thereof, wherein m is 2 and each $R^1$ is independently selected from halogen, —CN, $C_{1-6}$alkyl, $C_{1-6}$haloalkyl, —$NR^5R^6$, —$OR^7$, and heteroaryl. In some embodiments is a compound of Formula (III), or a pharmaceutically acceptable salt, solvate, or stereoisomer thereof, wherein m is 2 and each $R^1$ is independently selected from halogen, $C_{1-6}$haloalkyl, —$NR^5R^6$, —$OR^7$, thiazole, pyrazine, pyrimidine, and pyridine. In some embodiments is a compound of Formula (III), or a pharmaceutically acceptable salt, solvate, or stereoisomer thereof, wherein m is 2 and each $R^1$ is independently selected from halogen, $C_{1-6}$alkyl, $C_{1-6}$haloalkyl, $C_{3-8}$cycloalkyl, and —$OR^7$. In some embodiments is a compound of Formula (III), or a pharmaceutically acceptable salt, solvate, or stereoisomer thereof, wherein m is 2, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (III), or a pharmaceutically acceptable salt, solvate, or stereoisomer thereof, wherein m is 2, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$haloalkyl, $C_{3-8}$cycloalkyl, and heterocycloalkyl. In some embodiments is a compound of Formula (III), or a pharmaceutically acceptable salt, solvate, or stereoisomer thereof, wherein m is 3. In some embodiments is a compound of Formula (III), or a pharmaceutically acceptable salt, solvate, or stereoisomer thereof, wherein m is 3 and each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (III), or a pharmaceutically acceptable salt, solvate, or stereoisomer thereof, wherein m is 3 and each $R^1$ is independently selected from halogen, $C_{1-6}$alkyl, $C_{1-6}$haloalkyl, $C_{3-8}$cycloalkyl, —$NR^5R^6$, and —$OR^7$. In some embodiments is a compound of Formula (III), or a pharmaceutically acceptable salt, solvate, or stereoisomer thereof, m is 3 and each $R^1$ is independently selected from halogen, $C_{1-6}$alkyl, $C_{1-6}$haloalkyl, $C_{3-8}$cycloalkyl, and —$OR^7$. In some embodiments is a compound of Formula (III), or a pharmaceutically acceptable salt, solvate, or stereoisomer thereof, wherein m is 3, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (III), or a pharmaceutically acceptable salt, solvate, or stereoisomer thereof, wherein m is 3, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$haloalkyl, $C_{3-8}$cycloalkyl, and heterocycloalkyl.

In some embodiments is a compound of Formula (III), or a pharmaceutically acceptable salt, solvate, or stereoisomer thereof, wherein n is 0. In some embodiments is a compound of Formula (III), or a pharmaceutically acceptable salt, solvate, or stereoisomer thereof, wherein n is 1. In some embodiments is a compound of Formula (III), or a pharmaceutically acceptable salt, solvate, or stereoisomer thereof, wherein n is 1 and $R^1$ is selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (III), or a pharmaceutically acceptable salt, solvate, or stereoisomer thereof, wherein n is 1 and $R^1$ is selected from halogen, $C_{1-6}$alkyl, $C_{1-6}$haloalkyl, $C_{3-8}$cycloalkyl, —$NR^5R^6$, and —$OR^7$. In some embodiments is a compound of Formula (III), or a pharmaceutically acceptable salt, solvate, or stereoisomer thereof, wherein n is 1 and $R^1$ is selected from halogen, $C_{1-6}$alkyl, $C_{1-6}$haloalkyl, $C_{3-8}$cycloalkyl, and —$OR^7$. In some embodiments is a compound of Formula (III), or a pharmaceutically acceptable salt, solvate, or stereoisomer thereof, wherein n is 1 and $R^1$ is halogen. In some embodiments is a compound of Formula (III), or a pharmaceutically acceptable salt, solvate, or stereoisomer thereof, wherein n is 1 and $R^1$ is F. In some embodiments is a compound of Formula (III), or a pharmaceutically acceptable salt, solvate, or stereoisomer thereof, wherein n is 1 and $R^1$ is $C_1$. In some embodiments is a compound of Formula (III), or a pharmaceutically acceptable salt, solvate, or stereoisomer thereof, wherein n is 1 and $R^1$ is —CN. In some embodiments is a compound of Formula (III), or a pharmaceutically acceptable salt, solvate, or stereoisomer thereof, wherein n is 1 and $R^1$ is $C_{1-6}$alkyl. In some embodiments is a compound of Formula (III), or a pharmaceutically acceptable salt, solvate, or stereoisomer thereof, wherein n is 1 and $R^1$ is —$CH_3$. In some embodiments is a compound of Formula (III), or a pharmaceutically acceptable salt, solvate, or stereoisomer thereof, wherein n is 1 and $R^1$ is —C≡CH. In some embodiments is a compound of Formula (III), or a pharmaceutically acceptable salt, solvate, or stereoisomer thereof, wherein n is 1 and $R^1$ is $C_{1-6}$alkyl-$OR^7$. In some embodiments is a compound of Formula (III), or a pharmaceutically acceptable salt, solvate, or stereoisomer thereof, wherein n is 1 and $R^1$ is —$CH_2$—O—$CH_3$. In some embodiments is a compound of Formula (III), or a pharmaceutically acceptable salt, solvate, or stereoisomer thereof, wherein n is 1 and $R^1$ is $C_{1-6}$haloalkyl. In some embodiments is a compound of Formula (III), or a pharmaceutically acceptable salt, solvate, or stereoisomer thereof, wherein n is 1 and $R^1$ is —$CF_3$. In some embodiments is a compound of Formula (III), or a pharmaceutically acceptable salt, solvate, or stereoisomer thereof, wherein n is 1 and $R^1$ is $C_{3-8}$cycloalkyl. In some embodiments is a compound of Formula (III), or a pharmaceutically acceptable salt, solvate, or stereoisomer thereof, wherein n is 1 and $R^1$ is —$NR^5R^6$. In some embodiments is a compound of Formula (III), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl optionally substituted with one or two $R^{10}$. In some embodiments is a compound of Formula (III), or a pharmaceutically acceptable salt, solvate, or stereoisomer thereof, wherein n is 1, $R^1$ is —$NR^5R^6$, and $R^5$ and $R^6$, together with the nitrogen to which they are attached, form an unsubstituted heterocycloalkyl. In some embodiments is a compound of Formula (III), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, $C_{1-6}$haloalkyl, halogen, oxo, —C(O)$NR^8R^9$, —$SO_2R^8$, —$NR^9C(O)R^8$, and —$NR^9SO_2R^8$. In some embodiments is a compound of Formula (III), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, and —C(O)$NR^8R^9$. In some embodiments is a compound of Formula (III), or a pharmaceutically acceptable salt, solvate, or stereoisomer thereof, wherein n is 1 and $R^1$ is —$OR^7$. In some embodiments is a compound of Formula (III), or a pharmaceutically acceptable salt, solvate, or stereoisomer thereof, wherein n is 1, $R^1$ is —$OR^7$, and $R^7$ is selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (III), or a pharmaceutically acceptable salt, solvate, or stereoisomer thereof, wherein n is 1 and $R^1$ is —OCH3. In some embodiments is a compound of Formula (III), or a pharmaceutically acceptable salt, solvate, or stereoisomer thereof, wherein n is 1 and $R^1$ is —OCF$_3$. In some embodiments is a compound of Formula (III), or a pharmaceutically acceptable salt, solvate, or stereoisomer thereof, wherein n is 1 and $R^1$ is —SO$_2$R$^{12}$. In some embodiments is a compound of Formula (III), or a pharmaceutically acceptable salt, solvate, or stereoisomer thereof, wherein n is 1 and $R^1$ is —SF$_5$. In some embodiments is a compound of Formula (III), or a pharmaceutically acceptable salt, solvate, or stereoisomer thereof, wherein n is 1 and $R^1$ is —SR$^8$. In some embodiments is a compound of Formula (III), or a pharmaceutically acceptable salt, solvate, or stereoisomer thereof, wherein n is 1 and $R^1$ is aryl optionally substituted with one or two groups independently selected from halogen, C$_{1-6}$alkyl, C$_{1-6}$haloalkyl, and —C(O)NR$^8$R$^9$. In some embodiments is a compound of Formula (III), or a pharmaceutically acceptable salt, solvate, or stereoisomer thereof, wherein n is 1 and $R^1$ is heteroaryl optionally substituted with one or two groups independently selected from halogen, C$_{1-6}$alkyl, C$_{1-6}$haloalkyl, and —C(O)NR$^8$R$^9$. In some embodiments is a compound of Formula (III), or a pharmaceutically acceptable salt, solvate, or stereoisomer thereof, wherein n is 1 and $R^1$ is selected from thiazole, pyrazine, pyrimidine, and pyridine, optionally substituted with one or two groups independently selected from halogen, C$_{1-6}$alkyl, C$_{1-6}$haloalkyl, and —C(O)NR$^8$R$^9$. In some embodiments is a compound of Formula (III), or a pharmaceutically acceptable salt, solvate, or stereoisomer thereof, wherein n is 2. In some embodiments is a compound of Formula (III), or a pharmaceutically acceptable salt, solvate, or stereoisomer thereof, wherein n is 2 and each $R^1$ is independently selected from halogen, —CN, C$_{1-6}$alkyl, C$_{2-6}$alkynyl, C$_{1-6}$alkyl-OR$^7$, C$_{1-6}$haloalkyl, C$_{3-8}$cycloalkyl, —NR$^5$R$^6$, —OR$^7$, —SO$_2$R$^{12}$, —SF$_5$, —SR$^8$, aryl, and heteroaryl. In some embodiments is a compound of Formula (III), or a pharmaceutically acceptable salt, solvate, or stereoisomer thereof, wherein n is 2 and each $R^1$ is independently selected from halogen, C$_{1-6}$alkyl, C$_{1-6}$haloalkyl, C$_{3-8}$cycloalkyl, —NR$^5$R$^6$, and —OR$^7$. In some embodiments is a compound of Formula (III), or a pharmaceutically acceptable salt, solvate, or stereoisomer thereof, wherein n is 2 and each $R^1$ is independently selected from halogen, —CN, C$_{1-6}$alkyl, C$_{1-6}$haloalkyl, —NR$^5$R$^6$, —OR$^7$, and heteroaryl. In some embodiments is a compound of Formula (III), or a pharmaceutically acceptable salt, solvate, or stereoisomer thereof, wherein n is 2 and each $R^1$ is independently selected from halogen, C$_{1-6}$haloalkyl, —NR$^5$R$^6$, —OR$^7$, thiazole, pyrazine, pyrimidine, and pyridine. In some embodiments is a compound of Formula (III), or a pharmaceutically acceptable salt, solvate, or stereoisomer thereof, wherein n is 2 and each $R^1$ is independently selected from halogen, C$_{1-6}$alkyl, C$_{1-6}$haloalkyl, C$_{3-8}$cycloalkyl, and —OR$^7$. In some embodiments is a compound of Formula (III), or a pharmaceutically acceptable salt, solvate, or stereoisomer thereof, wherein n is 2, each $R^1$ is independently selected from halogen, C$_{1-6}$alkyl, C$_{1-6}$haloalkyl, C$_{3-8}$cycloalkyl, and —OR$^7$, and each $R^7$ is independently selected from C$_{1-6}$alkyl, C$_{1-6}$alkyl-O—C$_{1-6}$alkyl, C$_{1-6}$haloalkyl, C$_{3-8}$cycloalkyl, heterocycloalkyl, aryl, and heteroaryl. In some embodiments is a compound of Formula (III), or a pharmaceutically acceptable salt, solvate, or stereoisomer thereof, wherein n is 2, each $R^1$ is independently selected from halogen, C$_{1-6}$alkyl, C$_{1-6}$haloalkyl, C$_{3-8}$cycloalkyl, and —OR$^7$, and each $R^7$ is independently selected from C$_{1-6}$alkyl, C$_{1-6}$haloalkyl, C$_{3-8}$cycloalkyl, and heterocycloalkyl. In some embodiments is a compound of Formula (III), or a pharmaceutically acceptable salt, solvate, or stereoisomer thereof, wherein n is 3.

In some embodiments is a compound of Formula (IIIa):

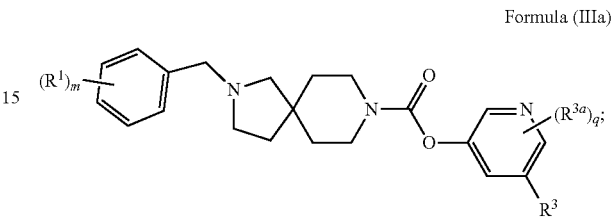

Formula (IIIa)

wherein:
each $R^1$ is independently selected from halogen, —CN, C$_{1-6}$alkyl, C$_{2-6}$alkynyl, C$_{1-6}$alkyl-OR$^7$, C$_{1-6}$haloalkyl, C$_{3-8}$cycloalkyl, —NR$^5$R$^6$, —C(O)NR$^5$R$^6$, —OR$^7$, —SO$_2$R$^{12}$, —SF$_5$, —SR$^8$, aryl, and heteroaryl, wherein aryl and heteroaryl are optionally substituted with one or two groups independently selected from halogen, C$_{1-6}$alkyl, C$_{1-6}$haloalkyl, and —C(O)NR$^8$R$^9$; or two adjacent $R^1$ form a heterocycloalkyl ring optionally substituted with one or two $R^{11}$;
$R^3$ is selected from halogen, —CN, C$_{1-6}$alkyl, C$_{1-6}$haloalkyl, —NR$^8$R$^9$, —C(O)NR$^8$R$^9$, —NR$^8$C(O)R$^9$, and —NR$^9$SO$_2$R$^8$; $R^{3a}$ is selected from halogen, C$_{1-6}$alkyl, and C$_{1-6}$haloalkyl;
each $R^5$ and $R^6$ is independently selected from H, C$_{1-6}$alkyl, and C$_{3-8}$cycloalkyl; or $R^5$ and $R^6$, together with the nitrogen to which they are attached, form a heterocycloalkyl optionally substituted with one or two $R^{10}$;
each $R^7$ is independently selected from H, C$_{1-6}$alkyl, C$_{1-6}$alkyl-O—C$_{1-6}$alkyl, C$_{1-6}$haloalkyl, C$_{3-8}$cycloalkyl, heterocycloalkyl, aryl, and heteroaryl, wherein heterocycloalkyl, aryl, and heteroaryl are optionally substituted with one or two groups independently selected from halogen, C$_{1-6}$alkyl, and C$_{1-6}$haloalkyl;
each $R^8$ and $R^9$ is independently selected from H, C$_{1-6}$alkyl, C$_{3-8}$cycloalkyl, aryl, and heteroaryl;
each $R^{10}$ is independently selected from C$_{1-6}$alkyl, C$_{3-8}$cycloalkyl, C$_{1-6}$haloalkyl, halogen, oxo, —CN, —C(O)OR$^8$, —C(O)R$^8$, —C(O)NR$^8$R$^9$, —SO$_2$R$^8$, —NR$^9$C(O)R$^8$, and —NR$^9$SO$_2$R$^8$;
each $R^{11}$ is independently selected from halogen and C$_{1-6}$alkyl;
each $R^{12}$ is independently selected from C$_{1-6}$alkyl and C$_{3-8}$cycloalkyl;
m is 0, 1, 2, 3, 4, or 5; and
q is 0 or 1;
or a pharmaceutically acceptable salt, solvate, or stereoisomer thereof.

In some embodiments is a compound of Formula (IIIa), or a pharmaceutically acceptable salt, solvate, or stereoisomer thereof, wherein $R^3$ is halogen. In some embodiments is a compound of Formula (IIIa), or a pharmaceutically acceptable salt, solvate, or stereoisomer thereof, wherein $R^3$ is —CN. In some embodiments is a compound of Formula (IIIa), or a pharmaceutically acceptable salt, solvate, or stereoisomer thereof, wherein $R^3$ is C$_{1-6}$alkyl. In some embodiments is a compound of Formula (IIIa), or a pharmaceutically acceptable salt, solvate, or stereoisomer thereof, wherein $R^3$ is —$CH_3$. In some embodiments is a compound of Formula (IIIa), or a pharmaceutically acceptable salt, solvate, or stereoisomer thereof, wherein $R^3$ is $C_{1-6}$haloalkyl. In some embodiments is a compound of Formula (IIIa), or a pharmaceutically acceptable salt, solvate, or stereoisomer thereof, wherein $R^3$ is —$CF_3$. In some embodiments is a compound of Formula (IIIa), or a pharmaceutically acceptable salt, solvate, or stereoisomer thereof, wherein $R^3$ is —$NR^8R^9$. In some embodiments is a compound of Formula (IIIa), or a pharmaceutically acceptable salt, solvate, or stereoisomer thereof, wherein $R^3$ is —$NH_2$. In some embodiments is a compound of Formula (IIIa), or a pharmaceutically acceptable salt, solvate, or stereoisomer thereof, wherein $R^3$ is —$C(O)NR^8R^9$. In some embodiments is a compound of Formula (IIIa), or a pharmaceutically acceptable salt, solvate, or stereoisomer thereof, wherein $R^3$ is —$C(O)NH_2$. In some embodiments is a compound of Formula (IIIa), or a pharmaceutically acceptable salt, solvate, or stereoisomer thereof, wherein $R^3$ is —$NR^8C(O)R^9$. In some embodiments is a compound of Formula (IIIa), or a pharmaceutically acceptable salt, solvate, or stereoisomer thereof, wherein $R^3$ is —$NHC(O)CH_3$. In some embodiments is a compound of Formula (IIIa), or a pharmaceutically acceptable salt, solvate, or stereoisomer thereof, wherein q is 0. In some embodiments is a compound of Formula (IIIa), or a pharmaceutically acceptable salt, solvate, or stereoisomer thereof, wherein q is 1. In some embodiments is a compound of Formula (IIIa), or a pharmaceutically acceptable salt, solvate, or stereoisomer thereof, wherein q is 1 and $R^{3a}$ is halogen. In some embodiments is a compound of Formula (IIIa), or a pharmaceutically acceptable salt, solvate, or stereoisomer thereof, wherein q is 1 and $R^{3a}$ is $C_{1-6}$alkyl. In some embodiments is a compound of Formula (IIIa), or a pharmaceutically acceptable salt, solvate, or stereoisomer thereof, wherein q is 1 and $R^{3a}$ is $C_{1-6}$haloalkyl.

In some embodiments is a compound of Formula (IIIa), or a pharmaceutically acceptable salt, solvate, or stereoisomer thereof, wherein m is 0. In some embodiments is a compound of Formula (IIIa), or a pharmaceutically acceptable salt, solvate, or stereoisomer thereof, wherein m is 1. In some embodiments is a compound of Formula (IIIa), or a pharmaceutically acceptable salt, solvate, or stereoisomer thereof, wherein m is 1 and $R^1$ selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (IIIa), or a pharmaceutically acceptable salt, solvate, or stereoisomer thereof, wherein m is 1 and $R^1$ is selected from halogen, $C_{1-6}$alkyl, $C_{1-6}$haloalkyl, $C_{3-8}$cycloalkyl, —$NR^5R^6$, and —$OR^7$. In some embodiments is a compound of Formula (IIIa), or a pharmaceutically acceptable salt, solvate, or stereoisomer thereof, wherein m is 1 and $R^1$ is selected from halogen, $C_{1-6}$alkyl, $C_{1-6}$haloalkyl, $C_{3-8}$cycloalkyl, and —$OR^7$. In some embodiments is a compound of Formula (IIIa), or a pharmaceutically acceptable salt, solvate, or stereoisomer thereof, wherein m is 1 and $R^1$ is halogen. In some embodiments is a compound of Formula (IIIa), or a pharmaceutically acceptable salt, solvate, or stereoisomer thereof, wherein m is 1 and $R^1$ is F. In some embodiments is a compound of Formula (IIIa), or a pharmaceutically acceptable salt, solvate, or stereoisomer thereof, wherein m is 1 and $R^1$ is Cl. In some embodiments is a compound of Formula (IIIa), or a pharmaceutically acceptable salt, solvate, or stereoisomer thereof, wherein m is 1 and $R^1$ is —CN. In some embodiments is a compound of Formula (IIIa), or a pharmaceutically acceptable salt, solvate, or stereoisomer thereof, wherein m is 1 and $R^1$ is $C_{1-6}$alkyl. In some embodiments is a compound of Formula (IIIa), or a pharmaceutically acceptable salt, solvate, or stereoisomer thereof, wherein m is 1 and $R^1$ is —$CH_3$. In some embodiments is a compound of Formula (IIIa), or a pharmaceutically acceptable salt, solvate, or stereoisomer thereof, wherein m is 1 and $R^1$ is —C≡CH. In some embodiments is a compound of Formula (IIIa), or a pharmaceutically acceptable salt, solvate, or stereoisomer thereof, wherein m is 1 and $R^1$ is $C_{1-6}$alkyl-$OR^7$. In some embodiments is a compound of Formula (IIIa), or a pharmaceutically acceptable salt, solvate, or stereoisomer thereof, wherein m is 1 and $R^1$ is —$CH_2$—O—$CH_3$. In some embodiments is a compound of Formula (IIIa), or a pharmaceutically acceptable salt, solvate, or stereoisomer thereof, wherein m is 1 and $R^1$ is $C_{1-6}$haloalkyl. In some embodiments is a compound of Formula (IIIa), or a pharmaceutically acceptable salt, solvate, or stereoisomer thereof, wherein m is 1 and $R^1$ is —$CF_3$. In some embodiments is a compound of Formula (IIIa), or a pharmaceutically acceptable salt, solvate, or stereoisomer thereof, wherein m is 1 and $R^1$ is $C_{3-8}$cycloalkyl. In some embodiments is a compound of Formula (IIIa), or a pharmaceutically acceptable salt, solvate, or stereoisomer thereof, wherein m is 1 and $R^1$ is —$NR^5R^6$. In some embodiments is a compound of Formula (IIIa), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl optionally substituted with one or two $R^{10}$. In some embodiments is a compound of Formula (IIIa), or a pharmaceutically acceptable salt, solvate, or stereoisomer thereof, wherein m is 1, $R^1$ is —$NR^5R^6$, and $R^5$ and $R^6$, together with the nitrogen to which they are attached, form an unsubstituted heterocycloalkyl. In some embodiments is a compound of Formula (IIIa), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, $C_{1-6}$haloalkyl, halogen, oxo, —$C(O)NR^8R^9$, —$SO_2R^8$, —$NR^9C(O)R^8$, and —$NR^9SO_2R^8$. In some embodiments is a compound of Formula (IIIa), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, and —$C(O)NR^8R^9$. In some embodiments is a compound of Formula (IIIa), or a pharmaceutically acceptable salt, solvate, or stereoisomer thereof, wherein m is 1 and $R^1$ is —$OR^7$. In some embodiments is a compound of Formula (IIIa), or a pharmaceutically acceptable salt, solvate, or stereoisomer thereof, wherein m is 1, $R^1$ is —$OR^7$, and $R^7$ is selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IIIa), or a pharmaceutically acceptable salt, solvate, or stereoisomer thereof, wherein m is 1 and $R^1$ is —$OCH_3$. In some embodiments is a compound of Formula (IIIa), or a pharmaceutically acceptable salt, solvate, or stereoisomer thereof, wherein m is 1 and $R^1$ is —$OCF_3$. In some embodiments is a compound of Formula (IIIa), or a pharmaceutically acceptable salt, solvate, or stereoisomer thereof, wherein m is 1 and $R^1$ is —$SO_2R^{12}$. In some embodiments is a compound of Formula (IIIa), or a pharmaceutically acceptable salt, solvate, or stereoisomer thereof, wherein m is 1 and $R^1$ is —$SF_5$. In some embodiments is a compound of Formula (IIIa), or a pharmaceutically acceptable salt, solvate, or stereoisomer thereof, wherein m is 1 and $R^1$ is —$SR^8$. In some embodiments is a compound of Formula (IIIa), or a pharmaceutically acceptable salt, solvate, or stereoisomer thereof, wherein m is 1 and $R^1$ is aryl optionally substituted with one or two groups independently selected from halogen, $C_{1-6}$alkyl, $C_{1-6}$haloalkyl, and —C(O)$NR^8R^9$. In some embodiments is a compound of Formula (IIIa), or a pharmaceutically acceptable salt, solvate, or stereoisomer thereof, wherein m is 1 and $R^1$ is heteroaryl optionally substituted with one or two groups independently selected from halogen, $C_{1-6}$alkyl, $C_{1-6}$haloalkyl, and —C(O)$NR^8R^9$. In some embodiments is a compound of Formula (IIIa), or a pharmaceutically acceptable salt, solvate, or stereoisomer thereof, wherein m is 1 and $R^1$ is selected from thiazole, pyrazine, pyrimidine, and pyridine, optionally substituted with one or two groups independently selected from halogen, $C_{1-6}$alkyl, $C_{1-6}$haloalkyl, and —C(O)$NR^8R^9$. In some embodiments is a compound of Formula (IIIa), or a pharmaceutically acceptable salt, solvate, or stereoisomer thereof, wherein m is 2. In some embodiments is a compound of Formula (IIIa), or a pharmaceutically acceptable salt, solvate, or stereoisomer thereof, wherein m is 2 and each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (IIIa), or a pharmaceutically acceptable salt, solvate, or stereoisomer thereof, wherein m is 2 and each $R^1$ is independently selected from halogen, $C_{1-6}$alkyl, $C_{1-6}$haloalkyl, $C_{3-8}$cycloalkyl, —$NR^5R^6$, and —$OR^7$. In some embodiments is a compound of Formula (IIIa), or a pharmaceutically acceptable salt, solvate, or stereoisomer thereof, wherein m is 2 and each $R^1$ is independently selected from halogen, —CN, $C_{1-6}$alkyl, $C_{1-6}$haloalkyl, —$NR^5R^6$, —$OR^7$, and heteroaryl. In some embodiments is a compound of Formula (IIIa), or a pharmaceutically acceptable salt, solvate, or stereoisomer thereof, wherein m is 2 and each $R^1$ is independently selected from halogen, $C_{1-6}$haloalkyl, —$NR^5R^6$, —$OR^7$, thiazole, pyrazine, pyrimidine, and pyridine. In some embodiments is a compound of Formula (IIIa), or a pharmaceutically acceptable salt, solvate, or stereoisomer thereof, wherein m is 2 and each $R^1$ is independently selected from halogen, $C_{1-6}$alkyl, $C_{1-6}$haloalkyl, $C_{3-8}$cycloalkyl, and —$OR^7$. In some embodiments is a compound of Formula (IIIa), or a pharmaceutically acceptable salt, solvate, or stereoisomer thereof, wherein m is 2, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IIIa), or a pharmaceutically acceptable salt, solvate, or stereoisomer thereof, wherein m is 2, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$haloalkyl, $C_{3-8}$cycloalkyl, and heterocycloalkyl. In some embodiments is a compound of Formula (IIIa), or a pharmaceutically acceptable salt, solvate, or stereoisomer thereof, wherein m is 3. In some embodiments is a compound of Formula (IIIa), or a pharmaceutically acceptable salt, solvate, or stereoisomer thereof, wherein m is 3 and each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (IIIa), or a pharmaceutically acceptable salt, solvate, or stereoisomer thereof, wherein m is 3 and each $R^1$ is independently selected from halogen, $C_{1-6}$alkyl, $C_{1-6}$haloalkyl, $C_{3-8}$cycloalkyl, —$NR^5R^6$, and —$OR^7$. In some embodiments is a compound of Formula (IIIa), or a pharmaceutically acceptable salt, solvate, or stereoisomer thereof, m is 3 and each $R^1$ is independently selected from halogen, $C_{1-6}$alkyl, $C_{1-6}$haloalkyl, $C_{3-8}$cycloalkyl, and —$OR^7$. In some embodiments is a compound of Formula (IIIa), or a pharmaceutically acceptable salt, solvate, or stereoisomer thereof, wherein m is 3, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IIIa), or a pharmaceutically acceptable salt, solvate, or stereoisomer thereof, wherein m is 3, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$haloalkyl, $C_{3-8}$cycloalkyl, and heterocycloalkyl.

In some embodiments is a compound of Formula (IIIa), or a pharmaceutically acceptable salt, solvate, or stereoisomer thereof, wherein n is 0. In some embodiments is a compound of Formula (IIIa), or a pharmaceutically acceptable salt, solvate, or stereoisomer thereof, wherein n is 1. In some embodiments is a compound of Formula (IIIa), or a pharmaceutically acceptable salt, solvate, or stereoisomer thereof, wherein n is 1 and $R^1$ is selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (IIIa), or a pharmaceutically acceptable salt, solvate, or stereoisomer thereof, wherein n is 1 and $R^1$ is selected from halogen, $C_{1-6}$alkyl, $C_{1-6}$haloalkyl, $C_{3-8}$cycloalkyl, —$NR^5R^6$, and —$OR^7$. In some embodiments is a compound of Formula (IIIa), or a pharmaceutically acceptable salt, solvate, or stereoisomer thereof, wherein n is 1 and $R^1$ is selected from halogen, $C_{1-6}$alkyl, $C_{1-6}$haloalkyl, $C_{3-8}$cycloalkyl, and —$OR^7$. In some embodiments is a compound of Formula (IIIa), or a pharmaceutically acceptable salt, solvate, or stereoisomer thereof, wherein n is 1 and $R^1$ is halogen. In some embodiments is a compound of Formula (IIIa), or a pharmaceutically acceptable salt, solvate, or stereoisomer thereof, wherein n is 1 and $R^1$ is F. In some embodiments is a compound of Formula (IIIa), or a pharmaceutically acceptable salt, solvate, or stereoisomer thereof, wherein n is 1 and $R^1$ is Cl. In some embodiments is a compound of Formula (IIIa), or a pharmaceutically acceptable salt, solvate, or stereoisomer thereof, wherein n is 1 and $R^1$ is —CN. In some embodiments is a compound of Formula (IIIa), or a pharmaceutically acceptable salt, solvate, or stereoisomer thereof, wherein n is 1 and $R^1$ is $C_{1-6}$alkyl. In some embodiments is a compound of Formula (IIIa), or a pharmaceutically acceptable salt, solvate, or stereoisomer thereof, wherein n is 1 and $R^1$ is —$CH_3$. In some embodiments is a compound of Formula (IIIa), or a pharmaceutically acceptable salt, solvate, or stereoisomer thereof, wherein n is 1 and $R^1$ is —C≡CH. In some embodiments is a compound of Formula (IIIa), or a pharmaceutically acceptable salt, solvate, or stereoisomer thereof, wherein n is 1 and $R^1$ is $C_{1-6}$alkyl-$OR^7$. In some embodiments is a compound of Formula (IIIa), or a pharmaceutically acceptable salt, solvate, or stereoisomer thereof, wherein n is 1 and $R^1$ is —$CH_2$—O—

CH$_3$. In some embodiments is a compound of Formula (IIIa), or a pharmaceutically acceptable salt, solvate, or stereoisomer thereof, wherein n is 1 and R$^1$ is C$_{1-6}$haloalkyl. In some embodiments is a compound of Formula (IIIa), or a pharmaceutically acceptable salt, solvate, or stereoisomer thereof, wherein n is 1 and R$^1$ is —CF$_3$. In some embodiments is a compound of Formula (IIIa), or a pharmaceutically acceptable salt, solvate, or stereoisomer thereof, wherein n is 1 and R$^1$ is C$_{3-8}$cycloalkyl. In some embodiments is a compound of Formula (IIIa), or a pharmaceutically acceptable salt, solvate, or stereoisomer thereof, wherein n is 1 and R$^1$ is —NR$^5$R$^6$. In some embodiments is a compound of Formula (IIIa), or a pharmaceutically acceptable salt, solvate, or stereoisomer thereof, wherein n is 1, R$^1$ is —NR$^5$R$^6$, and R$^5$ and R$^6$, together with the nitrogen to which they are attached, form a heterocycloalkyl optionally substituted with one or two R$^{10}$. In some embodiments is a compound of Formula (IIIa), or a pharmaceutically acceptable salt, solvate, or stereoisomer thereof, wherein n is 1, R$^1$ is —NR$^5$R$^6$, and R$^5$ and R$^6$, together with the nitrogen to which they are attached, form an unsubstituted heterocycloalkyl. In some embodiments is a compound of Formula (IIIa), or a pharmaceutically acceptable salt, solvate, or stereoisomer thereof, wherein n is 1, R$^1$ is —NR$^5$R$^6$, and R$^5$ and R$^6$, together with the nitrogen to which they are attached, form a heterocycloalkyl substituted with one or two R$^{10}$ independently selected from C$_{1-6}$alkyl, C$_{3-8}$cycloalkyl, C$_{1-6}$haloalkyl, halogen, oxo, —C(O)NR$^8$R$^9$, —SO$_2$R$^8$, —NR$^9$C(O)R$^8$, and —NR$^9$SO$_2$R$^8$. In some embodiments is a compound of Formula (IIIa), or a pharmaceutically acceptable salt, solvate, or stereoisomer thereof, wherein n is 1, R$^1$ is —NR$^5$R$^6$, and R$^5$ and R$^6$, together with the nitrogen to which they are attached, form a heterocycloalkyl substituted with one or two R$^{10}$ independently selected from C$_{1-6}$alkyl, C$_{3-8}$cycloalkyl, and —C(O)NR$^8$R$^9$. In some embodiments is a compound of Formula (IIIa), or a pharmaceutically acceptable salt, solvate, or stereoisomer thereof, wherein n is 1 and R$^1$ is —OR$^7$. In some embodiments is a compound of Formula (IIIa), or a pharmaceutically acceptable salt, solvate, or stereoisomer thereof, wherein n is 1, R$^1$ is —OR$^7$, and R$^7$ is selected from C$_{1-6}$alkyl, C$_{1-6}$alkyl-O—C$_{1-6}$alkyl, C$_{1-6}$haloalkyl, C$_{3-8}$cycloalkyl, heterocycloalkyl, aryl, and heteroaryl. In some embodiments is a compound of Formula (IIIa), or a pharmaceutically acceptable salt, solvate, or stereoisomer thereof, wherein n is 1 and R$^1$ is —OCH$_3$. In some embodiments is a compound of Formula (IIIa), or a pharmaceutically acceptable salt, solvate, or stereoisomer thereof, wherein n is 1 and R$^1$ is —OCF$_3$. In some embodiments is a compound of Formula (IIIa), or a pharmaceutically acceptable salt, solvate, or stereoisomer thereof, wherein n is 1 and R$^1$ is —SO$_2$R$^{12}$. In some embodiments is a compound of Formula (IIIa), or a pharmaceutically acceptable salt, solvate, or stereoisomer thereof, wherein n is 1 and R$^1$ is —SF$_5$. In some embodiments is a compound of Formula (IIIa), or a pharmaceutically acceptable salt, solvate, or stereoisomer thereof, wherein n is 1 and R$^1$ is —SR$^8$. In some embodiments is a compound of Formula (IIIa), or a pharmaceutically acceptable salt, solvate, or stereoisomer thereof, wherein n is 1 and R$^1$ is aryl optionally substituted with one or two groups independently selected from halogen, C$_{1-6}$alkyl, C$_{1-6}$haloalkyl, and —C(O)NR$^8$R$^9$. In some embodiments is a compound of Formula (IIIa), or a pharmaceutically acceptable salt, solvate, or stereoisomer thereof, wherein n is 1 and R$^1$ is heteroaryl optionally substituted with one or two groups independently selected from halogen, C$_{1-6}$alkyl, C$_{1-6}$haloalkyl, and —C(O)NR$^8$R$^9$. In some embodiments is a compound of Formula (IIIa), or a pharmaceutically acceptable salt, solvate, or stereoisomer thereof, wherein n is 1 and R$^1$ is selected from thiazole, pyrazine, pyrimidine, and pyridine, optionally substituted with one or two groups independently selected from halogen, C$_{1-6}$alkyl, C$_{1-6}$haloalkyl, and —C(O)NR$^8$R$^9$. In some embodiments is a compound of Formula (IIIa), or a pharmaceutically acceptable salt, solvate, or stereoisomer thereof, wherein n is 2. In some embodiments is a compound of Formula (IIIa), or a pharmaceutically acceptable salt, solvate, or stereoisomer thereof, wherein n is 2 and each R$^1$ is independently selected from halogen, —CN, C$_{1-6}$alkyl, C$_{2-6}$alkynyl, C$_{1-6}$alkyl-OR$^7$, C$_{1-6}$haloalkyl, C$_{3-8}$cycloalkyl, —NR$^5$R$^6$, —OR$^7$, —SO$_2$R$^{12}$, —SF$_5$, —SR$^8$, aryl, and heteroaryl. In some embodiments is a compound of Formula (IIIa), or a pharmaceutically acceptable salt, solvate, or stereoisomer thereof, wherein n is 2 and each R$^1$ is independently selected from halogen, C$_{1-6}$alkyl, C$_{1-6}$haloalkyl, C$_{3-8}$cycloalkyl, —NR$^5$R$^6$, and —OR$^7$. In some embodiments is a compound of Formula (IIIa), or a pharmaceutically acceptable salt, solvate, or stereoisomer thereof, wherein n is 2 and each R$^1$ is independently selected from halogen, —CN, C$_{1-6}$alkyl, C$_{1-6}$haloalkyl, —NR$^5$R$^6$, —OR$^7$, and heteroaryl. In some embodiments is a compound of Formula (IIIa), or a pharmaceutically acceptable salt, solvate, or stereoisomer thereof, wherein n is 2 and each R$^1$ is independently selected from halogen, C$_{1-6}$haloalkyl, —NR$^5$R$^6$, —OR$^7$, thiazole, pyrazine, pyrimidine, and pyridine. In some embodiments is a compound of Formula (IIIa), or a pharmaceutically acceptable salt, solvate, or stereoisomer thereof, wherein n is 2 and each R$^1$ is independently selected from halogen, C$_{1-6}$alkyl, C$_{1-6}$haloalkyl, C$_{3-8}$cycloalkyl, and —OR$^7$. In some embodiments is a compound of Formula (IIIa), or a pharmaceutically acceptable salt, solvate, or stereoisomer thereof, wherein n is 2, each R$^1$ is independently selected from halogen, C$_{1-6}$alkyl, C$_{1-6}$haloalkyl, C$_{3-8}$cycloalkyl, and —OR$^7$, and each R$^7$ is independently selected from C$_{1-6}$alkyl, C$_{1-6}$alkyl-O—C$_{1-6}$alkyl, C$_{1-6}$haloalkyl, C$_{3-8}$cycloalkyl, heterocycloalkyl, aryl, and heteroaryl. In some embodiments is a compound of Formula (IIIa), or a pharmaceutically acceptable salt, solvate, or stereoisomer thereof, wherein n is 2, each R$^1$ is independently selected from halogen, C$_{1-6}$alkyl, C$_{1-6}$haloalkyl, C$_{3-8}$cycloalkyl, and —OR$^7$, and each R$^7$ is independently selected from C$_{1-6}$alkyl, C$_{1-6}$haloalkyl, C$_{3-8}$cycloalkyl, and heterocycloalkyl. In some embodiments is a compound of Formula (IIIa), or a pharmaceutically acceptable salt, solvate, or stereoisomer thereof, wherein n is 3.

In some embodiments is a compound of Formula (IIIb):

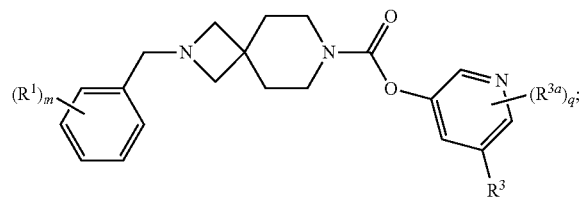

Formula (IIIb)

wherein:
each R$^1$ is independently selected from halogen, —CN, C$_{1-6}$alkyl, C$_{2-6}$alkynyl, C$_{1-6}$alkyl-OR$^7$, C$_{1-6}$haloalkyl, C$_{3-8}$cycloalkyl, —NR$^5$R$^6$, —C(O)NR$^5$R$^6$, —OR$^7$, —SO$_2$R$^{12}$, —SF$_5$, —SR$^8$, aryl, and heteroaryl, wherein aryl and heteroaryl are optionally substituted with one or two groups independently selected from halogen, $C_{1-6}$alkyl, $C_{1-6}$haloalkyl, and —C(O)NR$^8$R$^9$; or two adjacent R$^1$ form a heterocycloalkyl ring optionally substituted with one or two R$^{11}$;

R$^3$ is selected from halogen, —CN, $C_{1-6}$alkyl, $C_{1-6}$haloalkyl, —NR$^8$R$^9$, —C(O)NR$^8$R$^9$, —NR$^8$C(O)R$^9$, and —NR$^9$SO$_2$R$^8$;

R$^{3a}$ is selected from halogen, $C_{1-6}$alkyl, and $C_{1-6}$haloalkyl;

each R$^5$ and R$^6$ is independently selected from H, $C_{1-6}$alkyl, and $C_{3-8}$cycloalkyl; or R$^5$ and R$^6$, together with the nitrogen to which they are attached, form a heterocycloalkyl optionally substituted with one or two R$^{10}$;

each R$^7$ is independently selected from H, $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl, wherein heterocycloalkyl, aryl, and heteroaryl are optionally substituted with one or two groups independently selected from halogen, $C_{1-6}$alkyl, and $C_{1-6}$haloalkyl;

each R$^8$ and R$^9$ is independently selected from H, $C_{1-6}$alkyl, $C_{3-8}$cycloalkyl, aryl, and heteroaryl; each R$^{10}$ is independently selected from $C_{1-6}$alkyl, $C_{3-8}$cycloalkyl, $C_{1-6}$haloalkyl, halogen, oxo, —CN, —C(O)OR$^8$, —C(O)R$^8$, —C(O)NR$^8$R$^9$, —SO$_2$R$^8$, —NR$^9$C(O)R$^8$, and —NR$^9$SO$_2$R$^8$;

each R$^{11}$ is independently selected from halogen and $C_{1-6}$alkyl;

each R$^{12}$ is independently selected from $C_{1-6}$alkyl and $C_{3-8}$cycloalkyl;

m is 0, 1, 2, 3, 4, or 5; and q is 0 or 1;

or a pharmaceutically acceptable salt, solvate, or stereoisomer thereof.

In some embodiments is a compound of Formula (IIIb), or a pharmaceutically acceptable salt, solvate, or stereoisomer thereof, wherein R$^3$ is halogen. In some embodiments is a compound of Formula (IIIb), or a pharmaceutically acceptable salt, solvate, or stereoisomer thereof, wherein R$^3$ is —CN. In some embodiments is a compound of Formula (IIIb), or a pharmaceutically acceptable salt, solvate, or stereoisomer thereof, wherein R$^3$ is $C_{1-6}$alkyl. In some embodiments is a compound of Formula (IIIb), or a pharmaceutically acceptable salt, solvate, or stereoisomer thereof, wherein R$^3$ is —CH$_3$. In some embodiments is a compound of Formula (IIIb), or a pharmaceutically acceptable salt, solvate, or stereoisomer thereof, wherein R$^3$ is $C_{1-6}$haloalkyl. In some embodiments is a compound of Formula (IIIb), or a pharmaceutically acceptable salt, solvate, or stereoisomer thereof, wherein R$^3$ is —CF$_3$. In some embodiments is a compound of Formula (IIIb), or a pharmaceutically acceptable salt, solvate, or stereoisomer thereof, wherein R$^3$ is —NR$^8$R$^9$. In some embodiments is a compound of Formula (IIIb), or a pharmaceutically acceptable salt, solvate, or stereoisomer thereof, wherein R$^3$ is —NH$_2$. In some embodiments is a compound of Formula (IIIb), or a pharmaceutically acceptable salt, solvate, or stereoisomer thereof, wherein R$^3$ is —C(O)NR$^8$R$^9$. In some embodiments is a compound of Formula (IIIb), or a pharmaceutically acceptable salt, solvate, or stereoisomer thereof, wherein R$^3$ is —C(O)NH$_2$. In some embodiments is a compound of Formula (IIIb), or a pharmaceutically acceptable salt, solvate, or stereoisomer thereof, wherein R$^3$ is —NR$^8$C(O)R$^9$. In some embodiments is a compound of Formula (IIIb), or a pharmaceutically acceptable salt, solvate, or stereoisomer thereof, wherein R$^3$ is —NHC(O)CH$_3$. In some embodiments is a compound of Formula (IIIb), or a pharmaceutically acceptable salt, solvate, or stereoisomer thereof, wherein q is 0. In some embodiments is a compound of Formula (IIIb), or a pharmaceutically acceptable salt, solvate, or stereoisomer thereof, wherein q is 1. In some embodiments is a compound of Formula (IIIb), or a pharmaceutically acceptable salt, solvate, or stereoisomer thereof, wherein q is 1 and R$^{3a}$ is halogen. In some embodiments is a compound of Formula (IIIb), or a pharmaceutically acceptable salt, solvate, or stereoisomer thereof, wherein q is 1 and R$^{3a}$ is $C_{1-6}$alkyl. In some embodiments is a compound of Formula (IIIb), or a pharmaceutically acceptable salt, solvate, or stereoisomer thereof, wherein q is 1 and R$^{3a}$ is $C_{1-6}$haloalkyl.

In some embodiments is a compound of Formula (IIIb), or a pharmaceutically acceptable salt, solvate, or stereoisomer thereof, wherein m is 0. In some embodiments is a compound of Formula (IIIb), or a pharmaceutically acceptable salt, solvate, or stereoisomer thereof, wherein m is 1. In some embodiments is a compound of Formula (IIIb), or a pharmaceutically acceptable salt, solvate, or stereoisomer thereof, wherein m is 1 and R$^1$ is selected from halogen, —CN, $C_{1-6}$alkyl, $C_{2-6}$alkynyl, $C_{1-6}$alkyl-OR$^7$, $C_{1-6}$haloalkyl, $C_{3-8}$cycloalkyl, —NR$^5$R$^6$, —OR$^7$, —SO$_2$R$^{12}$, —SF$_5$, —SR$^8$, aryl, and heteroaryl. In some embodiments is a compound of Formula (IIIb), or a pharmaceutically acceptable salt, solvate, or stereoisomer thereof, wherein m is 1 and R$^1$ is selected from halogen, $C_{1-6}$alkyl, $C_{1-6}$haloalkyl, $C_{3-8}$cycloalkyl, —NR$^5$R$^6$, and —OR$^7$. In some embodiments is a compound of Formula (IIIb), or a pharmaceutically acceptable salt, solvate, or stereoisomer thereof, wherein m is 1 and R$^1$ is selected from halogen, $C_{1-6}$alkyl, $C_{1-6}$haloalkyl, $C_{3-8}$cycloalkyl, and —OR$^7$. In some embodiments is a compound of Formula (IIIb), or a pharmaceutically acceptable salt, solvate, or stereoisomer thereof, wherein m is 1 and R$^1$ is halogen. In some embodiments is a compound of Formula (IIIb), or a pharmaceutically acceptable salt, solvate, or stereoisomer thereof, wherein m is 1 and R$^1$ is F. In some embodiments is a compound of Formula (IIIb), or a pharmaceutically acceptable salt, solvate, or stereoisomer thereof, wherein m is 1 and R$^1$ is $C_1$. In some embodiments is a compound of Formula (IIIb), or a pharmaceutically acceptable salt, solvate, or stereoisomer thereof, wherein m is 1 and R$^1$ is —CN. In some embodiments is a compound of Formula (IIIb), or a pharmaceutically acceptable salt, solvate, or stereoisomer thereof, wherein m is 1 and R$^1$ is $C_{1-6}$alkyl. In some embodiments is a compound of Formula (IIIb), or a pharmaceutically acceptable salt, solvate, or stereoisomer thereof, wherein m is 1 and R$^1$ is —CH$_3$. In some embodiments is a compound of Formula (IIIb), or a pharmaceutically acceptable salt, solvate, or stereoisomer thereof, wherein m is 1 and R$^1$ is —C≡CH. In some embodiments is a compound of Formula (IIIb), or a pharmaceutically acceptable salt, solvate, or stereoisomer thereof, wherein m is 1 and R$^1$ is $C_{1-6}$alkyl-OR$^7$. In some embodiments is a compound of Formula (IIIb), or a pharmaceutically acceptable salt, solvate, or stereoisomer thereof, wherein m is 1 and R$^1$ is —CH$_2$—O—CH$_3$. In some embodiments is a compound of Formula (IIIb), or a pharmaceutically acceptable salt, solvate, or stereoisomer thereof, wherein m is 1 and R$^1$ is $C_{1-6}$haloalkyl. In some embodiments is a compound of Formula (IIIb), or a pharmaceutically acceptable salt, solvate, or stereoisomer thereof, wherein m is 1 and R$^1$ is —CF$_3$. In some embodiments is a compound of Formula (IIIb), or a pharmaceutically acceptable salt, solvate, or stereoisomer thereof, wherein m is 1 and R$^1$ is $C_{3-8}$cycloalkyl. In some embodiments is a compound of Formula (IIIb), or a pharmaceutically acceptable salt, solvate, or stereoisomer thereof, wherein m is 1 and R$^1$ is —NR$^5$R$^6$. In some embodiments is a compound of Formula (IIIb), or a pharmaceutically acceptable salt, solvate, or stereoisomer thereof, wherein m is 1, $R^1$ is $-NR^5R^6$, and $R^5$ and $R^6$, together with the nitrogen to which they are attached, form a heterocycloalkyl optionally substituted with one or two $R^{10}$. In some embodiments is a compound of Formula (IIIb), or a pharmaceutically acceptable salt, solvate, or stereoisomer thereof, wherein m is 1, $R^1$ is $-NR^5R^6$, and $R^5$ and $R^6$, together with the nitrogen to which they are attached, form an unsubstituted heterocycloalkyl. In some embodiments is a compound of Formula (IIIb), or a pharmaceutically acceptable salt, solvate, or stereoisomer thereof, wherein m is 1, $R^1$ is $-NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, $C_{1-6}$haloalkyl, halogen, oxo, $-C(O)NR^8R^9$, $-SO_2R^8$, $-NR^9C(O)R^8$, and $-NR^9SO_2R^8$. In some embodiments is a compound of Formula (IIIb), or a pharmaceutically acceptable salt, solvate, or stereoisomer thereof, wherein m is 1, $R^1$ is $-NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, and $-C(O)NR^8R^9$. In some embodiments is a compound of Formula (IIIb), or a pharmaceutically acceptable salt, solvate, or stereoisomer thereof, wherein m is 1 and $R^1$ is $-OR^7$. In some embodiments is a compound of Formula (IIIb), or a pharmaceutically acceptable salt, solvate, or stereoisomer thereof, wherein m is 1, $R^1$ is $-OR^7$, and $R^7$ is selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IIIb), or a pharmaceutically acceptable salt, solvate, or stereoisomer thereof, wherein m is 1 and $R^1$ is $-OCH_3$. In some embodiments is a compound of Formula (IIIb), or a pharmaceutically acceptable salt, solvate, or stereoisomer thereof, wherein m is 1 and $R^1$ is $-OCF_3$. In some embodiments is a compound of Formula (IIIb), or a pharmaceutically acceptable salt, solvate, or stereoisomer thereof, wherein m is 1 and $R^1$ is $-SO_2R^{12}$. In some embodiments is a compound of Formula (IIIb), or a pharmaceutically acceptable salt, solvate, or stereoisomer thereof, wherein m is 1 and $R^1$ is $-SF_5$. In some embodiments is a compound of Formula (IIIb), or a pharmaceutically acceptable salt, solvate, or stereoisomer thereof, wherein m is 1 and $R^1$ is $-SR^8$. In some embodiments is a compound of Formula (IIIb), or a pharmaceutically acceptable salt, solvate, or stereoisomer thereof, wherein m is 1 and $R^1$ is aryl optionally substituted with one or two groups independently selected from halogen, $C_{1-6}$alkyl, $C_{1-6}$haloalkyl, and $-C(O)NR^8R^9$. In some embodiments is a compound of Formula (IIIb), or a pharmaceutically acceptable salt, solvate, or stereoisomer thereof, wherein m is 1 and $R^1$ is heteroaryl optionally substituted with one or two groups independently selected from halogen, $C_{1-6}$alkyl, $C_{1-6}$haloalkyl, and $-C(O)NR^8R^9$. In some embodiments is a compound of Formula (IIIb), or a pharmaceutically acceptable salt, solvate, or stereoisomer thereof, wherein m is 1 and $R^1$ is selected from thiazole, pyrazine, pyrimidine, and pyridine, optionally substituted with one or two groups independently selected from halogen, $C_{1-6}$alkyl, $C_{1-6}$haloalkyl, and $-C(O)NR^8R^9$. In some embodiments is a compound of Formula (IIIb), or a pharmaceutically acceptable salt, solvate, or stereoisomer thereof, wherein m is 2. In some embodiments is a compound of Formula (IIIb), or a pharmaceutically acceptable salt, solvate, or stereoisomer thereof, wherein m is 2 and each $R^1$ is independently selected from halogen, $-CN$, $C_{1-6}$alkyl, $C_{2-6}$alkynyl, $C_{1-6}$alkyl-$OR^7$, $C_{1-6}$haloalkyl, $C_{3-8}$cycloalkyl, $-NR^5R^6$, $-OR^7$, $-SO_2R^{12}$, $-SF_5$, $-SR^8$, aryl, and heteroaryl. In some embodiments is a compound of Formula (IIIb), or a pharmaceutically acceptable salt, solvate, or stereoisomer thereof, wherein m is 2 and each $R^1$ is independently selected from halogen, $C_{1-6}$alkyl, $C_{1-6}$haloalkyl, $C_{3-8}$cycloalkyl, $-NR^5R^6$, and $-OR^7$. In some embodiments is a compound of Formula (IIIb), or a pharmaceutically acceptable salt, solvate, or stereoisomer thereof, wherein m is 2 and each $R^1$ is independently selected from halogen, $-CN$, $C_{1-6}$alkyl, $C_{1-6}$haloalkyl, $-NR^5R^6$, $-OR^7$, and heteroaryl. In some embodiments is a compound of Formula (IIIb), or a pharmaceutically acceptable salt, solvate, or stereoisomer thereof, wherein m is 2 and each $R^1$ is independently selected from halogen, $C_{1-6}$haloalkyl, $-NR^5R^6$, $-OR^7$, thiazole, pyrazine, pyrimidine, and pyridine. In some embodiments is a compound of Formula (IIIb), or a pharmaceutically acceptable salt, solvate, or stereoisomer thereof, wherein m is 2 and each $R^1$ is independently selected from halogen, $C_{1-6}$alkyl, $C_{1-6}$haloalkyl, $C_{3-8}$cycloalkyl, and $-OR^7$. In some embodiments is a compound of Formula (IIIb), or a pharmaceutically acceptable salt, solvate, or stereoisomer thereof, wherein m is 2, each $R^1$ is independently selected from halogen, $C_{1-6}$alkyl, $C_{1-6}$haloalkyl, $C_{3-8}$cycloalkyl, and $-OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IIIb), or a pharmaceutically acceptable salt, solvate, or stereoisomer thereof, wherein m is 2, each $R^1$ is independently selected from halogen, $C_{1-6}$alkyl, $C_{1-6}$haloalkyl, $C_{3-8}$cycloalkyl, and $-OR^7$, and each $R^7$ is independently selected from $C_{1-6}$alkyl, $C_{1-6}$haloalkyl, $C_{3-8}$cycloalkyl, and heterocycloalkyl. In some embodiments is a compound of Formula (IIIb), or a pharmaceutically acceptable salt, solvate, or stereoisomer thereof, wherein m is 3. In some embodiments is a compound of Formula (IIIb), or a pharmaceutically acceptable salt, solvate, or stereoisomer thereof, wherein m is 3 and each $R^1$ is independently selected from halogen, $-CN$, $C_{1-6}$alkyl, $C_{2-6}$alkynyl, $C_{1-6}$alkyl-$OR^7$, $C_{1-6}$haloalkyl, $C_{3-8}$cycloalkyl, $-NR^5R^6$, $-OR^7$, $-SO_2R^{12}$, $-SF_5$, $-SR^8$, aryl, and heteroaryl. In some embodiments is a compound of Formula (IIIb), or a pharmaceutically acceptable salt, solvate, or stereoisomer thereof, wherein m is 3 and each $R^1$ is independently selected from halogen, $C_{1-6}$alkyl, $C_{1-6}$haloalkyl, $C_{3-8}$cycloalkyl, $-NR^5R^6$, and $-OR^7$. In some embodiments is a compound of Formula (IIIb), or a pharmaceutically acceptable salt, solvate, or stereoisomer thereof, m is 3 and each $R^1$ is independently selected from halogen, $C_{1-6}$alkyl, $C_{1-6}$haloalkyl, $C_{3-8}$cycloalkyl, and $-OR^7$. In some embodiments is a compound of Formula (IIIb), or a pharmaceutically acceptable salt, solvate, or stereoisomer thereof, wherein m is 3, each $R^1$ is independently selected from halogen, $C_{1-6}$alkyl, $C_{1-6}$haloalkyl, $C_{3-8}$cycloalkyl, and $-OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IIIb), or a pharmaceutically acceptable salt, solvate, or stereoisomer thereof, wherein m is 3, each $R^1$ is independently selected from halogen, $C_{1-6}$alkyl, $C_{1-6}$haloalkyl, $C_{3-8}$cycloalkyl, and $-OR^7$, and each $R^7$ is independently selected from $C_{1-6}$alkyl, $C_{1-6}$haloalkyl, $C_{3-8}$cycloalkyl, and heterocycloalkyl.

In some embodiments is a compound of Formula (IIIb), or a pharmaceutically acceptable salt, solvate, or stereoisomer thereof, wherein n is 0. In some embodiments is a compound of Formula (IIIb), or a pharmaceutically acceptable salt, solvate, or stereoisomer thereof, wherein n is 1. In some embodiments is a compound of Formula (IIIb), or a pharmaceutically acceptable salt, solvate, or stereoisomer thereof, wherein n is 1 and $R^1$ is selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (IIIb), or a pharmaceutically acceptable salt, solvate, or stereoisomer thereof, wherein n is 1 and $R^1$ is selected from halogen, $C_{1-6}$alkyl, $C_{1-6}$haloalkyl, $C_{3-8}$cycloalkyl, —$NR^5R^6$, and —$OR^7$. In some embodiments is a compound of Formula (IIIb), or a pharmaceutically acceptable salt, solvate, or stereoisomer thereof, wherein n is 1 and $R^1$ is selected from halogen, $C_{1-6}$alkyl, $C_{1-6}$haloalkyl, $C_{3-8}$cycloalkyl, and —$OR^7$. In some embodiments is a compound of Formula (IIIb), or a pharmaceutically acceptable salt, solvate, or stereoisomer thereof, wherein n is 1 and $R^1$ is halogen. In some embodiments is a compound of Formula (IIIb), or a pharmaceutically acceptable salt, solvate, or stereoisomer thereof, wherein n is 1 and $R^1$ is F. In some embodiments is a compound of Formula (IIIb), or a pharmaceutically acceptable salt, solvate, or stereoisomer thereof, wherein n is 1 and $R^1$ is Cl. In some embodiments is a compound of Formula (IIIb), or a pharmaceutically acceptable salt, solvate, or stereoisomer thereof, wherein n is 1 and $R^1$ is —CN. In some embodiments is a compound of Formula (IIIb), or a pharmaceutically acceptable salt, solvate, or stereoisomer thereof, wherein n is 1 and $R^1$ is $C_{1-6}$alkyl. In some embodiments is a compound of Formula (IIIb), or a pharmaceutically acceptable salt, solvate, or stereoisomer thereof, wherein n is 1 and $R^1$ is —$CH_3$. In some embodiments is a compound of Formula (IIIb), or a pharmaceutically acceptable salt, solvate, or stereoisomer thereof, wherein n is 1 and $R^1$ is —C≡CH. In some embodiments is a compound of Formula (IIIb), or a pharmaceutically acceptable salt, solvate, or stereoisomer thereof, wherein n is 1 and $R^1$ is $C_{1-6}$alkyl-$OR^7$. In some embodiments is a compound of Formula (IIIb), or a pharmaceutically acceptable salt, solvate, or stereoisomer thereof, wherein n is 1 and $R^1$ is —$CH_2$—O—$CH_3$. In some embodiments is a compound of Formula (IIIb), or a pharmaceutically acceptable salt, solvate, or stereoisomer thereof, wherein n is 1 and $R^1$ is $C_{1-6}$haloalkyl. In some embodiments is a compound of Formula (IIIb), or a pharmaceutically acceptable salt, solvate, or stereoisomer thereof, wherein n is 1 and $R^1$ is —$CF_3$. In some embodiments is a compound of Formula (IIIb), or a pharmaceutically acceptable salt, solvate, or stereoisomer thereof, wherein n is 1 and $R^1$ is $C_{3-8}$cycloalkyl. In some embodiments is a compound of Formula (IIIb), or a pharmaceutically acceptable salt, solvate, or stereoisomer thereof, wherein n is 1 and $R^1$ is —$NR^5R^6$. In some embodiments is a compound of Formula (IIIb), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl optionally substituted with one or two $R^{10}$. In some embodiments is a compound of Formula (IIIb), or a pharmaceutically acceptable salt, solvate, or stereoisomer thereof, wherein n is 1, $R^1$ is —$NR^5R^6$, and $R^5$ and $R^6$, together with the nitrogen to which they are attached, form an unsubstituted heterocycloalkyl. In some embodiments is a compound of Formula (IIIb), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, $C_{1-6}$haloalkyl, halogen, oxo, —C(O)$NR^8R^9$, —$SO_2R^8$, —$NR^9C(O)R^8$, and —$NR^9SO_2R^8$. In some embodiments is a compound of Formula (IIIb), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, and —C(O)$NR^8R^9$. In some embodiments is a compound of Formula (IIIb), or a pharmaceutically acceptable salt, solvate, or stereoisomer thereof, wherein n is 1 and $R^1$ is —$OR^7$. In some embodiments is a compound of Formula (IIIb), or a pharmaceutically acceptable salt, solvate, or stereoisomer thereof, wherein n is 1, $R^1$ is —$OR^7$, and $R^7$ is selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IIIb), or a pharmaceutically acceptable salt, solvate, or stereoisomer thereof, wherein n is 1 and $R^1$ is —$OCH_3$. In some embodiments is a compound of Formula (IIIb), or a pharmaceutically acceptable salt, solvate, or stereoisomer thereof, wherein n is 1 and $R^1$ is —$OCF_3$. In some embodiments is a compound of Formula (IIIb), or a pharmaceutically acceptable salt, solvate, or stereoisomer thereof, wherein n is 1 and $R^1$ is —$SO_2R^{12}$. In some embodiments is a compound of Formula (IIIb), or a pharmaceutically acceptable salt, solvate, or stereoisomer thereof, wherein n is 1 and $R^1$ is —$SF_5$. In some embodiments is a compound of Formula (IIIb), or a pharmaceutically acceptable salt, solvate, or stereoisomer thereof, wherein n is 1 and $R^1$ is —$SR^8$. In some embodiments is a compound of Formula (IIIb), or a pharmaceutically acceptable salt, solvate, or stereoisomer thereof, wherein n is 1 and $R^1$ is aryl optionally substituted with one or two groups independently selected from halogen, $C_{1-6}$alkyl, $C_{1-6}$haloalkyl, and —C(O)$NR^8R^9$. In some embodiments is a compound of Formula (IIIb), or a pharmaceutically acceptable salt, solvate, or stereoisomer thereof, wherein n is 1 and $R^1$ is heteroaryl optionally substituted with one or two groups independently selected from halogen, $C_{1-6}$alkyl, $C_{1-6}$haloalkyl, and —C(O)$NR^8R^9$. In some embodiments is a compound of Formula (IIIb), or a pharmaceutically acceptable salt, solvate, or stereoisomer thereof, wherein n is 1 and $R^1$ is selected from thiazole, pyrazine, pyrimidine, and pyridine, optionally substituted with one or two groups independently selected from halogen, $C_{1-6}$alkyl, $C_{1-6}$haloalkyl, and —C(O)$NR^8R^9$. In some embodiments is a compound of Formula (IIIb), or a pharmaceutically acceptable salt, solvate, or stereoisomer thereof, wherein n is 2. In some embodiments is a compound of Formula (IIIb), or a pharmaceutically acceptable salt, solvate, or stereoisomer thereof, wherein n is 2 and each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (IIIb), or a pharmaceutically acceptable salt, solvate, or stereoisomer thereof, wherein n is 2 and each $R^1$ is independently selected from halogen, $C_{1-6}$alkyl, $C_{1-6}$haloalkyl, $C_{3-8}$cycloalkyl, —$NR^5R^6$, and —$OR^7$. In some embodiments is a compound of Formula (IIIb), or a pharmaceutically acceptable salt, solvate, or stereoisomer thereof, wherein n is 2 and each $R^1$ is independently selected from halogen, —CN, $C_{1-6}$alkyl, $C_{1-6}$haloalkyl, —$NR^5R^6$, —$OR^7$, and heteroaryl. In some embodiments is a compound of Formula (IIIb), or a pharmaceutically acceptable salt, solvate, or stereoisomer thereof, wherein n is 2 and each $R^1$ is independently selected from halogen, $C_{1-6}$haloalkyl, —$NR^5R^6$, —$OR^7$, thiazole, pyrazine, pyrimidine, and pyridine. In some embodiments is a compound of Formula (IIIb), or a pharmaceutically acceptable salt, solvate, or stereoisomer thereof, wherein n is 2 and each $R^1$ is independently selected from halogen, $C_{1-6}$alkyl, $C_{1-6}$haloalkyl, $C_{3-8}$cycloalkyl, and $-OR^7$. In some embodiments is a compound of Formula (IIIb), or a pharmaceutically acceptable salt, solvate, or stereoisomer thereof, wherein n is 2, each $R^1$ is independently selected from halogen, $C_{1-6}$alkyl, $C_{1-6}$haloalkyl, $C_{3-8}$cycloalkyl, and $-OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IIIb), or a pharmaceutically acceptable salt, solvate, or stereoisomer thereof, wherein n is 2, each $R^1$ is independently selected from halogen, $C_{1-6}$alkyl, $C_{1-6}$haloalkyl, $C_{3-8}$cycloalkyl, and $-OR^7$, and each $R^7$ is independently selected from $C_{1-6}$alkyl, $C_{1-6}$haloalkyl, $C_{3-8}$cycloalkyl, and heterocycloalkyl. In some embodiments is a compound of Formula (IIIb), or a pharmaceutically acceptable salt, solvate, or stereoisomer thereof, wherein n is 3.

In some embodiments is a compound of Formula (IV):

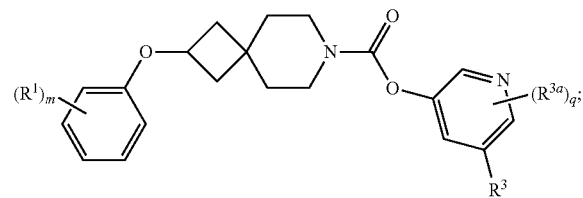

Formula (IV)

wherein:
each $R^1$ is independently selected from halogen, —CN, $C_{1-6}$alkyl, $C_{2-6}$alkynyl, $C_{1-6}$alkyl-OR$^7$, $C_{1-6}$haloalkyl, $C_{3-8}$cycloalkyl, —NR$^5$R$^6$, —C(O)NR$^5$R$^6$, —OR$^7$, —SO$_2$R$^{12}$, —SF$_5$, —SR$^8$, aryl, and heteroaryl, wherein aryl and heteroaryl are optionally substituted with one or two groups independently selected from halogen, $C_{1-6}$alkyl, $C_{1-6}$haloalkyl, and —C(O)NR$^8$R$^9$; or two adjacent $R^1$ form a heterocycloalkyl ring optionally substituted with one or two $R^{11}$;
$R^3$ is selected from halogen, —CN, $C_{1-6}$alkyl, $C_{1-6}$haloalkyl, —NR$^8$R$^9$, —C(O)NR$^8$R$^9$, —NR$^8$C(O)R$^9$, and —NR$^9$SO$_2$R$^8$;
$R^{3a}$ is selected from halogen, $C_{1-6}$alkyl, and $C_{1-6}$haloalkyl;
each $R^5$ and $R^6$ is independently selected from H, $C_{1-6}$alkyl, and $C_{3-8}$cycloalkyl; or $R^5$ and $R^6$, together with the nitrogen to which they are attached, form a heterocycloalkyl optionally substituted with one or two $R^{10}$;
each $R^7$ is independently selected from H, $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl, wherein heterocycloalkyl, aryl, and heteroaryl are optionally substituted with one or two groups independently selected from halogen, $C_{1-6}$alkyl, and $C_{1-6}$haloalkyl;
each $R^8$ and $R^9$ is independently selected from H, $C_{1-6}$alkyl, $C_{3-8}$cycloalkyl, aryl, and heteroaryl;
each $R^{10}$ is independently selected from $C_{1-6}$alkyl, $C_{3-8}$cycloalkyl, $C_{1-6}$haloalkyl, halogen, oxo, —CN, —C(O)OR$^8$, —C(O)R$^8$, —C(O)NR$^8$R$^9$, —SO$_2$R$^8$, —NR$^9$C(O)R$^8$, and —NR$^9$SO$_2$R$^8$;
each $R^{11}$ is independently selected from halogen and $C_{1-6}$alkyl;

each $R^{12}$ is independently selected from $C_{1-6}$alkyl and $C_{3-8}$cycloalkyl;
m is 0, 1, 2, 3, 4, or 5; and
q is 0 or 1;
or a pharmaceutically acceptable salt, solvate, or stereoisomer thereof.

In some embodiments is a compound of Formula (IV), or a pharmaceutically acceptable salt, solvate, or stereoisomer thereof, wherein $R^3$ is halogen. In some embodiments is a compound of Formula (IV), or a pharmaceutically acceptable salt, solvate, or stereoisomer thereof, wherein $R^3$ is —CN. In some embodiments is a compound of Formula (IV), or a pharmaceutically acceptable salt, solvate, or stereoisomer thereof, wherein $R^3$ is $C_{1-6}$alkyl. In some embodiments is a compound of Formula (IV), or a pharmaceutically acceptable salt, solvate, or stereoisomer thereof, wherein $R^3$ is —CH$_3$. In some embodiments is a compound of Formula (IV), or a pharmaceutically acceptable salt, solvate, or stereoisomer thereof, wherein $R^3$ is $C_{1-6}$haloalkyl. In some embodiments is a compound of Formula (IV), or a pharmaceutically acceptable salt, solvate, or stereoisomer thereof, wherein $R^3$ is —CF$_3$. In some embodiments is a compound of Formula (IV), or a pharmaceutically acceptable salt, solvate, or stereoisomer thereof, wherein $R^3$ is —NR$^8$R$^9$. In some embodiments is a compound of Formula (IV), or a pharmaceutically acceptable salt, solvate, or stereoisomer thereof, wherein $R^3$ is —NH$_2$. In some embodiments is a compound of Formula (IV), or a pharmaceutically acceptable salt, solvate, or stereoisomer thereof, wherein $R^3$ is —C(O)NR$^8$R$^9$. In some embodiments is a compound of Formula (IV), or a pharmaceutically acceptable salt, solvate, or stereoisomer thereof, wherein $R^3$ is —C(O)NH$_2$. In some embodiments is a compound of Formula (IV), or a pharmaceutically acceptable salt, solvate, or stereoisomer thereof, wherein $R^3$ is —NR$^8$C(O)R$^9$. In some embodiments is a compound of Formula (IV), or a pharmaceutically acceptable salt, solvate, or stereoisomer thereof, wherein $R^3$ is —NHC(O)CH$_3$. In some embodiments is a compound of Formula (IV), or a pharmaceutically acceptable salt, solvate, or stereoisomer thereof, wherein q is 0. In some embodiments is a compound of Formula (IV), or a pharmaceutically acceptable salt, solvate, or stereoisomer thereof, wherein q is 1. In some embodiments is a compound of Formula (IV), or a pharmaceutically acceptable salt, solvate, or stereoisomer thereof, wherein q is 1 and $R^{3a}$ is halogen. In some embodiments is a compound of Formula (IV), or a pharmaceutically acceptable salt, solvate, or stereoisomer thereof, wherein q is 1 and $R^{3a}$ is $C_{1-6}$alkyl. In some embodiments is a compound of Formula (IV), or a pharmaceutically acceptable salt, solvate, or stereoisomer thereof, wherein q is 1 and $R^{3a}$ is $C_{1-6}$haloalkyl.

In some embodiments is a compound of Formula (IV), or a pharmaceutically acceptable salt, solvate, or stereoisomer thereof, wherein m is 0. In some embodiments is a compound of Formula (IV), or a pharmaceutically acceptable salt, solvate, or stereoisomer thereof, wherein m is 1. In some embodiments is a compound of Formula (IV), or a pharmaceutically acceptable salt, solvate, or stereoisomer thereof, wherein m is 1 and $R^1$ is selected from halogen, —CN, $C_{1-6}$alkyl, $C_{2-6}$alkynyl, $C_{1-6}$alkyl-OR$^7$, $C_{1-6}$haloalkyl, $C_{3-8}$cycloalkyl, —NR$^5$R$^6$, —OR$^7$, —SO$_2$R$^{12}$, —SF$_5$, —SR$^8$, aryl, and heteroaryl. In some embodiments is a compound of Formula (IV), or a pharmaceutically acceptable salt, solvate, or stereoisomer thereof, wherein m is 1 and $R^1$ is selected from halogen, $C_{1-6}$alkyl, $C_{1-6}$haloalkyl, $C_{3-8}$cycloalkyl, —NR$^5$R$^6$, and —OR$^7$. In some embodiments is a pharmaceutically acceptable salt, solvate, or stereoisomer thereof, wherein m is 1 and $R^1$ is selected from halogen, $C_{1-6}$alkyl, $C_{1-6}$haloalkyl, $C_{3-8}$cycloalkyl, and —$OR^7$. In some embodiments is a compound of Formula (IV), or a pharmaceutically acceptable salt, solvate, or stereoisomer thereof, wherein m is 1 and $R^1$ is halogen. In some embodiments is a compound of Formula (IV), or a pharmaceutically acceptable salt, solvate, or stereoisomer thereof, wherein m is 1 and $R^1$ is F. In some embodiments is a compound of Formula (IV), or a pharmaceutically acceptable salt, solvate, or stereoisomer thereof, wherein m is 1 and $R^1$ is Cl. In some embodiments is a compound of Formula (IV), or a pharmaceutically acceptable salt, solvate, or stereoisomer thereof, wherein m is 1 and $R^1$ is —CN. In some embodiments is a compound of Formula (IV), or a pharmaceutically acceptable salt, solvate, or stereoisomer thereof, wherein m is 1 and $R^1$ is $C_{1-6}$alkyl. In some embodiments is a compound of Formula (IV), or a pharmaceutically acceptable salt, solvate, or stereoisomer thereof, wherein m is 1 and $R^1$ is —$CH_3$. In some embodiments is a compound of Formula (IV), or a pharmaceutically acceptable salt, solvate, or stereoisomer thereof, wherein m is 1 and $R^1$ is —C≡CH. In some embodiments is a compound of Formula (IV), or a pharmaceutically acceptable salt, solvate, or stereoisomer thereof, wherein m is 1 and $R^1$ is $C_{1-6}$alkyl-$OR^7$. In some embodiments is a compound of Formula (IV), or a pharmaceutically acceptable salt, solvate, or stereoisomer thereof, wherein m is 1 and $R^1$ is —$CH_2$—O—$CH_3$. In some embodiments is a compound of Formula (IV), or a pharmaceutically acceptable salt, solvate, or stereoisomer thereof, wherein m is 1 and $R^1$ is $C_{1-6}$haloalkyl. In some embodiments is a compound of Formula (IV), or a pharmaceutically acceptable salt, solvate, or stereoisomer thereof, wherein m is 1 and $R^1$ is —$CF_3$. In some embodiments is a compound of Formula (IV), or a pharmaceutically acceptable salt, solvate, or stereoisomer thereof, wherein m is 1 and $R^1$ is $C_{3-8}$cycloalkyl. In some embodiments is a compound of Formula (IV), or a pharmaceutically acceptable salt, solvate, or stereoisomer thereof, wherein m is 1 and $R^1$ is —$NR^5R^6$. In some embodiments is a compound of Formula (IV), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl optionally substituted with one or two $R^{10}$. In some embodiments is a compound of Formula (IV), or a pharmaceutically acceptable salt, solvate, or stereoisomer thereof, wherein m is 1, $R^1$ is —$NR^5R^6$, and $R^5$ and $R^6$, together with the nitrogen to which they are attached, form an unsubstituted heterocycloalkyl. In some embodiments is a compound of Formula (IV), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, $C_{1-6}$haloalkyl, halogen, oxo, —C(O)$NR^8R^9$, —$SO_2R^8$, —$NR^9C(O)R^8$, and —$NR^9SO_2R^8$. In some embodiments is a compound of Formula (IV), or a pharmaceutically acceptable salt, solvate, or stereoisomer thereof, wherein m is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, and —C(O)$NR^8R^9$. In some embodiments is a compound of Formula (IV), or a pharmaceutically acceptable salt, solvate, or stereoisomer thereof, wherein m is 1 and $R^1$ is —$OR^7$. In some embodiments is a compound of Formula (IV), or a pharmaceutically acceptable salt, solvate, or stereoisomer thereof, wherein m is 1, $R^1$ is —$OR^7$, and $R^7$ is selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IV), or a pharmaceutically acceptable salt, solvate, or stereoisomer thereof, wherein m is 1 and $R^1$ is —$OCH_3$. In some embodiments is a compound of Formula (IV), or a pharmaceutically acceptable salt, solvate, or stereoisomer thereof, wherein m is 1 and $R^1$ is —$OCF_3$. In some embodiments is a compound of Formula (IV), or a pharmaceutically acceptable salt, solvate, or stereoisomer thereof, wherein m is 1 and $R^1$ is —$SO_2R^{12}$. In some embodiments is a compound of Formula (IV), or a pharmaceutically acceptable salt, solvate, or stereoisomer thereof, wherein m is 1 and $R^1$ is —$SF_5$. In some embodiments is a compound of Formula (IV), or a pharmaceutically acceptable salt, solvate, or stereoisomer thereof, wherein m is 1 and $R^1$ is —$SR^8$. In some embodiments is a compound of Formula (IV), or a pharmaceutically acceptable salt, solvate, or stereoisomer thereof, wherein m is 1 and $R^1$ is aryl optionally substituted with one or two groups independently selected from halogen, $C_{1-6}$alkyl, $C_{1-6}$haloalkyl, and —C(O)$NR^8R^9$. In some embodiments is a compound of Formula (IV), or a pharmaceutically acceptable salt, solvate, or stereoisomer thereof, wherein m is 1 and $R^1$ is heteroaryl optionally substituted with one or two groups independently selected from halogen, $C_{1-6}$alkyl, $C_{1-6}$haloalkyl, and —C(O)$NR^8R^9$. In some embodiments is a compound of Formula (IV), or a pharmaceutically acceptable salt, solvate, or stereoisomer thereof, wherein m is 1 and $R^1$ is selected from thiazole, pyrazine, pyrimidine, and pyridine, optionally substituted with one or two groups independently selected from halogen, $C_{1-6}$alkyl, $C_{1-6}$haloalkyl, and —C(O)$NR^8R^9$. In some embodiments is a compound of Formula (IV), or a pharmaceutically acceptable salt, solvate, or stereoisomer thereof, wherein m is 2. In some embodiments is a compound of Formula (IV), or a pharmaceutically acceptable salt, solvate, or stereoisomer thereof, wherein m is 2 and each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (IV), or a pharmaceutically acceptable salt, solvate, or stereoisomer thereof, wherein m is 2 and each $R^1$ is independently selected from halogen, $C_{1-6}$alkyl, $C_{1-6}$haloalkyl, $C_{3-8}$cycloalkyl, —$NR^5R^6$, and —$OR^7$. In some embodiments is a compound of Formula (IV), or a pharmaceutically acceptable salt, solvate, or stereoisomer thereof, wherein m is 2 and each $R^1$ is independently selected from halogen, —CN, $C_{1-6}$alkyl, $C_{1-6}$haloalkyl, —$NR^5R^6$, —$OR^7$, and heteroaryl. In some embodiments is a compound of Formula (IV), or a pharmaceutically acceptable salt, solvate, or stereoisomer thereof, wherein m is 2 and each $R^1$ is independently selected from halogen, $C_{1-6}$haloalkyl, —$NR^5R^6$, —$OR^7$, thiazole, pyrazine, pyrimidine, and pyridine. In some embodiments is a compound of Formula (IV), or a pharmaceutically acceptable salt, solvate, or stereoisomer thereof, wherein m is 2 and each $R^1$ is independently selected from halogen, $C_{1-6}$alkyl, $C_{1-6}$haloalkyl, $C_{3-8}$cycloalkyl, and —$OR^7$. In some embodiments is a compound of Formula (IV), or a pharmaceutically acceptable salt, solvate, or stereoisomer thereof, wherein m is 2, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IV), or a pharmaceutically acceptable salt, solvate, or stereoisomer thereof, wherein m is 2, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$haloalkyl, $C_{3-8}$cycloalkyl, and heterocycloalkyl. In some embodiments is a compound of Formula (IV), or a pharmaceutically acceptable salt, solvate, or stereoisomer thereof, wherein m is 3. In some embodiments is a compound of Formula (IV), or a pharmaceutically acceptable salt, solvate, or stereoisomer thereof, wherein m is 3 and each $R^1$ is independently selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (IV), or a pharmaceutically acceptable salt, solvate, or stereoisomer thereof, wherein m is 3 and each $R^1$ is independently selected from halogen, $C_{1-6}$alkyl, $C_{1-6}$haloalkyl, $C_{3-8}$cycloalkyl, —$NR^5R^6$, and —$OR^7$. In some embodiments is a compound of Formula (IV), or a pharmaceutically acceptable salt, solvate, or stereoisomer thereof, m is 3 and each $R^1$ is independently selected from halogen, $C_{1-6}$alkyl, $C_{1-6}$haloalkyl, $C_{3-8}$cycloalkyl, and —$OR^7$. In some embodiments is a compound of Formula (IV), or a pharmaceutically acceptable salt, solvate, or stereoisomer thereof, wherein m is 3, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IV), or a pharmaceutically acceptable salt, solvate, or stereoisomer thereof, wherein m is 3, each $R^1$ is independently selected from halogen, $C_{1-6}$alkyl, $C_{1-6}$haloalkyl, $C_{3-8}$cycloalkyl, and —$OR^7$, and each $R^7$ is independently selected from $C_{1-6}$alkyl, $C_{1-6}$haloalkyl, $C_{3-8}$cycloalkyl, and heterocycloalkyl.

In some embodiments is a compound of Formula (IV), or a pharmaceutically acceptable salt, solvate, or stereoisomer thereof, wherein n is 0. In some embodiments is a compound of Formula (IV), or a pharmaceutically acceptable salt, solvate, or stereoisomer thereof, wherein n is 1. In some embodiments is a compound of Formula (IV), or a pharmaceutically acceptable salt, solvate, or stereoisomer thereof, wherein n is 1 and $R^1$ is selected from halogen, —CN, $C_{1-6}$alkyl, $C_{2-6}$alkynyl, $C_{1-6}$alkyl-$OR^7$, $C_{1-6}$haloalkyl, $C_{3-8}$cycloalkyl, —$NR^5R^6$, —$OR^7$, —$SO_2R^{12}$, —$SF_5$, —$SR^8$, aryl, and heteroaryl. In some embodiments is a compound of Formula (IV), or a pharmaceutically acceptable salt, solvate, or stereoisomer thereof, wherein n is 1 and $R^1$ is selected from halogen, $C_{1-6}$alkyl, $C_{1-6}$haloalkyl, $C_{3-8}$cycloalkyl, —$NR^5R^6$, and —$OR^7$. In some embodiments is a compound of Formula (IV), or a pharmaceutically acceptable salt, solvate, or stereoisomer thereof, wherein n is 1 and $R^1$ is selected from halogen, $C_{1-6}$alkyl, $C_{1-6}$haloalkyl, $C_{3-8}$cycloalkyl, and —$OR^7$. In some embodiments is a compound of Formula (IV), or a pharmaceutically acceptable salt, solvate, or stereoisomer thereof, wherein n is 1 and $R^1$ is halogen. In some embodiments is a compound of Formula (IV), or a pharmaceutically acceptable salt, solvate, or stereoisomer thereof, wherein n is 1 and $R^1$ is F. In some embodiments is a compound of Formula (IV), or a pharmaceutically acceptable salt, solvate, or stereoisomer thereof, wherein n is 1 and $R^1$ is $C_1$. In some embodiments is a compound of Formula (IV), or a pharmaceutically acceptable salt, solvate, or stereoisomer thereof, wherein n is 1 and $R^1$ is —CN. In some embodiments is a compound of Formula (IV), or a pharmaceutically acceptable salt, solvate, or stereoisomer thereof, wherein n is 1 and $R^1$ is $C_{1-6}$alkyl.

In some embodiments is a compound of Formula (IV), or a pharmaceutically acceptable salt, solvate, or stereoisomer thereof, wherein n is 1 and $R^1$ is —$CH_3$. In some embodiments is a compound of Formula (IV), or a pharmaceutically acceptable salt, solvate, or stereoisomer thereof, wherein n is 1 and $R^1$ is —C≡CH. In some embodiments is a compound of Formula (IV), or a pharmaceutically acceptable salt, solvate, or stereoisomer thereof, wherein n is 1 and $R^1$ is $C_{1-6}$alkyl-$OR^7$. In some embodiments is a compound of Formula (IV), or a pharmaceutically acceptable salt, solvate, or stereoisomer thereof, wherein n is 1 and $R^1$ is —$CH_2$—O—$CH_3$. In some embodiments is a compound of Formula (IV), or a pharmaceutically acceptable salt, solvate, or stereoisomer thereof, wherein n is 1 and $R^1$ is $C_{1-6}$haloalkyl. In some embodiments is a compound of Formula (IV), or a pharmaceutically acceptable salt, solvate, or stereoisomer thereof, wherein n is 1 and $R^1$ is —$CF_3$. In some embodiments is a compound of Formula (IV), or a pharmaceutically acceptable salt, solvate, or stereoisomer thereof, wherein n is 1 and $R^1$ is $C_{3-8}$cycloalkyl. In some embodiments is a compound of Formula (IV), or a pharmaceutically acceptable salt, solvate, or stereoisomer thereof, wherein n is 1 and $R^1$ is —$NR^5R^6$. In some embodiments is a compound of Formula (IV), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl optionally substituted with one or two $R^{10}$. In some embodiments is a compound of Formula (IV), or a pharmaceutically acceptable salt, solvate, or stereoisomer thereof, wherein n is 1, $R^1$ is —$NR^5R^6$, and $R^5$ and $R^6$, together with the nitrogen to which they are attached, form an unsubstituted heterocycloalkyl. In some embodiments is a compound of Formula (IV), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, $C_{1-6}$haloalkyl, halogen, oxo, —$C(O)NR^8R^9$, —$SO_2R^8$, —$NR^9C(O)R^8$, and —$NR^9SO_2R^8$. In some embodiments is a compound of Formula (IV), or a pharmaceutically acceptable salt, solvate, or stereoisomer thereof, wherein n is 1, $R^1$ is —$NR^5R^6$, and $R^5$ and $R^6$, together with the nitrogen to which they are attached, form a heterocycloalkyl substituted with one or two $R^{10}$ independently selected from $C_{1-6}$alkyl, $C_{3-8}$cycloalkyl, and —$C(O)NR^8R^9$. In some embodiments is a compound of Formula (IV), or a pharmaceutically acceptable salt, solvate, or stereoisomer thereof, wherein n is 1 and $R^1$ is —$OR^7$. In some embodiments is a compound of Formula (IV), or a pharmaceutically acceptable salt, solvate, or stereoisomer thereof, wherein n is 1, $R^1$ is —$OR^7$, and $R^7$ is selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IV), or a pharmaceutically acceptable salt, solvate, or stereoisomer thereof, wherein n is 1 and $R^1$ is —$OCH_3$. In some embodiments is a compound of Formula (IV), or a pharmaceutically acceptable salt, solvate, or stereoisomer thereof, wherein n is 1 and $R^1$ is —$OCF_3$. In some embodiments is a compound of Formula (IV), or a pharmaceutically acceptable salt, solvate, or stereoisomer thereof, wherein n is 1 and $R^1$ is —$SO_2R^{12}$. In some embodiments is a compound of Formula (IV), or a pharmaceutically acceptable salt, solvate, or stereoisomer thereof, wherein n is 1 and $R^1$ is —$SF_5$. In some embodiments is a compound of Formula (IV), or a pharmaceutically acceptable salt, solvate, or stereoisomer thereof, wherein n is 1 and $R^1$ is —$SR^8$. In some embodiments is a compound of Formula (IV), or a pharmaceutically acceptable salt, solvate, or stereoisomer thereof, wherein n is 1 and $R^1$ is aryl optionally substituted with one or two groups independently selected from halogen, $C_{1-6}$alkyl, $C_{1-6}$haloalkyl, and —C(O)NR$^8$R$^9$. In some embodiments is a compound of Formula (IV), or a pharmaceutically acceptable salt, solvate, or stereoisomer thereof, wherein n is 1 and $R^1$ is heteroaryl optionally substituted with one or two groups independently selected from halogen, $C_{1-6}$alkyl, $C_{1-6}$haloalkyl, and —C(O)NR$^8$R$^9$. In some embodiments is a compound of Formula (IV), or a pharmaceutically acceptable salt, solvate, or stereoisomer thereof, wherein n is 1 and $R^1$ is selected from thiazole, pyrazine, pyrimidine, and pyridine, optionally substituted with one or two groups independently selected from halogen, $C_{1-6}$alkyl, $C_{1-6}$haloalkyl, and —C(O)NR$^8$R$^9$. In some embodiments is a compound of Formula (IV), or a pharmaceutically acceptable salt, solvate, or stereoisomer thereof, wherein n is 2. In some embodiments is a compound of Formula (IV), or a pharmaceutically acceptable salt, solvate, or stereoisomer thereof, wherein n is 2 and each $R^1$ is independently selected from halogen, —CN, $C_{1-6}$alkyl, $C_{2-6}$alkynyl, $C_{1-6}$alkyl-OR$^7$, $C_{1-6}$haloalkyl, $C_{3-8}$cycloalkyl, —NR$^5$R$^6$, —OR$^7$, —SO$_2$R$^{12}$, —SF$_5$, —SR$^8$, aryl, and heteroaryl. In some embodiments is a compound of Formula (IV), or a pharmaceutically acceptable salt, solvate, or stereoisomer thereof, wherein n is 2 and each $R^1$ is independently selected from halogen, $C_{1-6}$alkyl, $C_{1-6}$haloalkyl, $C_{3-8}$cycloalkyl, —NR$^5$R$^6$, and —OR$^7$. In some embodiments is a compound of Formula (IV), or a pharmaceutically acceptable salt, solvate, or stereoisomer thereof, wherein n is 2 and each $R^1$ is independently selected from halogen, —CN, $C_{1-6}$alkyl, $C_{1-6}$haloalkyl, —NR$^5$R$^6$, —OR$^7$, and heteroaryl. In some embodiments is a compound of Formula (IV), or a pharmaceutically acceptable salt, solvate, or stereoisomer thereof, wherein n is 2 and each $R^1$ is independently selected from halogen, $C_{1-6}$haloalkyl, —NR$^5$R$^6$, —OR$^7$, thiazole, pyrazine, pyrimidine, and pyridine. In some embodiments is a compound of Formula (IV), or a pharmaceutically acceptable salt, solvate, or stereoisomer thereof, wherein n is 2 and each $R^1$ is independently selected from halogen, $C_{1-6}$alkyl, $C_{1-6}$haloalkyl, $C_{3-8}$cycloalkyl, and —OR$^7$. In some embodiments is a compound of Formula (IV), or a pharmaceutically acceptable salt, solvate, or stereoisomer thereof, wherein n is 2, each $R^1$ is independently selected from halogen, $C_{1-6}$alkyl, $C_{1-6}$haloalkyl, $C_{3-8}$cycloalkyl, and —OR$^7$, and each $R^7$ is independently selected from $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl. In some embodiments is a compound of Formula (IV), or a pharmaceutically acceptable salt, solvate, or stereoisomer thereof, wherein n is 2, each $R^1$ is independently selected from halogen, $C_{1-6}$alkyl, $C_{1-6}$haloalkyl, $C_{3-8}$cycloalkyl, and —OR$^7$, and each $R^7$ is independently selected from $C_{1-6}$alkyl, $C_{1-6}$haloalkyl, $C_{3-8}$cycloalkyl, and heterocycloalkyl. In some embodiments is a compound of Formula (IV), or a pharmaceutically acceptable salt, solvate, or stereoisomer thereof, wherein n is 3.

Further embodiments provided herein include combinations of one or more of the particular embodiments set forth above.

In some embodiments, the compound disclosed herein is a compound of any one of Examples 1-86, or a pharmaceutically acceptable salt, solvate, or stereoisomer thereof.

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds described herein include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, esters, solvate, hydrates, or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i. e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Solvates

In some embodiments, the compounds described herein exist as solvates. In some embodiments, are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or methanol. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. Further described herein are methods of treating diseases by administering such prodrugs. Also described herein are methods of treating diseases by administering such prodrugs as pharmaceutical compositions.

In some embodiments, prodrugs include compounds wherein an amino acid residue, or a polypeptide chain of two or more (e.g., two, three, or four) amino acid residues is covalently joined through an amide or ester bond to a free amino, hydroxy or carboxylic acid group of compounds described herein. The amino acid residues include, but are not limited to, the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound described herein.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts, and sulfonate esters. In some embodiments, compounds having free amino, amido, hydroxy, or carboxylic groups are converted into prodrugs. For instance, free carboxyl groups are derivatized as amides or alkyl esters. In certain instances, all of these prodrug moieties incorporate groups including, but not limited to, ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters, and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to, the following groups and combinations of groups:

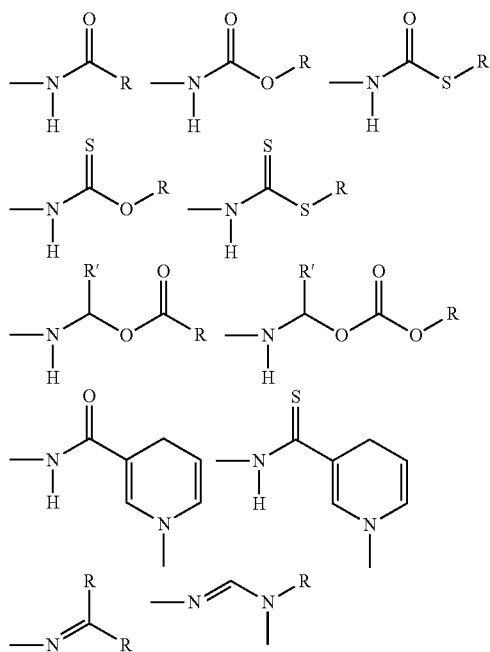

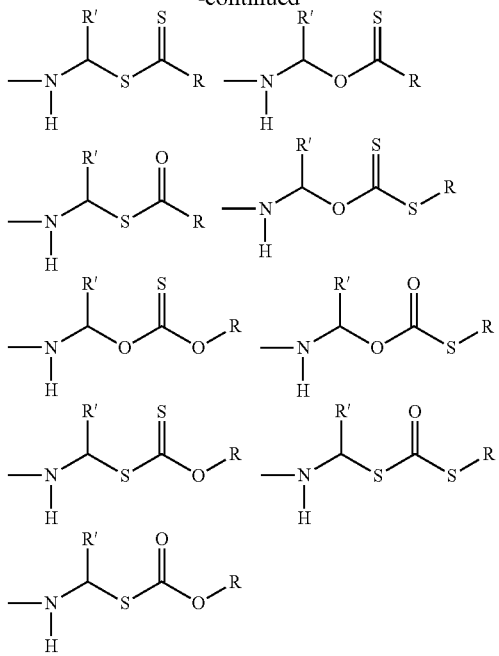

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Pharmaceutical Compositions

In certain embodiments, the compound of Formula (I), (II), (III), (IIIa), (IIIb), or (IV) as described herein is administered as a pure chemical. In some embodiments, the compound of Formula (I), (II), (III), (IIIa), (IIIb), or (IV) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one compound of Formula (I), (II), (III), (IIIa), (IIIb), or (IV) described herein, or a pharmaceutically acceptable salt, solvate, or stereoisomer thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof.

One embodiment provides a pharmaceutical composition comprising a pharmaceutically acceptable excipient and a compound of Formula (II), or a pharmaceutically acceptable salt thereof.

One embodiment provides a pharmaceutical composition comprising a pharmaceutically acceptable excipient and a compound of Formula (III), or a pharmaceutically acceptable salt thereof.

One embodiment provides a pharmaceutical composition comprising a pharmaceutically acceptable excipient and a compound of Formula (IIIa), or a pharmaceutically acceptable salt thereof.

One embodiment provides a pharmaceutical composition comprising a pharmaceutically acceptable excipient and a compound of Formula (IIIb), or a pharmaceutically acceptable salt thereof.

One embodiment provides a pharmaceutical composition comprising a pharmaceutically acceptable excipient and a compound of Formula (IV), or a pharmaceutically acceptable salt thereof.

Another embodiment provides a pharmaceutical composition consisting essentially of a pharmaceutically acceptable excipient and a compound of Formula (I), or a pharmaceutically acceptable salt thereof. Another embodiment provides a pharmaceutical composition consisting essentially of a pharmaceutically acceptable excipient and a compound of Formula (II), or a pharmaceutically acceptable salt thereof. Another embodiment provides a pharmaceutical composition consisting essentially of a pharmaceutically acceptable excipient and a compound of Formula (III), or a pharmaceutically acceptable salt thereof. Another embodiment provides a pharmaceutical composition consisting essentially of a pharmaceutically acceptable excipient and a compound of Formula (IIIa), or a pharmaceutically acceptable salt thereof. Another embodiment provides a pharmaceutical composition consisting essentially of a pharmaceutically acceptable excipient and a compound of Formula (IIIb), or a pharmaceutically acceptable salt thereof. Another embodiment provides a pharmaceutical composition consisting essentially of a pharmaceutically acceptable excipient and a compound of Formula (IV), or a pharmaceutically acceptable salt thereof.

In certain embodiments, the compound of Formula (I), (II), (III), (IIIa), (IIIb), or (IV) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These pharmaceutical compositions include those suitable for oral, rectal, topical, buccal, parenteral (e.g., subcutaneous, intramuscular, intradermal, or intravenous), vaginal, ophthalmic, or aerosol administration.

Exemplary pharmaceutical compositions are used in the form of a pharmaceutical preparation, for example, in solid, semisolid, or liquid form, which includes one or more of a disclosed compound, as an active ingredient, in a mixture with an organic or inorganic carrier or excipient suitable for external, enteral, or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills, and capsules.

In solid dosage forms for oral administration (capsules, tablets, pills, dragees, powders, granules, and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose, and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol, and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets, and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills, and granules, are scored or prepared with coatings and shells, such as enteric coatings and other coatings.

Compositions for inhalation or insufflation include solutions and suspensions in pharmaceutically acceptable aqueous or organic solvents, or mixtures thereof, and powders. Liquid dosage forms for oral administration include pharmaceutically acceptable emulsions, microemulsions, solutions, suspensions, syrups, and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins, and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils such as olive oil, and injectable organic esters such as ethyl oleate, and cyclodextrins. Proper fluidity is maintained, for example, by the use of coating materials, such as lecithin, by the maintenance of the required particle size in the case of dispersions, and by the use of surfactants.

Also contemplated are enteral pharmaceutical formulations including a disclosed compound, an enteric material, and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I), (II), (III), (IIIa), (IIIb), or (IV) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods and Uses

Disclosed herein are in vitro (ex vivo) and in vivo methods of modulating the activity of MAGL and/or FAAH. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (II), (III), (IIIa), (IIIb), or (IV), or a pharmaceutically acceptable salt, solvate, or stereoisomer thereof. The ability of compounds described herein to modulate or inhibit MAGL and FAAH is evaluated by procedures known in the art and/or described herein. Embodiments of the invention also relate to a compound of Formula (I), (II), (III), (IIIa), (IIIb), or (IV) described herein and any subgroup thereof, or a pharmaceutically acceptable salt, solvate, or stereoisomer thereof, for use in a method of treating conditions which are characterized by unhealthy or abnormal levels of MAGL and/or FAAH. Conditions "characterized by unhealthy or abnormal levels of MAGL and FAAH" include those like neuropathic pain, anxiety and inflammatory bowel diseases, as well as the proliferation and migration of cancer cells.

In some embodiments is a method of treating pain in a patient in need thereof, comprising administering to the patient a therapeutically effective amount of a compound of Formula (I), (II), (III), (IIIa), (IIIb), or (IV) described herein, or a pharmaceutically acceptable salt, solvate, or stereoisomer thereof. Embodiments of the invention also relate to a compound of Formula (I), (II), (III), (IIIa), (IIIb), or (IV) described herein and any subgroup thereof, or a pharmaceutically acceptable salt, solvate, or stereoisomer thereof, for use in a method of treating pain in a patient. In some embodiments is a method of treating pain in a patient in need thereof, comprising administering to the patient a therapeutically effective amount of a compound of Formula (I) described herein, or a pharmaceutically acceptable salt, solvate, or stereoisomer thereof. In some embodiments is a method of treating pain in a patient in need thereof, comprising administering to the patient a therapeutically effective amount of a compound of Formula (II) described herein, or a pharmaceutically acceptable salt, solvate, or stereoisomer thereof. In some embodiments is a method of treating pain in a patient in need thereof, comprising administering to the patient a therapeutically effective amount of a compound of Formula (III) described herein, or a pharmaceutically acceptable salt, solvate, or stereoisomer thereof. In some embodiments is a method of treating pain in a patient in need thereof, comprising administering to the patient a therapeutically effective amount of a compound of Formula (IIIa) described herein, or a pharmaceutically acceptable salt, solvate, or stereoisomer thereof. In some embodiments is a method of treating pain in a patient in need thereof, comprising administering to the patient a therapeutically effective amount of a compound of Formula (IIIb) described herein, or a pharmaceutically acceptable salt, solvate, or stereoisomer thereof. In some embodiments is a method of treating pain in a patient in need thereof, comprising administering to the patient a therapeutically effective amount of a compound of Formula (IV) described herein, or a pharmaceutically acceptable salt, solvate, or stereoisomer thereof.

In some embodiments is a method of treating a neurological disorder in a patient in need thereof, comprising administering to the patient a therapeutically effective amount of a compound of Formula (I), (II), (III), (IIIa), (IIIb), or (IV) described herein, or a pharmaceutically acceptable salt, solvate, or stereoisomer thereof. Embodiments of the invention also relate to a compound of Formula (I), (II), (III), (IIIa), (IIIb), or (IV) described herein and any subgroup thereof, or a pharmaceutically acceptable salt, solvate, or stereoisomer thereof, for use in a method of treating a neurological disorder in a patient. In some embodiments is a method of treating a neurological disorder in a patient in need thereof, comprising administering to the patient a therapeutically effective amount of a compound of Formula (I) described herein, or a pharmaceutically acceptable salt, solvate, or stereoisomer thereof. In some embodiments is a method of treating a neurological disorder in a patient in need thereof, comprising administering to the patient a therapeutically effective amount of a compound of Formula (II) described herein, or a pharmaceutically acceptable salt, solvate, or stereoisomer thereof. In some embodiments is a method of treating a neurological disorder in a patient in need thereof, comprising administering to the patient a therapeutically effective amount of a compound of Formula (III) described herein, or a pharmaceutically acceptable salt, solvate, or stereoisomer thereof. In some embodiments is a method of treating a neurological disorder in a patient in need thereof, comprising administering to the patient a therapeutically effective amount of a compound of Formula (IIIa) described herein, or a pharmaceutically acceptable salt, solvate, or stereoisomer thereof. In some embodiments is a method of treating a neurological disorder in a patient in need thereof, comprising administering to the patient a therapeutically effective amount of a compound of Formula (IIIb) described herein, or a pharmaceutically acceptable salt, solvate, or stereoisomer thereof. In some embodiments is a method of treating a neurological disorder in a patient in need thereof, comprising administering to the patient a therapeutically effective amount of a compound of Formula (IV) described herein, or a pharmaceutically acceptable salt, solvate, or stereoisomer thereof.

In certain embodiments, a disclosed compound utilized by one or more of the foregoing methods is one of the generic, subgeneric, or specific compounds described herein, such as a compound of Formula (I), (II), (III), (IIIa), (IIIb), or (IV). Embodiments of the invention also relate to a compound of Formula (I), (II), (III), (IIIa), (IIIb), or (IV) described herein and any subgroup thereof, or a pharmaceutically acceptable salt, solvate, or stereoisomer thereof, for use in one or more of the foregoing methods of treatment. Embodiments of the invention also relate to a compound of Formula (I), (II), (III), (IIIa), (IIIb), or (IV) described herein and any subgroup thereof, or a pharmaceutically acceptable salt, solvate, or stereoisomer thereof, for use in a method of treatment by therapy.

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray, or rectally in dosage unit formulations containing conventional non-toxic pharmaceutically acceptable carriers, adjuvants, and vehicles. Parenteral administration include subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months, or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

For example, e.g., for contemplated treatment of pain, a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered, include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN or MeCN acetonitrile
Bn benzyl
BOC or Boc tert-butyl carbamate
CDI 1,1'-carbonyldiimidazole
Cy cyclohexyl
DCE dichloroethane ($ClCH_2CH_2Cl$)
DCM dichloromethane ($CH_2Cl_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
EtOH ethanol
EtOAc ethyl acetate
HATU 1-[bis(dimethylamino)methylene]-1H-1,2,3-triazolo[4,5-b]pyridinium 3-oxid hexafluorophosphate
HPLC high performance liquid chromatography
LAH lithium aluminum hydride
Me methyl
MeOH methanol
MS mass spectroscopy
NMM N-methylmorpholine
NMR nuclear magnetic resonance
PMB para-methoxybenzyl
TEA triethylamine
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For proton spectra the solvent peak was used as the reference peak.

Example 1: 5-(Trifluoromethyl)pyridin-3-yl 2-(3-(trifluoromethyl)phenoxy)-7-azaspiro[3.5]nonane-7-carboxylate

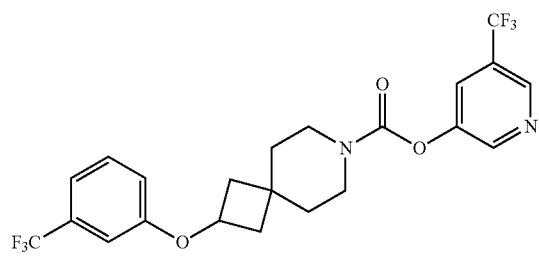 [SMILES: O=C(Oc1cncc(C(F)(F)F)c1)N1CCC2(CC1)CC(Oc1cccc(C(F)(F)F)c1)C2]

Step 1: Preparation of tert-butyl 2-((methylsulfonyl)oxy)-7-azaspiro[3.5]nonane-7-carboxylate

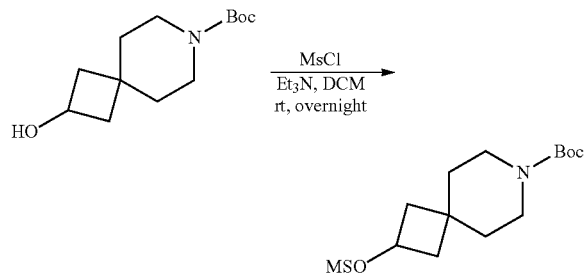

A 250-mL round-bottom flask was charged with tert-butyl 2-hydroxy-7-azaspiro[3.5]nonane-7-carboxylate (3.00 g, 12.4 mmol, 1.00 equiv), triethylamine (3.77 g, 37.3 mmol, 3.00 equiv), and dichloromethane (50 mL). Methanesulfonyl chloride (2.13 g, 18.7 mmol, 1.50 equiv) was added at 0° C. The reaction was stirred overnight at room temperature and quenched with water (100 mL). The resulting solution was extracted with dichloromethane (3×100 mL) and the organic layers were combined, washed with brine (3×100 mL), dried over anhydrous sodium sulfate, filtered, and concentrated under reduced pressure to provide 4.55 g of tert-butyl 2-((methylsulfonyl)oxy)-7-azaspiro[3.5]nonane-7-carboxylate as a brown oil. LCMS (ESI, m/z): 320 [M+H]$^+$.

Step 2: Preparation of tert-butyl 2-(3-(trifluoromethyl)phenoxy)-7-azaspiro[3.5]nonane-7-carboxylate

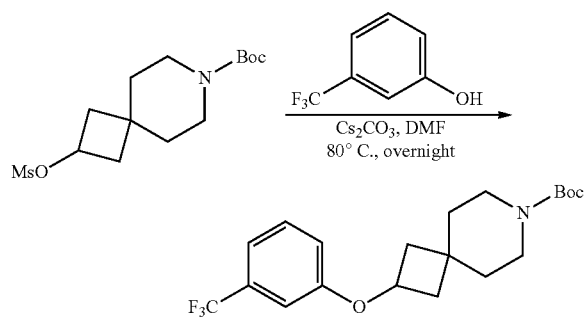

A 50-mL round-bottom flask was charged with tert-butyl 2-((methylsulfonyl)oxy)-7-azaspiro[3.5]nonane-7-carboxylate (0.909 g, 2.85 mmol, 1.00 equiv), 3-(trifluoromethyl)phenol (0.554 g, 3.42 mmol, 1.20 equiv), cesium carbonate (2.79 g, 8.55 mmol, 3.00 equiv), and DMF (20 mL). The reaction was stirred overnight at 80° C. and quenched with water (20 mL). The resulting solution was extracted with ethyl acetate (3×20 mL) and the organic layers were combined, washed with brine (1×100 mL), dried over anhydrous sodium sulfate, filtered, and concentrated under reduced pressure. The residue was chromatographed on a silica gel column to provide 0.880 g (80% yield) of tert-butyl 2-(3-(trifluoromethyl)phenoxy)-7-azaspiro[3.5]nonane-7-carboxylate as a light yellow oil. LCMS (ESI, m/z): 386 [M+H]$^+$.

Step 3: Preparation of 2-(3-(trifluoromethyl)phenoxy)-7-azaspiro[3.5]nonane

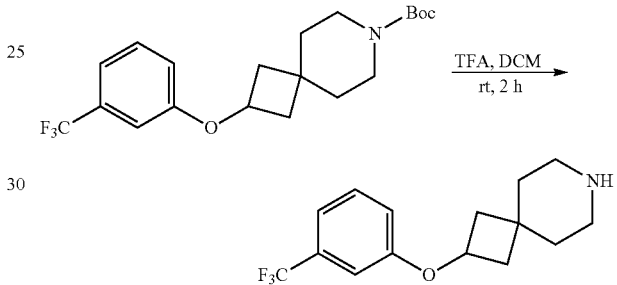

A 50-mL round-bottom flask was charged with tert-butyl 2-(3-(trifluoromethyl)phenoxy)-7-azaspiro[3.5]nonane-7-carboxylate (880 mg, 2.28 mmol, 1.00 equiv), dichloromethane (20 mL), and trifluoroacetic acid (12 mL). The resulting solution was stirred for 2 hours at room temperature and concentrated under reduced pressure. The crude product was dissolved in 1M sodium hydroxide solution (10 mL) and extracted with dichloromethane (3×20 mL). The organic layers were combined, washed with brine (10 mL), dried over anhydrous sodium sulfate, filtered, and concentrated under reduced pressure to provide 638 mg (98% yield) of 2-(3-(trifluoromethyl)phenoxy)-7-azaspiro[3.5]nonane as a yellow oil. LCMS (ESI, m/z): 286 [M+H]$^+$.

Step 4: Preparation of 5-(trifluoromethyl)pyridin-3-yl 2-(3-(trifluoromethyl)phenoxy)-7-azaspiro[3.5]nonane-7-carboxylate

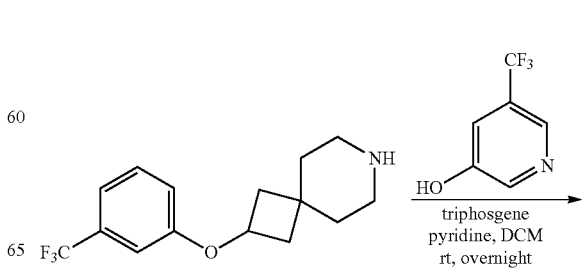

-continued

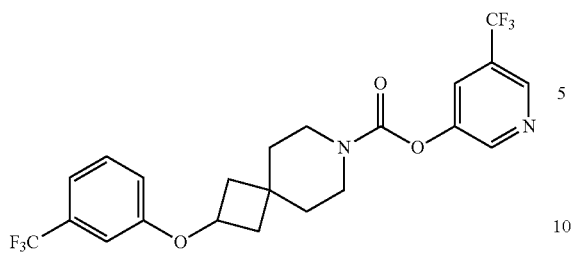

A 50-mL round-bottom flask was charged with triphosgene (158 mg, 0.530 mmol, 0.70 equiv) and dichloromethane (20 mL). 5-(Trifluoromethyl)pyridin-3-ol (248 mg, 1.52 mmol, 2.00 equiv) and pyridine were added in sequence at 0° C., and the mixture continued to stir for 2 hours at 0° C. before the addition of 2-(3-(trifluoromethyl)phenoxy)-7-azaspiro[3.5]nonane (217 mg, 0.760 mmol, 1.00 equiv). The resulting solution was stirred overnight at room temperature and quenched with water (20 mL). The mixture was extracted with dichloromethane (3×20 mL) and the organic layers were combined, washed with brine (1×100 mL), dried over anhydrous sodium sulfate, filtered, and concentrated under reduced pressure. The crude product (900 mg) was purified by preparative HPLC to afford 206.5 mg (57% yield) of 5-(trifluoromethyl)pyridin-3-yl 2-(3-(trifluoromethyl)phenoxy)-7-azaspiro[3.5]nonane-7-carboxylate as a brown oil. ¹H NMR (300 MHz, Chloroform-d) δ 8.75 (s, 1H), 8.66 (s, 1H), 7.81 (s, 1H), 7.38-7.43 (m, 1H), 7.22-7.25 (m, 1H), 6.99-7.04 (m, 2H), 4.74-4.82 (m, 1H), 3.51-3.68 (m, 4H), 2.49-2.56 (m, 2H), 2.03-2.10 (m, 2H), 1.78 (s, 4H). LCMS (ESI, m/z): 516 [M+H+MeCN]⁺.

Example 2: 5-(Trifluoromethyl)pyridin-3-yl 2-(4-(3-chlorophenoxy)benzyl)-2,7-diazaspiro[3.5]nonane-7-carboxylate

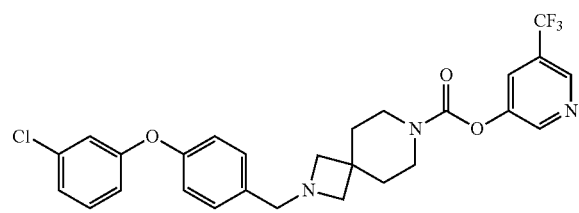 [SMILES: O=C(Oc1cncc(C(F)(F)F)c1)N1CCC2(CC1)CN(Cc1ccc(Oc3cccc(Cl)c3)cc1)C2]

Step 1: Preparation of 3-(benzyloxy)-5-(trifluoromethyl)pyridine

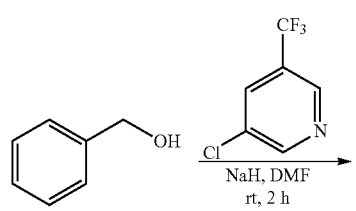

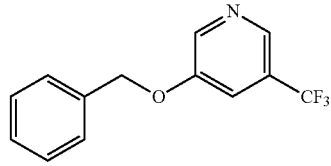

A 250-mL 3-necked round-bottom flask was charged with 3-chloro-5-(trifluoromethyl)pyridine (5.04 g, 27.5 mmol, 1.00 equiv), phenylmethanol (2.98 g, 27.6 mmol, 1.00 equiv), and DMF (30 mL) under nitrogen. Sodium hydride (60% dispersion in mineral oil, 2.32 g, 55.8 mmol, 2.00 equiv) was added portion-wise at 0° C. The resulting solution was stirred for 2 hours at 40° C. and quenched with water (20 mL). The mixture was extracted with dichloromethane (3×30 mL) and the organic layers were combined, washed with water (3×30 mL), dried over anhydrous sodium sulfate, filtered, and concentrated under reduced pressure to provide 3.00 g (43% yield) of 3-(benzyloxy)-5-(trifluoromethyl)pyridine as a yellow oil. LCMS (ESI, m/z): 254 [M+H]⁺.

Step 2: Preparation of 5-(trifluoromethyl)pyridin-3-ol

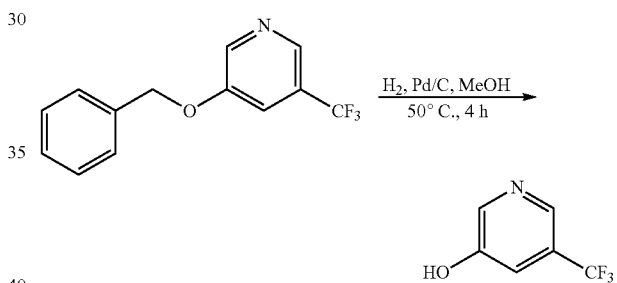

A 250-mL 3-necked round-bottom flask was charged with 3-(benzyloxy)-5-(trifluoromethyl)pyridine (3.00 g, 11.9 mmol, 1.00 equiv), methanol (30 mL) and 10% palladium carbon (150 mg). The resulting solution was stirred for 4 hours at 50° C. under hydrogen. Solids were filtered and washed with methanol (3×30 mL). The filtrate was concentrated under reduced pressure to provide 1.60 g (83% yield) of 5-(trifluoromethyl)pyridin-3-ol as a white solid. LCMS (ESI, m/z): 164 [M+H]⁺.

Step 3: Preparation of 2-(tert-butyl) 7-(5-(trifluoromethyl)pyridin-3-yl) 2,7-diazaspiro[3.5]nonane-2,7-dicarboxylate

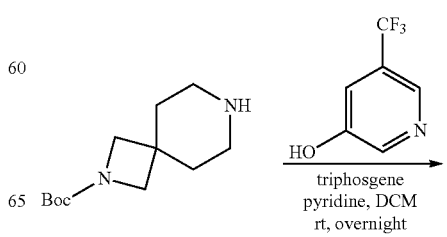

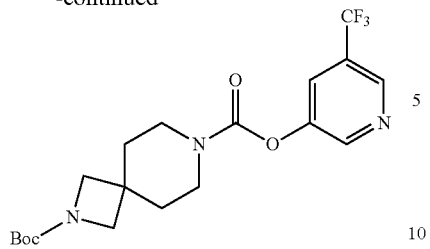

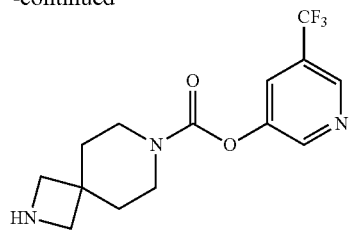

A 100-mL round-bottom flask was charged with triphosgene (0.971 mg, 3.27 mmol, 0.37 equiv), 5-(trifluoromethyl)pyridin-3-yl chloroformate (2.08 g, 8.87 mmol, 1.10 equiv) and dichloromethane (30 mL). Pyridine (1.94 g, 24.5 mmol, 3.00 equiv) was added dropwise at 0° C. The resulting solution was stirred for 2 hours at 0° C. prior to addition of tert-butyl 2,7-diazaspiro[3.5]nonane-2-carboxylate (1.85 g, 8.17 mmol, 1.00 equiv). The reaction was stirred overnight at room temperature and quenched with water (10 mL). The mixture was extracted with dichloromethane (3×20 mL) and the organic layers were combined, washed with water (3×20 mL), dried over anhydrous sodium sulfate, filtered, and concentrated under reduced pressure. The residue was chromatographed on a silica gel column to provide 1.40 g (41% yield) of 2-(tert-butyl) 7-(5-(trifluoromethyl)pyridin-3-yl) 2,7-diazaspiro[3.5]nonane-2,7-dicarboxylate as a yellow oil. LCMS (ESI, m/z): 416 [M+H]+.

Step 4: Preparation of 5-(trifluoromethyl)pyridin-3-yl 2,7-diazaspiro[3.5]nonane-7-carboxylate

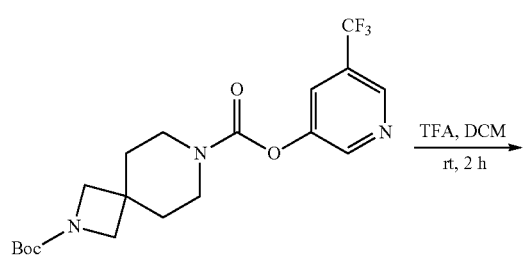

A 100-mL round-bottom flask was charged with 2-(tert-butyl) 7-(5-(trifluoromethyl)pyridin-3-yl) 2,7-diazaspiro[3.5]nonane-2,7-dicarboxylate (1.40 g, 3.37 mmol, 1.00 equiv), dichloromethane (20 mL) and trifluoroacetic acid (10 mL). The resulting solution was stirred for 2 hours at room temperature and concentrated under reduced pressure to provide 1.02 g of 5-(trifluoromethyl)pyridin-3-yl 2,7-diazaspiro[3.5]nonane-7-carboxylate as a yellow oil. LCMS (ESI, m/z): 316 [M+H]+.

Step 5: Preparation of 5-(trifluoromethyl)pyridin-3-yl 2-(4-(3-chlorophenoxy)benzyl)-2,7-diazaspiro[3.5]nonane-7-carboxylate

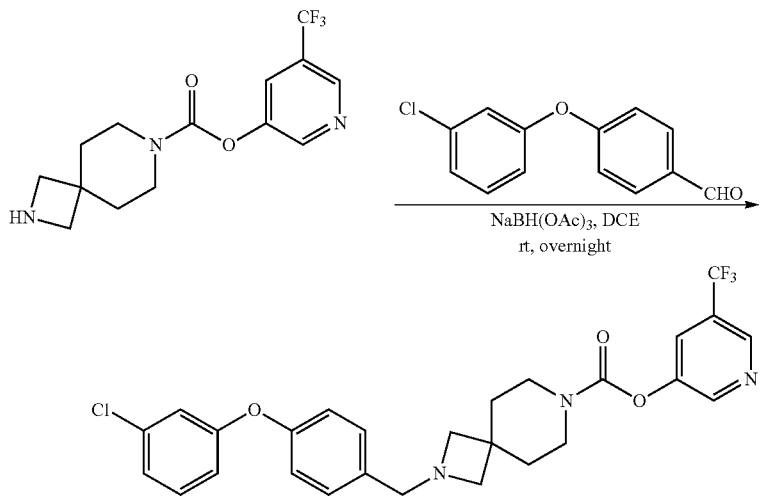

A 40-mL round-bottom flask was charged with 4-(3-chlorophenoxy)benzaldehyde (100 mg, 0.431 mmol, 1.00 equiv), 5-(trifluoromethyl)pyridin-3-yl 2,7-diazaspiro[3.5]nonane-7-carboxylate (164 mg, 0.522 mmol, 1.20 equiv), triethylamine (130 mg, 1.28 mmol, 3.0 equiv), and 1,2-dichloroethane (10 mL). The resulting solution was stirred for 2 hours at room temperature prior to addition of sodium triacetoxyborohydride (228 mg, 1.08 mmol, 2.50 equiv). The reaction was stirred overnight at room temperature and quenched with water (10 mL). The mixture was extracted with dichloromethane (3×10 mL) and the organic layers were combined, washed with water (3×10 mL), dried over anhydrous sodium sulfate, filtered, and concentrated under reduced pressure. The crude product was purified by preparative HPLC to afford 36.4 mg (16% yield) of 5-(trifluoromethyl)pyridin-3-yl 2-(4-(3-chlorophenoxy)benzyl)-2,7-diazaspiro[3.5]nonane-7-carboxylate as a colorless oil. 1H NMR (300 MHz, Chloroform-d) δ 8.72 (s, 1H), 8.62 (s, 1H), 7.77 (s, 1H), 7.28-7.31 (m, 2H), 7.22-7.27 (m, 1H), 7.05-7.12 (m, 1H), 6.90-7.00 (m, 3H), 6.88-6.90 (m, 1H), 3.68 (s, 2H), 3.61 (br, 2H), 3.50 (br, 2H), 3.04-3.15 (m, 4H), 1.87 (br, 4H). LCMS (ESI, m/z): 532 [M+H]+.

Example 3: 5-Carbamoylpyridin-3-yl 2-(3-chloro-5-(trifluoromethyl)benzyl)-2,8-diazaspiro[4.5]decane-8-carboxylate

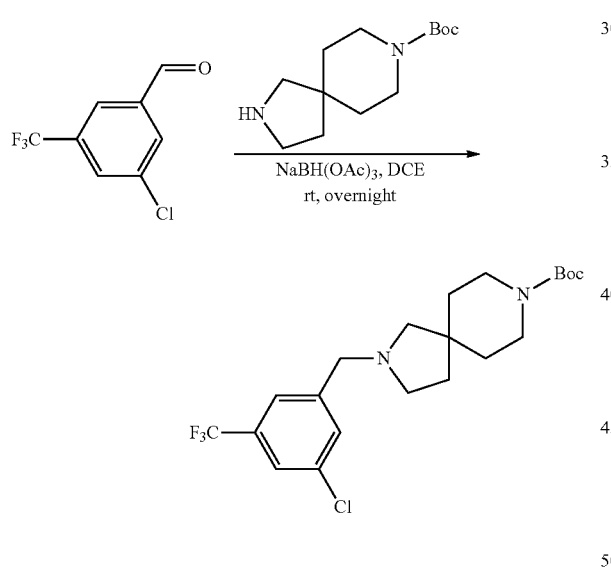

Step 1: Preparation of tert-butyl 2-(3-chloro-5-(trifluoromethyl)benzyl)-2,8-diazaspiro[4.5]decane-8-carboxylate

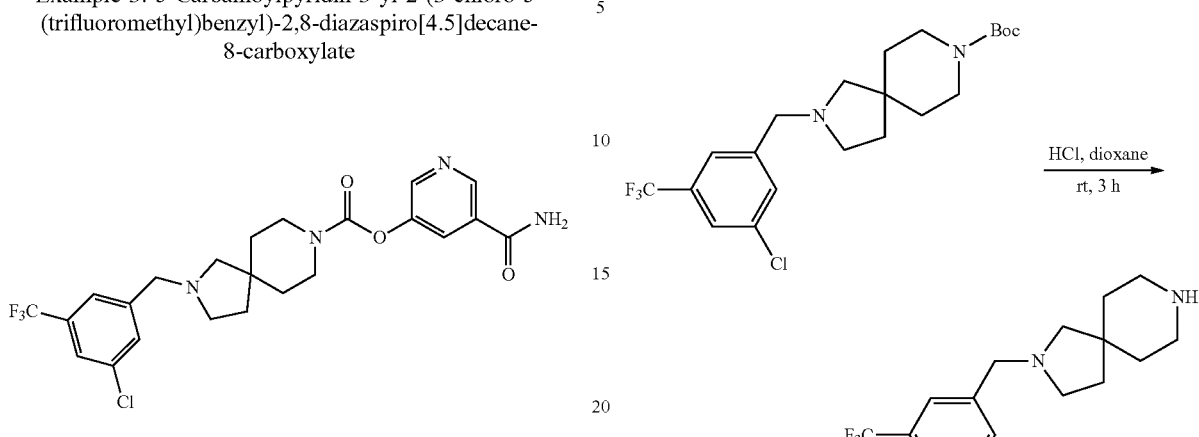

A 250-mL round-bottom flask was charged with 3-chloro-5-(trifluoromethyl)benzaldehyde (2.08 g, 10.0 mmol, 1.00 equiv), tert-butyl 2,8-diazaspiro[4.5]decane-8-carboxylate (2.40 g, 10.0 mmol, 1.00 equiv), and 1,2-dichloroethane (50 mL). The resulting solution was stirred for 2 hours at room temperature prior to addition of sodium triacetoxyborohydride (4.24 g, 20.0 mmol, 2.00 equiv). The reaction was stirred overnight at room temperature and quenched with water (150 mL). The mixture was extracted with dichloromethane (3×100 mL) and the organic layers were combined, washed with brine (3×100 mL), dried over anhydrous sodium sulfate, filtered, and concentrated under reduced pressure. The residue was chromatographed on a silica gel to provide 3.67 g (90% yield) of tert-butyl 2-(3-chloro-5-(trifluoromethyl)benzyl)-2,8-diazaspiro[4.5]decane-8-carboxylate as a white solid. LCMS (ESI, m/z): 433 [M+H]+.

Step 2: Preparation of 2-(3-chloro-5-(trifluoromethyl)benzyl)-2,8-diazaspiro[4.5]decane

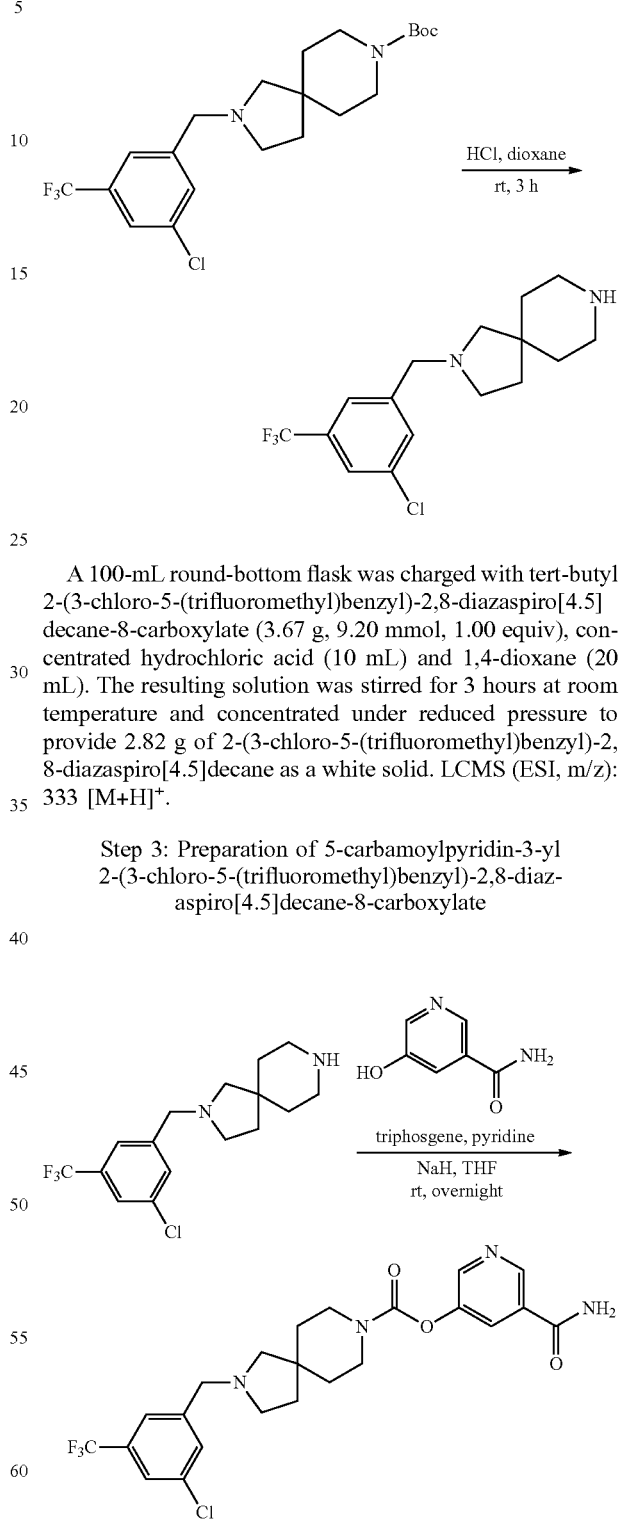

A 100-mL round-bottom flask was charged with tert-butyl 2-(3-chloro-5-(trifluoromethyl)benzyl)-2,8-diazaspiro[4.5]decane-8-carboxylate (3.67 g, 9.20 mmol, 1.00 equiv), concentrated hydrochloric acid (10 mL) and 1,4-dioxane (20 mL). The resulting solution was stirred for 3 hours at room temperature and concentrated under reduced pressure to provide 2.82 g of 2-(3-chloro-5-(trifluoromethyl)benzyl)-2,8-diazaspiro[4.5]decane as a white solid. LCMS (ESI, m/z): 333 [M+H]+.

Step 3: Preparation of 5-carbamoylpyridin-3-yl 2-(3-chloro-5-(trifluoromethyl)benzyl)-2,8-diazaspiro[4.5]decane-8-carboxylate A 40-mL vial was charged with 5-hydroxypyridine-3-carboxamide (207 mg, 1.50 mmol, 1.50 equiv), triphosgene (93.0 mg, 0.330 mmol, 0.33 equiv) and tetrahydrofuran (5 mL). Pyridine (395 mg, 4.99 mmol, 5.00 equiv) was added dropwise at 0° C. and the resulting solution was stirred for 3 hours at 0° C. 2-(3-chloro-5-(trifluoromethyl)benzyl)-2,8-diazaspiro[4.5]decane (333 mg, 1.00 mmol, 1.00 equiv) was combined with sodium hydride (60% dispersion in mineral oil, 48.0 mg, 1.20 mol, 1.20 equiv) in tetrahydrofuran (5 mL) and this solution was added to the reaction. The reaction was stirred overnight at room temperature and quenched with water (20 mL). The mixture was extracted with ethyl acetate (3×10 mL) and the organic layers were combined, washed with brine (3×10 mL), dried over anhydrous sodium sulfate, filtered, and concentrated under reduced pressure. The crude product was purified by preparative HPLC to provide 50.1 mg (10% yield) of 5-carbamoylpyridin-3-yl 2-(3-chloro-5-(trifluoromethyl)benzyl)-2,8-diazaspiro[4.5]decane-8-carboxylate as a white solid. $^1$H NMR (300 MHz, Chloroform-d) δ 8.83 (s, 1H), 8.57 (d, J=2.3 Hz, 1H), 7.96 (t, J=2.2 Hz, 1H), 7.50-7.61 (m, 3H), 6.29 (br, 1H), 5.91 (br, 1H), 3.45-3.70 (m, 6H), 2.64 (br, 2H), 2.44 (br, 2H), 1.67-1.76 (m, 6H). LCMS (ESI, m/z): 497 [M+H]$^+$.

Example 4: 5-Carbamoylpyridin-3-yl 2-(5-chloro-2-(trifluoromethyl)benzyl)-2,8-diazaspiro[4.5]decane-8-carboxylate

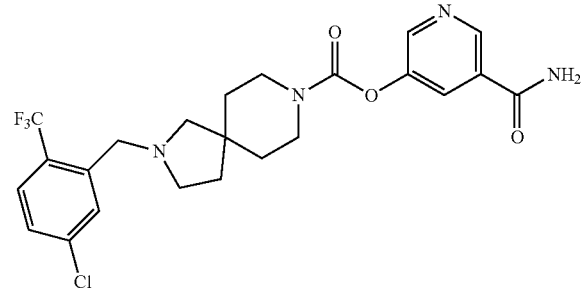 [SMILES: NC(=O)c1cncc(OC(=O)N2CCC3(CCN(Cc4cc(Cl)ccc4C(F)(F)F)C3)CC2)c1]

Step 1: Preparation of tert-butyl 2-(5-chloro-2-(trifluoromethyl)benzyl)-2,8-diazaspiro[4.5]decane-8-carboxylate

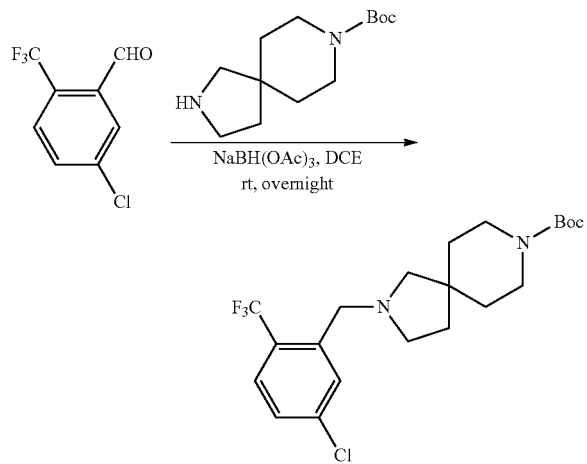

A 250-mL round-bottom flask was charged with 5-chloro-2-(trifluoromethyl)benzaldehyde (0.860 g, 4.12 mmol, 1.00 equiv), tert-butyl 2,8-diazaspiro[4.5]decane-8-carboxylate (1.00 g, 4.16 mmol, 1.00 equiv), and 1,2-dichloroethane (50 mL). The mixture was stirred for 2 hours at room temperature prior to addition of sodium triacetoxyborohydride (3.90 g, 18.4 mmol, 2.00 equiv). The resulting solution was stirred overnight at room temperature and quenched with water (50 mL). The mixture was extracted with dichloromethane (3×50 mL) and the organic layers were combined, washed with water (3×50 mL), dried over anhydrous sodium sulfate, filtered, and concentrated under reduced pressure. The residue was chromatographed on a silica gel column to provide 1.50 g (84% yield) of tert-butyl 2-(5-chloro-2-(trifluoromethyl)benzyl)-2,8-diazaspiro[4.5]decane-8-carboxylate as a white oil. LCMS (ESI, m/z): 433 [M+H]$^+$.

Step 2: Preparation of 2-(5-chloro-2-(trifluoromethyl)benzyl)-2,8-diazaspiro[4.5]decane

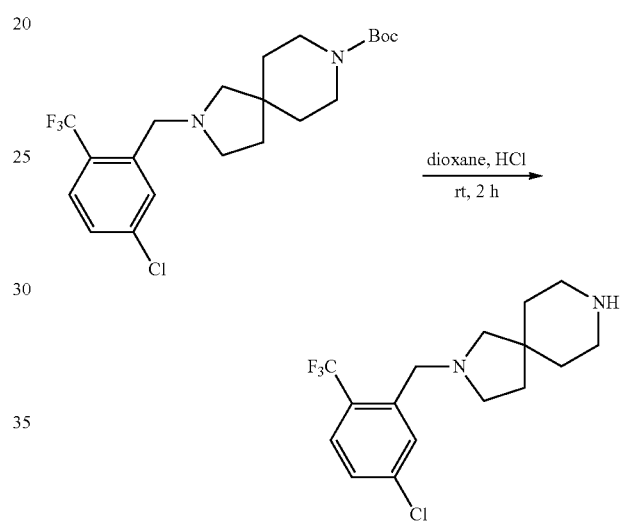

A 250-mL round-bottom flask was charged with tert-butyl 2-(5-chloro-2-(trifluoromethyl)benzyl)-2,8-diazaspiro[4.5]decane-8-carboxylate (1.50 g, 3.46 mmol, 1.00 equiv), 1,4-dioxane (50 mL) and concentrated hydrogen chloride (20 mL). The resulting solution was stirred for 2 hours at room temperature and concentrated under reduced pressure to provide 1.20 g of 2-(5-chloro-2-(trifluoromethyl)benzyl)-2,8-diazaspiro[4.5]decane as a white solid. LCMS (ESI, m/z): 333 [M+H]$^+$.

Step 3: Preparation of 2-(5-chloro-2-(trifluoromethyl)benzyl)-2,8-diazaspiro[4.5]decane-8-carbonyl Chloride

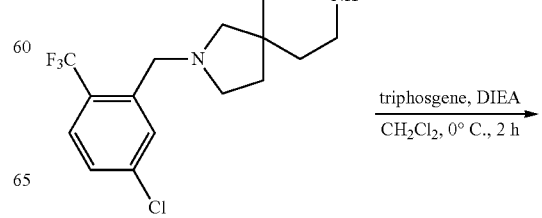

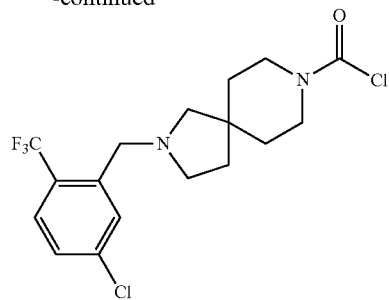

A 40-mL round-bottom flask was charged with 2-(5-chloro-2-(trifluoromethyl)benzyl)-2,8-diazaspiro[4.5]decane (1.00 g, 3.00 mmol, 1.00 equiv), triphosgene (0.358 g, 1.21 mmol, 0.40 equiv) and dichloromethane (10 mL). DIPEA (0.777 g, 6.01 mmol, 2.00 equiv) was added dropwise at 0° C., and the resulting solution was stirred for 2 hours at 0° C. before quenching with water (5 mL). The mixture was extracted with dichloromethane (3×10 mL) and the organic layers were combined, washed with water (3×10 mL), dried over anhydrous sodium sulfate, filtered, and concentrated under reduced pressure to provide 1.18 g of 2-(5-chloro-2-(trifluoromethyl)benzyl)-2,8-diazaspiro[4.5]decane-8-carbonyl chloride as a yellow oil.

Step 4: Preparation of 5-carbamoylpyridin-3-yl 2-(5-chloro-2-(trifluoromethyl)benzyl)-2,8-diazaspiro[4.5]decane-8-carboxylate

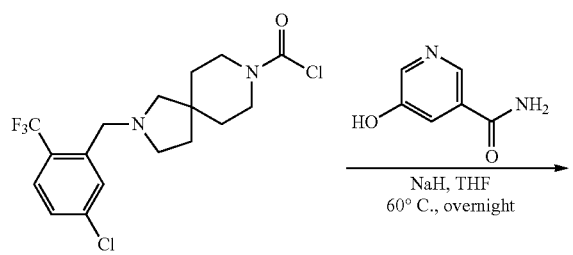

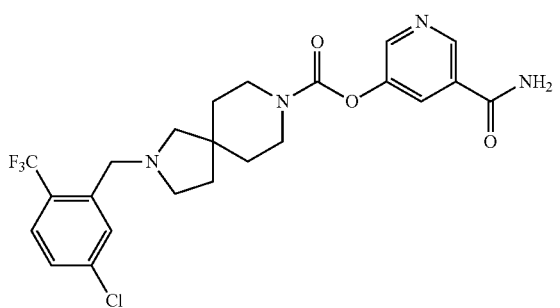

A 40-mL vial was charged with 5-hydroxypyridine-3-carboxamide (83.0 mg, 0.600 mmol, 1.00 equiv), sodium hydride (60% dispersion in mineral oil, 120 mg, 3.00 mmol, 3.00 equiv), and tetrahydrofuran (10 mL) under nitrogen. The mixture was stirred for 2 hours at room temperature prior to addition of 2-(5-chloro-2-(trifluoromethyl)benzyl)-2,8-diazaspiro[4.5]decane-8-carbonyl chloride (237 mg, 0.600 mmol, 1.00 equiv). The resulting solution was stirred overnight at 60° C. and quenched with water (30 mL). The mixture was extracted with dichloromethane (3×20 mL), and the organic layers were combined, washed with water (3×20 mL), dried over anhydrous sodium sulfate, filtered, and concentrated under reduced pressure. The crude product was purified by preparative HPLC to provide 42.6 mg (14% yield) of 5-carbamoylpyridin-3-yl 2-(5-chloro-2-(trifluoromethyl)benzyl)-2,8-diazaspiro[4.5]decane-8-carboxylate as a white solid. $^1$H NMR (300 MHz, Chloroform-d) δ 8.84 (d, J=1.8 Hz, 1H), 8.60 (d, J=2.4 Hz, 1H), 7.98-8.00 (m, 1H), 7.84-7.86 (m, 1H), 7.60 (d, J=8.4 Hz, 1H), 7.28-7.36 (m, 1H), 5.70-6.40 (m, 2H), 3.50-3.80 (m, 6H), 2.50-2.72 (m, 4H), 1.66-1.74 (m, 6H). LCMS (ESI, m/z): 497 [M+H]$^+$.

Example 5: 5-Carbamoylpyridin-3-yl 2-(3-(4-chlorophenoxy)benzyl)-2,7-diazaspiro[3.5]nonane-7-carboxylate

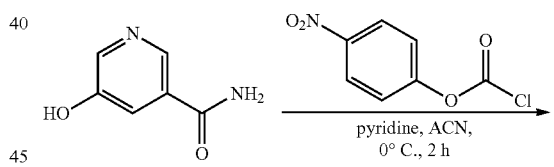

Step 1: Preparation of 5-carbamoylpyridin-3-yl (4-nitrophenyl) carbonate

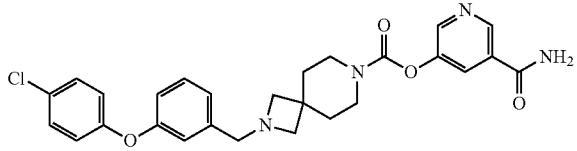 [SMILES: NC(=O)c1cncc(OC(=O)N2CCC3(CC2)CN(Cc2cccc(Oc4ccc(Cl)cc4)c2)C3)c1]

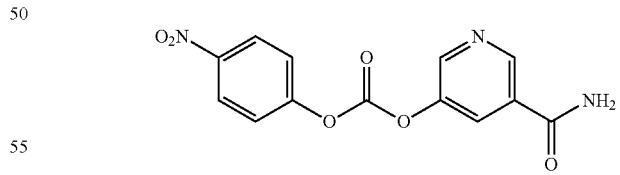

A 40-mL vial was charged with 5-hydroxypyridine-3-carboxamide (138 mg, 1.00 mmol, 1.00 equiv), pyridine (158 mg, 2.00 mmol, 2.00 equiv) and acetonitrile (5 mL). 4-Nitrophenyl chloroformate (222 mg, 1.10 mmol, 1.10 equiv) was added at 0° C. The resulting solution was stirred for 2 hours at 0° C. and concentrated under reduced pressure to provide 303 mg of 5-carbamoylpyridin-3-yl (4-nitrophenyl) carbonate as a yellow solid.

Step 2: Preparation of tert-butyl 2-(3-(4-chlorophenoxy)benzyl)-2,7-diazaspiro[3.5]nonane-7-carboxylate

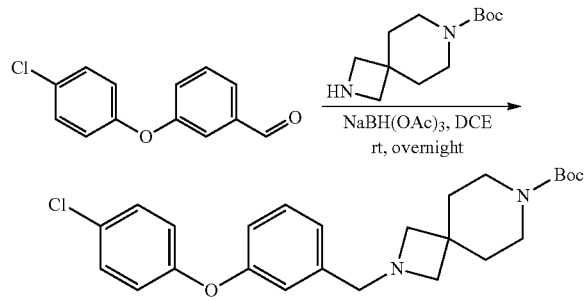

A 100-mL round-bottom flask was charged with tert-butyl 2,7-diazaspiro[3.5]nonane-7-carboxylate (452 mg, 2.00 mmol, 1.00 equiv), 3-(4-chlorophenoxy)benzaldehyde (466 mg, 2.00 mmol, 1.00 equiv) and 1,2-dichloroethane (10 mL). The mixture was stirred for 2 h at room temperature prior to addition of sodium triacetoxyborohydride (848 mg, 4.00 mmol, 2.00 equiv). The resulting solution was stirred overnight at room temperature and quenched with water (50 mL). The mixture was extracted with dichloromethane (3×50 mL) and the organic layers were combined, washed with brine (3×50 mL), dried over anhydrous sodium sulfate, filtered, and concentrated under reduced pressure. The residue was chromatographed on a silica gel column to provide 700 mg (79% yield) of tert-butyl 2-(3-(4-chlorophenoxy)benzyl)-2,7-diazaspiro[3.5]nonane-7-carboxylate as a white semi-solid. LCMS (ESI, m/z): 443 [M+H]$^+$.

Step 3: Preparation of 2-(3-(4-chlorophenoxy)benzyl)-2,7-diazaspiro[3.5]nonane

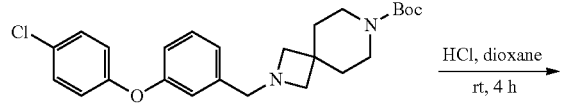

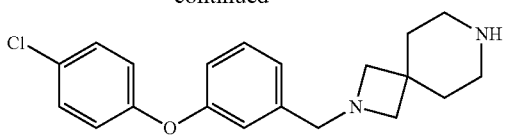

A 100-mL round-bottom flask was charged with tert-butyl 2-(3-(4-chlorophenoxy)benzyl)-2,7-diazaspiro[3.5]nonane (443 mg, 1.00 mmol, 1.00 equiv), 1,4-dioxane (20 mL) and concentrated hydrogen chloride (5 mL). The resulting solution was stirred for 4 hours at room temperature and concentrated under reduced pressure to provide 343 mg of 2-(3-(4-chlorophenoxy)benzyl)-2,7-diazaspiro[3.5]nonane as a white solid. LCMS (ESI, m/z): 343 [M+H]$^+$.

Step 4: Preparation of 5-carbamoylpyridin-3-yl 2-(3-(4-chlorophenoxy)benzyl)-2,7-diazaspiro[3.5]nonane-7-carboxylate

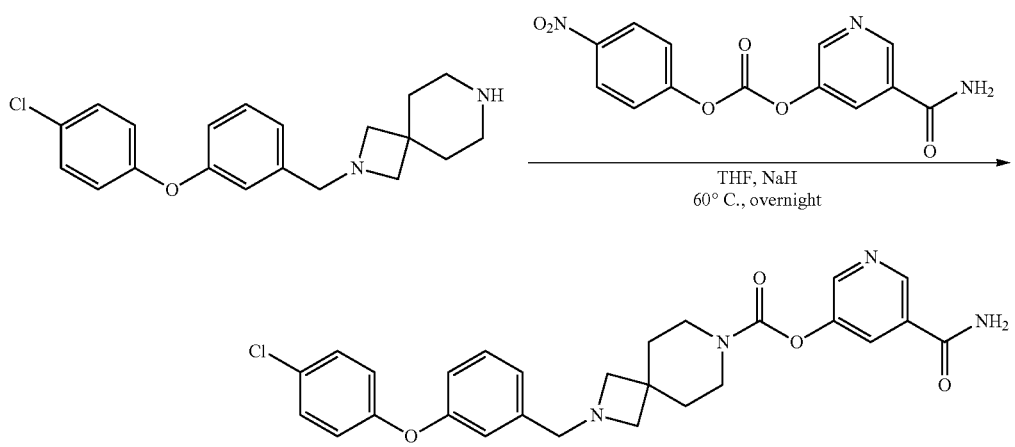

A 40-mL vial was charged with 2-(3-(4-chlorophenoxy)benzyl)-2,7-diazaspiro[3.5]nonane (343 mg, 1.00 mmol, 1.00 equiv), tetrahydrofuran (5 mL) and sodium hydride (60% dispersion in mineral oi, 100 mg, 2.50 mmol, 2.50 equiv) under nitrogen. The resulting solution was stirred for 30 minutes at room temperature prior to addition of 5-carbamoylpyridin-3-yl 4-nitrophenyl carbonate (303 mg, 1.00 mmol, 1.00 equiv). The reaction was stirred overnight at 60° C. and quenched with water (10 mL). The mixture was extracted with ethyl acetate (3×10 mL) and the organic layers were combined, washed with brine (3×10 mL), dried over anhydrous sodium sulfate, filtered, and concentrated under reduced pressure. The crude product was purified by preparative HPLC to provide 21.2 mg (4% yield) of 5-carbamoylpyridin-3-yl 2-(3-(4-chlorophenoxy)benzyl)-2,7-diazaspiro[3.5]nonane-7-carboxylate as a white solid. $^1$H NMR (300 MHz, Chloroform-d) δ 8.83 (d, J=1.8 Hz, 1H), 8.57 (d, J=2.5 Hz, 1H), 7.94 (t, J=2.2 Hz, 1H), 7.26-7.32 (m, 3H), 7.05-7.08 (m, 1H), 6.86-6.96 (m, 4H), 6.23 (br, 1H), 5.78 (br, 1H), 3.39-3.74 (m, 6H), 3.27 (br, 4H), 1.87 (br, 4H). LCMS (ESI, m/z): 507 [M+H]$^+$.

Example 6: 5-Aminopyridin-3-yl 4-(4-chloro-3-isopropoxybenzyl)piperazine-1-carboxylate

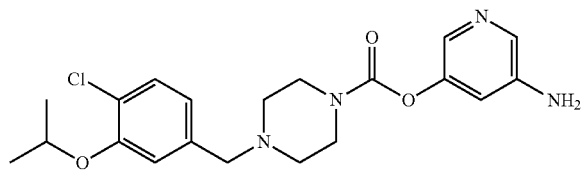 [SMILES: CC(C)Oc1cc(CN2CCN(C(=O)Oc3cncc(N)c3)CC2)ccc1Cl]

Step 1: Preparation of 4-chloro-3-isopropoxybenzaldehyde

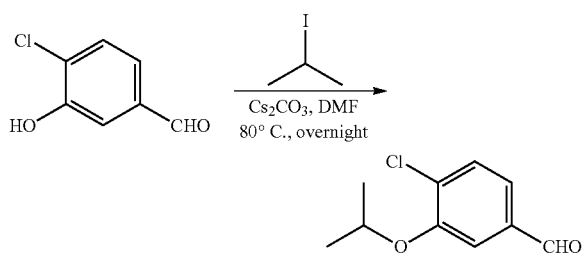

A 250-mL round-bottom flask was charged with 4-chloro-3-hydroxybenzaldehyde (2.00 g, 12.8 mmol, 1.00 equiv), 2-iodopropane (4.30 g, 25.3 mmol, 2.00 equiv), cesium carbonate (12.4 g, 38.1 mmol, 3.00 equiv) and DMF (80 mL). The resulting solution was stirred overnight at 80° C. and quenched with water (50 mL). The mixture was extracted with ethyl acetate (3×100 mL) and the organic layers were combined, washed with water (3×30 mL), dried over anhydrous sodium sulfate, filtered, and concentrated under reduced pressure. The residue was chromatographed on a silica gel column to provide 2.37 g (93% yield) of 4-chloro-3-isopropoxybenzaldehyde as a yellow oil. LCMS (ESI, m/z): 199 [M+H]$^+$.

Step 2: Preparation of tert-butyl 4-(4-chloro-3-isopropoxybenzyl)piperazine-1-carboxylate

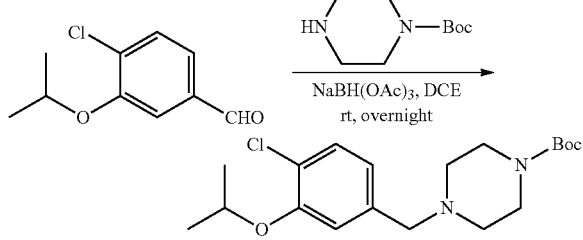

A 100-mL round-bottom flask was charged with 4-chloro-3-isopropoxybenzaldehyde (1.00 g, 5.03 mmol, 1.00 equiv), tert-butyl piperazine-1-carboxylate (1.40 g, 7.52 mmol, 1.50 equiv) and 1,2-dichloroethane (30 mL). The resulting solution was stirred for 1 hour at room temperature prior to addition of sodium triacetoxyborohydride (2.20 g, 10.4 mmol, 2.00 equiv). The reaction was stirred overnight at room temperature and quenched with water (30 mL). The mixture was extracted with dichloromethane (3×50 mL), and the organic layers were combined, washed with water (3×30 mL), dried over anhydrous sodium sulfate, filtered, and concentrated under reduced pressure. The residue was chromatographed on a silica gel column to provide 1.49 g (80% yield) of tert-butyl 4-(4-chloro-3-isopropoxybenzyl)piperazine-1-carboxylate as a yellow oil. LCMS (ESI, m/z): 369 [M+H]$^+$.

Step 3: Preparation of 1-(4-chloro-3-isopropoxybenzyl)piperazine

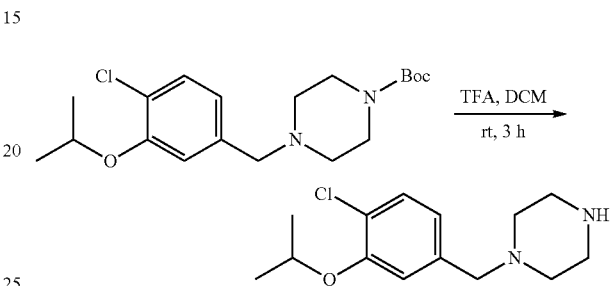

A 50-mL round-bottom flask was charged with tert-butyl 4-(4-chloro-3-isopropoxybenzyl)piperazine-1-carboxylate (1.11 g, 3.00 mmol, 1.00 equiv), trifluoroacetic acid (1 mL) and dichloromethane (10 mL). The resulting solution was stirred for 3 hours at room temperature and concentrated under reduced pressure to provide 0.807 g of 1-(4-chloro-3-isopropoxybenzyl)piperazine as a yellow oil. LCMS (ESI, m/z): 269 [M+H]$^+$.

Step 4: Preparation of 4-(4-chloro-3-isopropoxybenzyl)piperazine-1-carbonyl Chloride

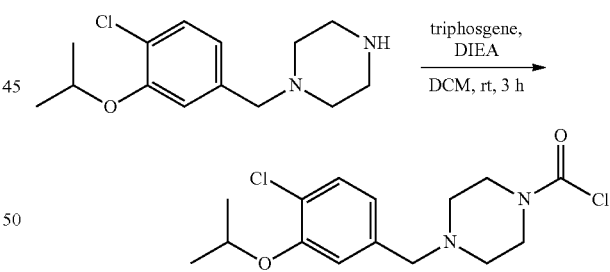

A 50-mL round-bottom flask was charged with 1-(4-chloro-3-isopropoxybenzyl)piperazine (538 mg, 2.00 mmol, 1.00 equiv), triphosgene (298 mg, 1.00 mmol, 0.50 equiv), and dichloromethane (10 mL). DIPEA (516 mg, 4.00 mmol, 2.00 equiv) was added dropwise at 0° C. The resulting solution was stirred for 3 hours at room temperature and quenched with water (10 mL). The mixture was extracted with dichloromethane (3×30 mL) and the organic layers were combined, washed with water (3×10 mL), dried over anhydrous sodium sulfate, filtered, and concentrated under reduced pressure to provide 662 mg of 4-(4-chloro-3-isopropoxybenzyl)piperazine-1-carbonyl chloride as a yellow solid.

Step 5: Preparation of 5-aminopyridin-3-yl 4-(4-chloro-3-isopropoxybenzyl)piperazine-1-carboxylate

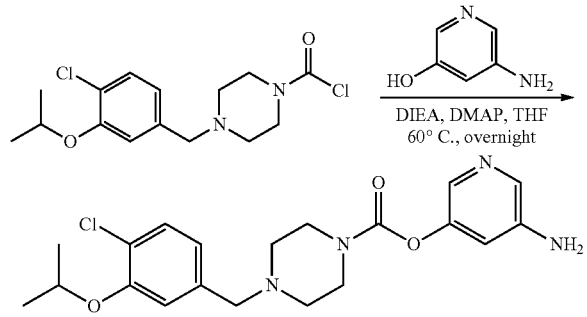

A 50-mL round-bottom flask was charged with 4-(4-chloro-3-isopropoxybenzyl)piperazine-1-carbonyl chloride (390 mg, 1.18 mmol, 1.20 equiv), 5-aminopyridin-3-ol (108 mg, 0.980 mmol, 1.00 equiv), 4-dimethylaminopyridine (23.9 mg, 0.200 mmol, 0.20 equiv), DIPEA (457 mg, 3.54 mmol, 3.00 equiv) and tetrahydrofuran (10 mL). The resulting solution was stirred overnight at 60° C. and quenched with water (10 mL). The mixture was extracted with ethyl acetate (3×30 mL) and the organic layers were combined, washed with water (3×10 mL), dried over anhydrous sodium sulfate, filtered, and concentrated under reduced pressure. The crude product was purified by preparative HPLC to afford 249.0 mg (63% yield) of 5-aminopyridin-3-yl 4-(4-chloro-3-isopropoxybenzyl)piperazine-1-carboxylate as a yellow solid. $^1$H NMR: (300 MHz, Chloroform-d) δ 7.71-7.93 (m, 2H), 7.34-7.38 (m, 1H), 6.89-7.01 (s, 1H), 6.74-6.89 (m, 2H), 4.42-4.71 (m, 1H), 3.34-3.90 (m, 8H), 2.30-2.61 (m, 4H), 1.24-1.40 (m, 6H). LCMS (ESI, m/z): 405 [M+H]$^+$.

Example 7: 5-(Trifluoromethyl)pyridin-3-yl 2-(3-(benzo[d]thiazol-2-yloxy)benzyl)-2,7-diazaspiro[3.5]nonane-7-carboxylate

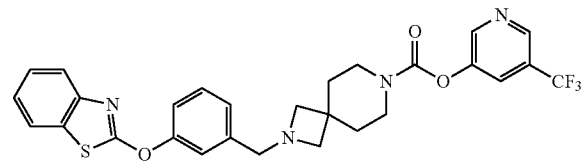 [SMILES: O=C(Oc1cncc(C(F)(F)F)c1)N1CCC2(CC1)CN(Cc1cccc(Oc3nc4ccccc4s3)c1)C2]

Step 1: Preparation of 3-(benzo[d]thiazol-2-yloxy)benzaldehyde

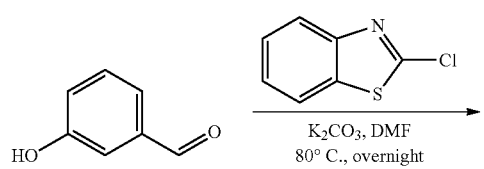

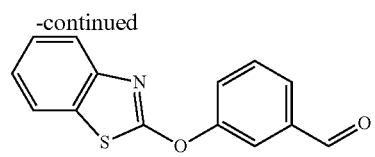

A 100-mL round-bottom flask was charged with 3-hydroxybenzaldehyde (1.00 g, 8.20 mmol, 1.00 equiv), 2-chlorobenzo[d]thiazole (2.08 g, 12.3 mmol, 1.50 equiv), DMF (25 mL), and potassium carbonate (3.40 g, 24.6 mmol, 3.00 equiv) under nitrogen. The reaction was stirred overnight at 80° C. and quenched with water (25 mL). The resulting solution was extracted with ethyl acetate (3×25 mL) and the organic layers were combined, washed with brine (2×50 mL), dried over anhydrous sodium sulfate, filtered, and concentrated under reduced pressure. The residue was chromatographed on a silica gel column to provide 0.800 g (38% yield) of 3-(benzo[d]thiazol-2-yloxy)benzaldehyde as a yellow oil. LCMS (ESI, m/z): 256 [M+H]$^+$.

Step 2: Preparation of 2-(tert-butyl) 7-(5-(trifluoromethyl)pyridin-3-yl) 2,7-diazaspiro[3.5]nonane-2,7-dicarboxylate

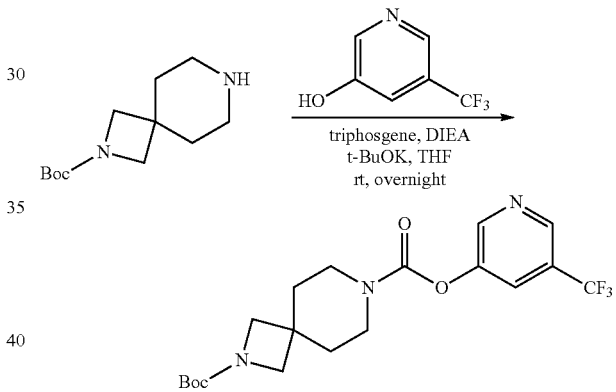

A 100-mL round-bottom flask was charged with triphosgene (0.986 g, 3.32 mmol, 0.50 equiv), and tetrahydrofuran (15 mL). tert-Butyl 2,7-diazaspiro[3.5]nonane-2-carboxylate (1.50 g, 6.64 mmol, 1.00 equiv) was added at 0° C. followed by DIPEA (3.43 g, 26.6 mmol, 4.00 equiv). The reaction was stirred for 2 hours at room temperature and quenched with water (15 mL). The resulting solution was extracted with dichloromethane (3×15 mL) and the organic layers were combined, washed with brine (2×50 mL), dried over anhydrous sodium sulfate, filtered, and concentrated under reduced pressure. The crude product was dissolved in tetrahydrofuran (15 mL) and 5-(trifluoromethyl)pyridin-3-ol (1.30 g, 7.97 mmol, 1.20 equiv) and potassium tert-butoxide (1.12 g, 9.96 mmol, 1.50 equiv) were added. The resulting solution was stirred overnight at room temperature and quenched with water (15 mL). The mixture was extracted with dichloromethane (3×100 mL) and the organic layers were combined, washed with brine (2×75 mL), dried over anhydrous sodium sulfate, filtered, and concentrated under reduced pressure. The residue was chromatographed on a silica gel column to provide 1.60 g (58% yield) of 2-(tert-butyl) 7-(5-(trifluoromethyl)pyridin-3-yl) 2,7-diazaspiro[3.5]nonane-2,7-dicarboxylate as a yellow oil. LCMS (ESI, m/z): 416 [M+H]$^+$.

Step 3: Preparation of 5-(trifluoromethyl)pyridin-3-yl 2-(3-(benzo[d]thiazol-2-yloxy)benzyl)-2,7-diazaspiro[3.5]nonane-7-carboxylate

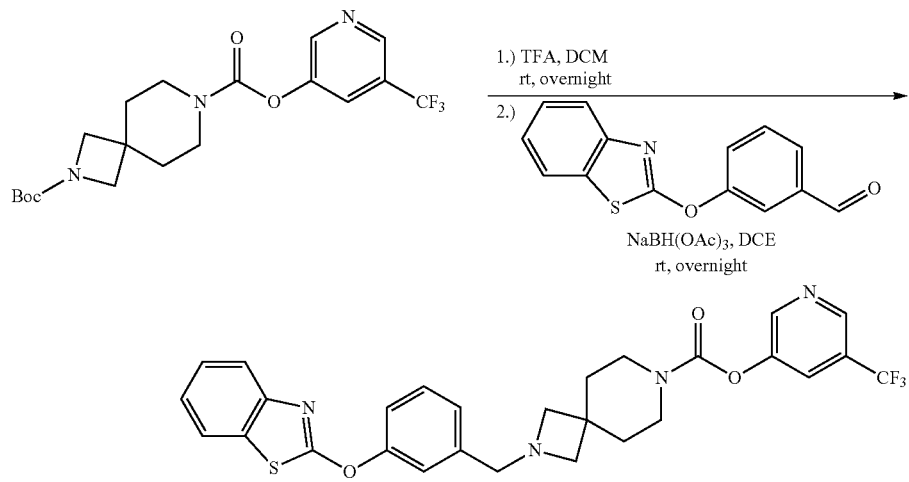

The title compound was synthesized as described in Example 2, Steps 4-5, using 3-(benzo[d]thiazol-2-yloxy)benzaldehyde in Step 5 to afford 111 mg (50% yield) of 5-(trifluoromethyl)pyridin-3-yl 2-(3-(benzo[d]thiazol-2-yloxy)benzyl)-2,7-diazaspiro[3.5]nonane-7-carboxylate as a colorless oil. $^1$H NMR (300 MHz, Chloroform-d) δ 8.62-8.71 (m, 2H), 7.66-7.76 (m, 3H), 7.30-7.48 (m, 2H), 7.32 (s, 1H), 7.12-7.24 (m, 3H), 3.71 (s, 2H), 3.59 (br, 2H), 3.49 (br, 2H), 3.11-3.14 (m, 4H), 1.75-1.85 (m, 4H). LCMS (ESI, m/z): 555 [M+H]$^+$.

Example 8: 5-(Trifluoromethyl)pyridin-3-yl 2-(4-(2-chlorophenoxy)benzyl)-2,7-diazaspiro[3.5]nonane-7-carboxylate

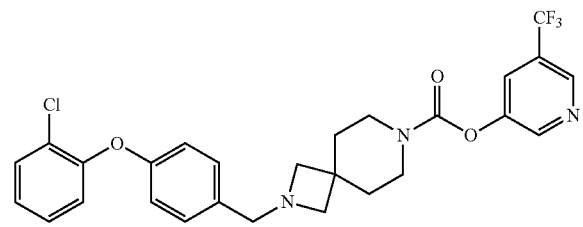 [SMILES: O=C(Oc1cncc(C(F)(F)F)c1)N1CCC2(CC1)CN(Cc1ccc(Oc3ccccc3Cl)cc1)C2]

Step 1: Preparation of 4-(2-chlorophenoxy)benzaldehyde

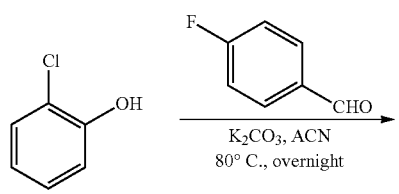

-continued

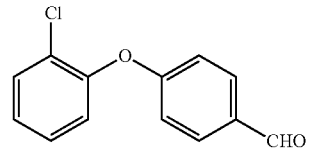

A 250-mL round-bottom flask was charged with potassium carbonate (4.30 g, 31.1 mmol, 2.00 equiv), 2-chlorophenol (2.00 g, 15.6 mmol, 1.00 equiv), 4-fluorobenzaldehyde (1.94 g, 15.6 mmol, 1.00 equiv) and acetonitrile (50 mL) under nitrogen. The resulting solution was stirred overnight at 80° C. and quenched with water (100 mL). The mixture was extracted with dichloromethane (3×50 mL) and the organic layers were combined, washed with water (3×50 mL), dried over anhydrous sodium sulfate, filtered, and concentrated under reduced pressure. The residue was chromatographed on a silica gel column to provide 2.20 g (61% yield) of 4-(2-chlorophenoxy)benzaldehyde as a yellow oil. LCMS (ESI, m/z): 233 [M+H]$^+$.

Step 2: Preparation of 5-(trifluoromethyl)pyridin-3-yl 2-(4-(2-chlorophenoxy)benzyl)-2,7-diazaspiro[3.5]nonane-7-carboxylate

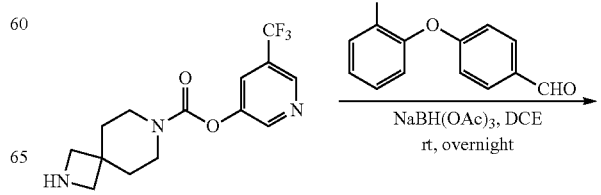

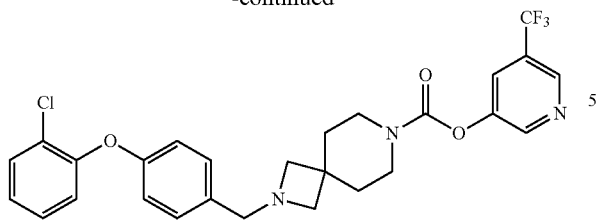

A 50-mL round-bottom flask was charged with 4-(2-chlorophenoxy)benzaldehyde (100 mg, 0.432 mmol, 1.00 equiv), 5-(trifluoromethyl)pyridin-3-yl 2,7-diazaspiro[3.5]nonane-7-carboxylate (164 mg, 0.522 mmol, 1.20 equiv, prepared as described in Example 2, Steps 1-4), triethylamine (130 mg, 1.28 mmol, 3.00 equiv), and 1,2-dichloroethane (10 mL). The resulting solution was stirred fpr 2 hours at room temperature prior to the addition of sodium triacetoxyborohydride (228 mg, 1.08 mmol, 2.50 equiv). The reaction was stirred overnight at room temperature and quenched with water (10 mL). The mixture was extracted with dichloromethane (3×10 mL) and the organic layers were combined, washed with water (3×10 mL), dried over anhydrous sodium sulfate, filtered, and concentrated under reduced pressure. The crude product was purified by preparative HPLC to afford 56.2 mg (25% yield) of 5-(trifluoromethyl)pyridin-3-yl 2-(4-(2-chlorophenoxy)benzyl)-2,7-diazaspiro[3.5]nonane-7-carboxylate as a yellow oil. $^1$H NMR (300 MHz, Chloroform-d) δ 8.72 (s, 1H), 8.62 (s, 1H), 7.76 (s, 1H), 7.44-7.48 (m, 1H), 7.19-7.26 (m, 3H), 7.06-7.11 (m, 1H), 6.90-7.00 (m, 3H), 3.50-3.64 (m, 4H), 3.49 (br, 2H), 3.10-3.11 (m, 4H), 1.85-1.97 (m, 4H). LCMS (ESI, m/z): 532 [M+H]$^+$.

Example 9: 5-(Trifluoromethyl)pyridin-3-yl 2-(3-(2-chlorophenoxy)benzyl)-2,7-diazaspiro[3.5]nonane-7-carboxylate

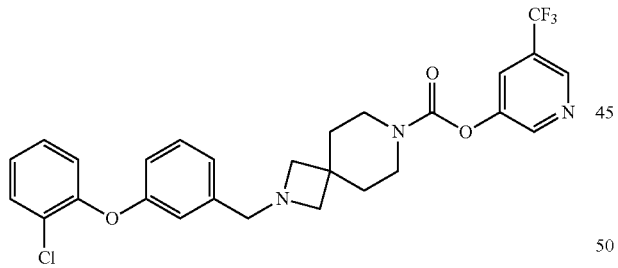

Step 1: Preparation of 3-(2-chlorophenoxy)benzaldehyde

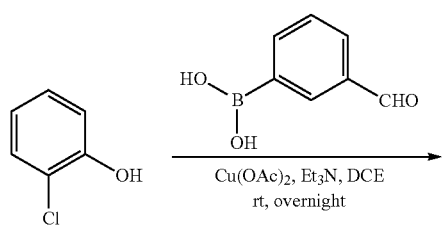

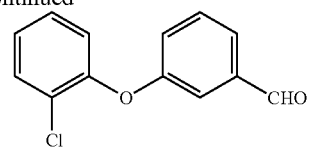

A 250-mL round-bottom flask was charged with 2-chlorophenol (1.28 g, 9.96 mmol, 1.00 equiv), (3-formylphenyl)boronic acid (1.50 g, 10.0 mmol, 1.00 equiv), triethylamine (5.05 g, 49.9 mmol, 5.00 equiv), 1,2-dichloroethane (100 mL) and copper(II) acetate (1.82 g, 10.0 mmol, 1.00 equiv). The resulting solution was stirred overnight at room temperature and concentrated under reduced pressure. The residue was chromatographed on a silica gel column to provide 760 mg (33% yield) of 3-(2-chlorophenoxy)benzaldehyde as a yellow oil. LCMS (ESI, m/z): 233 [M+H]$^+$.

Step 2: Preparation of 5-(trifluoromethyl)pyridin-3-yl 2-(3-(2-chlorophenoxy)benzyl)-2,7-diazaspiro[3.5]nonane-7-carboxylate

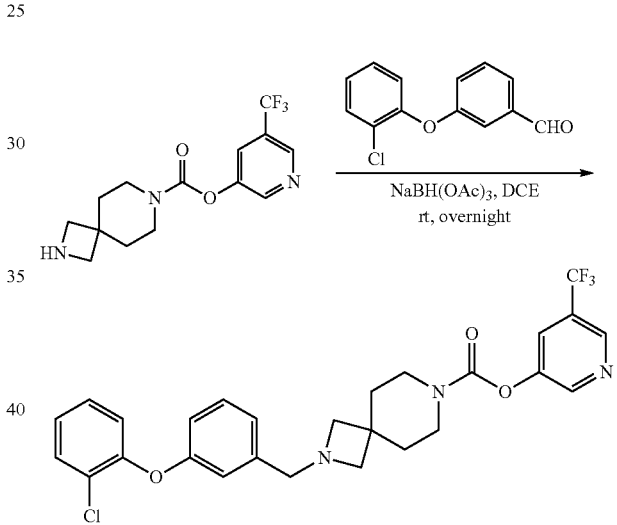

A 50-mL round-bottom flask was charged with 3-(2-chlorophenoxy)benzaldehyde (100 mg, 0.432 mmol, 1.00 equiv), 5-(trifluoromethyl)pyridin-3-yl 2,7-diazaspiro[3.5]nonane-7-carboxylate (164 mg, 0.522 mmol, 1.20 equiv, prepared as described in Example 2, Steps 1-4), triethylamine (130 mg, 1.28 mmol, 3.00 equiv), and 1,2-dichloroethane (10 mL). The resulting solution was stirred for 2 hours at room temperature prior to addition of sodium triacetoxyborohydride (228 mg, 1.08 mmol, 2.50 equiv). The reaction was stirred overnight at room temperature and quenched with water (5 mL). The mixture was extracted with dichloromethane (3×10 mL) and the organic layers were combined, washed with water (3×10 mL), dried over anhydrous sodium sulfate, filtered, and concentrated under reduced pressure. The crude product was purified by preparative HPLC to provide 16.5 mg (7% yield) of 5-(trifluoromethyl)pyridin-3-yl 2-(3-(2-chlorophenoxy)benzyl)-2,7-diazaspiro[3.5]nonane-7-carboxylate as a colorless oil. $^1$H NMR (300 MHz, Chloroform-d) δ 8.72 (s, 1H), 8.62 (s, 1H), 7.76 (s, 1H), 7.48-7.60 (m, 1H), 7.36-7.45 (m, 1H), 7.26-7.31 (m, 1H), 7.07-7.20 (m, 2H), 7.01-7.05 (m, 1H), 6.94-6.99 (m, 1H), 6.84-6.91 (m, 1H), 3.71 (s, 2H), 3.40-3.59 (m, 4H), 3.01-3.35 (m, 4H), 1.86 (br, 4H). LCMS (ESI, m/z): 532 [M+H]+.

Example 10: 5-(Trifluoromethyl)pyridin-3-yl 2-(3-(3-chlorophenoxy)benzyl)-2,7-diazaspiro[3.5]nonane-7-carboxylate

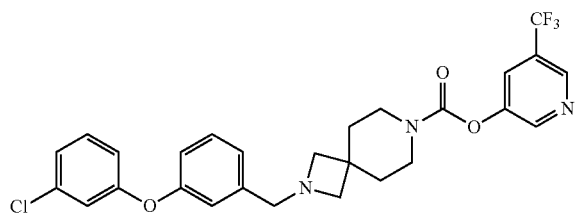 [SMILES: O=C(Oc1cncc(C(F)(F)F)c1)N1CCC2(CC1)CN(Cc1cccc(Oc3cccc(Cl)c3)c1)C2]

Step 1: Preparation of 3-(3-chlorophenoxy)benzaldehyde

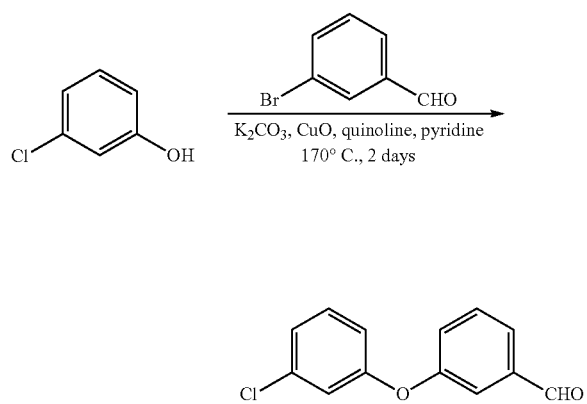

A 500-mL round-bottom flask was charged with 3-chlorophenol (1.53 g, 11.9 mmol, 1.10 equiv), potassium carbonate (11.2 g, 81.0 mmol, 8.00 equiv), 3-bromobenzaldehyde (2.00 g, 10.8 mmol, 1.00 equiv), quinoline (50 mL), pyridine (100 mL) and copper(II) oxide (6.50 g, 81.2 mmol, 8.00 equiv) under nitrogen. The resulting solution was stirred for 2 days at 170° C., concentrated under reduced pressure and diluted with water (100 mL). The mixture was extracted with ethyl acetate (3×100 mL) and the organic layers were combined, washed with brine (3×100 mL), dried over anhydrous sodium sulfate, filtered, and concentrated under reduced pressure. The residue was chromatographed on a silica gel column to provide 500 mg (20% yield) of 3-(3-chlorophenoxy)benzaldehyde as a yellow oil. LCMS (ESI, m/z): 233 [M+H]+.

Step 2: Preparation of 5-(trifluoromethyl)pyridin-3-yl 2-(3-(3-chlorophenoxy)benzyl)-2,7-diazaspiro[3.5]nonane-7-carboxylate

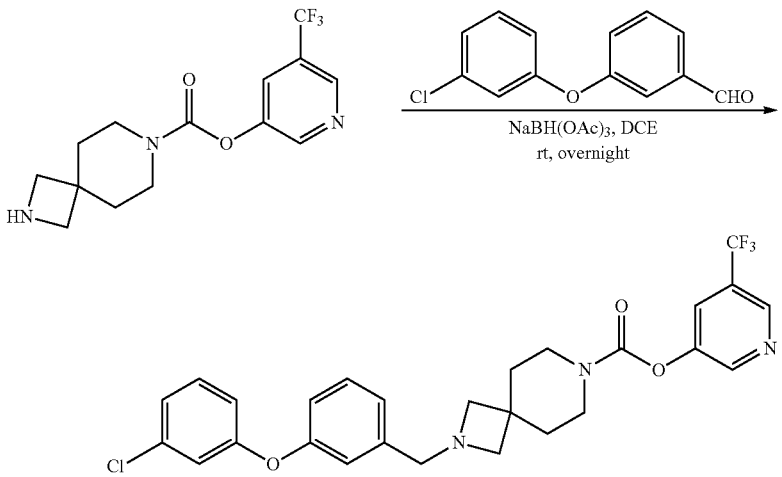

A 50-mL round-bottom flask was charged with 3-(3-chlorophenoxy)benzaldehyde (100 mg, 0.432 mmol, 0.83 equiv), 5-(trifluoromethyl)pyridin-3-yl 2,7-diazaspiro[3.5]nonane-7-carboxylate (164 mg, 0.522 mmol, 1.00 equiv, prepared as described in Example 2, Steps 1-4), triethylamine (130 mg, 1.28 mmol, 2.50 equiv), and 1,2-dichloroethane (10 mL). The resulting solution was stirred for 2 hours at room temperature prior to addition of sodium triacetoxyborohydride (228 mg, 1.08 mmol, 2.50 equiv). The reaction was stirred overnight at room temperature and quenched with water (10 mL). The mixture was extracted with dichloromethane (3×10 mL) and the organic layers were combined, washed with water (3×10 mL), dried over anhydrous sodium sulfate, filtered, and concentrated under reduced pressure. The crude product was purified by preparative HPLC to afford 10.8 mg (4% yield) of 5-(trifluoromethyl)pyridin-3-yl 2-(3-(3-chlorophenoxy)benzyl)-2,7-diazaspiro[3.5]nonane-7-carboxylate as a colorless oil. $^1$H NMR (300 MHz, Chloroform-d) δ 8.12 (s, 1H), 8.62 (s, 1H), 7.76 (s, 1H), 7.31 (m, 1H), 7.28-7.31 (m, 1H), 7.00-7.12 (m, 2H), 6.88-6.98 (m, 4H), 3.87 (s, 2H), 3.49-3.77 (m, 4H), 3.14-3.42 (m, 4H), 1.87-1.89 (m, 4H). LCMS (ESI, m/z): 532 [M+H]+.

Example 11: 5-(Trifluoromethyl)pyridin-3-yl 2-(3-(pyrimidin-5-yloxy)benzyl)-2,7-diazaspiro[3.5]nonane-7-carboxylate

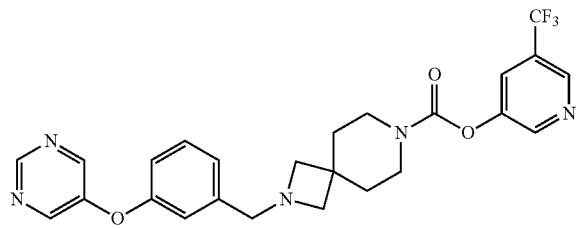 [SMILES: O=C(Oc1cncc(C(F)(F)F)c1)N1CCC2(CC1)CN(Cc1cccc(Oc3cncnc3)c1)C2]

Step 1: Preparation of 3-(pyrimidin-5-yloxy)benzaldehyde

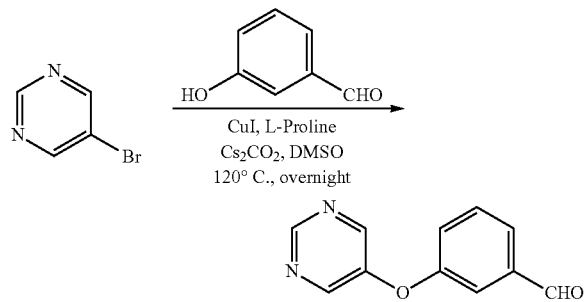

A 250-mL round-bottom flask was charged with 5-bromopyrimidine (3.18 g, 20.0 mmol, 1.00 equiv), 3-hydroxybenzaldehyde (2.44 g, 20.0 mmol, 1.00 equiv), cesium carbonate (13.0 g, 40.0 mmol, 2.00 equiv), copper(I) iodide (380 mg, 2.00 mmol, 0.10 equiv), L-proline (460 mg, 4.00 mmol, 0.20 equiv), and dimethyl sulfoxide (10 mL) under nitrogen. The resulting solution was stirred overnight at 120° C. and quenched with water (50 mL). The mixture was extracted with ethyl acetate (3×50 mL) and the organic layers were combined, washed with brine (3×50 mL), dried over anhydrous sodium sulfate, filtered, and concentrated under reduced pressure. The residue was chromatographed on a silica gel column to provide 1.00 g (25% yield) of 3-(pyrimidin-5-yloxy)benzaldehyde as a yellow oil. LCMS (ESI, m/z): 201 [M+H]+.

Step 2: Preparation of 5-(trifluoromethyl)pyridin-3-yl 2-(3-(pyrimidin-5-yloxy)benzyl)-2,7-diazaspiro[3.5]nonane-7-carboxylate

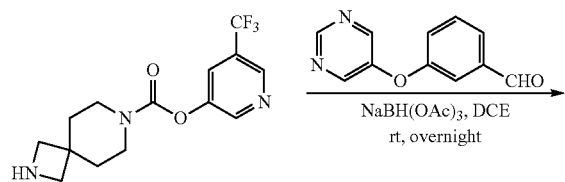

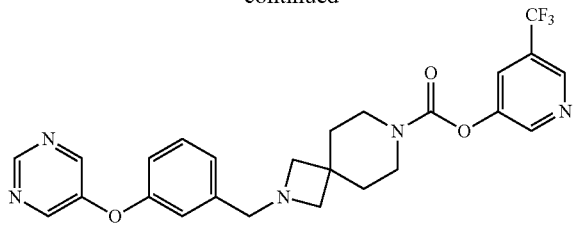

A 50-mL round-bottom flask was charged with 3-(pyrimidin-5-yloxy)benzaldehyde (100 mg, 0.501 mmol, 1.00 equiv), 5-(trifluoromethyl)pyridin-3-yl 2,7-diazaspiro[3.5]nonane-7-carboxylate (189 mg, 0.602 mmol, 1.20 equiv, prepared as described in Example 2, Steps 1-4), triethylamine (151 mg, 1.49 mmol, 3.00 equiv), and 1,2-dichloroethane (10 mL). The resulting solution was stirred for 2 hours at room temperature prior to addition of sodium triacetoxyborohydride (265 mg, 1.25 mmol, 2.50 equiv). The resulting solution was stirred overnight at room temperature and quenched with water (10 mL). The mixture was extracted with dichloromethane (3×10 mL) and the organic layers were combined, washed with water (3×10 mL), dried over anhydrous sodium sulfate, filtered, and concentrated under reduced pressure. The crude product was purified by preparative HPLC to provide 36.5 mg (15% yield) of 5-(trifluoromethyl)pyridin-3-yl 2-(3-(pyrimidin-5-yloxy)benzyl)-2,7-diazaspiro[3.5]nonane-7-carboxylate as a gray semisolid. $^1$H NMR (300 MHz, Chloroform-d) δ 8.98 (s, 1H), 8.72 (s, 1H), 8.62 (s, 1H), 8.48 (s, 2H), 7.77 (s, 1H), 7.34-7.39 (m, 1H), 7.15-7.18 (m, 1H), 7.05 (s, 1H), 6.95-6.98 (m, 1H), 3.70 (s, 2H), 3.49-3.60 (m, 4H), 3.14 (br, 4H), 1.87 (br, 4H). LCMS (ESI, m/z): 500 [M+H]+.

Example 12: 5-(Trifluoromethyl)pyridin-3-yl 2-(3-((6-(trifluoromethyl)pyridin-2-yl)oxy)benzyl)-2,7-diazaspiro[3.5]nonane-7-carboxylate

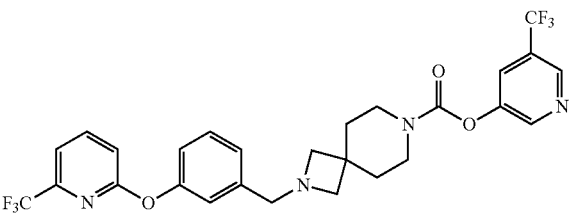 [SMILES: O=C(Oc1cncc(C(F)(F)F)c1)N1CCC2(CC1)CN(Cc1cccc(Oc3cccc(C(F)(F)F)n3)c1)C2]

Step 1: Preparation of 3-((6-(trifluoromethyl)pyridin-2-yl)oxy)benzaldehyde

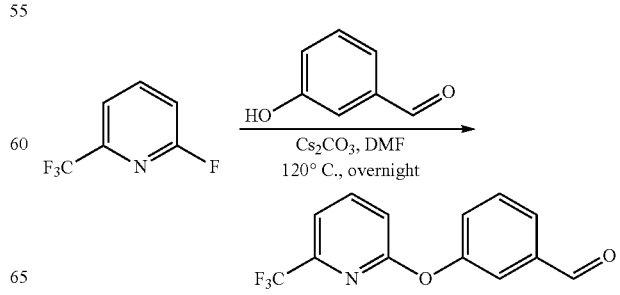

A 100-mL round-bottom flask was charged with 2-fluoro-6-(trifluoromethyl)pyridine (0.330 g, 2.00 mmol, 1.00 equiv), 3-hydroxybenzaldehyde (0.244 g, 2.00 mmol, 1.00 equiv), cesium carbonate (1.30 g, 4.00 mmol, 2.00 equiv), and DMF (15 mL) under nitrogen. The resulting solution was stirred overnight at 120° C. and quenched with water (40 mL). The mixture was extracted with dichloromethane (3×50 mL) and the organic layers were combined, washed with water (3×20 mL), dried over anhydrous sodium sulfate, filtered, and concentrated under reduced pressure. The residue was chromatographed on a silica gel column to provide 0.438 g (82% yield) of 3-((6-(trifluoromethyl)pyridin-2-yl)oxy)benzaldehyde as a yellow solid. LCMS (ESI, m/z): 268 [M+H]$^+$.

Step 2: Preparation of 5-(trifluoromethyl)pyridin-3-yl 2-(3-((6-(trifluoromethyl)pyridin-2-yl)oxy)benzyl)-2,7-diazaspiro[3.5]nonane-7-carboxylate

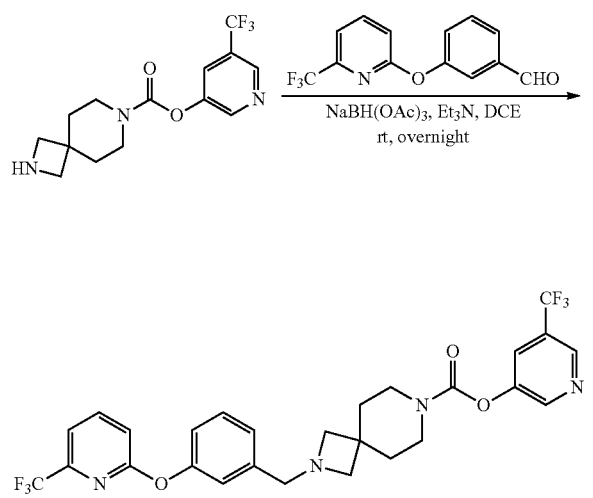

A 50-mL round-bottom flask was charged with 3-((6-(trifluoromethyl)pyridin-2-yl)oxy)benzaldehyde (160 mg, 0.601 mmol, 1.00 equiv), 5-(trifluoromethyl)pyridin-3-yl 2,7-diazaspiro[3.5]nonane-7-carboxylate (189 mg, 0.601 mmol, 1.00 equiv, prepared as described in Example 2, Steps 1-4), triethylamine (121 mg, 1.20 mmol, 2.00 equiv), and 1,2-dichloroethane (10 mL). The resulting solution was stirred for 2 hours at room temperature prior to addition of sodium triacetoxyborohydride (382 mg, 1.80 mmol, 3.00 equiv). The reaction was stirred overnight at room temperature and quenched with water (40 mL). The mixture was extracted with dichloromethane (3×50 mL) and the organic layers were combined, washed with water (3×20 mL), dried over anhydrous sodium sulfate, filtered, and concentrated under reduced pressure. The crude product was purified by preparative HPLC to provide 86.4 mg (25% yield) of 5-(trifluoromethyl)pyridin-3-yl 2-(3-((6-(trifluoromethyl)pyridin-2-yl)oxy)benzyl)-2,7-diazaspiro[3.5]nonane-7-carboxylate as a colorless oil. $^1$H NMR (300 MHz, Chloroform-d) δ 8.50-8.80 (m, 2H), 7.68-7.95 (m, 2H), 7.30-7.50 (m, 2H), 7.10-7.25 (m, 2H), 6.98-7.10 (m, 2H), 3.68 (s, 2H), 3.37-3.63 (m, 4H), 2.92-3.23 (m, 4H), 1.72-1.92 (d, J=3.0 Hz, 4H). LCMS (ESI, m/z): 567 [M+H]$^+$.

Example 13: 5-(Trifluoromethyl)pyridin-3-yl 2-(2-chloro-3-(2-chlorophenoxy)benzyl)-2,7-diazaspiro[3.5]nonane-7-carboxylate

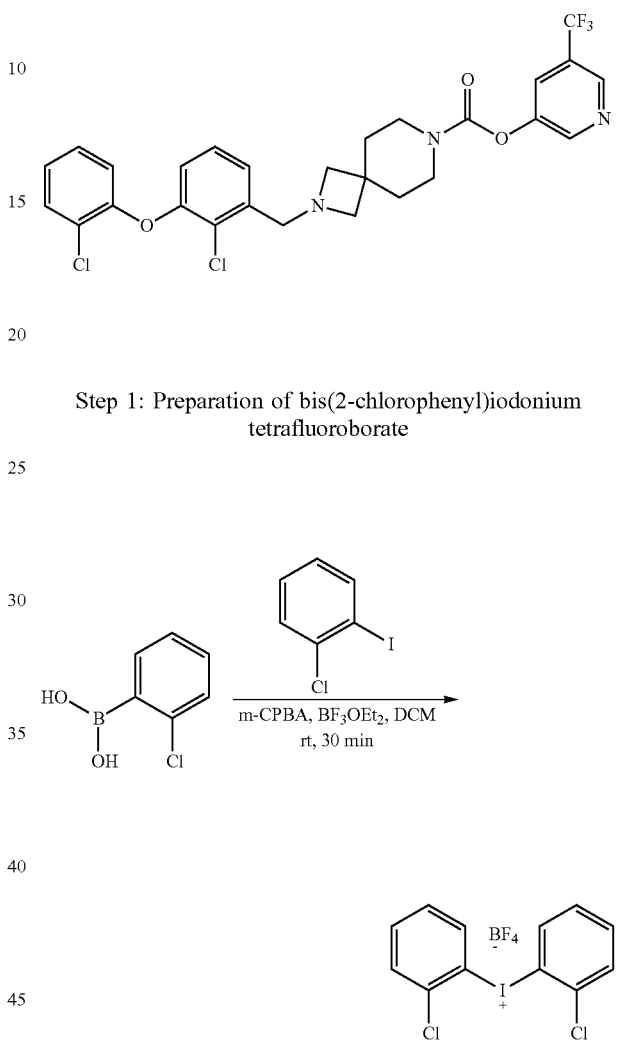

Step 1: Preparation of bis(2-chlorophenyl)iodonium tetrafluoroborate

A 100-mL round-bottom flask was charged with 3-chloroperoxybenzoic acid (1.20 g, 6.94 mmol, 1.12 equiv), 1-chloro-2-iodobenzene (1.48 mg, 6.20 mmol, 1.00 equiv), boron trifluoride etherate (2.18 g, 15.5 mmol, 2.50 equiv), and dichloromethane (30 mL). The resulting solution was stirred at room temperature for 30 minutes, and cooled to 0° C. prior to addition of (2-chlorophenyl)boronic acid (1.08 g, 6.91 mmol, 1.12 equiv). The reaction was stirred for 30 minutes at room temperature and quenched with water (40 mL). The mixture was extracted with dichloromethane (3×50 mL) and the organic layers were combined, washed with water (3×20 mL), dried over anhydrous sodium sulfate, filtered, and concentrated under reduced pressure. The residue was chromatographed on a silica gel column to provide 1.36 g (50% yield) of bis(2-chlorophenyl)iodonium tetrafluoroborate as a yellow oil. LCMS (ESI, m/z): 349 [M-BF$_4$]$^+$.

Step 2: Preparation of 2-chloro-3-(2-chlorophenoxy)benzaldehyde

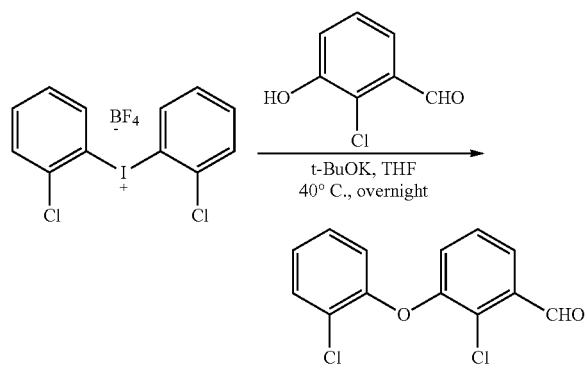

A 100-mL round-bottom flask was charged with 2-chloro-3-hydroxybenzaldehyde (0.366 g, 2.34 mmol, 1.00 equiv), potassium tert-butoxide (0.289 g, 2.58 mmol, 1.10 equiv), bis(2-chlorophenyl)iodonium tetrafluoroborate (1.23 g, 2.82 mmol, 1.20 equiv), and tetrahydrofuran (10 mL). The resulting solution was stirred overnight at 40° C. and quenched with water (40 mL). The mixture was extracted with dichloromethane (3×30 mL) and the organic layers were combined, washed with water (3×10 mL), dried over anhydrous sodium sulfate, filtered, and concentrated under reduced pressure to provide 0.481 g of 2-chloro-3-(2-chlorophenoxy)benzaldehyde as a yellow solid. LCMS (ESI, m/z): 267 [M+H]$^+$.

Step 3: Preparation of 5-(trifluoromethyl)pyridin-3-yl 2-(2-chloro-3-(2-chlorophenoxy)benzyl)-2,7-diazaspiro[3.5]nonane-7-carboxylate

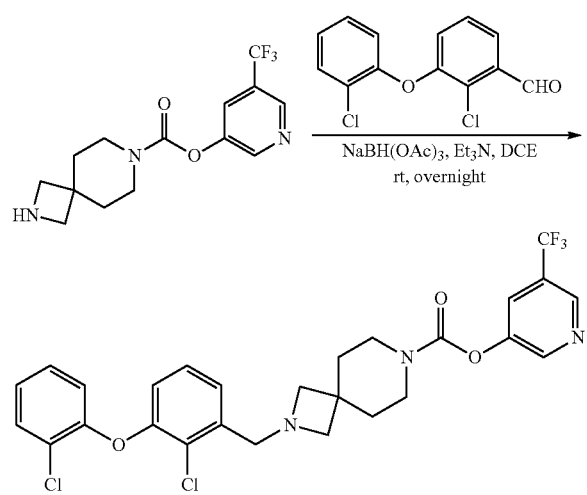

A 50-mL round-bottom flask was charged with 2-chloro-3-(2-chlorophenoxy)benzaldehyde (120 mg, 0.451 mmol, 1.00 equiv), 5-(trifluoromethyl)pyridin-3-yl 2,7-diazaspiro[3.5]nonane-7-carboxylate (141 mg, 0.451 mmol, 1.00 equiv, prepared as described by Example 2, Steps 1-4), triethylamine (91.1 mg, 0.902 mmol, 2.00 equiv), and 1,2-dichloroethane (10 mL). The resulting solution was stirred for 2 hours at room temperature prior to addition of sodium triacetoxyborohydride (286 mg, 1.35 mmol, 3.00 equiv). The reaction was stirred overnight at room temperature and quenched with water (40 mL). The mixture was extracted with dichloromethane (3×50 mL) and the organic layers were combined, washed with water (3×20 mL), dried over anhydrous sodium sulfate, filtered, and concentrated under reduced pressure. The crude product was purified by preparative HPLC to provide 52.8 mg (21% yield) of 5-(trifluoromethyl)pyridin-3-yl 2-(2-chloro-3-(2-chlorophenoxy)benzyl)-2,7-diazaspiro[3.5]nonane-7-carboxylate as a white solid. $^1$H NMR (400 MHz, Chloroform-d) δ 8.72 (s, 1H), 8.63 (d, J=2.4 Hz, 1H), 7.78 (s, 1H), 7.48 (m, 1H), 7.14-7.26 (m, 3H), 7.01-7.14 (m, 1H), 6.81-6.93 (m, 1H), 6.68-6.81 (m, 1H), 3.84 (s, 2H), 3.57-3.70 (m, 2H), 3.45-3.57 (m, 2H), 3.22 (s, 4H), 1.81-2.00 (m, 4H). LCMS (ESI, m/z): 566 [M+H]$^+$.

Example 14: 5-(Trifluoromethyl)pyridin-3-yl 2-(2,4-dichloro-3-phenoxybenzyl)-2,7-diazaspiro[3.5]nonane-7-carboxylate

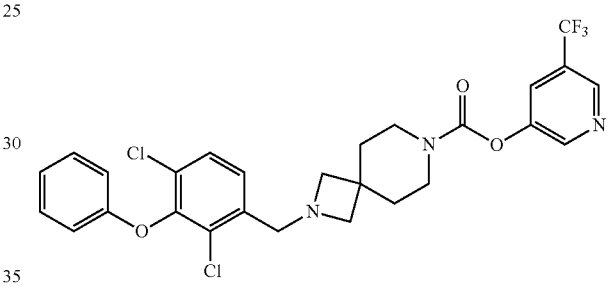

Step 1: Preparation of 2,4-dichloro-3-phenoxybenzaldehyde

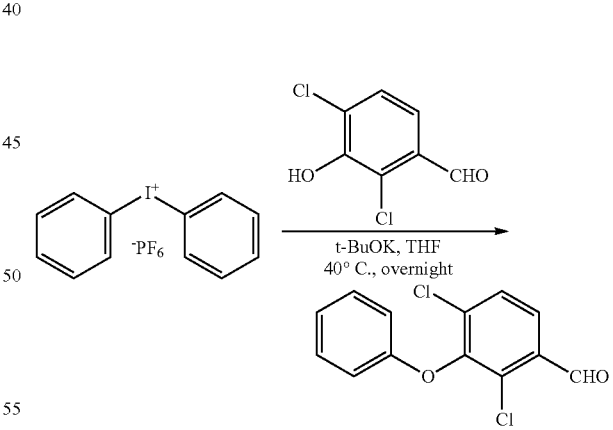

A 100-mL round-bottom flask was charged with 2,4-dichloro-3-hydroxybenzaldehyde (0.380 g, 1.99 mmol, 1.00 equiv), potassium tert-butoxide (0.246 g, 2.19 mmol, 1.10 equiv), diphenyliodonium hexafluorophosphate (1.02 g, 2.39 mmol, 1.20 equiv), and tetrahydrofuran (10 mL). The resulting solution was stirred overnight at 40° C. and quenched with water (40 mL). The mixture was extracted with dichloromethane (3×30 mL) and the organic layers were combined, washed with water (3×10 mL), dried over anhydrous sodium sulfate, filtered, and concentrated under reduced pressure to provide 0.380 g of 2,4-dichloro-3-phenoxybenzaldehyde as a yellow solid. LCMS (ESI, m/z): 267 [M+H]+.

Step 2: Preparation of 5-(trifluoromethyl)pyridin-3-yl 2-(2,4-dichloro-3-phenoxybenzyl)-2,7-diazaspiro[3.5]nonane-7-carboxylate

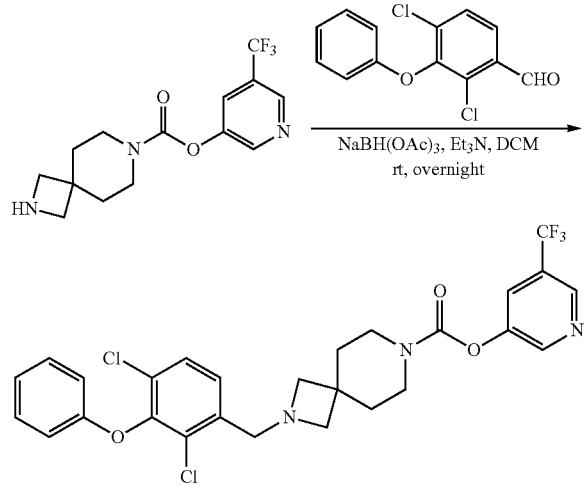

A 50-mL round-bottom flask was charged with 2,4-dichloro-3-phenoxybenzaldehyde (134 mg, 0.500 mmol, 1.00 equiv), 5-(trifluoromethyl)pyridin-3-yl 2,7-diazaspiro[3.5]nonane-7-carboxylate (158 mg, 0.500 mmol, 1.00 equiv, prepared as described in Example 2, Steps 1-4), triethylamine (152 mg, 1.50 mmol, 3.00 equiv), and 1,2-dichloroethane (20 mL). The resulting solution was stirred for 2 hours at room temperature prior to addition of sodium triacetoxyborohydride (318 mg, 1.50 mmol, 3.00 equiv). The reaction was stirred overnight at room temperature and quenched with water (40 mL). The mixture was extracted with dichloromethane (3×50 mL) and the organic layers were combined, washed with water (3×20 mL), dried over anhydrous sodium sulfate, filtered, and concentrated under reduced pressure. The crude product was purified by preparative HPLC to afford 60.3 mg (21% yield) of 5-(trifluoromethyl)pyridin-3-yl 2-(2,4-dichloro-3-phenoxybenzyl)-2,7-diazaspiro[3.5]nonane-7-carboxylate as a white solid. $^1$H NMR (400 MHz, Chloroform-d) δ 8.74 (s, 1H), 8.40-8.68 (d, J=2.3 Hz, 1H), 7.78 (s, 1H), 7.28-7.48 (m, 4H), 6.99-7.15 (m, 1H), 6.73-6.93 (m, 2H), 3.80 (s, 2H), 3.49-3.68 (m, 4H), 3.20 (s, 4H), 1.90 (s, 4H). LCMS (ESI, m/z): 566 [M+H]+.

Example 15: 5-(Methylsulfonamido)pyridin-3-yl 4-(4-chloro-3-isopropoxybenzyl)piperazine-1-carboxylate

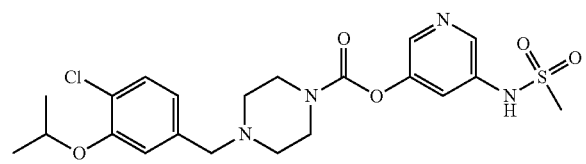 [SMILES: CC(C)Oc1cc(CN2CCN(C(=O)Oc3cncc(NS(C)(=O)=O)c3)CC2)ccc1Cl]

Step 1: Preparation of 5-(methylsulfonamido)pyridin-3-yl 4-(4-chloro-3-isopropoxybenzyl)piperazine-1-carboxylate

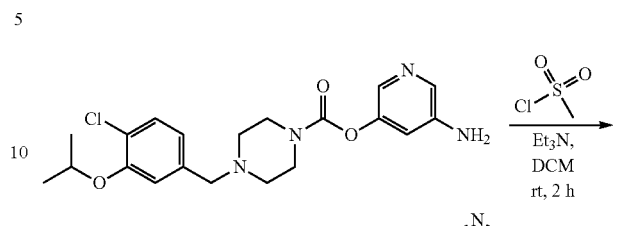

A 50-mL round-bottom flask was charged with 5-aminopyridin-3-yl 4-(4-chloro-3-isopropoxybenzyl)piperazine-1-carboxylate (83.0 mg, 0.200 mmol, 1.00 equiv, prepared as described in Example 6, Steps 1-5), triethylamine (63.6 mg, 0.630 mmol, 3.00 equiv) and dichloromethane (5 mL). Methylsulfonyl chloride (36.2 mg, 0.310 mmol, 1.50 equiv) was added at 0° C. The resulting solution was stirred for 2 hours at room temperature and concentrated under reduced pressure. The crude product was purified by preparative HPLC to provide 83.4 mg (84% yield) of 5-(methylsulfonamido)pyridin-3-yl 4-(4-chloro-3-isopropoxybenzyl)piperazine-1-carboxylate as a yellow solid. $^1$H NMR (300 MHz, Chloroform-d) δ 8.14-8.35 (m, 2H), 7.87-8.14 (m, 1H), 7.52-7.67 (m, 1H), 7.26-7.37 (m, 1H), 6.98 (s, 1H), 6.73-6.91 (m, 1H), 4.45-4.67 (m, 1H), 3.42-3.78 (m, 6H), 3.04 (s, 3H), 2.35-2.57 (m, 4H), 1.30-1.47 (m, 6H). LCMS (ESI, m/z): 483 [M+H]+.

Example 16: 5-Carbamoylpyridin-3-yl 4-(3-carbamoyl-4-chlorobenzyl)piperazine-1-carboxylate

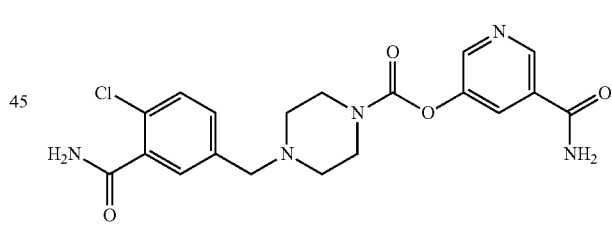

Step 1: Preparation of 2-chloro-5-formylbenzamide

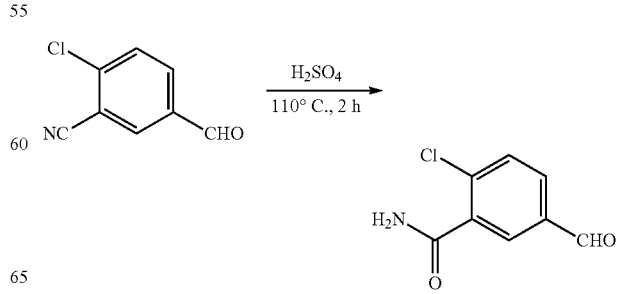

A 50-mL round-bottom flask was charged with 2-chloro-5-formylbenzonitrile (500 mg, 3.00 mmol, 1.00 equiv) and sulfuric acid (10 mL). The resulting solution was stirred for 2 hours at 110° C. and poured into ice-water (20 mL). The mixture was extracted with ethyl acetate (3×30 mL), washed with water (3×10 mL), dried over anhydrous sodium sulfate, filtered, and concentrated under reduced pressure to provide 430 mg (78% yield) of 2-chloro-5-formylbenzamide as a yellow solid.

Step 2: Preparation of 5-carbamoylpyridin-3-yl 4-(3-carbamoyl-4-chlorobenzyl)piperazine-1-carboxylate

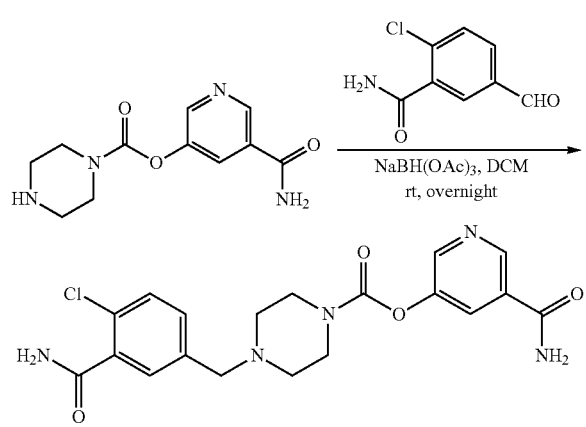

A 40-mL vial was charged with 5-carbamoylpyridin-3-yl piperazine-1-carboxylate (100 mg, 0.400 mmol, 1.00 equiv), 2-chloro-5-formylbenzamide (135 mg, 0.740 mmol, 1.00 equiv) and dichloromethane (10 mL). The resulting solution was stirred for 1 hour at room temperature prior to addition of sodium triacetoxyborohydride (228 mg, 1.08 mmol, 2.00 equiv). The reaction was stirred overnight at room temperature and quenched with water (10 mL). The mixture was extracted with dichloromethane (3×20 mL) and the organic layers were combined, washed with water (3×10 mL), dried over anhydrous sodium sulfate, filtered, and concentrated under reduced pressure. The crude product was purified by preparative HPLC to provide 61.4 mg (37% yield) of 5-carbamoylpyridin-3-yl 4-(3-carbamoyl-4-chlorobenzyl) piperazine-1-carboxylate as a white solid. $^1$H NMR (300 MHz, Methanol-$d_4$) δ 8.82-8.99 (m, 1H), 8.50-8.65 (m, 1H), 8.03-8.14 (m, 1H), 7.48-7.60 (m, 1H), 7.38-7.48 (m, 2H), 3.67-3.85 (m, 2H), 3.51-3.67 (m, 4H), 2.48-2.67 (m, 4H). LCMS (ESI, m/z): 418 [M+H]$^+$.

Example 17: 5-Carbamoylpyridin-3-yl 4-(4-(2-methylpyrrolidin-1-yl)-2-(trifluoromethoxy)benzyl) piperazine-1-carboxylate

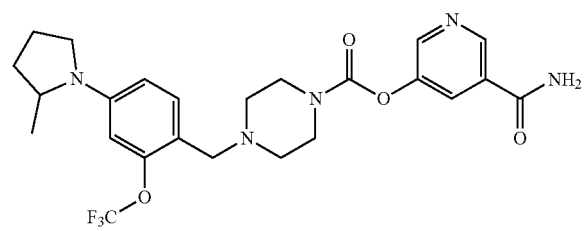 [SMILES: CC1CCCN1c1ccc(CN2CCN(C(=O)Oc3cncc(C(N)=O)c3)CC2)c(OC(F)(F)F)c1]

Step 1: Preparation of 4-(2-methylpyrrolidin-1-yl)-2-(trifluoromethoxy)benzaldehyde

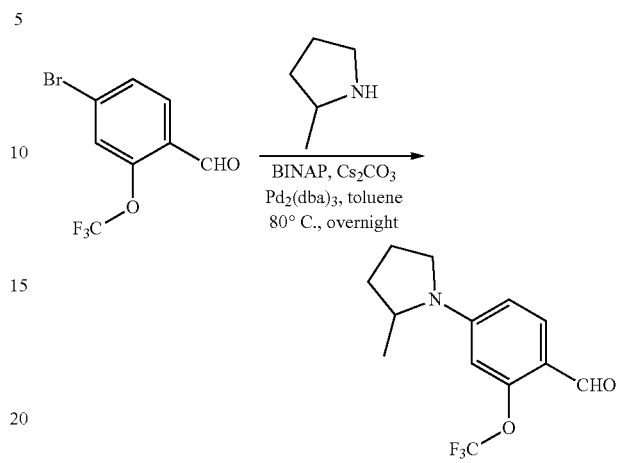

A 50-mL round-bottom flask was charged with 4-bromo-2-(trifluoromethoxy)benzaldehyde (0.500 g, 1.86 mmol, 1.00 equiv), cesium carbonate (1.82 g, 5.59 mmol, 3.00 equiv), 2-methylpyrrolidine (0.367 g, 4.31 mmol, 2.00 equiv), 2,2'-bis(diphenylphosphino)-1,1'-binaphthyl (0.116 g, 0.190 mmol, 0.10 equiv), tris(dibenzylideneacetone)dipalladium (0.100 g, 0.110 mmol, 0.05 equiv), and toluene (10 mL) under nitrogen. The resulting solution was stirred overnight at 80° C. under nitrogen atmosphere and quenched with water (20 mL). The mixture was extracted with ethyl acetate (3×30 mL) and the organic layers were combined, washed with water (3×10 mL), dried over anhydrous sodium sulfate, filtered, and concentrated under reduced pressure. The residue was chromatographed on a silica gel column to provide 0.300 g (59% yield) of 4-(2-methylpyrrolidin-1-yl)-2-(trifluoromethoxy)benzaldehyde as a white oil. LCMS (ESI, m/z): 274 [M+H]$^+$.

Step 2: Preparation of tert-butyl 4-(chlorocarbonyl)piperazine-1-carboxylate

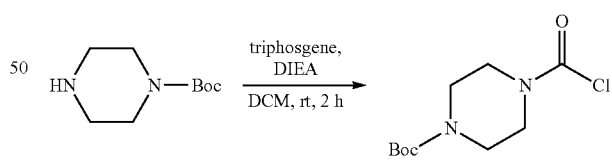

A 100-mL round-bottom flask was charged with tert-butyl piperazine-1-carboxylate (2.86 g, 15.4 mmol, 1.00 equiv), triphosgene (2.29 g, 7.71 mmol, 0.50 equiv) and dichloromethane (20 mL). DIPEA (7.95 g, 61.5 mmol, 4.00 equiv) was added at 0° C. and the resulting solution was stirred for 2 hours at room temperature. The reaction was quenched with water (20 mL), extracted with dichloromethane (3×30 mL), and the organic layers were combined, washed with water (3×10 mL), dried over anhydrous sodium sulfate, filtered, and concentrated under reduced pressure to provide 3.82 g of tert-butyl 4-(chlorocarbonyl)piperazine-1-carboxylate as a yellow solid.

Step 3: Preparation of 1-(tert-butyl) 4-(5-carbamoylpyridin-3-yl) piperazine-1,4-dicarboxylate

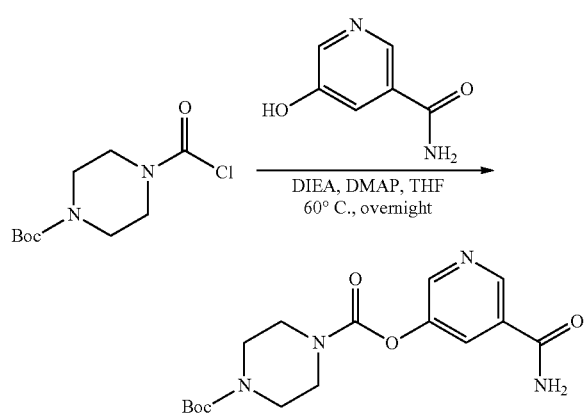

A 50-mL round-bottom flask was charged with 5-hydroxypyridine-3-carboxamide (276 mg, 2.00 mmol, 1.00 equiv), tert-butyl 4-(chlorocarbonyl)piperazine-1-carboxylate (598 mg, 2.40 mmol, 1.20 equiv), 4-dimethylaminopyridine (48.8 mg, 0.400 mmol, 0.20 equiv), DIPEA (774 mg, 5.99 mmol, 3.00 equiv) and tetrahydrofuran (10 mL). The resulting solution was stirred overnight at 60° C. and quenched with water (20 mL). The mixture was extracted with ethyl acetate (3×30 mL) and the organic layers were combined, washed with water (3×10 mL), dried over anhydrous sodium sulfate, filtered, and concentrated under reduced pressure. The residue was chromatographed on a silica gel column to provide 437 mg (62% yield) of 1-(tert-butyl) 4-(5-carbamoylpyridin-3-yl) piperazine-1,4-dicarboxylate as a white oil. LCMS (ESI, m/z): 351 [M+H]+.

Step 4: Preparation of 5-carbamoylpyridin-3-yl piperazine-1-carboxylate

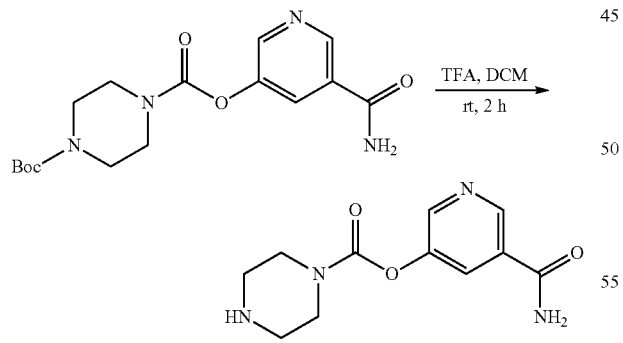

A 50-mL round-bottom flask was charged with 1-(tert-butyl) 4-(5-carbamoylpyridin-3-yl) piperazine-1,4-dicarboxylate (200 mg, 0.570 mmol, 1.00 equiv), trifluoroacetic acid (1 mL) and dichloromethane (4 mL). The resulting solution was stirred for 2 hours at room temperature and concentrated under reduced pressure to provide 143 mg of 5-carbamoylpyridin-3-yl piperazine-1-carboxylate as a white oil. LCMS (ESI, m/z): 251 [M+H]+.

Step 5: Preparation of 5-carbamoylpyridin-3-yl 4-(4-(2-methylpyrrolidin-1-yl)-2-(trifluoromethoxy)benzyl)piperazine-1-carboxylate

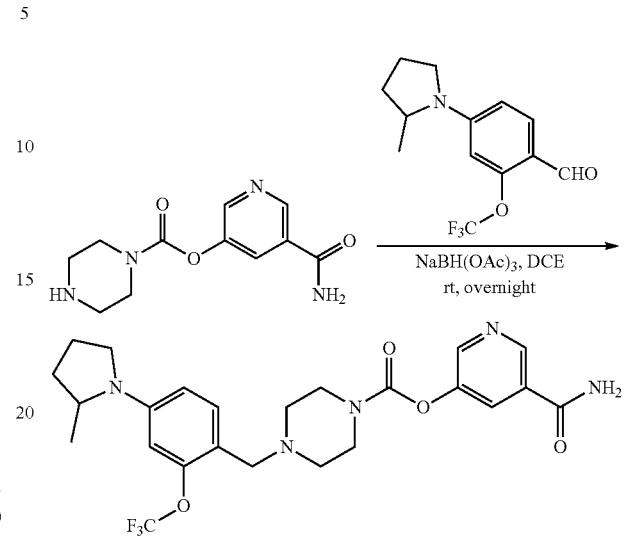

A 50-mL round-bottom flask was charged with 5-carbamoylpyridin-3-yl piperazine-1-carboxylate (107 mg, 0.430 mmol, 1.00 equiv), 4-(2-methylpyrrolidin-1-yl)-2-(trifluoromethoxy)benzaldehyde (117 mg, 0.430 mmol, 1.00 equiv) and 1,2-dichloroethane (5 mL). The resulting solution was stirred for 1 hour at room temperature prior to addition of sodium triacetoxyborohydride (182 mg, 0.860 mmol, 2.00 equiv). The reaction was stirred overnight at room temperature and quenched with water (10 mL). The mixture was extracted with dichloromethane (3×30 mL) and the organic layers were combined, washed with water (3×10 mL), dried over anhydrous sodium sulfate, filtered, and concentrated under reduced pressure. The crude product was purified by preparative HPLC to provide 14.5 mg (8% yield) of 5-carbamoylpyridin-3-yl 4-(4-(2-methylpyrrolidin-1-yl)-2-(trifluoromethoxy)benzyl)piperazine-1-carboxylate as a white solid. 1H NMR (300 MHz, Chloroform-d) δ 8.75-8.87 (m, 1H), 8.50-8.61 (m, 1H), 7.92-7.98 (m, 1H), 7.16-7.25 (m, 1H), 6.43-6.50 (m, 1H), 6.38 (s, 1H), 6.05-6.31 (m, 1H), 5.59-5.95 (m, 1H), 3.34-3.92 (m, 8H), 3.05-3.22 (m, 1H), 2.50 (s, 4H), 1.91-2.17 (m, 3H), 3.78-2.87 (m, 1H), 1.10-1.24 (m, 3H). LCMS (ESI, m/z): 508 [M+H]+.

Example 18: 5-Carbamoylpyridin-3-yl 4-(4-isopropoxy-2-(trifluoromethoxy)benzyl)piperazine-1-carboxylate

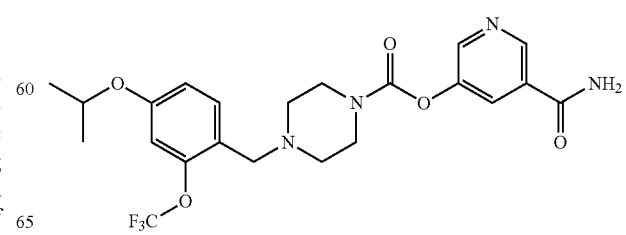

Step 1: Preparation of tert-butyl 4-(4-bromo-2-(trifluoromethoxy)benzyl)piperazine-1-carboxylate

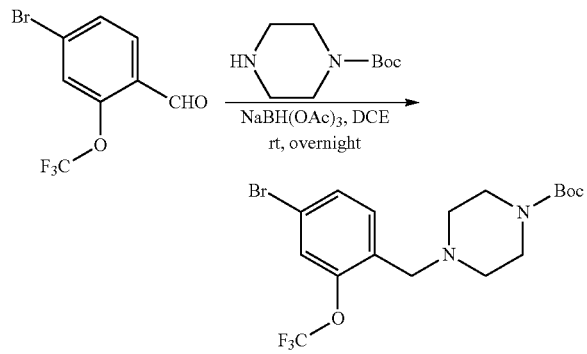

A 100-mL round-bottom flask was charged with 4-bromo-2-(trifluoromethoxy)benzaldehyde (1.08 g, 4.00 mmol, 1.00 equiv), tert-butyl piperazine-1-carboxylate (0.823 g, 4.42 mmol, 1.10 equiv) and 1,2-dichloroethane (50 mL). The resulting solution was stirred for 1 hour at room temperature prior to addition of sodium triacetoxyborohydride (1.70 g, 8.00 mmol, 2.00 equiv). The resulting solution was stirred overnight at room temperature and quenched with water (30 mL). The mixture was extracted with dichloromethane (3×50 mL) and the organic layers were combined, washed with water (3×30 mL), dried over anhydrous sodium sulfate, filtered, and concentrated under reduced pressure. The residue was chromatographed on a silica gel column to provide 0.980 g (55.6% yield) of tert-butyl 4-(4-bromo-2-(trifluoromethoxy)benzyl)piperazine-1-carboxylate as a white solid. LCMS (ESI, m/z): 439 [M+H]$^+$.

Step 2: Preparation of tert-butyl 4-(4-hydroxy-2-(trifluoromethoxy)benzyl)piperazine-1-carboxylate

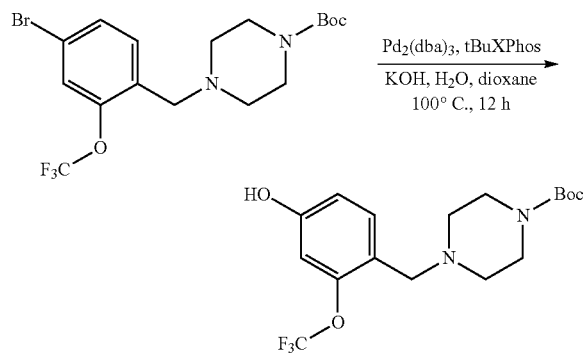

A 40-mL vial was charged with tert-butyl 4-(4-bromo-2-(trifluoromethoxy)benzyl)piperazine-1-carboxylate (880 mg, 2.00 mmol, 1.00 equiv), tris(dibenzylideneacetone)dipalladium (183 mg, 0.200 mmol, 0.10 equiv), 2-di-tert-butylphosphino-2',4',6'-triisopropylbiphenyl (85.1 mg, 0.200 mmol, 0.10 equiv), potassium hydroxide (449 mg, 8.01 mmol, 4.00 equiv), water (2 mL) and 1,4-dioxane (8 mL) under nitrogen atmosphere. The resulting solution was stirred for 12 hours at 100° C. and quenched with water (10 mL). The mixture was extracted with dichloromethane (3×30 mL) and the organic layers were combined, washed with water (3×20 mL), dried over anhydrous sodium sulfate, filtered, and concentrated under reduced pressure. The residue was chromatographed on a silica gel column to provide 661 mg (87.7% yield) of tert-butyl 4-(4-hydroxy-2-(trifluoromethoxy)benzyl)piperazine-1-carboxylate as a white solid. LCMS (ESI, m/z): 377 [M+H]$^+$.

Step 3: Preparation of tert-butyl 4-(4-isopropoxy-2-(trifluoromethoxy)benzyl)piperazine-1-carboxylate

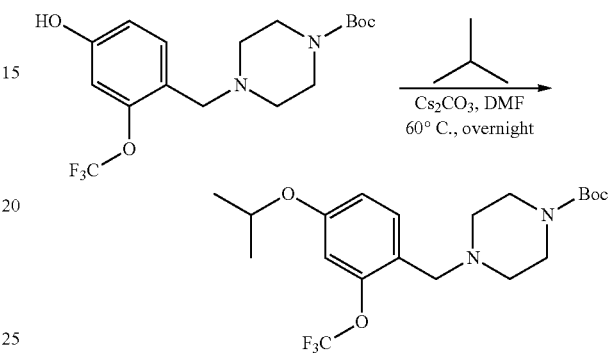

A 40-mL vial was charged with tert-butyl 4-(4-hydroxy-2-(trifluoromethoxy)benzyl)piperazine-1-carboxylate (0.500 g, 1.33 mmol, 1.00 equiv), 2-iodopropane (0.248 g, 1.46 mmol, 1.10 equiv), cesium carbonate (1.30 g, 3.98 mmol, 3.00 equiv) and dimethyl formamide (15 mL). The reaction was stirred overnight at 60° C. and diluted with water (5 mL). The resulting solution was extracted with ethyl acetate (3×30 mL) and the organic layers were combined, washed with brine (2×20 mL), dried over anhydrous sodium sulfate, filtered, and concentrated under reduced pressure. The residue was chromatographed on a silica gel column to provide 420 mg (76% yield) of tert-butyl 4-(4-isopropoxy-2-(trifluoromethoxy)benzyl)piperazine-1-carboxylate as a yellow oil. LCMS (ESI, m/z): 419 [M+H]$^+$.

Step 4: Preparation of 4-(4-isopropoxy-2-(trifluoromethoxy)benzyl)piperazine-1-carbonyl chloride

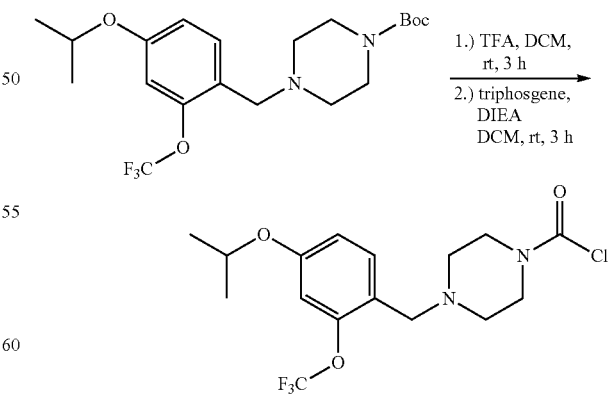

A 40-mL vial was charged with tert-butyl 4-(4-isopropoxy-2-(trifluoromethoxy)benzyl)piperazine-1-carboxylate (200 mg, 0.480 mmol, 1.00 equiv), dichloromethane (10 mL) and trifluoroacetic acid (2 mL). The resulting solution was stirred for 3 hours at room temperature and concentrated under reduced pressure to provide 152 mg of 1-(4-isopropoxy-2-(trifluoromethoxy)benzyl)piperazine as a white solid (LCMS (ESI, m/z): 319 [M+H]+). This crude product was transferred to a 40-mL vial to which triphosgene (71.3 mg, 0.240 mmol, 0.50 equiv) and dichloromethane (15 mL) were added. DIPEA (278 mg, 2.16 mmol, 4.50 equiv) was added dropwise at 0° C. The reaction was stirred for 2 hours at room temperature and diluted with water (5 mL). The mixture was extracted with dichloromethane (3×5 mL) and the organic layers were combined, washed with brine (3×5 mL) and dried over anhydrous sodium sulfate, filtered, and concentrated under reduced pressure to provide 182 mg of 4-(4-isopropoxy-2-(trifluoromethoxy)benzyl)piperazine-1-carbonyl chloride as a yellow solid.

Step 5: Preparation of 5-carbamoylpyridin-3-yl 4-(4-isopropoxy-2-(trifluoromethoxy)benzyl)piperazine-1-carboxylate

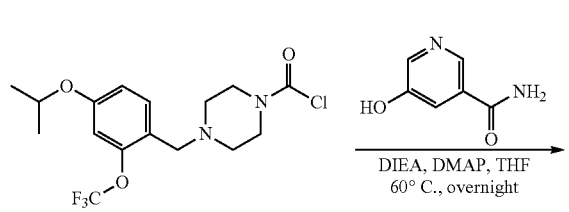

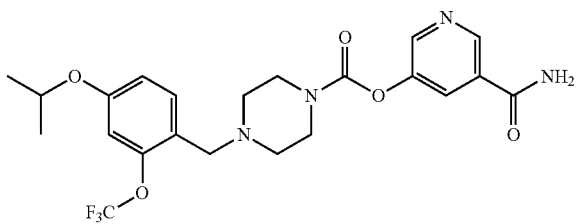 [SMILES: CC(C)Oc1ccc(CN2CCN(C(=O)Oc3cncc(C(N)=O)c3)CC2)c(OC(F)(F)F)c1]

A 40-mL vial was charged with 4-(4-isopropoxy-2-(trifluoromethoxy)benzyl)piperazine-1-carbonyl chloride (182 mg, 0.480 mmol, 1.00 equiv), 5-hydroxypyridine-3-carboxamide (66.0 mg, 0.480 mmol, 1.00 equiv), 4-dimethylaminopyridine (11.7 mg, 0.100 mmol, 0.20 equiv), DIPEA (124 mg, 0.960 mmol, 2.00 equiv) and tetrahydrofuran (15 mL). The resulting solution was stirred overnight at 60° C. and quenched with water (20 mL). The mixture was extracted with dichloromethane (3×30 mL) and the organic layers were combined, washed with water (3×10 mL), dried over anhydrous sodium sulfate, filtered, and concentrated under reduced pressure. The crude product was purified by preparative HPLC to afford 60.3 mg (26% yield) of 5-carbamoylpyridin-3-yl 4-(4-isopropoxy-2-(trifluoromethoxy)benzyl)piperazine-1-carboxylate as a white solid. $^1$H NMR (300 MHz, Methanol-$d_4$) δ 8.89-8.90 (m, 1H), 8.56-8.57 (m, 1H), 8.08-8.10 (m, 1H), 7.45-7.49 (m, 1H), 6.92-6.95 (m, 1H), 6.81-6.82 (m, 1H), 4.59-4.67 (m, 1H), 3.75 (br, 2H), 3.58 (br, 4H), 2.56 (br, 4H), 1.33-1.35 (m, 6H). LCMS (ESI, m/z): 483 [M+H]+.

Example 19: 5-Cyanopyridin-3-yl (R)-2-methyl-4-((4-(trifluoromethyl)pyridin-3-yl)methyl)piperazine-1-carboxylate

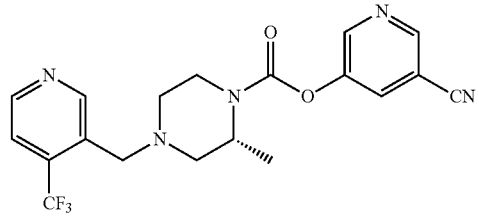 [SMILES: C[C@@H]1CN(Cc2cnccc2C(F)(F)F)CCN1C(=O)Oc1cncc(C#N)c1]

Step 1: Preparation of tert-butyl (R)-4-(chlorocarbonyl)-3-methylpiperazine-1-carboxylate

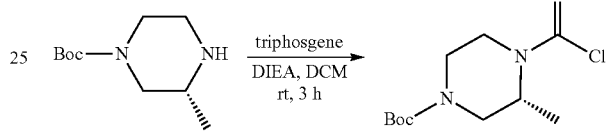

A 100-mL round-bottom flask was charged with triphosgene (0.743 g, 2.50 mmol, 0.50 equiv), tert-butyl (R)-3-methylpiperazine-1-carboxylate (1.00 g, 5.00 mmol, 1.00 equiv), and dichloromethane (10 mL). DIPEA (1.94 g, 15.0 mmol, 3.00 equiv) was added at 0° C. The reaction was stirred for 3 hours at room temperature and quenched with water (80 mL). The mixture was extracted with dichloromethane (2×100 mL) and the organic layers were combined, washed with brine (2×80 mL), dried over anhydrous sodium sulfate, filtered, and concentrated under reduced pressure to provide 1.40 g of tert-butyl (R)-4-(chlorocarbonyl)-3-methylpiperazine-1-carboxylate as a yellow oil. LCMS (ESI, m/z): 263 [M+H]+.

Step 2: Preparation of 4-(tert-butyl) 1-(5-cyanopyridin-3-yl) (R)-2-methylpiperazine-1,4-dicarboxylate

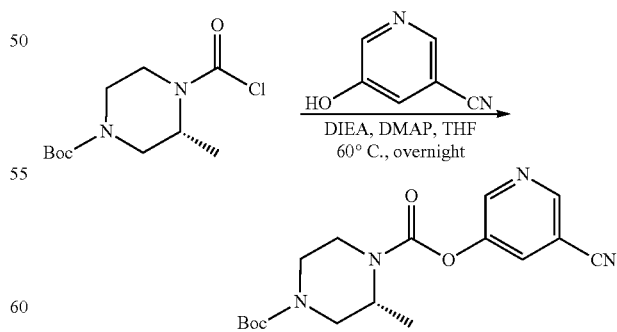

A 50-mL round-bottom flask was charged with tert-butyl (R)-4-(chlorocarbonyl)-3-methylpiperazine-1-carboxylate (1.31 g, 5.00 mmol, 1.00 equiv), 5-hydroxypyridine-3-carbonitrile (0.720 g, 6.00 mmol, 1.20 equiv), DIPEA (1.94 g, 15.0 mmol, 3.00 equiv), 4-dimethylaminopyridine (0.122 g, 1.00 mmol, 0.20 equiv), and tetrahydrofuran (10 mL). The reaction was stirred overnight at 60° C. and quenched with water (50 mL). The resulting solution was extracted with dichloromethane (2×80 mL) and the organic layers were combined, washed with brine (2×50 mL), dried over anhydrous sodium sulfate, filtered, and concentrated under reduced pressure. The residue was chromatographed on a silica gel column to provide 1.30 g (75% yield) of 4-(tert-butyl) 1-(5-cyanopyridin-3-yl) (R)-2-methylpiperazine-1,4-dicarboxylate as a yellow solid. LCMS (ESI, m/z): 347 [M+H]+.

Step 3: Preparation of 5-cyanopyridin-3-yl (R)-2-methylpiperazine-1-carboxylate

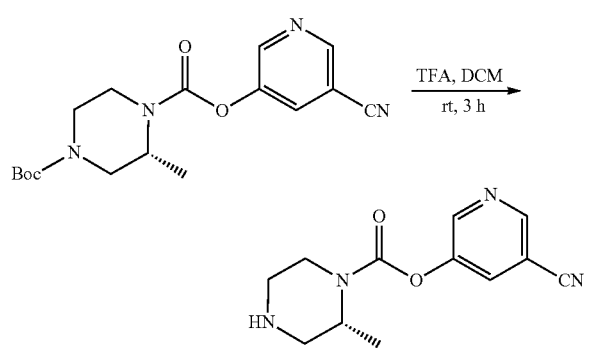

A 50-mL round-bottom flask was charged with 4-(tert-butyl) 1-(5-cyanopyridin-3-yl) (R)-2-methylpiperazine-1,4-dicarboxylate (750 mg, 2.17 mmol, 1.00 equiv), dichloromethane (10 mL), and trifluoroacetic acid (2 mL). The resulting solution was stirred for 3 hours at room temperature and concentrated under reduced pressure to provide 800 mg of 5-cyanopyridin-3-yl (R)-2-methylpiperazine-1-carboxylate as a yellow oil. LCMS (ESI, m/z): 247 [M+H]+.

Step 4: Preparation of 5-cyanopyridin-3-yl (R)-2-methyl-4-((4-(trifluoromethyl)pyridin-3-yl)methyl) piperazine-1-carboxylate

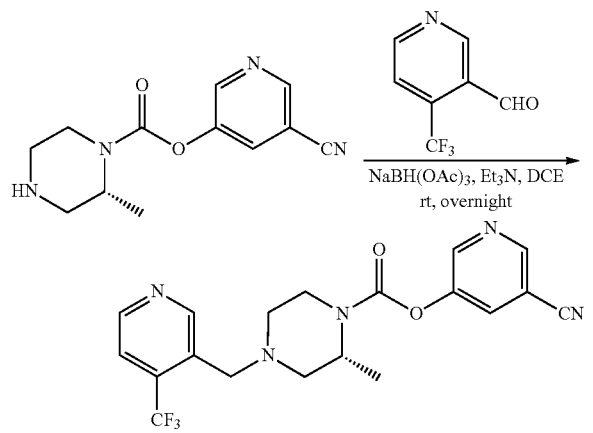

A 50-mL round-bottom flask was charged with 5-cyanopyridin-3-yl (R)-2-methylpiperazine-1-carboxylate (179 mg, 0.727 mmol, 1.20 equiv), 4-(trifluoromethyl)pyridine-3-carbaldehyde (106 mg, 0.606 mmol, 1.00 equiv), triethylamine (184 mg, 1.82 mmol, 3.00 equiv), and 1,2-dichloroethane (10 mL). The mixture was stirred for 1 hour at room temperature prior to addition of sodium triacetoxyborohydride (386 mg, 1.82 mmol, 3.00 equiv). The reaction was stirred overnight at room temperature and quenched with water (30 mL). The resulting solution was extracted with dichloromethane (2×50 mL) and the organic layers were combined, washed with brine (2×30 mL), dried over anhydrous sodium sulfate, filtered, and concentrated under reduced pressure. The crude product (300 mg) was purified by preparative HPLC to afford 94.9 mg (39% yield) of 5-cyanopyridin-3-yl (R)-2-methyl-4-((4-(trifluoromethyl) pyridin-3-yl)methyl)piperazine-1-carboxylate as a yellow oil. $^1$H NMR (300 MHz, Chloroform-d) δ 9.02 (s, 1H), 8.71-8.73 (m, 2H), 8.64 (s, 1H), 7.84 (s, 1H), 7.54 (d, J=5.1 Hz, 1H), 4.41 (br, 1H), 3.99-4.03 (m, 1H), 3.73 (s, 2H), 3.48 (br, 1H), 2.84-2.87 (m, 1H), 2.69-2.73 (m, 1H), 2.42-2.47 (m, 1H), 2.01-2.31 (m, 1H), 1.41-1.42 (m, 3H). LCMS (ESI, m/z): 406 [M+H]+.

Example 20: 5-Carbamoylpyridin-3-yl (R)-4-(3-fluoro-5-(trifluoromethyl)benzyl)-2-methylpiperazine-1-carboxylate

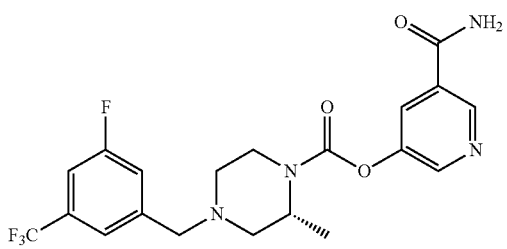 [SMILES: C[C@@H]1CN(Cc2cc(F)cc(C(F)(F)F)c2)CCN1C(=O)Oc1cncc(C(N)=O)c1]

Step 1: Preparation of tert-butyl (R)-4-(3-fluoro-5-(trifluoromethyl)benzyl)-2-methylpiperazine-1-carboxylate

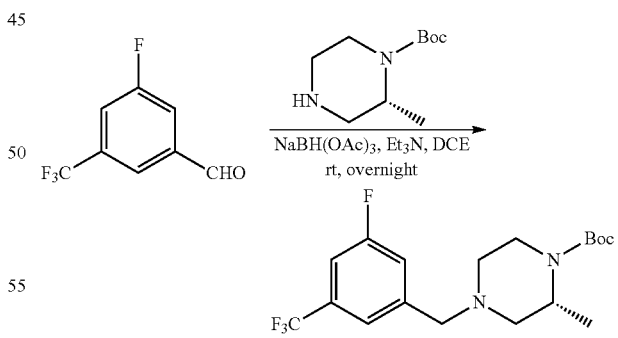

A 100-mL round-bottom flask was charged with 3-fluoro-5-(trifluoromethyl)benzaldehyde (2.00 g, 10.4 mmol, 1.00 equiv), tert-butyl (R)-2-methylpiperazine-1-carboxylate (2.50 g, 12.5 mmol, 1.20 equiv), triethylamine (3.16 g, 31.2 mmol, 3.00 equiv), and 1,2-dichloroethane (20 mL). The mixture was stirred for 30 minutes at room temperature prior to addition of sodium triacetoxyborohydride (6.63 g, 31.2 mmol, 3.00 equiv). The reaction was stirred overnight at room temperature and quenched with water (20 mL). The resulting solution was extracted with dichloromethane (3×30 mL) and the organic layers were combined, washed with brine (2×10 mL), dried over anhydrous sodium sulfate, filtered, and concentrated under reduced pressure. The residue was chromatographed on a silica gel column to provide 3.00 g (77% yield) of tert-butyl (R)-4-(3-fluoro-5-(trifluoromethyl)benzyl)-2-methylpiperazine-1-carboxylate as a colorless oil. LCMS (ESI, m/z): 377 [M+H]$^+$.

Step 2: Preparation of (R)-1-(3-fluoro-5-(trifluoromethyl)benzyl)-3-methylpiperazine

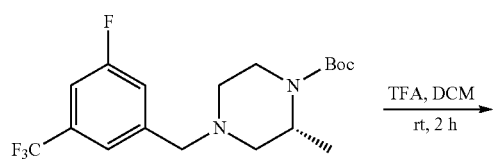

A 100-mL round-bottom flask was charged with tert-butyl (R)-4-(3-fluoro-5-(trifluoromethyl)benzyl)-2-methylpiperazine-1-carboxylate (2.00 g, 5.31 mmol, 1.00 equiv), dichloromethane (20 mL), and trifluoroacetic acid (5 mL). The resulting solution was stirred for 2 hours at room temperature and concentrated under reduced pressure. The crude product was dissolved in saturated NaHCO$_3$ solution (20 mL) and extracted with dichloromethane (3×60 mL). The organic layers were combined, washed with brine (2×20 mL), dried over anhydrous sodium sulfate, filtered, and concentrated under reduced pressure to provide 1.87 g of (R)-1-(3-fluoro-5-(trifluoromethyl)benzyl)-3-methylpiperazine as a light yellow oil. LCMS (ESI, m/z): 277 [M+H]$^+$.

Step 3: Preparation of (R)-4-(3-fluoro-5-(trifluoromethyl)benzyl)-2-methylpiperazine-1-carbonyl Chloride

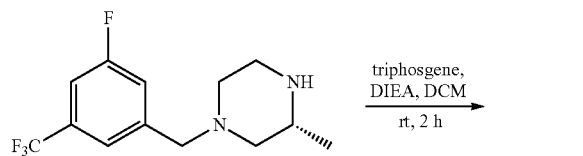

A 50-mL round-bottom flask was charged with triphosgene (646 mg, 2.18 mmol, 0.50 equiv), dichloromethane (10 mL), (R)-1-(3-fluoro-5-(trifluoromethyl)benzyl)-3-methylpiperazine (1.20 g, 4.34 mmol, 1.00 equiv). DIPEA (2.24 g, 17.4 mmol, 4.00 equiv) was added dropwise 0° C. The reaction was stirred for 2 hours at room temperature and quenched with water (10 mL). The resulting solution was extracted with dichloromethane (3×20 mL) and the organic layers were combined, washed with brine (2×10 mL), dried over anhydrous sodium sulfate, filtered, and concentrated under reduced pressure to provide 1.40 g (95% yield) of (R)-4-(3-fluoro-5-(trifluoromethyl)benzyl)-2-methylpiperazine-1-carbonyl chloride as a yellow oil. LCMS (ESI, m/z): 339 [M+H]$^+$.

Step 4: Preparation of 5-carbamoylpyridin-3-yl (R)-4-(3-fluoro-5-(trifluoromethyl)benzyl)-2-methylpiperazine-1-carboxylate

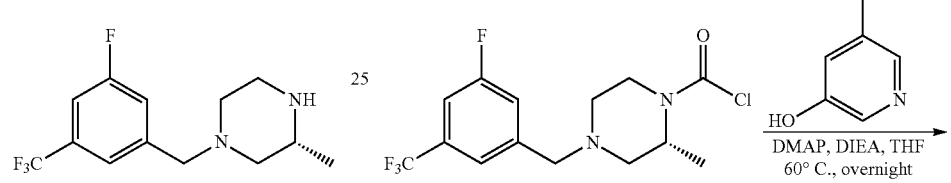

A 25-mL round-bottom flask was charged with (R)-4-(3-fluoro-5-(trifluoromethyl)benzyl)-2-methylpiperazine-1-carbonyl chloride (350 mg, 1.03 mmol, 1.00 equiv), 5-hydroxypyridine-3-carboxamide (171 mg, 1.24 mmol, 1.20 equiv), 4-dimethylaminopyridine (25.2 mg, 0.206 mmol, 0.20 equiv), DIPEA (400 mg, 3.10 mmol, 3.00 equiv), and tetrahydrofuran (5 mL). The reaction was stirred overnight at 60° C. and quenched with water (10 mL). The resulting solution was extracted with dichloromethane (3×20 mL) and the organic layers were combined, washed with brine (2×10 mL), dried over anhydrous sodium sulfate, filtered, and concentrated under reduced pressure. The crude product (400 mg) was purified by preparative HPLC to provide 96.9 mg (21% yield) of 5-carbamoylpyridin-3-yl (R)-4-(3-fluoro-5-(trifluoromethyl)benzyl)-2-methylpiperazine-1-carboxylate as an off-white solid. $^1$H NMR (300 MHz, Chloroform-d) δ 8.83 (d, J=1.5 Hz, 1H), 8.58 (d, J=2.4 Hz, 1H), 7.98 (t, J=2.2 Hz, 1H), 7.44 (s, 1H), 7.31 (d, J=9.3 Hz, 1H), 7.24 (d, J=8.4 Hz, 1H), 6.03-6.41 (m, 2H), 4.40 (br, 1H), 4.02 (br, 1H), 3.62-3.66 (m, 1H), 3.31-3.53 (m, 2H), 2.84-2.88 (m, 1H), 2.64-2.68 (m, 1H), 2.18-2.35 (m, 2H), 1.41 (d, J=5.7 Hz, 3H). LCMS (ESI, m/z): 441 [M+H]$^+$.

Example 21: 5-Cyano-2-methylpyridin-3-yl (R)-2-methyl-4-(2-methyl-3-(trifluoromethyl)benzyl)piperazine-1-carboxylate

Step 1: Preparation of 5-hydroxy-6-methylnicotinonitrile

Step 2: Preparation of 5-cyano-2-methylpyridin-3-yl (R)-2-methyl-4-(2-methyl-3-(trifluoromethyl)benzyl)piperazine-1-carboxylate

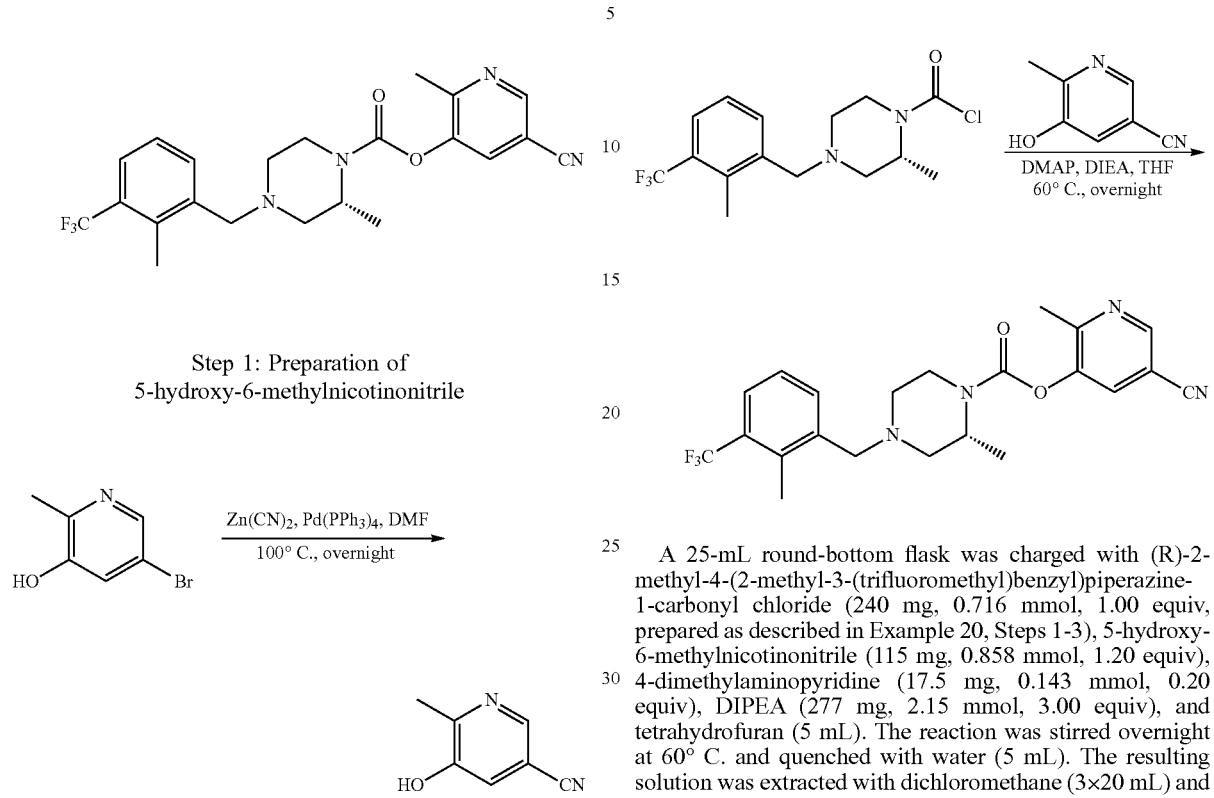

A 50-mL round-bottom flask was charged with 5-bromo-2-methylpyridin-3-ol (1.00 g, 5.32 mmol, 1.00 equiv), zinc cyanide (802 mg, 6.83 mmol, 1.30 equiv), tetrakis(triphenylphosphane)palladium (615 mg, 0.532 mmol, 0.10 equiv), and DMF (10 mL). The reaction was stirred overnight at 100° C. and quenched with water (10 mL). The resulting solution was extracted with ethyl acetate (3×20 mL) and the organic layers were combined, washed with brine (2×5 mL), dried over anhydrous sodium sulfate, filtered, and concentrated under reduced pressure. The residue was chromatographed on a silica gel column to provide 250 mg (35% yield) of 5-hydroxy-6-methylnicotinonitrile as a brown solid. LCMS (ESI, m/z): 135 [M+H]+.

A 25-mL round-bottom flask was charged with (R)-2-methyl-4-(2-methyl-3-(trifluoromethyl)benzyl)piperazine-1-carbonyl chloride (240 mg, 0.716 mmol, 1.00 equiv, prepared as described in Example 20, Steps 1-3), 5-hydroxy-6-methylnicotinonitrile (115 mg, 0.858 mmol, 1.20 equiv), 4-dimethylaminopyridine (17.5 mg, 0.143 mmol, 0.20 equiv), DIPEA (277 mg, 2.15 mmol, 3.00 equiv), and tetrahydrofuran (5 mL). The reaction was stirred overnight at 60° C. and quenched with water (5 mL). The resulting solution was extracted with dichloromethane (3×20 mL) and the organic layers were combined, washed with brine (2×10 mL), dried over anhydrous sodium sulfate, filtered, and concentrated under reduced pressure. The crude product (300 mg) was purified by preparative HPLC to afford 95.3 mg (31% yield) of 5-cyano-2-methylpyridin-3-yl (R)-2-methyl-4-(2-methyl-3-(trifluoromethyl)benzyl)piperazine-1-carboxylate as a white solid. $^1$H NMR (300 MHz, Chloroform-d) δ 8.61 (d, J=1.8 Hz, 1H), 7.74 (d, J=1.8 Hz, 1H), 7.59 (d, J=7.8 Hz, 1H), 7.45 (d, J=7.5 Hz, 1H), 7.22-7.26 (m, 1H), 4.41 (br, 1H), 3.98 (br, 1H), 3.49-3.59 (m, 2H), 3.28-3.32 (m, 1H), 2.81-2.85 (m, 1H), 2.68-2.71 (m, 1H), 2.48-2.53 (m, 6H), 2.34-2.38 (m, 1H), 2.12-2.21 (m, 1H), 1.38 (br, 3H). LCMS (ESI, m/z): 433 [M+H]+.

Examples 22-86

Examples 22-86 were prepared by similar procedures as described in Examples 1-21.

| Ex | Name | Structure | NMR ($^1$H NMR, 300 MHz or 400 MHz, Chloroform-d) | MS [M + H]+ |
|---|---|---|---|---|
| 22 | 5-(Trifluoromethyl)pyridin-3-yl 2-(3-isopropoxybenzyl)-2,7-diazaspiro[3.5]nonane-7-carboxylate | 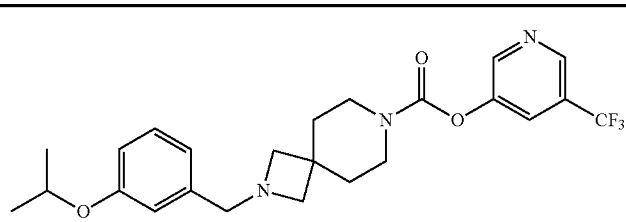 | δ 8.62-8.71 (m, 2H), 7.77 (s, 1H), 7.21-7.24 (m, 1H), 6.77-6.85 (m, 3H), 4.52-4.60 (m, 1H), 3.59-3.64 (m, 4H), 3.48 (br, 2H), 3.10-3.12 (m, 4H), 1.74-1.85 (m, 4H), 1.34 (t, J = 6.0 Hz, 6H). | 464 |

-continued

| Ex | Name | Structure | NMR (¹H NMR, 300 MHz or 400 MHz, Chloroform-d) | MS [M + H]⁺ |
|---|---|---|---|---|
| 23 | 5-(Trifluoromethyl)pyridin-3-yl 2-(3-(benzo[d]thiazol-2-yloxy)-5-chlorobenzyl)-2,7-diazaspiro[3.5]nonane-7-carboxylate | 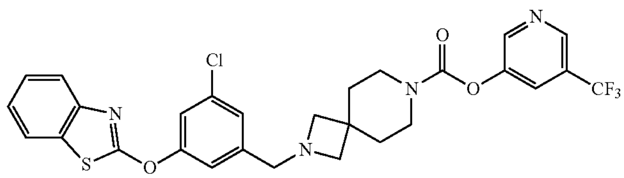 [SMILES: O=C(Oc1cncc(C(F)(F)F)c1)N1CCC2(CC1)CN(Cc1cc(Cl)cc(Oc3nc4ccccc4s3)c1)C2] | δ 8.72 (s, 1H), 8.62 (s, 1H), 7.69-7.76 (m, 3H), 7.39-7.44 (m, 1H), 7.27-7.31 (m, 2H), 7.23 (s, 2H), 3.67 (s, 2H), 3.60 (br, 2H), 3.49 (br, 2H), 3.11-3.13 (m, 4H), 1.86 (br, 4H). | 589 |
| 24 | 5-(Trifluoromethyl)pyridin-3-yl 2-(3-chloro-5-isopropoxybenzyl)-2,7-diazaspiro[3.5]nonane-7-carboxylate | 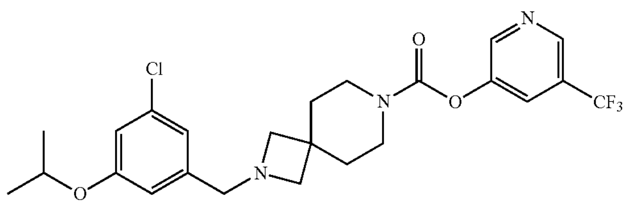 [SMILES: CC(C)Oc1cc(Cl)cc(CN2CC3(CCN(C(=O)Oc4cncc(C(F)(F)F)c4)CC3)C2)c1] | δ 8.62-8.71 (m, 2H), 7.77 (s, 1H), 6.84 (s, 1H), 6.71-6.76 (m, 2H), 4.48-4.56 (m, 1H), 3.57 (s, 4H), 3.49 (br, 2H), 3.08-3.10 (m, 4H), 1.85 (br, 4H), 1.33 (t, J = 6.0 Hz, 6H). | 498 |
| 25 | 5-(Trifluoromethyl)pyridin-3-yl 2-(3,5-dichlorophenoxy)-7-azaspiro[3.5]nonane-7-carboxylate | 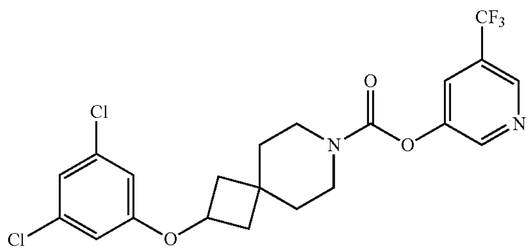 [SMILES: O=C(Oc1cncc(C(F)(F)F)c1)N1CCC2(CC1)CC(Oc1cc(Cl)cc(Cl)c1)C2] | δ 8.74 (s, 1H), 8.66 (s, 1H), 7.80 (s, 1H), 6.97 (s, 1H) 6.71 (s, 2H), 4.65-4.74 (m, 1H), 3.52-3.67 (m, 4H), 2.46-2.53 (m, 2H), 2.00-2.06 (m, 2H), 1.75 (s, 4H). | 475 |
| 26 | 5-(Trifluoromethyl)pyridin-3-yl 2-(3-(pyrrolidine-1-carbonyl)phenoxy)-7-azaspiro[3.5]nonane-7-carboxylate | 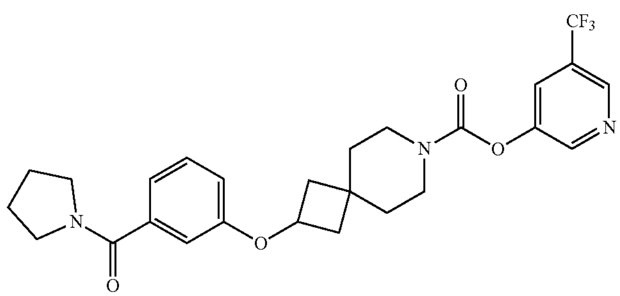 [SMILES: O=C(Oc1cncc(C(F)(F)F)c1)N1CCC2(CC1)CC(Oc1cccc(C(=O)N3CCCC3)c1)C2] | δ 8.72 (s, 1H), 8.64 (s, 1H), 7.79 (s, 1H), 7.27-7.32 (m, 1H), 7.06-7.09 (m, 1H), 6.95 (s, 1H), 6.86-6.88 (m, 1H), 4.71-4.80 (m, 1H), 3.48-3.67 (m, 6H), 3.42-3.46 (m, 2H), 2.46-2.53 (m, 2H), 1.84-2.07 (m, 6H), 1.75 (s, 4H). | 504 |
| 27 | 5-(Trifluoromethyl)pyridin-3-yl 2-(2,5-dichlorophenoxy)-7-azaspiro[3.5]nonane-7-carboxylate | 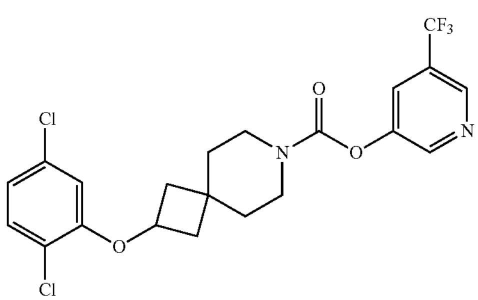 [SMILES: O=C(Oc1cncc(C(F)(F)F)c1)N1CCC2(CC1)CC(Oc1cc(Cl)ccc1Cl)C2] | δ 8.75 (s, 1H), 8.66 (s, 1H), 7.82 (s, 1H), 7.29-7.30 (m, 1H), 6.90-6.93 (m, 1H), 6.73-6.74 (m, 1H), 4.72-4.81 (m, 1H), 3.51-3.70 (m, 4H), 2.50-2.57 (m, 2H), 2.10-2.16 (m, 2H), 1.75-1.81 (m, 4H). | 516 [M + H + MeCN]⁺ |
| 28 | 5-(Trifluoromethyl)pyridin-3-yl 2-([1,1'-biphenyl]-4-yloxy)-7-azaspiro[3.5]nonane-7-carboxylate | 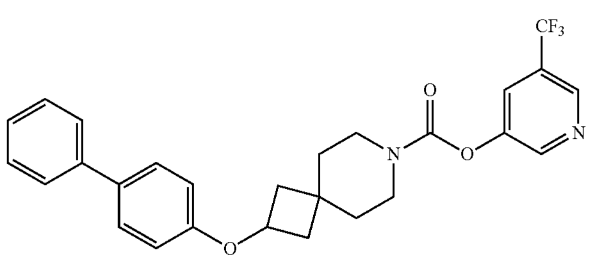 [SMILES: O=C(Oc1cncc(C(F)(F)F)c1)N1CCC2(CC1)CC(Oc1ccc(-c3ccccc3)cc1)C2] | δ 8.67-8.76 (m, 2H), 7.82 (s, 1H), 7.54-7.62 (m, 4H), 7.43-7.48 (m, 2H), 7.32-7.36 (m, 1H), 6.90-6.93 (m, 2H), 4.76-4.84 (m, 1H), 3.52-3.69 (m, 4H), 2.50-2.57 (m, 2H), 2.02-2.13 (m, 2H), 1.76-1.80 (m, 4H). | 483 |

| Ex | Name | Structure | NMR (¹H NMR, 300 MHz or 400 MHz, Chloroform-d) | MS [M + H]⁺ |
|----|------|-----------|---------------------------------------------|-------|
| 29 | 5-(Trifluoromethyl)pyridin-3-yl 2-(3-((4-chlorophenoxy)methyl)phenoxy)-7-azaspiro[3.5]nonane-7-carboxylate | 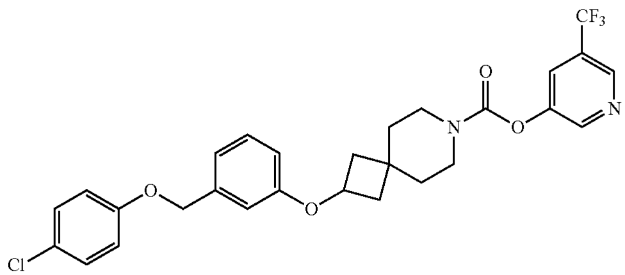 [SMILES: O=C(Oc1cncc(C(F)(F)F)c1)N1CCC2(CC1)CC(Oc1cccc(COc3ccc(Cl)cc3)c1)C2] | δ 8.75 (s, 1H), 8.66 (s, 1H), 7.81 (s, 1H), 7.29-7.34 (m, 1H), 7.24-7.26 (m, 2H), 7.01 (d, J = 7.8 Hz, 1H), 6.88-6.94 (m, 3H), 6.77-6.80 (m, 1H), 5.04 (s, 2H), 4.71-4.80 (m, 1H), 3.50-3.69 (m, 4H), 2.45-2.52 (m, 2H), 2.01-2.08 (m, 2H), 1.76 (br, 4H). | 547 |
| 30 | 5-(Trifluoromethyl)pyridin-3-yl 2-(4-(4-chlorophenoxy)benzyl)-2,7-diazaspiro[3.5]nonane-7-carboxylate | 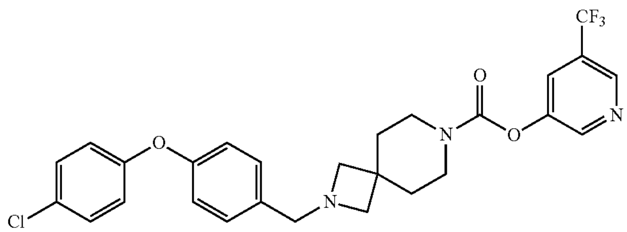 [SMILES: O=C(Oc1cncc(C(F)(F)F)c1)N1CCC2(CC1)CN(Cc1ccc(Oc3ccc(Cl)cc3)cc1)C2] | δ 8.72 (s, 1H), 8.62-8.65 (m, 1H), 7.76 (s, 1H), 7.23-7.40 (m, 4H), 6.92-7.02 (m, 4H), 3.68-3.75 (m, 2H), 3.40-3.60 (m, 4H), 3.06-3.29 (m, 4H), 1.88 (br, 4H). | 532 |
| 31 | 5-(Trifluoromethyl)pyridin-3-yl 2-(3-(4-chlorophenoxy)benzyl)-2,7-diazaspiro[3.5]nonane-7-carboxylate | 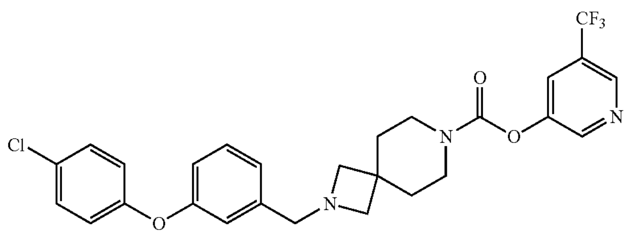 [SMILES: O=C(Oc1cncc(C(F)(F)F)c1)N1CCC2(CC1)CN(Cc1cccc(Oc3ccc(Cl)cc3)c1)C2] | δ 8.97 (s, 1H), 8.72 (s, 1H), 7.76 (s, 1H), 7.26-7.33 (m, 3H), 7.07-7.10 (m, 1H), 6.88-6.97 (m, 4H), 3.70 (s, 2H), 3.49-3.60 (m, 4H), 3.00-3.28 (m, 4H), 1.87 (br, 4H). | 532 |
| 32 | 5-(Trifluoromethyl)pyridin-3-yl 2-(4-(pyridazin-4-yloxy)benzyl)-2,7-diazaspiro[3.5]nonane-7-carboxylate | 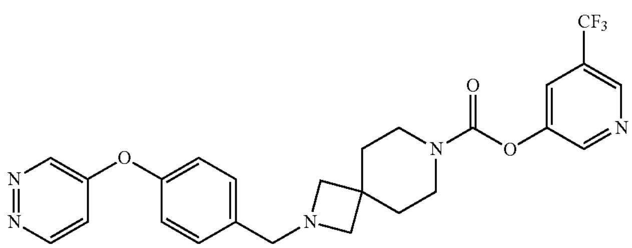 [SMILES: O=C(Oc1cncc(C(F)(F)F)c1)N1CCC2(CC1)CN(Cc1ccc(Oc3ccnnc3)cc1)C2] | δ 8.72 (s, 1H), 8.62 (s, 1H), 8.18-8.21 (m, 1H), 8.03-8.04 (m, 1H), 7.73-7.76 (m, 1H), 7.50-7.66 (m, 4H), 6.59-6.63 (m, 1H), 3.75-3.83 (m, 2H), 3.39-3.61 (m, 4H), 3.15 (br, 4H), 1.88 (br, 4H). | 500 |
| 33 | 5-(Trifluoromethyl)pyridin-3-yl 2-(3-(pyridazin-4-yloxy)benzyl)-2,7-diazaspiro[3.5]nonane-7-carboxylate | 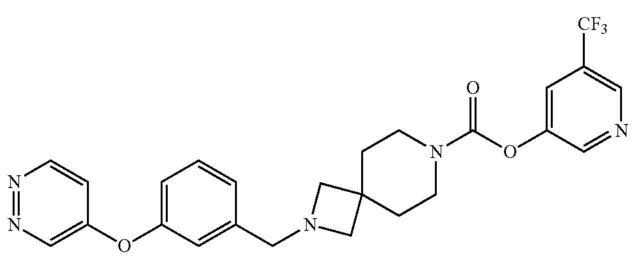 [SMILES: O=C(Oc1cncc(C(F)(F)F)c1)N1CCC2(CC1)CN(Cc1cccc(Oc3ccnnc3)c1)C2] | δ 8.72 (s, 1H), 8.62 (s, 1H), 8.23-8.26 (m, 1H), 8.04-8.05 (m, 1H), 7.76 (s, 1H), 7.50-7.53 (m, 1H), 7.46-7.48 (m, 2H), 7.31-7.38 (m, 1H), 6.60-6.64 (m, 1H), 3.77 (s, 2H), 3.36-3.61 (m, 4H), 3.17 (s, 4H), 1.89 (br, 4H). | 500 |
| 34 | 5-(Trifluoromethyl)pyridin-3-yl 2-(4-(pyrimidin-5-yloxy)benzyl)-2,7-diazaspiro[3.5]nonane-7-carboxylate | 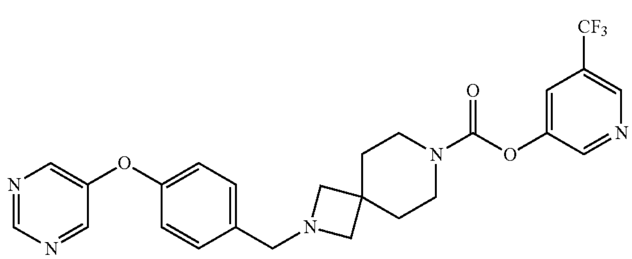 [SMILES: O=C(Oc1cncc(C(F)(F)F)c1)N1CCC2(CC1)CN(Cc1ccc(Oc3cncnc3)cc1)C2] | δ 8.97 (s, 1H), 8.72 (s, 1H), 8.63 (s, 1H), 8.47 (s, 2H), 7.77 (s, 1H), 7.33-7.36 (m, 2H), 7.01-7.04 (m, 2H), 3.76 (s, 2H), 3.50-3.69 (m, 4H), 3.13-3.15 (m, 4H), 1.88 (br, 4H). | 500 |

| Ex | Name | Structure | NMR (¹H NMR, 300 MHz or 400 MHz, Chloroform-d) | MS [M + H]⁺ |
|---|---|---|---|---|
| 35 | 5-(Trifluoromethyl)pyridin-3-yl 2-(3-(3,5-dichlorophenoxy)benzyl)-2,7-diazaspiro[3.5]nonane-7-carboxylate | 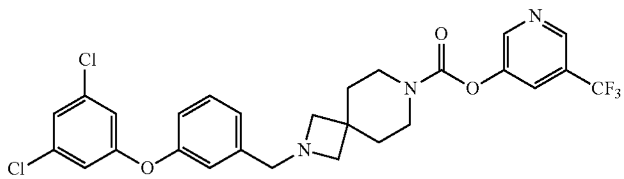 [SMILES: O=C(Oc1cncc(C(F)(F)F)c1)N1CCC2(CC1)CN(Cc1cccc(Oc3cc(Cl)cc(Cl)c3)c1)C2] | δ 8.73 (s, 1H), 8.62 (d, J = 2.3 Hz, 1H), 7.78 (s, 1H), 7.27-7.37 (m, 1H), 7.07-7.14 (m, 2H), 7.01 (s, 1H), 6.92-6.95 (m, 1H), 6.87 (d, J = 1.8 Hz, 2H), 3.68 (s, 2H), 3.61 (br, 2H), 3.50 (br, 2H), 3.11 (br, 4H), 1.86 (br, 4H). | 566 |
| 36 | 5-Carbamoylpyridin-3-yl 2-(3,4-dichlorobenzyl)-2,8-diazaspiro[4.5]decane-8-carboxylate | 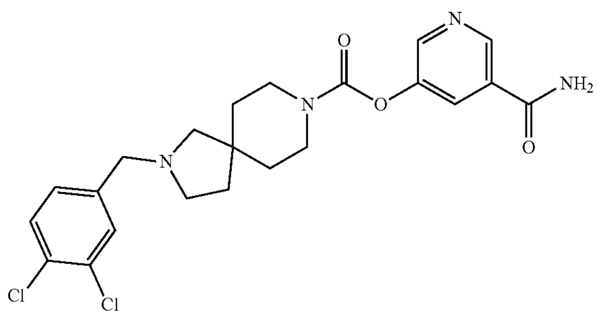 [SMILES: NC(=O)c1cncc(OC(=O)N2CCC3(CCN(Cc4ccc(Cl)c(Cl)c4)C3)CC2)c1] | δ 8.82 (s, 1H), 8.56 (d, J = 2.4 Hz, 1H), 7.95 (s, 1H), 7.61 (s, 1H), 7.37-7.44 (m, 1H), 7.16-7.19 (m, 1H), 6.28 (br, 1H), 5.86 (br, 1H), 3.45-3.69 (m, 6H), 2.62 (br, 2H), 2.43 (br, 2H), 1.66-1.90 (m, 6H). | 463 |
| 37 | 5-(Trifluoromethyl)pyridin-3-yl 2-(3-((5-(trifluoromethyl)pyridin-2-yl)oxy)benzyl)-2,7-diazaspiro[3.5]nonane-7-carboxylate | 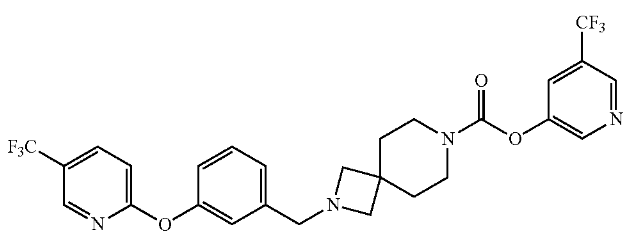 [SMILES: O=C(Oc1cncc(C(F)(F)F)c1)N1CCC2(CC1)CN(Cc1cccc(Oc3ccc(C(F)(F)F)cn3)c1)C2] | δ 8.72 (s, 1H), 8.62 (d, J = 2.3 Hz, 1H), 8.45 (s, 1H), 7.82-7.96 (m, 1H), 7.77 (s, 1H), 7.32-7.48 (d, J = 15.6 Hz, 1H), 7.15-7.23 (d, J = 7.6 Hz, 1H), 7.11 (s, 1H), 6.83-7.09 (m, 2H), 3.70 (s, 2H), 3.40-3.65 (m, 4H), 3.01-3.20 (d, J = 4.3 Hz, 4H), 1.73-1.96 (d, J = 3.2 Hz, 4H). | 567 |
| 38 | 5-(Trifluoromethyl)pyridin-3-yl 2-(3-((5-(trifluoromethyl)pyridin-3-yl)oxy)benzyl)-2,7-diazaspiro[3.5]nonane-7-carboxylate | 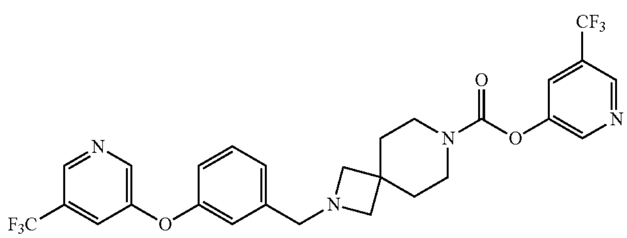 [SMILES: O=C(Oc1cncc(C(F)(F)F)c1)N1CCC2(CC1)CN(Cc1cccc(Oc3cncc(C(F)(F)F)c3)c1)C2] | δ 8.72 (s, 1H), 8.62 (t, J = 4.6 Hz, 2H), 8.57 (d, J = 2.6 Hz, 1H), 7.77 (s, 1H), 7.45 (s, 1H), 7.30-7.40 (t, J = 15.7 Hz, 1H), 7.16 (d, J = 7.6 Hz, 1H), 7.03 (d, J = 11.9 Hz, 1H), 6.87-7.00 (m, 1H), 3.67 (s, 2H), 3.54-3.63 (t, J = 10.4 Hz, 2H), 3.38-3.54 (t, J = 10.7 Hz, 2H), 3.03-3.18 (m, 4H), 1.75-1.93 (m, 4H). | 567 |
| 39 | 5-(Trifluoromethyl)pyridin-3-yl 2-(3-((6-(trifluoromethyl)pyridin-3-yl)oxy)benzyl)-2,7-diazaspiro[3.5]nonane-7-carboxylate | 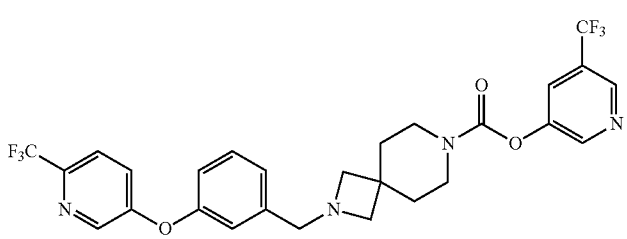 [SMILES: O=C(Oc1cncc(C(F)(F)F)c1)N1CCC2(CC1)CN(Cc1cccc(Oc3ccc(C(F)(F)F)nc3)c1)C2] | δ 8.72 (s, 1H), 8.62 (d, J = 2.4 Hz, 1H), 8.46 (d, J = 2.6 Hz, 1H), 7.77 (s, 1H), 7.64 (d, J = 8.6 Hz, 1H), 7.31-7.42 (m, 2H), 7.17 (d, J = 7.6 Hz, 1H), 7.05 (s, 1H), 6.88-7.01 (d, J = 2.1 Hz, 1H), 3.40-3.70 (m, 6H), 3.00-3.18 (m, 4H), 1.80-1.90 (m, 4H). | 567 |
| 40 | 5-(Trifluoromethyl)pyridin-3-yl 2-(2-chloro-3-(3-chlorophenoxy)benzyl)-2,7-diazaspiro[3.5]nonane-7-carboxylate | 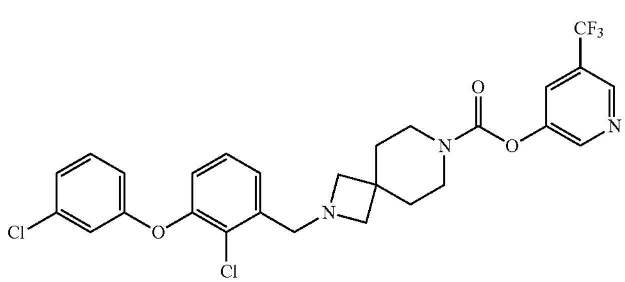 [SMILES: O=C(Oc1cncc(C(F)(F)F)c1)N1CCC2(CC1)CN(Cc1cccc(Oc3cccc(Cl)c3)c1Cl)C2] | δ 8.73 (s, 1H), 7.63 (d, J = 2.3 Hz, 1H), 7.78 (s, 1H), 7.22-7.34 (m, 3H), 7.02-7.10 (m, 1H), 6.92-7.00 (m, 1H), 6.88-6.92 (m, 1H), 6.78-6.88 (m, 1H), 3.83 (s, 2H), 3.43-3.72 (m, 4H), 3.22 (s, 4H), 1.76-2.00 (m, 4H). | 566 |

-continued

| Ex | Name | Structure | NMR (¹H NMR, 300 MHz or 400 MHz, Chloroform-d) | MS [M + H]⁺ |
|---|---|---|---|---|
| 41 | 5-(Trifluoromethyl)pyridin-3-yl 2-(2-chloro-3-phenoxybenzyl)-2,7-diazaspiro[3.5]nonane-7-carboxylate | 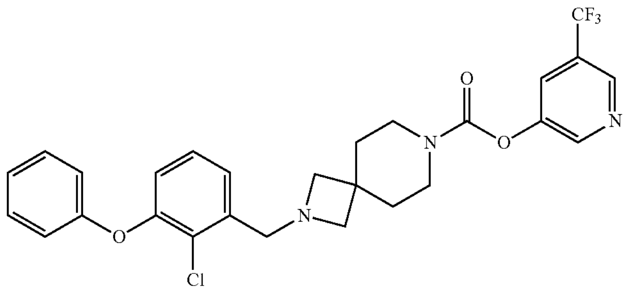 [SMILES: O=C(Oc1cncc(C(F)(F)F)c1)N1CCC2(CC1)CN(Cc1cccc(Oc3ccccc3)c1Cl)C2] | δ 8.73 (s, 1H), 8.50-8.69 (d, J = 2.3 Hz, 1H), 7.77 (s, 1H), 7.29-7.40 (m, 2H), 7.17-7.25 (m, 2H), 7.04-7.15 (m, 1H), 6.92-7.01 (m, 2H), 6.82-6.92 (m, 1H), 3.83 (s, 2H), 3.59-3.72 (m, 2H), 3.43-3.59 (m, 2H), 3.21 (s, 4H), 1.85-1.98 (m, 4H). | 532 |
| 42 | 5-Fluoropyridin-3-yl 4-(5-chloro-2-(trifluoromethyl)benzyl)piperazine-1-carboxylate | 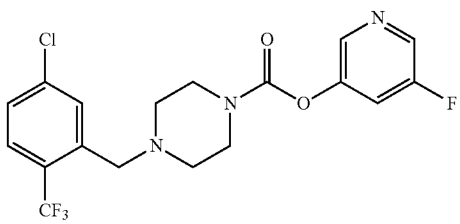 [SMILES: O=C(Oc1cncc(F)c1)N1CCN(Cc2cc(Cl)ccc2C(F)(F)F)CC1] | δ 8.30-8.36 (m, 2H), 7.83 (s, 1H), 7.58 (d, J = 8.4 Hz, 1H), 7.34-7.38 (m, 2H), 3.63-3.72 (m, 6H), 2.55-2.58 (m, 4H). | 418 |
| 43 | 5-Cyanopyridin-3-yl 4-(5-chloro-2-(trifluoromethyl)benzyl)piperazine-1-carboxylate | 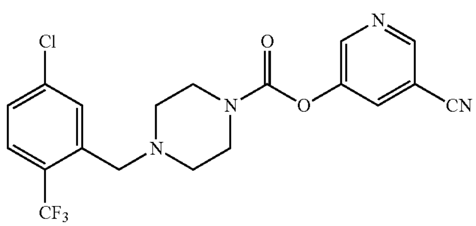 [SMILES: N#Cc1cncc(OC(=O)N2CCN(Cc3cc(Cl)ccc3C(F)(F)F)CC2)c1] | δ 8.66-8.72 (m, 2H), 7.83-7.86 (m, 2H), 7.59 (d, J = 8.7 Hz, 1H), 7.35 (d, J = 8.4 Hz, 1H), 3.64-3.73 (m, 6H), 2.58 (t, J = 4.8 Hz, 4H). | 425 |
| 44 | 5-(Trifluoromethyl)pyridin-3-yl 4-(5-chloro-2-(trifluoromethyl)benzyl)piperazine-1-carboxylate | 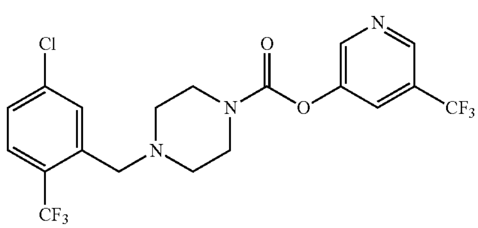 [SMILES: O=C(Oc1cncc(C(F)(F)F)c1)N1CCN(Cc2cc(Cl)ccc2C(F)(F)F)CC1] | δ 8.65-8.73 (m, 2H), 7.80-7.84 (m, 2H), 7.58 (d, J = 8.4 Hz, 1H), 7.33-7.36 (m, 1H), 3.70-3.76 (m, 4H), 3.64 (t, J = 4.8 Hz, 2H), 2.58 (t, J = 5.1 Hz, 4H). | 468 |
| 45 | 5-Fluoropyridin-3-yl 4-(4-methoxy-3-(trifluoromethyl)benzyl)piperazine-1-carboxylate | 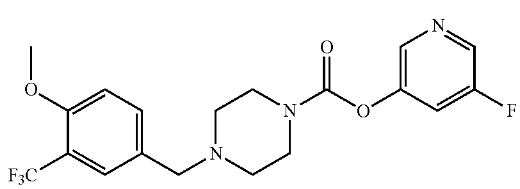 [SMILES: COc1ccc(CN2CCN(C(=O)Oc3cncc(F)c3)CC2)cc1C(F)(F)F] | δ 8.34-8.35 (m, 1H), 8.29-8.30 (m, 1H), 7.54-7.55 (m, 1H), 7.46 (d, J = 8.1 Hz, 1H), 7.26-7.37 (m, 1H), 6.98 (d, J = 8.4 Hz, 1H), 3.91 (s, 3H), 3.53-3.68 (m, 6H), 2.50 (br, 4H). | 414 |
| 46 | 5-Fluoropyridin-3-yl 4-((2,2-difluorobenzo[d][1,3]dioxol-5-yl)methyl)piperazine-1-carboxylate | 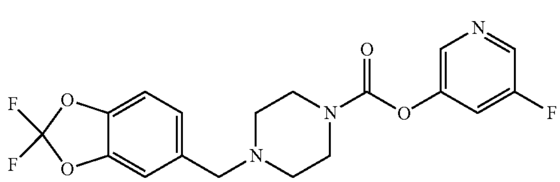 [SMILES: O=C(Oc1cncc(F)c1)N1CCN(Cc2ccc3c(c2)OC(F)(F)O3)CC1] | δ 8.29-8.35 (m, 2H), 7.33-7.37 (m, 1H), 7.27 (s, 1H), 6.98-7.04 (m, 2H), 3.54-3.68 (m, 6H), 2.49-2.52 (m, 4H). | 396 |
| 47 | 5-Fluoropyridin-3-yl 4-(4-chloro-3-ethoxybenzyl)piperazine-1-carboxylate | 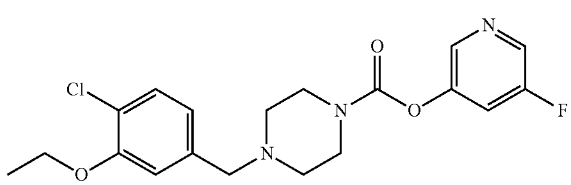 [SMILES: CCOc1cc(CN2CCN(C(=O)Oc3cncc(F)c3)CC2)ccc1Cl] | δ 8.35 (d, J = 2.4 Hz, 1H), 8.29 (d, J = 1.8 Hz, 1H), 7.27-7.37 (m, 2H), 6.94 (d, J = 2.4 Hz, 1H), 6.83-6.86 (m, 1H), 4.09-4.16 (m, 2H), 3.57-3.69 (m, 4H), 3.51 (s, 2H), 2.48-2.51 (m, 4H), 1.48 (t, J = 6.9 Hz, 3H). | 394 |

| Ex | Name | Structure | NMR (¹H NMR, 300 MHz or 400 MHz, Chloroform-d) | MS [M + H]⁺ |
|---|---|---|---|---|
| 48 | 5-Fluoropyridin-3-yl 4-((4-(trifluoromethyl)pyridin-3-yl)methyl)piperazine-1-carboxylate | 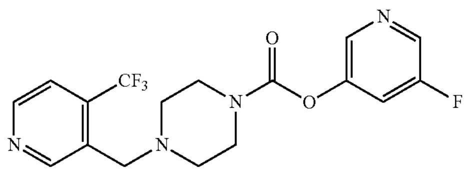 [SMILES: O=C(Oc1cncc(F)c1)N1CCN(Cc2cnccc2C(F)(F)F)CC1] | δ 9.02 (s, 1H), 8.71 (d, J = 4.8 Hz, 1H), 8.30-8.35 (m, 2H), 7.53 (d, J = 5.1 Hz, 1H), 7.34-7.38 (m, 1H), 3.60-3.76 (m, 6H), 2.58 (t, J = 4.8 Hz, 4H). | 385 |
| 49 | 5-Fluoropyridin-3-yl 4-(4-isopropoxy-2-methylbenzyl)piperazine-1-carboxylate | 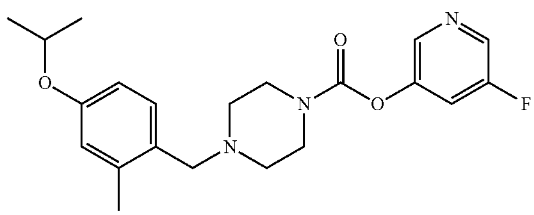 [SMILES: Cc1cc(OC(C)C)ccc1CN1CCN(C(=O)Oc2cncc(F)c2)CC1] | δ 8.29-8.34 (m, 2H), 7.32-7.37 (m, 1H), 7.11 (d, J = 8.4 Hz, 1H), 6.65-6.73 (m, 2H), 4.49-4.57 (m, 1H), 3.55-3.64 (m, 4H), 3.45 (s, 2H), 2.47-2.50 (m, 4H), 2.35 (s, 3H), 1.33 (d, J = 6.3 Hz, 6H). | 388 |
| 50 | 5-Cyanopyridin-3-yl 4-(3-(pyrimidin-2-yloxy)benzyl)piperazine-1-carboxylate | 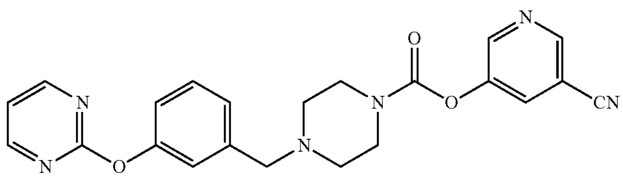 [SMILES: N#Cc1cncc(OC(=O)N2CCN(Cc3cccc(Oc4ncccn4)c3)CC2)c1] | δ 8.71 (d, J = 1.8 Hz, 1H), 8.65 (d, J = 2.4 Hz, 1H), 8.58 (d, J = 4.8 Hz, 2H), 7.83-7.85 (m, 1H), 7.38-7.44 (m, 1H), 7.22-7.27 (m, 2H), 7.12-7.16 (m, 1H), 7.04-7.07 (m, 1H), 3.58-3.70 (m, 6H), 2.53-2.56 (m, 4H). | 417 |
| 51 | 5-Carbamoylpyridin-3-yl 4-(3-carbamoyl-5-chlorobenzyl)piperazine-1-carboxylate | 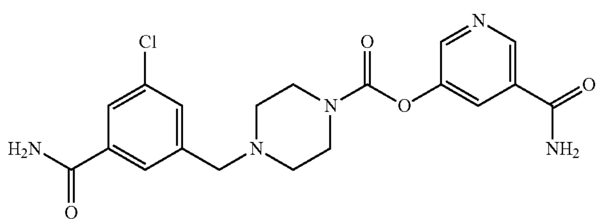 [SMILES: NC(=O)c1cc(Cl)cc(CN2CCN(C(=O)Oc3cncc(C(N)=O)c3)CC2)c1] | δ 8.89 (s, 1H), 8.56 (d, J = 2.7 Hz, 1H), 8.18 (br, 1H), 8.09 (br, 1H), 8.02-8.03 (m, 1H), 7.80-7.83 (m, 2H), 7.68 (s, 1H), 7.53-7.56 (m, 2H), 3.60-3.65 (m, 4H), 3.48 (br, 2H), 2.49-2.51 (m, 4H). | 418 |
| 52 | 5-Acetamidopyridin-3-yl 4-(4-chloro-3-isopropoxybenzyl)piperazine-1-carboxylate | 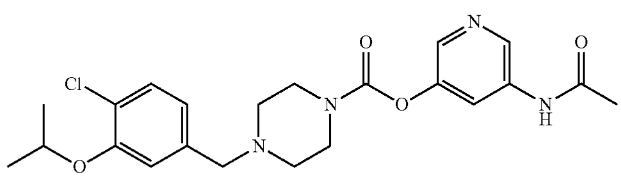 [SMILES: CC(=O)Nc1cncc(OC(=O)N2CCN(Cc3ccc(Cl)c(OC(C)C)c3)CC2)c1] | δ 8.11 (s, 3H), 7.95 (s, 1H), 7.25-7.40 (m, 1H), 6.95 (s, 1H), 6.73-6.92 (m, 1H), 4.45-4.72 (m, 1H), 3.26-3.93 (m, 6H), 2.58 (s, 4H), 2.15 (s, 3H), 1.34-1.47 (m, 6H). | 447 |
| 53 | 5-Carbamoylpyridin-3-yl 4-(4-chloro-3-isopropoxybenzyl)piperazine-1-carboxylate | 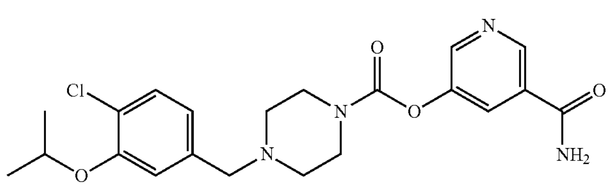 [SMILES: CC(C)Oc1cc(CN2CCN(C(=O)Oc3cncc(C(N)=O)c3)CC2)ccc1Cl] | δ 8.84 (s, 1H), 8.50-8.61 (m, 1H), 8.01 (s, 1H), 7.25-7.34 (m, 1H), 6.98 (s, 1H), 6.81-6.88 (m, 1H), 5.73-6.60 (m, 2H), 4.51-4.64 (m, 1H), 3.51-3.74 (m, 4H), 3.48 (s, 2H), 2.41-2.73 (m, 4H), 1.24-1.51 (m, 6H). | 433 |
| 54 | 5-Carbamoylpyridin-3-yl (R)-4-(3-carbamoyl-4-chlorobenzyl)-2-methylpiperazine-1-carboxylate | 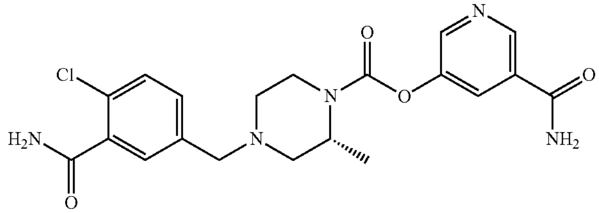 [SMILES: C[C@@H]1CN(Cc2ccc(Cl)c(C(N)=O)c2)CCN1C(=O)Oc1cncc(C(N)=O)c1] | (Methanol-d₄) δ 8.82-8.95 (m, 1H), 8.52-8.62 (m, 1H), 8.01-8.17 (m, 1H), 7.50-7.62 (m, 1H), 7.30-7.50 (m, 2H), 4.28-4.57 (m, 1H), 3.90-4.19 (m, 1H), 3.48-3.67 (m, 2H), 3.35-3.48 (m, 1H), 2.84-2.97 (m, 1H), 2.69-2.82 (m, 1H), 2.28-2.39 (m, 1H), 2.08-2.25 (m, 1H), 1.35-1.55 (m, 3H). | 432 |

| Ex | Name | NMR (¹H NMR, 300 MHz or 400 MHz, Chloroform-d) | MS [M + H]⁺ |
|---|---|---|---|
| 55 | 5-Carbamoylpyridin-3-yl (S)-4-(3-carbamoyl-4-chlorobenzyl)-2-methylpiperazine-1-carboxylate | (Methanol-$d_4$) δ 8.89-9.05 (m, 1H), 8.65-8.81 (m, 1H), 8.18-8.39 (m, 1H), 7.49-7.85 (m, 3H), 4.18-4.77 (m, 4H), 3.33-3.88 (m, 5H), 1.28-1.78 (m, 3H). | 432 |
| 56 | (R)-5-Carbamoylpyridin-3-yl 4-(4-chloro-3-isopropoxybenzyl)-2-methylpiperazine-1-carboxylate | (Methanol-$d_4$) δ 8.90 (m, 1H), 8.57 (m, 1H), 8.10 (m, 1H), 7.32 (m, 1H), 7.13 (m, 1H), 6.91 (m, 1H), 4.65 (m, 1H), 4.27-4.54 (br, 1H), 3.86-4.18 (br, 1H), 3.56-3.66 (m, 1H), 3.36-3.51 (m, 2H), 2.86-2.99 (d, J = 11.4 Hz, 1H), 2.70-2.80 (d, J = 11.5 Hz, 1H), 2.12-2.34 (m, 2H), 1.40-1.50 (m, 3H), 1.37 (m, 6H). | 447 |
| 57 | (S)-5-Carbamoylpyridin-3-yl 4-(4-chloro-3-isopropoxybenzyl)-2-methylpiperazine-1-carboxylate | (Methanol-$d_4$) δ 8.90 (m, 1H), 8.57 (m, 1H), 8.10 (m, 1H), 7.32 (m, 1H), 7.13 (m, 1H), 6.91 (m, 1H), 4.65 (m, 1H), 4.27-4.54 (br, 1H), 3.86-4.18 (br, 1H), 3.56-3.66 (m, 1H), 3.36-3.51 (m, 2H), 2.86-2.99 (d, J = 11.4 Hz, 1H), 2.70-2.80 (d, J = 11.5 Hz, 1H), 2.12-2.34 (m, 2H), 1.40-1.50 (m, 3H), 1.37 (m, 6H). | 447 |
| 58 | (R)-5-Carbamoylpyridin-3-yl 2-methyl-4-(2-methyl-3-(trifluoromethyl)benzyl)piperazine-1-carboxylate | (Methanol-$d_4$) δ 8.90 (m, 1H), 8.57 (m, 1H), 8.10 (m, 1H), 7.49-7.70 (m, 2H), 7.22-7.40 (m, 1H), 4.28-4.59 (br, 1H), 3.87-4.19 (br, 1H), 3.60 (s, 2H), 3.37-3.50 (m, 1H), 2.80-2.91 (m, 1H), 2.70-2.80 (m, 1H), 2.58 (s, 3H), 2.31-2.41 (m, 1H), 2.10-2.28 (m, 1H), 1.38 (s, 3H). | 437 |
| 59 | (S)-5-Carbamoylpyridin-3-yl 2-methyl-4-(2-methyl-3-(trifluoromethyl)benzyl)piperazine-1-carboxylate | (Methanol-$d_4$) δ 8.90 (m, 1H), 8.57 (m, 1H), 8.10 (m, 1H), 7.49-7.70 (m, 2H), 7.22-7.40 (m, 1H), 4.28-4.59 (br, 1H), 3.87-4.19 (br, 1H), 3.60 (s, 2H), 3.37-3.50 (m, 1H), 2.80-2.91 (m, 1H), 2.70-2.80 (m, 1H), 2.58 (s, 3H), 2.31-2.41 (m, 1H), 2.10-2.28 (m, 1H), 1.38 (s, 3H). | 437 |
| 60 | 5-Carbamoylpyridin-3-yl 4-(2-methyl-3-(trifluoromethyl)benzyl)piperazine-1-carboxylate | δ 8.84 (s, 1H), 8.60 (s, 1H), 7.95-8.04 (m, 1H), 7.51-7.64 (m, 1H), 7.37-7.50 (m, 1H), 7.17-7.26 (m, 1H), 5.79-6.26 (m, 1H), 6.26-6.67 (m, 1H), 3.46-3.79 (m, 6H), 2.45-2.62 (m, 7H). | 423 |

| Ex | Name | Structure | NMR (¹H NMR, 300 MHz or 400 MHz, Chloroform-d) | MS [M + H]⁺ |
|---|---|---|---|---|
| 61 | (S)-5-Aminopyridin-3-yl 4-(4-chloro-3-isopropoxybenzyl)-2-methylpiperazine-1-carboxylate | 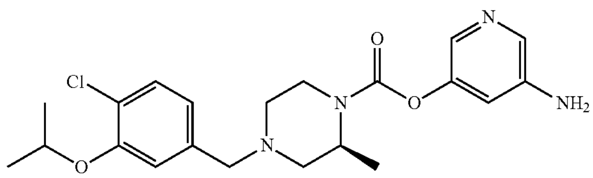 [SMILES: CC(C)Oc1cc(CN2CCN(C(=O)Oc3cncc(N)c3)[C@@H](C)C2)ccc1Cl] | δ 8.89-8.99 (m, 1H), 8.82-8.86 (m, 1H), 7.28-7.33 (m, 1H), 6.98-7.18 (m, 1H), 6.79-6.94 (m, 2H), 4.50-4.71 (m, 1H), 4.28-4.35 (m, 1H), 3.26-4.08 (m, 6H), 2.58-3.11 (m, 2H), 2.07-2.41 (m, 2H), 1.35-1.45 (m, 9H). | 419 |
| 62 | (R)-5-Aminopyridin-3-yl 4-(4-chloro-3-isopropoxybenzyl)-2-methylpiperazine-1-carboxylate | 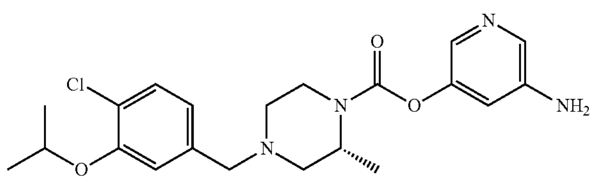 [SMILES: CC(C)Oc1cc(CN2CCN(C(=O)Oc3cncc(N)c3)[C@H](C)C2)ccc1Cl] | δ 8.89-8.97 (m, 1H), 8.82-8.87 (m, 1H), 7.28-7.33 (m, 1H), 6.98-7.12 (m, 1H), 6.79-6.88 (m, 2H), 4.50-4.71 (m, 1H), 4.28-4.35 (m, 1H), 3.18-4.15 (m, 6H), 2.52-3.01 (m, 2H), 2.07-2.38 (m, 2H), 1.25-1.48 (m, 9H). | 419 |
| 63 | 5-Carbamoylpyridin-3-yl 4-((4-(trifluoromethyl)pyridin-3-yl)methyl)piperazine-1-carboxylate | 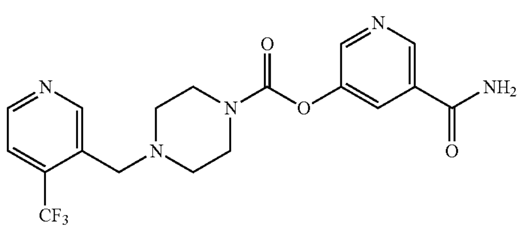 [SMILES: NC(=O)c1cncc(OC(=O)N2CCN(Cc3cnccc3C(F)(F)F)CC2)c1] | (Methanol-d₄) δ 9.04 (s, 1H), 8.85-8.93 (m, 1H), 8.67-8.76 (m,1H), 8.53-8.62 (m, 1H), 8.04-8.14 (m, 1H), 7.67-7.77 (m, 1H), 3.82-3.91 (m, 2H), 3.70-3.82 (m, 2H), 3.54-3.66 (m, 2H), 2.57-2.67 (m, 4H), 1.88-2.02 (m, 2H). | 410 |
| 64 | 5-Carbamoylpyridin-3-yl 4-(4-chloro-3-ethoxyphenoxy)piperidine-1-carboxylate | 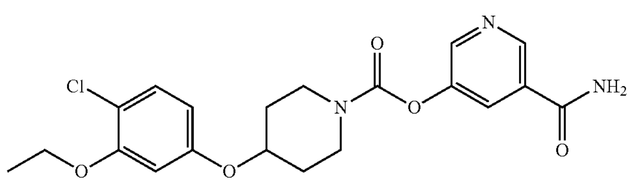 [SMILES: CCOc1cc(OC2CCN(C(=O)Oc3cncc(C(N)=O)c3)CC2)ccc1Cl] | (Methanol-d₄) δ 8.82-8.96 (m, 1H), 8.49-8.66 (m, 1H), 7.99-8.15 (m, 1H), 7.12-7.28 (m, 1H), 6.48-6.72 (m, 2H), 4.53-4.72 (m, 1H), 3.51-4.18 (m, 6H), 1.78-2.19 (m, 4H), 1.38-1.51 (m, 3H). | 420 |
| 65 | (R)-5-Carbamoylpyridin-3-yl 4-(3-chloro-5-(trifluoromethyl)benzyl)-2-methylpiperazine-1-carboxylate | 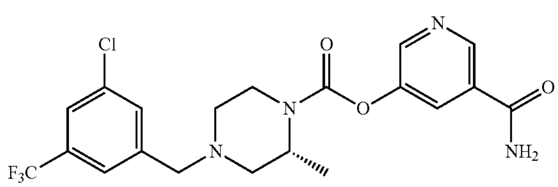 [SMILES: C[C@@H]1CN(Cc2cc(Cl)cc(C(F)(F)F)c2)CCN1C(=O)Oc1cncc(C(N)=O)c1] | (Methanol-d₄) δ 8.90-8.91 (m, 1H), 8.57-8.58 (m, 1H), 8.09-8.10 (m, 1H), 7.62-7.72 (m, 3H), 4.25-4.61 (m, 1H), 3.83-4.25 (m, 1H), 3.67-3.77 (m, 1H), 3.54-3.67 (m, 1H), 3.38-3.54 (m, 1H), 2.83-2.98 (m, 1H), 2.62-2.80 (m, 1H), 2.18-2.45 (m, 2H), 1.30-1.56 (m, 3H). | 457 |
| 66 | (R)-5-Carbamoylpyridin-3-yl 4-(2-chloro-3-(trifluoromethyl)benzyl)-2-methylpiperazine-1-carboxylate | 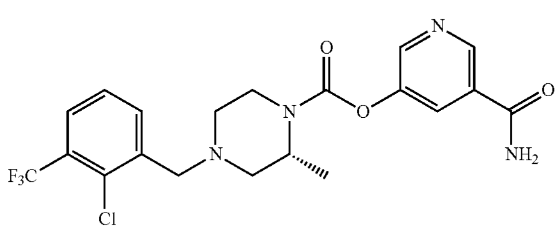 [SMILES: C[C@@H]1CN(Cc2cccc(C(F)(F)F)c2Cl)CCN1C(=O)Oc1cncc(C(N)=O)c1] | (Methanol-d₄) δ 8.86-8.95 (m, 1H), 8.52-8.60 (m, 1H), 8.05-8.14 (m, 1H), 7.82-7.93 (m, 1H), 7.69-7.78 (m, 1H), 7.44-7.56 (m, 1H), 4.24-4.69 (m, 1H), 3.84-4.24 (m, 1H), 3.65-3.84 (br, 2 H), 3.38-3.57 (m, 1H), 2.85-2.98 (m, 1H), 2.70-2.85 (m, 1H), 2.38-2.54 (m, 1H), 2.17-2.38 (m, 1H), 1.32-1.56 (m, 3H). | 457 |

| Ex | Name | Structure | NMR (¹H NMR, 300 MHz or 400 MHz, Chloroform-d) | MS [M + H]⁺ |
|---|---|---|---|---|
| 67 | (R)-5-Cyanopyridin-3-yl 4-(5-chloro-2-(trifluoromethyl)benzyl)-2-methylpiperazine-1-carboxylate | 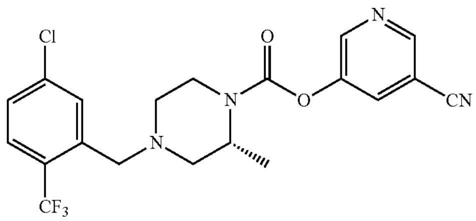 | δ 8.71 (s, 1H), 8.65 (s, 1H), 7.85 (s, 2H), 7.59 (d, J = 8.7 Hz, 1H), 7.36 (d, J = 8.4 Hz, 1H), 4.41 (br, 1H), 4.00-4.04 (m, 1H), 3.67 (s, 2H), 3.43 (br, 1H), 2.85-2.88 (m, 1H), 2.67-2.71 (m, 1H), 2.40-2.42 (m, 1H), 2.25-2.32 (m, 1H), 1.44-1.46 (m, 3H). | 439 |
| 68 | (R)-5-Cyanopyridin-3-yl 2-methyl-4-(2-methyl-3-(trifluoromethyl)benzyl)piperazine-1-carboxylate | 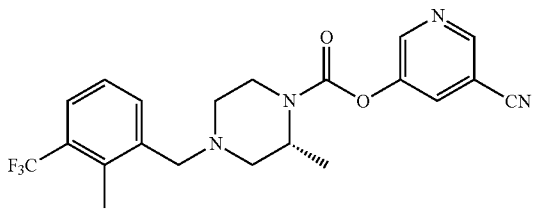 [SMILES: Cc1c(CN2CCN(C(=O)Oc3cncc(C#N)c3)[C@H](C)C2)cccc1C(F)(F)F] | δ 8.70 (s, 1H), 8.64 (s, 1H), 7.84 (s, 1H), 7.59 (d, J = 7.8 Hz, 1H), 7.44-7.46 (m, 1H), 7.23-7.27 (m, 1H), 4.40 (br, 1H), 3.96-4.00 (m, 1H), 3.54 (s, 2H), 3.32 (br, 1H), 2.81-2.84 (m, 1H), 2.67-2.71 (m, 1H), 2.51 (s, 3H), 2.35-2.38 (m, 1H), 2.13-2.21 (m, 1H), 1.38 (br, 3H). | 419 |
| 69 | (R)-5-Fluoropyridin-3-yl 4-(5-chloro-2-(trifluoromethyl)benzyl)-2-methylpiperazine-1-carboxylate | 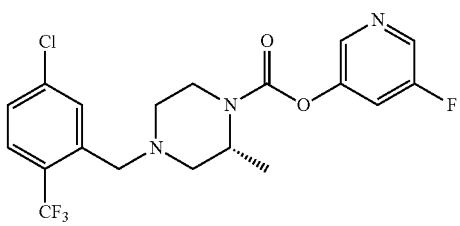 [SMILES: C[C@@H]1CN(Cc2cc(Cl)ccc2C(F)(F)F)CCN1C(=O)Oc1cncc(F)c1] | δ 8.35 (d, J = 2.4 Hz, 1H), 8.30 (s, 1H), 7.85 (br, 1H), 7.59 (d, J = 8.7 Hz, 1H), 7.34-7.37 (m, 2H), 4.41 (br, 1H), 4.01-4.05 (m, 1H), 3.66 (s, 2H), 3.49 (br, 1H), 2.84-2.88 (m, 1H), 2.70-2.76 (m, 1H), 2.39-2.42 (m, 1H), 2.24-2.28 (m, 1H), 1.43-1.45 (m, 3H). | 432 |
| 70 | (R)-5-Fluoropyridin-3-yl 2-methyl-4-((4-(trifluoromethyl)pyridin-3-yl)methyl)piperazine-1-carboxylate | 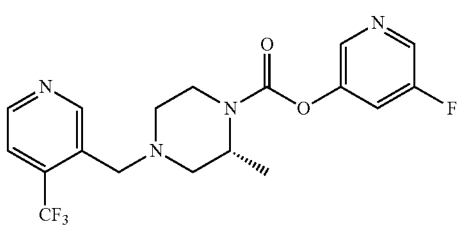 [SMILES: C[C@@H]1CN(Cc2cnccc2C(F)(F)F)CCN1C(=O)Oc1cncc(F)c1] | δ 9.01 (s, 1H), 8.72 (d, J = 4.8 Hz, 1H), 8.35 (d, J = 2.4 Hz, 1H), 8.29 (s, 1H), 7.54 (d, J = 5.1 Hz, 1H), 7.33-7.38 (m, 1H), 4.41 (br, 1H), 3.99-4.09 (m, 1H), 3.71 (s, 2H), 3.49 (br, 1H), 2.82-2.85 (m, 1H), 2.68-2.71 (m, 1H), 2.41-2.46 (m, 2H), 2.21-2.30 (m, 1H), 1.41-1.47 (m, 3H). | 399 |
| 71 | (R)-5-Fluoropyridin-3-yl 2-methyl-4-(2-methyl-3-(trifluoromethyl)benzyl)piperazine-1-carboxylate | 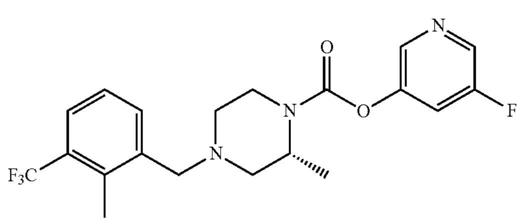 [SMILES: Cc1c(CN2CCN(C(=O)Oc3cncc(F)c3)[C@H](C)C2)cccc1C(F)(F)F] | δ 8.34 (d, J = 2.4 Hz, 1H), 8.29 (s, 1H), 7.58 (d, J = 7.8 Hz, 1H), 7.45 (d, J = 7.5 Hz, 1H), 7.33-7.38 (m, 1H), 7.22-7.30 (m, 1H), 4.39 (br, 1H), 3.96-4.00 (m, 1H), 3.52-3.58 (m, 2H), 3.30 (br, 1H), 2.80-2.83 (m, 1H), 2.65-2.69 (m, 1H), 2.51 (s, 3H), 2.20-2.38 (m, 1H), 2.11-2.19 (m, 1H), 1.35-1.37 (m, 3H). | 412 |
| 72 | 5-fluoro-4-methylpyridin-3-yl 4-(5-chloro-2-(trifluoromethyl)benzyl)piperazine-1-carboxylate | 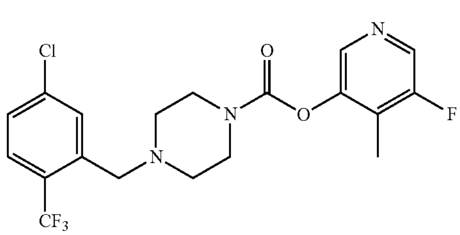 [SMILES: Cc1c(F)cncc1OC(=O)N1CCN(Cc2cc(Cl)ccc2C(F)(F)F)CC1] | δ 8.29 (s, 1H), 8.22 (s, 1H), 7.84 (br, 1H), 7.59 (d, J = 8.4 Hz, 1H), 7.34-7.36 (m, 1H), 3.76 (br, 2H), 3.71 (br, 2H), 3.63 (br, 2H), 2.56-2.59 (m, 4H), 2.18 (s, 3H). | 432 |

-continued

| Ex | Name | Structure | NMR (¹H NMR, 300 MHz or 400 MHz, Chloroform-d) | MS [M + H]⁺ |
|---|---|---|---|---|
| 73 | 5-Cyano-4-methylpyridin-3-yl 4-(5-chloro-2-(trifluoromethyl)benzyl)piperazine-1-carboxylate | 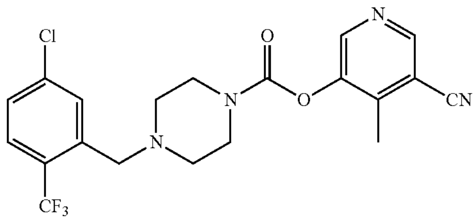 [SMILES: Cc1c(C#N)cncc1OC(=O)N1CCN(Cc2cc(Cl)ccc2C(F)(F)F)CC1] | δ 8.66 (s, 1H), 8.54 (s, 1H), 7.83 (br, 1H), 7.59 (d, J = 8.4 Hz, 1H), 7.34-7.37 (m, 1H), 3.72-3.76 (m, 4H), 3.64 (br, 2H), 2.58-2.65 (m, 4H), 2.44 (s, 3H). | 439 |
| 74 | (R)-5-Carbamoylpyridin-3-yl 2-methyl-4-(3-(trifluoromethoxy)benzyl)piperazine-1-carboxylate | 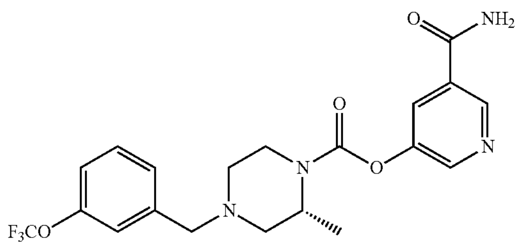 [SMILES: C[C@@H]1CN(Cc2cccc(OC(F)(F)F)c2)CCN1C(=O)Oc1cncc(C(N)=O)c1] | δ 8.83 (d, J = 1.8 Hz, 1H), 8.58 (d, J = 2.7 Hz, 1H), 7.97 (t, J = 2.1 Hz, 1H), 7.36 (t, J = 4.0 Hz, 1H), 7.26-7.28 (m, 2H), 7.12 (d, J = 7.8 Hz, 1H), 6.36 (br, 1H), 5.90 (br, 1H), 4.38 (br, 1H), 3.99-4.03 (m, 1H), 3.60-3.65 (m, 1H), 3.37-3.49 (m, 2H), 2.85-2.88 (m, 1H), 2.65-2.69 (m, 1H), 2.15-2.31 (m, 2H), 1.40 (d, J = 6.0 Hz, 3H). | 439 |
| 75 | (R)-5-Cyanopyridin-3-yl 2-methyl-4-(3-(trifluoromethoxy)benzyl)piperazine-1-carboxylate | 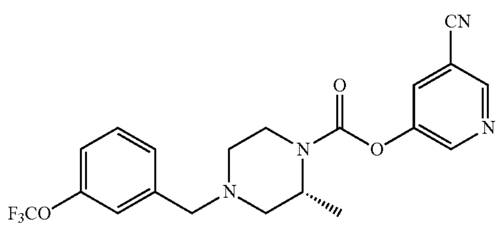 | δ 8.64-8.71 (m, 2H), 7.84 (t, J = 2.1 Hz, 1H), 7.36 (t, J = 7.8 Hz, 1H), 7.26-7.27 (m, 2H), 7.13 (d, J = 7.8 Hz, 1H), 4.37 (br, 1H), 3.98-4.02 (m, 1H), 3.60-3.65 (m, 1H), 3.40-3.49 (m, 2H), 2.86-2.89 (m, 1H), 2.66-2.70 (m, 1H), 2.16-2.31 (m, 2H), 1.40 (d, J = 5.7 Hz, 3H). | 421 |
| 76 | (R)-5-Fluoropyridin-3-yl 2-methyl-4-(3-(trifluoromethoxy)benzyl)piperazine-1-carboxylate | 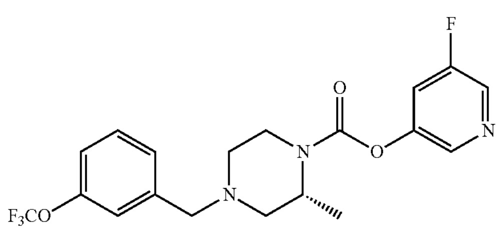 [SMILES: C[C@@H]1CN(Cc2cccc(OC(F)(F)F)c2)CCN1C(=O)Oc1cncc(F)c1] | δ 8.29-8.34 (m, 2H), 7.33-7.38 (m, 2H), 7.26-7.27 (m, 2H), 7.12 (d, J = 8.1 Hz, 1H), 4.38 (br, 1H), 3.98-4.03 (m, 1H), 3.60-3.64 (m, 1H), 3.37-3.48 (m, 2H), 2.84-2.88 (m, 1H), 2.64-2.68 (m, 1H), 2.15-2.30 (m, 2H), 1.39 (d, J = 6.6 Hz, 3H). | 414 |
| 77 | 5-Aminopyridin-3-yl (R)-2-methyl-4-(3-(trifluoromethoxy)benzyl)piperazine-1-carboxylate | 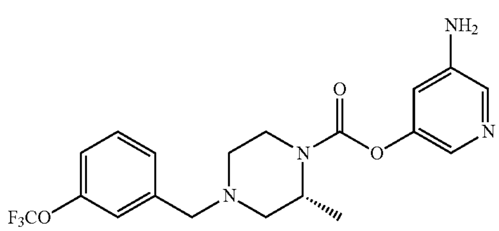 [SMILES: C[C@@H]1CN(Cc2cccc(OC(F)(F)F)c2)CCN1C(=O)Oc1cncc(N)c1] | δ 7.84-7.92 (m, 2H), 7.35 (t, J = 8.0 Hz, 1H), 7.26-7.27 (m, 2H), 7.12 (d, J = 7.8 Hz, 1H), 6.83 (t, J = 2.2 Hz, 1H), 4.37 (br, 1H), 3.92-4.02 (m, 1H), 3.34-3.71 (m, 3H), 2.82-2.86 (m, 1H), 2.65-2.67 (m, 1H), 2.13-2.29 (m, 2H), 1.40 (d, J = 6.9 Hz, 3H). | 411 |
| 78 | 5-Cyanopyridin-3-yl (R)-4-(3-fluoro-5-(trifluoromethyl)benzyl)-2-methylpiperazine-1-carboxylate | 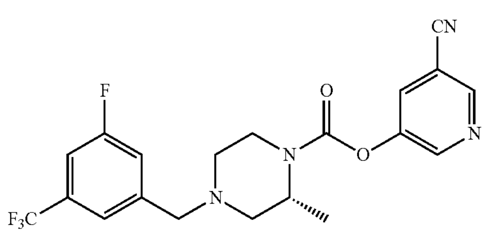 [SMILES: C[C@@H]1CN(Cc2cc(F)cc(C(F)(F)F)c2)CCN1C(=O)Oc1cncc(C#N)c1] | δ 8.71 (s, 1H), 8.64 (s, 1H), 7.84 (t, J = 1.8 Hz, 1H), 7.43 (s, 1H), 7.31 (d, J = 9.0 Hz, 1H), 7.23 (s, 1H), 4.39 (br, 1H), 4.00-4.04 (m, 1H), 3.40-3.67 (m, 3H), 2.85-2.89 (m, 1H), 2.65-2.69 (m, 1H), 2.19-2.36 (m, 2H), 1.42 (d, J = 6.3 Hz, 3H). | 423 |

-continued

| Ex | Name | Structure | NMR (¹H NMR, 300 MHz or 400 MHz, Chloroform-d) | MS [M + H]⁺ |
|---|---|---|---|---|
| 79 | 5-Fluoropyridin-3-yl (R)-4-(3-fluoro-5-(trifluoromethyl)benzyl)-2-methylpiperazine-1-carboxylate | 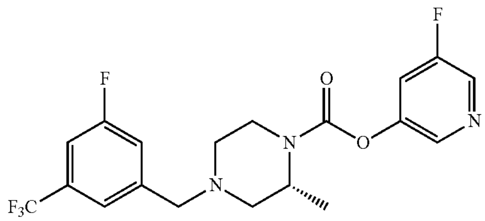 [SMILES: C[C@@H]1CN(Cc2cc(F)cc(C(F)(F)F)c2)CCN1C(=O)Oc1cncc(F)c1] | δ 8.29-8.35 (m, 2H), 7.43 (s, 1H), 7.29-7.43 (m, 2H), 7.23 (s, 1H), 4.40 (br, 1H), 4.00-4.04 (m, 1H), 3.61-3.66 (m, 1H), 3.39-3.53 (m, 2H), 2.83-2.87 (m, 1H), 2.64-2.68 (m, 1H), 2.18-2.35 (m, 2H), 1.41 (d, J = 6.6 Hz, 3H). | 416 |
| 80 | 5-Aminopyridin-3-yl (R)-4-(3-fluoro-5-(trifluoromethyl)benzyl)-2-methylpiperazine-1-carboxylate | 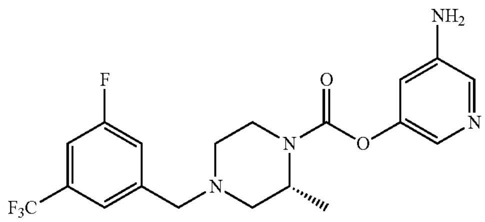 | δ 7.84-7.92 (m, 2H), 7.43 (s, 1H), 7.31 (d, J = 9.3 Hz, 1H), 7.24 (d, J = 8.4 Hz, 1H), 6.83 (t, J = 2.2 Hz, 1H), 4.39 (br, 1H), 3.99-4.04 (m, 1H), 3.73 (br, 2H), 3.47-3.65 (m, 2H), 3.35 (br, 1H), 2.82-2.85 (m, 1H), 2.62-2.66 (m, 1H), 2.16-2.33 (m, 2H), 1.39 (d, J = 6.9 Hz, 3H). | 413 |
| 81 | 5-Aminopyridin-3-yl (R)-2-methyl-4-(2-methyl-3-(trifluoromethyl)benzyl)piperazine-1-carboxylate | 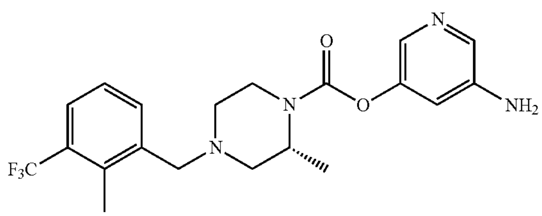 [SMILES: Cc1c(CN2CCN(C(=O)Oc3cncc(N)c3)[C@H](C)C2)cccc1C(F)(F)F] | δ 7.93 (d, J = 2.4 Hz, 1H), 7.84 (d, J = 2.1 Hz, 1H), 7.58 (d, J = 7.8 Hz, 1H), 7.44 (d, J = 7.5 Hz, 1H), 7.23 (d, J = 7.5 Hz, 1H), 6.84 (t, J = 2.2 Hz, 1H), 4.39 (br, 1H), 3.95-3.99 (m, 1H), 3.46-3.74 (m, 4H), 3.26 (br, 1H), 2.77-2.81 (m, 1H), 2.64-2.67 (m, 1H), 2.51 (s, 3H), 2.31-2.36 (m, 1H), 2.10-2.18 (m, 1H), 1.34 (d, J = 6.9 Hz, 3H). | 409 |
| 82 | 5-Carbamoyl-4-methylpyridin-3-yl (R)-2-methyl-4-(2-methyl-3-(trifluoromethyl)benzyl)piperazine-1-carboxylate | 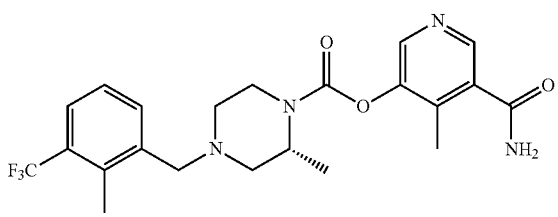 [SMILES: Cc1c(OC(=O)N2CCN(Cc3cccc(C(F)(F)F)c3C)C[C@H]2C)cncc1C(N)=O] | δ 8.48 (s, 1H), 8.38 (s, 1H), 7.59 (d, J = 7.8 Hz, 1H), 7.46 (d, J = 7.5 Hz, 1H), 7.22-7.26 (m, 1H), 6.01-6.21 (m, 2H), 4.41-4.45 (m, 1H), 3.99 (br, 1H), 3.47-3.59 (m, 2H), 3.28-3.31 (m, 1H), 2.80-2.84 (m, 1H), 2.67-2.71 (m, 1H), 2.51 (s, 3H), 2.34-2.38 (m, 4H), 2.13-2.21 (m, 1H), 1.38 (br, 3H). | 451 |
| 83 | 5-Cyano-4-methylpyridin-3-yl (R)-2-methyl-4-(2-methyl-3-(trifluoromethyl)benzyl)piperazine-1-carboxylate | 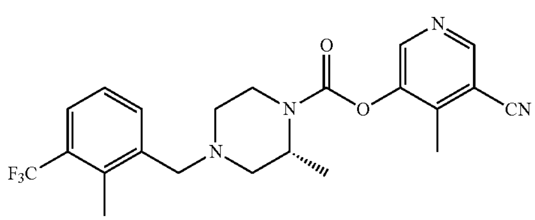 [SMILES: Cc1c(C#N)cncc1OC(=O)N1CCN(Cc2cccc(C(F)(F)F)c2C)C[C@H]1C] | δ 8.65 (s, 1H), 8.53 (s, 1H), 7.59 (d, J = 7.8 Hz, 1H), 7.45 (d, J = 7.5 Hz, 1H), 7.22-7.26 (m, 1H), 4.42-4.43 (m, 1H), 3.99 (br, 1H), 3.49-3.59 (m, 2H), 3.25-3.39 (m, 1H), 2.82-2.85 (m, 1H), 2.68-2.72 (m, 1H), 2.51 (s, 3H), 2.34-2.43 (m, 4H), 2.13-2.22 (m, 1H), 1.38 (br, 3H). | 433 |
| 84 | 5-Cyanopyridin-3-yl (R)-2-methyl-4-(3-(pyrimidin-2-yloxy)benzyl)piperazine-1-carboxylate | 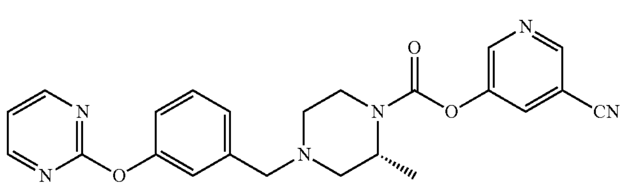 [SMILES: C[C@@H]1CN(Cc2cccc(Oc3ncccn3)c2)CCN1C(=O)Oc1cncc(C#N)c1] | δ 8.74 (d, J = 3.0 Hz, 1H), 8.66 (d, J = 3.0 Hz, 1H), 8.57-8.60 (m, 2H), 7.85-7.86 (m, 1H), 7.42-7.48 (m, 1H), 7.28-7.33 (m, 2H), 7.08-7.08 (m, 1H), 6.93-7.07 (m, 1H), 4.45 (br, 1H), 4.05 (br, 1H), 3.64-3.89 (m, 3H), 2.83-3.12 (m, 2H), 2.32-2.42 (m, 2H), 1.47 (br, 3H). | 431 |

| Ex | Name | Structure | NMR (¹H NMR, 300 MHz or 400 MHz, Chloroform-d) | MS [M + H]⁺ |
|---|---|---|---|---|
| 85 | 5-Carbamoylpyridin-3-yl (R)-4-(3-chloro-5-fluorobenzyl)-2-methylpiperazine-1-carboxylate | 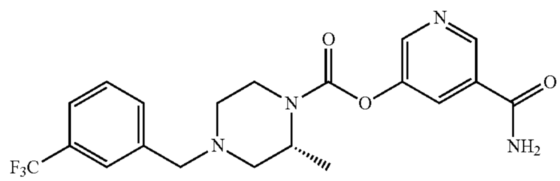 [SMILES: C[C@@H]1CN(Cc2cccc(C(F)(F)F)c2)CCN1C(=O)Oc1cncc(C(N)=O)c1] | δ 8.83 (s, 1H), 8.57 (s, 1H), 7.98 (s, 1H), 7.16 (s, 1H), 7.03-7.00 (m, 2H), 6.49 (br, 1H), 6.12 (br, 1H), 4.40 (s, 1H), 4.01 (s, 1H), 3.55-3.52 (m, 1H), 3.46-3.38 (m, 2H), 2.85-2.83 (m, 1H), 2.69-2.66 (m, 1H), 2.32-2.30 (m, 1H), 2.21-2.15 (m, 1H), 1.41 (d, J = 3.2 Hz, 3H). | 407 |
| 86 | 5-Cyanopyridin-3-yl (R)-4-(3-chloro-5-(pyrimidin-2-yloxy)benzyl)-2-methylpiperazine-1-carboxylate | 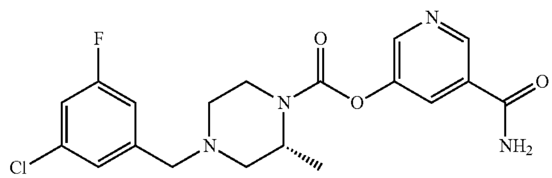 [SMILES: C[C@@H]1CN(Cc2cc(F)cc(Cl)c2)CCN1C(=O)Oc1cncc(C(N)=O)c1] | (Methanol-d4) δ 8.80-8.73 (m, 1H), 8.72-8.60 (m, 1H), 8.60-8.58 (m, 2H), 8.13-8.08 (m, 1H), 7.39-7.31 (m, 1H), 7.31-7.22 (m, 1H), 7.22-7.14 (m, 2H), 4.61-4.23 (m, 1H), 4.18-3.85 (m, 1H), 3.71-3.60 (m, 1H), 3.60-3.49 (m, 1 H), 3.49-3.37 (m, 1H), 3.01-2.87 (m, 1H), 2.87-2.70 (m, 1H), 2.41-2.28 (m, 1H), 2.28-2.11 (m, 1 H), 1.55-1.27 (m, 3 H). | 487 [M + Na]⁺ |

II. Biological Evaluation

Compounds were tested to assess their MAGL and FAAH activity using the following in vitro and in vivo assays.

In Vitro Competitive Activity-Based Protein Profiling.

Proteomes (mouse brain membrane fraction or cell lysates for mouse assays; human prefrontal cortex or cell membrane fractions for human assays) (50 μL, 1.0 mg/mL total protein concentration) were preincubated with varying concentrations of inhibitors at 37° C. After 30 min, FP—Rh or HT-01 (1.0 μL, 50 μM in DMSO) was added and the mixture was incubated for another 30 min at 37° C. Reactions were quenched with SDS loading buffer (15 μL-4×) and run on SDS-PAGE. Following gel imaging, serine hydrolase activity was determined by measuring fluorescent intensity of gel bands corresponding to MAGL and FAAH using ImageJ 1.43u software. $IC_{50}$ data from this assay is shown in Table 1.

Preparation of Mouse Brain Proteomes from Inhibitor Treated Mice.

Inhibitors were administered to wild-type C57Bl/6J by oral gavage in a vehicle of polyethylene glycol. Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44).

Compounds demonstrated activity in the assays described herein as indicated in Table 1.

TABLE 1

| Ex | FAAH (human) % inh. 1 μM | MAGL (human) % inh. 1 μM | FAAH (human) $IC_{50}$ (μM) | MAGL (human) $IC_{50}$ (μM) | FAAH (mouse) % inh. 5 mg/kg | MAGL (mouse) % inh. 5 mg/kg |
|---|---|---|---|---|---|---|
| 1 | A | A | *** | *** | | |
| 2 | | | * | ** | | |
| 3 | A | A | *** | *** | | |
| 4 | A | A | *** | *** | A | A |
| 5 | A | A | *** | *** | | |
| 6 | A | A | *** | ** | A | D |
| 7 | A | A | *** | *** | A | C |
| 8 | | | ** | *** | | |
| 9 | | | ** | ** | | |
| 10 | | | *** | *** | | |
| 11 | | | ** | ** | | |
| 12 | B | A | | | | |
| 13 | B | A | | | | |
| 14 | B | A | | | | |
| 15 | A | A | *** | ** | D | D |
| 16 | A | C | | | | |
| 17 | A | A | ** | *** | | |
| 18 | A | A | ** | ** | A | A |
| 19 | A | A | *** | * | A | D |
| 20 | A | A | *** | *** | A | A |
| 21 | A | C | ** | * | | |
| 22 | B | C | | | | |
| 23 | A | A | *** | *** | | |
| 24 | A | A | | | | |
| 25 | A | A | ** | *** | | |
| 26 | A | A | ** | *** | | |
| 27 | A | A | *** | *** | | |
| 28 | A | A | *** | *** | | |
| 29 | A | A | *** | ** | | |

TABLE 1-continued

| Ex | FAAH (human) % inh. 1 μM | MAGL (human) % inh. 1 μM | FAAH (human) IC$_{50}$ (μM) | MAGL (human) IC$_{50}$ (μM) | FAAH (mouse) % inh. 5 mg/kg | MAGL (mouse) % inh. 5 mg/kg |
|---|---|---|---|---|---|---|
| 30 | | | * | ** | | |
| 31 | | | *** | ** | | |
| 32 | A (10 μM) | A (10 μM) | | | | |
| 33 | C | B | | | | |
| 34 | | | * | ** | | |
| 35 | A | A | | | | |
| 36 | A | A | *** | *** | A | C |
| 37 | A | A | | | | |
| 38 | A | A | *** | *** | A | D |
| 39 | A | A | ** | ** | | |
| 40 | A | A | ** | *** | | |
| 41 | A | A | | | | |
| 42 | A | A | *** | *** | | |
| 43 | A | A | *** | *** | | |
| 44 | A | A | ** | ** | | |
| 45 | A | A | *** | *** | | |
| 46 | A | A | | | | |
| 47 | A | A | | | | |
| 48 | A | A | *** | ** | | |
| 49 | A | A | *** | ** | | |
| 50 | A | A | ** | *** | | |
| 51 | A | A | ** | * | D | D |
| 52 | A | A | ** | *** | A | D |
| 53 | A | A | *** | *** | A | B |
| 54 | A | C (10 μM) | | | | |
| 55 | A (50 μM) | B | | | | |
| 56 | A | A | ** | ** | | |
| 57 | A (10 μM) | A | | | | |
| 58 | A | A | *** | ** | | |
| 59 | B | A | | | | |
| 60 | A | A | | | | |
| 61 | A (10 μM) | A | | | | |
| 62 | A | C | *** | * | | |
| 63 | A | A (10 μM) | | | | |
| 64 | A | A | *** | *** | A | A |
| 65 | A | A | ** | ** | A | A |
| 66 | A | A | *** | *** | | |
| 67 | A | A | *** | ** | | |
| 68 | A | A | *** | *** | | |
| 69 | A | A (10 μM) | | | | |
| 70 | A | B (10 μM) | | | | |
| 71 | A | B | *** | ** | A | D |
| 72 | A | A | *** | * | | |
| 73 | A | A | *** | *** | | |
| 74 | A | C | *** | ** | A | A |
| 75 | A | A | *** | *** | | |
| 76 | A | A (50 μM) | *** | * | | |
| 77 | A | D | | | | |
| 78 | A | A | *** | *** | | |
| 79 | A | A (10 μM) | *** | ** | | |
| 80 | A | C (50 μM) | | | | |
| 81 | A | D | | | | |
| 82 | A | D | | | | |
| 83 | A | A | *** | ** | | |
| 84 | A | A | ** | *** | | |
| 85 | A | A | *** | ** | A | A |
| 86 | A | A | *** | ** | A | A |

*** IC$_{50}$ is less than or equal to 100 nM;
** IC$_{50}$ is greater than 100 nM and less than 1 μM;
* IC$_{50}$ is greater than or equal to 1 μM and less or equal to 10 μM.
A = % inhibition is greater than or equal to 75%; B = % inhibition is greater than or equal to 50% and less than 75%; C = % inhibition is greater than or equal to 25% and less than 50%; D = % inhibition is greater than or equal to 0% and less than 25%.

What is claimed is:

1. A method of treating a neurological disorder in a subject in need thereof, the method comprising administering to the subject a therapeutically effective amount of a compound having the structure of Formula (I):

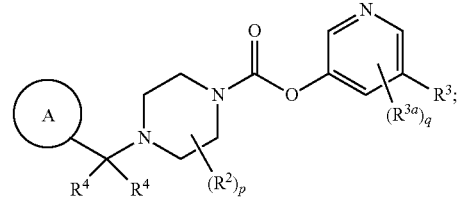

Formula (I)

wherein:

is

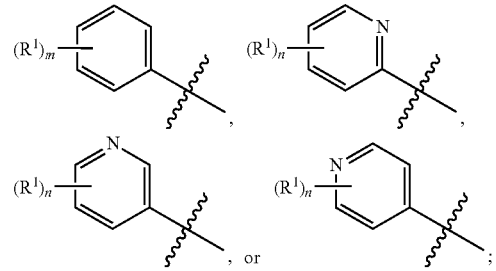

each $R^1$ is independently selected from halogen, —CN, $C_{1-6}$alkyl, $C_{2-6}$alkynyl, $C_{1-6}$alkyl-OR$^7$, $C_{1-6}$haloalkyl, $C_{3-8}$cycloalkyl, —NR$^5$R$^6$, —C(O)NR$^5$R$^6$, —OR$^7$, —SO$_2$R$^{12}$, —SF$_5$, —SR$^8$, aryl, and heteroaryl, wherein aryl and heteroaryl are optionally substituted with one or two groups independently selected from halogen, $C_{1-6}$alkyl, $C_{1-6}$haloalkyl, and —C(O)NR$^8$R$^9$; or two adjacent $R^1$ form a heterocycloalkyl ring optionally substituted with one or two $R^{11}$;

$R^2$ is $C_{1-6}$alkyl;

$R^3$ is selected from halogen, —CN, $C_{1-6}$alkyl, $C_{1-6}$haloalkyl, —NR$^8$R$^9$, —C(O)NR$^8$R$^9$, —NR$^8$C(O)R$^9$, and —NR$^9$SO$_2$R$^8$;

$R^{3a}$ is selected from halogen, $C_{1-6}$alkyl, and $C_{1-6}$haloalkyl;

each $R^4$ is independently selected from H and $C_{1-6}$alkyl;

each $R^5$ and $R^6$ is independently selected from H, $C_{1-6}$alkyl, and $C_{3-8}$cycloalkyl; or $R^5$ and $R^6$, together with the nitrogen to which they are attached, form a heterocycloalkyl optionally substituted with one or two $R^{10}$;

each $R^7$ is independently selected from H, $C_{1-6}$alkyl, $C_{1-6}$alkyl-O—$C_{1-6}$alkyl, $C_{1-6}$haloalkyl, $C_{3-8}$cycloalkyl, heterocycloalkyl, aryl, and heteroaryl, wherein heterocycloalkyl, aryl, and heteroaryl are optionally substituted with one or two groups independently selected from halogen, $C_{1-6}$alkyl, and $C_{1-6}$haloalkyl;

each $R^8$ and $R^9$ is independently selected from H, $C_{1-6}$alkyl, $C_{3-8}$cycloalkyl, aryl, and heteroaryl;

each $R^{10}$ is independently selected from $C_{1-6}$alkyl, $C_{3-8}$cycloalkyl, $C_{1-6}$haloalkyl, halogen, oxo, —CN, —C(O)OR$^8$, —C(O)R$^8$, —C(O)NR$^8$R$^9$, —SO$_2$R$^8$, —NR$^9$C(O)R$^8$, and —NR$^9$SO$_2$R$^8$;

each $R^{11}$ is independently selected from halogen and $C_{1-6}$alkyl;

each $R^{12}$ is independently selected from $C_{1-6}$alkyl and $C_{3-8}$cycloalkyl;

m is 0, 1, 2, 3, 4, or 5;

n is 0, 1, 2, or 3;

p is 0 or 1; and q is 0 or 1;

or a pharmaceutically acceptable salt or solvate thereof, wherein the level of monoacylglycerol lipase (MAGL) and/or the level of fatty acid amide hydrolase (FAAH) in a biological sample from the subject is decreased after administration of the therapeutically effective amount of the compound to the subject as compared to the level of MAGL and/or the level of FAAH in a biological sample from the subject prior to the administration, thereby treating the subject.

2. The method of claim 1, wherein $R^2$ is —CH$_3$.

3. The method of claim 1, wherein

is

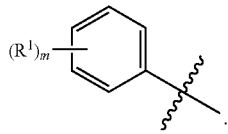

4. The method of claim 3, wherein m is 1 or 2.
5. The method of claim 1, wherein $R^3$ is $C_{1-6}$haloalkyl.
6. The method of claim 5, wherein $R^3$ is —CF$_3$.
7. The method of claim 1, wherein $R^3$ is halogen.
8. The method of claim 1, wherein $R^3$ is —C(O)NH$_2$.
9. The method of claim 1, wherein $R^3$ is —CN.
10. The method of claim 1, wherein q is 0.
11. The method of claim 1, wherein q is 1.
12. The method of claim 1, wherein each $R^1$ is independently selected from halogen, $C_{1-6}$alkyl, $C_{1-6}$haloalkyl, and —OR$^7$.
13. The method of claim 12, wherein $R^7$ is independently selected from $C_{1-6}$alkyl, $C_{1-6}$haloalkyl, $C_{3-8}$cycloalkyl, aryl, and heteroaryl.
14. The method of claim 13, wherein $R^7$ is independently selected from $C_{1-6}$alkyl and $C_{1-6}$haloalkyl.
15. The method of claim 1, wherein each $R^4$ is H.
16. The method of claim 1, wherein the compound having the structure of Formula (I) is selected from:

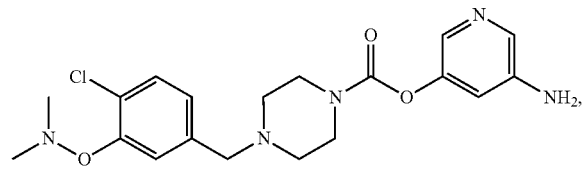

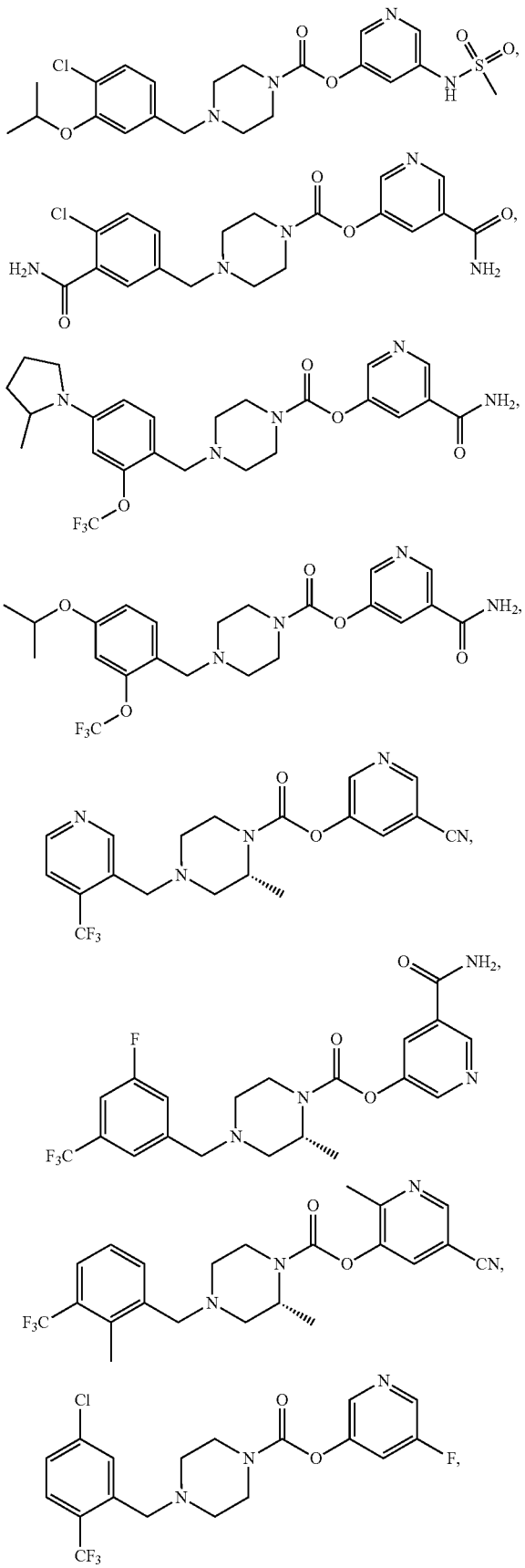

-continued
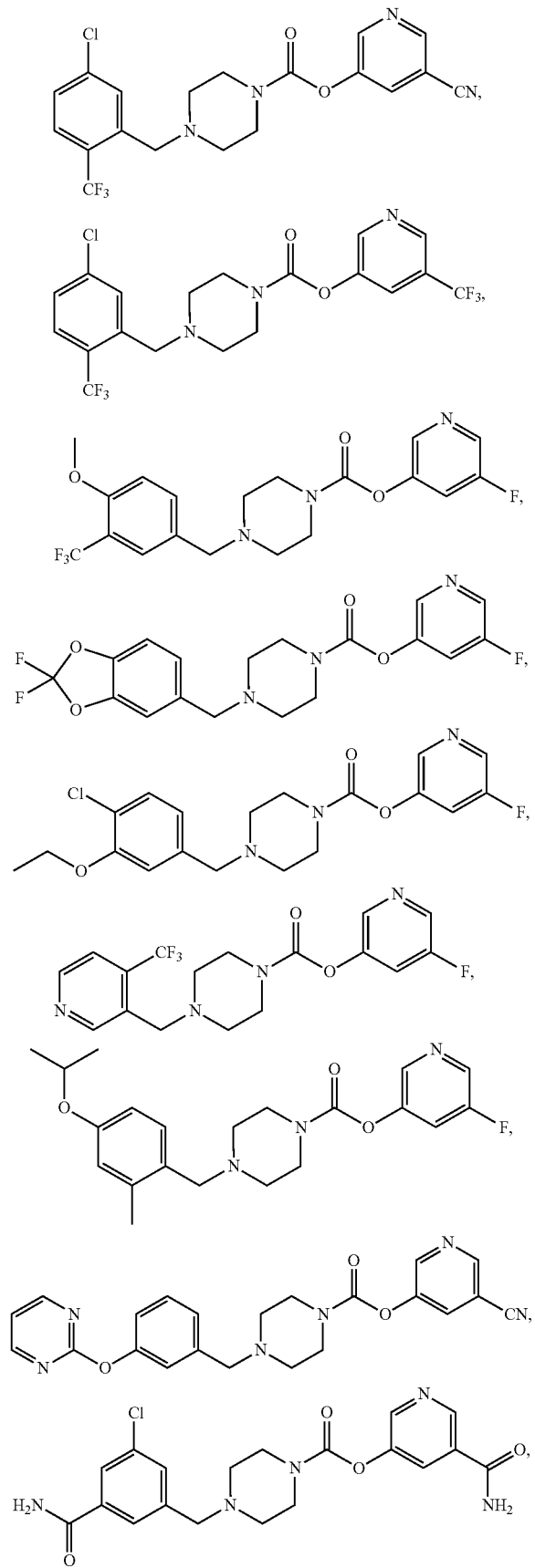
-continued
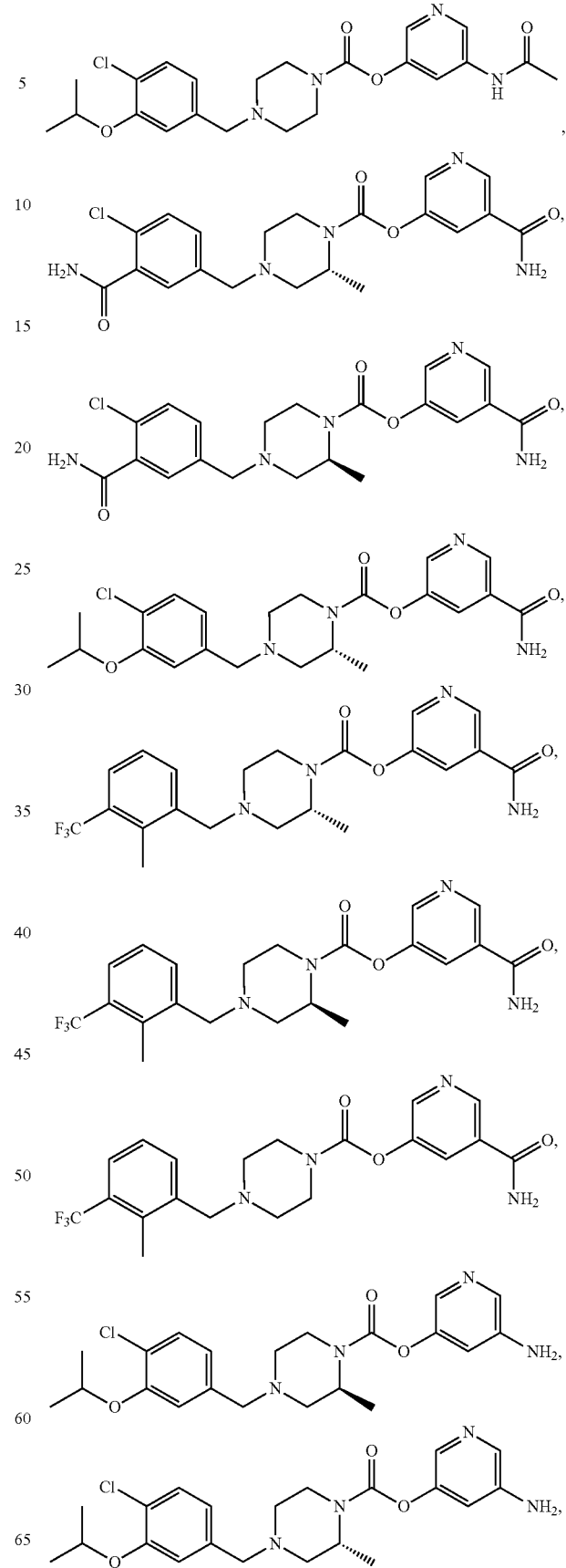

149
-continued
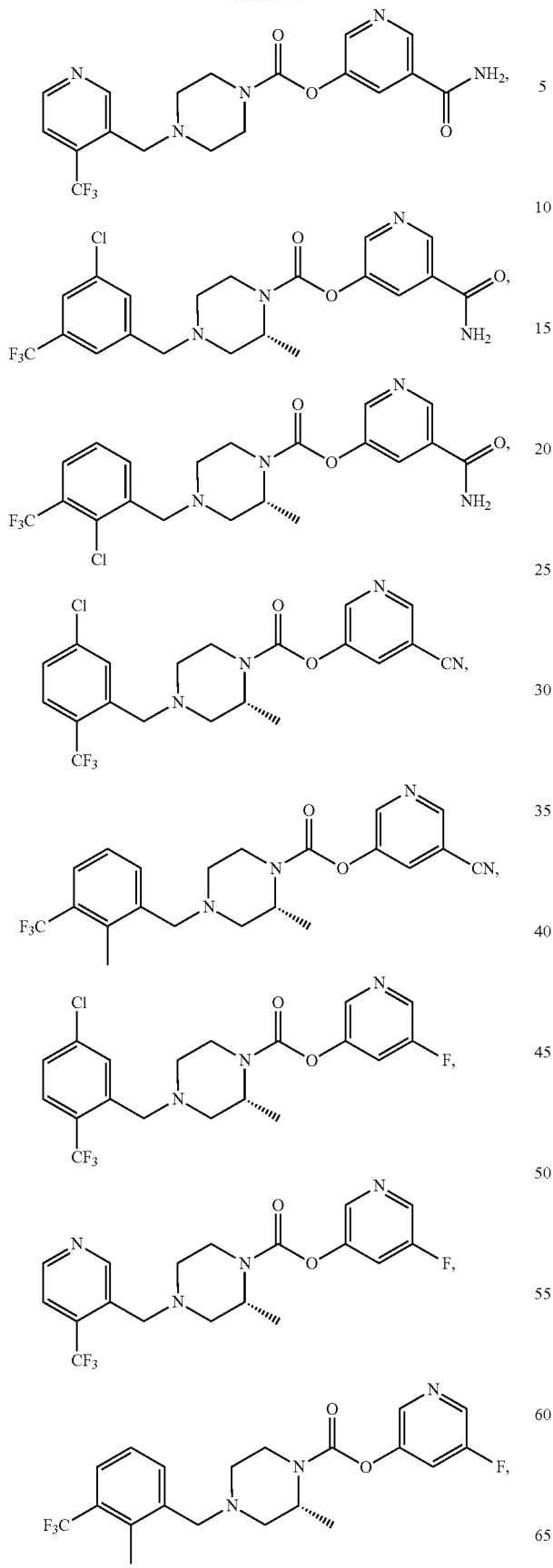
150
-continued
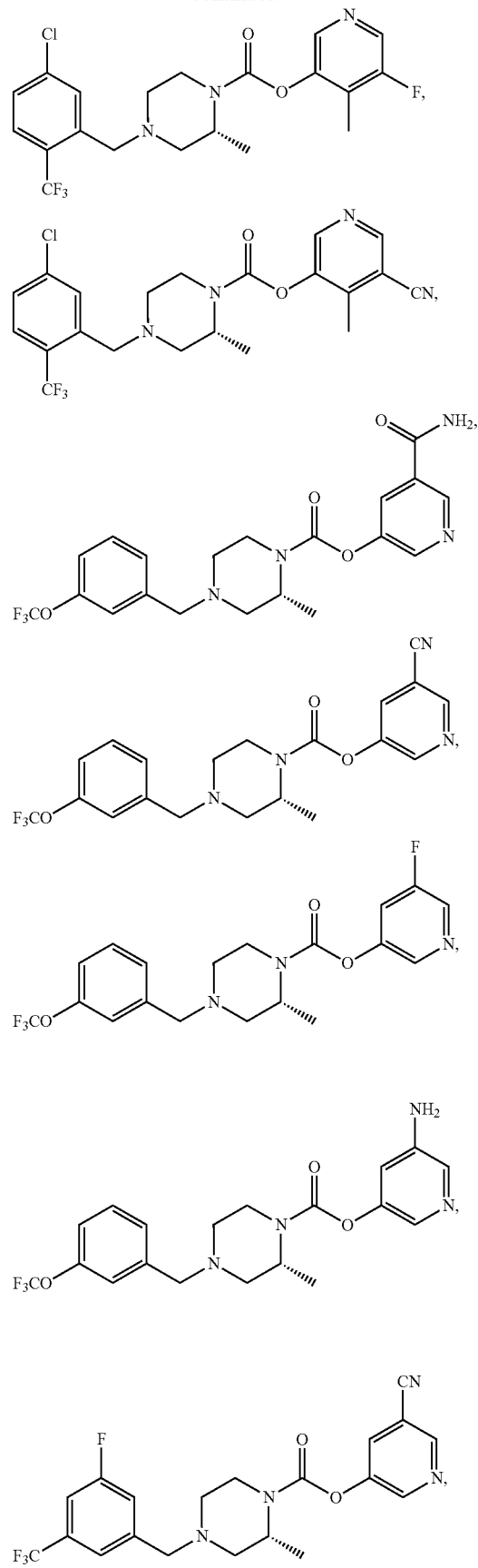

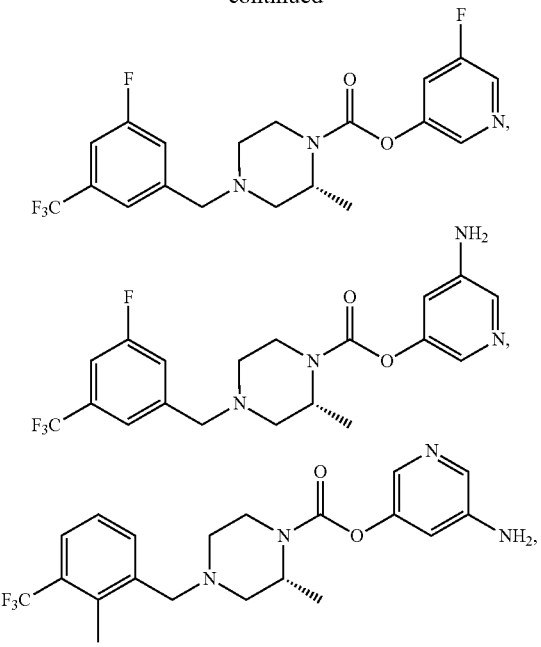
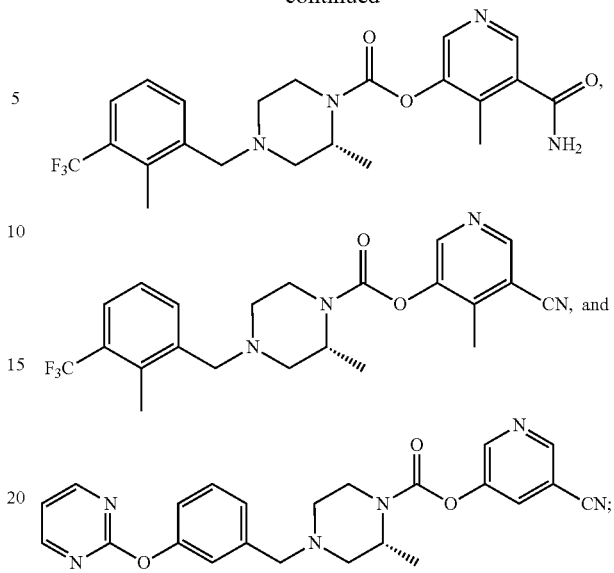
or a pharmaceutically acceptable salt or solvate thereof.
* * * * *